US008637576B2

(12) United States Patent
Powers et al.

(10) Patent No.: US 8,637,576 B2
(45) Date of Patent: *Jan. 28, 2014

(54) BENZAMIDE DERIVATIVES AND USES RELATED THERETO

(75) Inventors: Jay P. Powers, Pacifica, CA (US); Michael R. Degraffenreid, San Francisco, CA (US); Xiao He, Foster City, CA (US); Lisa D. Julian, Denver, CO (US); Dustin L. McMinn, Pacifica, CA (US); Daqing Sun, Foster City, CA (US); Yosup Rew, Foster City, CA (US); Xuelei Yan, Foster City, CA (US)

(73) Assignee: Amgen Inc., Thousand Oaks, CA (US)

( * ) Notice: Subject to any disclaimer, the term of this patent is extended or adjusted under 35 U.S.C. 154(b) by 536 days.

This patent is subject to a terminal disclaimer.

(21) Appl. No.: 12/582,535

(22) Filed: Oct. 20, 2009

(65) Prior Publication Data
US 2010/0069447 A1    Mar. 18, 2010

Related U.S. Application Data

(63) Continuation of application No. 11/448,986, filed on Jun. 8, 2006, now Pat. No. 7,605,289.

(60) Provisional application No. 60/691,244, filed on Jun. 17, 2005.

(51) Int. Cl.
*A61K 31/165*  (2006.01)
*A61K 31/44*   (2006.01)

(52) U.S. Cl.
USPC ............ 514/617; 514/212.01; 514/231.2; 514/247; 514/330; 514/423

(58) Field of Classification Search
USPC ............ 564/176, 177; 548/530; 546/225; 544/358; 540/484; 514/617, 423, 330, 514/247, 231.2, 212.01
See application file for complete search history.

(56) References Cited

U.S. PATENT DOCUMENTS

| 7,605,289 B2 * | 10/2009 | Powers et al. ............ 564/177 |
| 2007/0293478 A1 * | 12/2007 | Zimmermann et al. ...... 514/218 |

FOREIGN PATENT DOCUMENTS

| GB | 1 495 287 A | 12/1977 |
| JP | 08 311032 A | 11/1996 |
| JP | 09 309879 A | 12/1997 |
| WO | WO 02/058690 A2 | 8/2002 |
| WO | WO 2004/065351 A1 | 8/2004 |
| WO | WO 2004/089896 A1 | 10/2004 |
| WO | WO 2006/138508 | 12/2006 |

OTHER PUBLICATIONS

Draper et al. "1 lb-Hydroxysteroid dehydrogenase and the pre-receptor regulation of corticosteroid hormone action" J. Endocrinology, 2005, 186, 251-271.*
Wolff, M.E. "Burger's Medicinal Chemistry 4th Ed. Part I", Wiley: New York, 1979, 336-337.*
Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996, pp. 451 and 596.*
West, Anthony R., Solid State Chemistry and its Applications, Wiley, New York, 1988, pp. 358 & 365.*
Herve Allain et al, Neuropsychiatric Disease and Treatment, 2007:3(1), 103-116.*
Office Action received in the related European Patent Application No. 06 773 288.3, dated Dec. 29, 2009.
Lacombe, et al., "Nitrogen-bridged substituted 8-arylquinolines as potent PDE IV inhibitors", *Bioorganic & Medicinal Chemistry Letters*, vol. 16, 2006, pp. 2608-2612.
Rossi et al., "Spectroscopic Characterisation of Fluorinated/Hydrogenated Mixed Vesicles Containing Fluorinated Mn(III)-Porphyrin" *Inorganica Chimica Acta*, vol. 272, No. 1-2, Elsevier Science, May 1, 1998, pp. 274-282.

* cited by examiner

*Primary Examiner* — Shailendra Kumar
(74) *Attorney, Agent, or Firm* — Elsa D. Lemoine

(57) ABSTRACT

Benzamide derivatives of formulae I and II, and pharmaceutically acceptable salts, solvates, stereoisomers, and prodrugs thereof, and pharmaceutical compositions comprising the same, are described and have therapeutic utility, particularly in the treatment of diabetes, obesity, and related conditions and disorders:

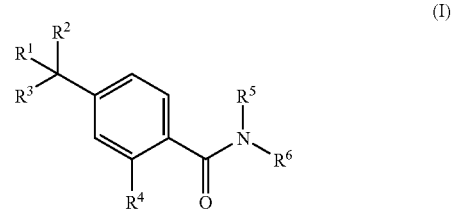

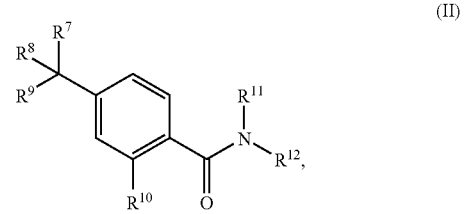

wherein $R^1$, $R^2$, $R^3$, $R^4$, $R^5$, $R^6$, $R^7$, $R^8$, $R^9$, $R^{10}$, $R^{11}$, and $R^{12}$ are defined as provided herein.

4 Claims, No Drawings

BENZAMIDE DERIVATIVES AND USES RELATED THERETO

This application is a CON of Ser. No. 11/448,986, filed Jun. 8, 2006, now U.S. Pat. No. 7,605,289, which claims benefit of 60/691,244, filed Jun. 17, 2005.

BACKGROUND OF THE INVENTION

This invention is generally directed to novel compounds, compositions, and the use of either in methods for modulating hydroxysteroid dehydrogenases, such as 11β-HSD1, and for treating or preventing diseases associated with the modulation of hydroxysteroid dehydrogenases, such as diabetes and obesity. The methods comprise the administration, to a patient in need thereof, of a therapeutically effective amount of a benzamide derivative. Novel benzamide derivatives or pharmaceutically acceptable salts, solvates, stereoisomers, or prodrugs thereof are presented herein.

Hydroxysteroid dehydrogenases (HSDs) regulate the occupancy and activation of steroid hormone receptors by converting steroid hormones into their inactive metabolites. For a recent review, see Nobel et al., Eur. J. Biochem. 2001, 268:4113-4125.

There exist numerous classes of HSDs. The 11-beta-hydroxysteroid dehydrogenases (11β-HSDs) catalyze the interconversion of active glucocorticoids (such as cortisol and corticosterone), and their inert forms (such as cortisone and 11-dehydrocorticosterone). The isoform 11-beta-hydroxysteroid dehydrogenase type 1 (11β-HSD1) is expressed in liver, adipose tissue, brain, lung and other glucocorticoid tissue and is a potential target for therapy directed at numerous disorders that may be ameliorated by reduction of glucocorticoid action, such as diabetes, obesity and age-related cognitive dysfunction. Seckl, et al., Endocrinology, 2001, 142:1371-1376.

It is well known that glucocorticoids play a central role in the development of diabetes and that glucocorticoids enable the effect of glucagon on the liver. Long et al., J. Exp. Med. 1936, 63: 465-490; and Houssay, Endocrinology 1942, 30: 884-892. In addition, it has been well substantiated that 11β-HSD1 plays an important role in the regulation of local glucocorticoid effect and of glucose production in the liver. Jamieson et al., J. Endocrinol. 2000, 165:685-692.

Furthermore, the hypothesized mechanism of action of HSDs in the treatment of diabetes has been supported by various experiments conducted in mice and rats. These studies showed that the mRNA levels and activities of two key enzymes in hepatic glucose production, phosphoenolpyruvate carboxykinase (PEPCK), and glucose-6-phosphatase (G6Pase) were reduced upon administration of HSD inhibitors. In addition, blood glucose levels and hepatic glucose production were shown to be reduced in 11β-HSD1 knockout mice. Additional data gathered using this murine knockout model also confirm that inhibition of 11β-HSD1 will not cause hypoglycemia, since the basal levels of PEPCK and G6Pase are regulated independently of glucocorticoids. Kotelevtsev et al., Proc. Natl. Acad. Sci. USA 1997, 94: 14924-14929.

HSDs also play a role in obesity. Obesity is an important factor in Syndrome X as well as type II (non-insulin dependent) diabetes, and omental fat appears to be of central importance in the development of both of these disease, as abdominal obesity has been linked with glucose intolerance, hyperinsulinemia, hypertriglyceridemia, and other factors of Syndrome X (e.g., raised blood pressure, decreased levels of HDL and increased levels of VLDL). Montague et al., Diabetes 2000, 49:883-888, 2000. It has also been reported that inhibition of the 11β-HSDs in pre-adipocytes (stromal cells) resulted in a decreased rate of differentiation into adipocytes. This is predicted to result in diminished expansion (possibly reduction) of the omental fat depot, which may lead to reduced central obesity. Bujalska et al., Lancet 1997, 349: 1210-1213.

Inhibition of 11β-HSD1 in mature adipocytes is expected to attenuate secretion of the plasminogen activator inhibitor 1 (PAI-1), which is an independent cardiovascular risk factor, as reported in Halleux et al., J. Clin. Endocrinol. Metab. 1999, 84:4097-4105. In addition, a correlation has been shown to exist between glucocorticoid activity and certain cardiovascular risk factors. This suggests that a reduction of the glucocorticoid effects would be beneficial in the treatment or prevention of certain cardiovascular diseases. Walker et al., Hypertension 1998, 31:891-895; and Fraser et al., Hypertension 1999, 33:1364-1368.

HSDs have also been implicated in the process of appetite control and therefore are believed to play an additional role in weight-related disorders. It is known that adrenalectomy attenuates the effect of fasting to increase both food intake and hypothalamic neuropeptide Y expression. This suggests that glucocorticoids play a role in promoting food intake and that inhibition of 11β-HSD1 in the brain may increase satiety, thus resulting in a decreased food intake. Woods et al., Science 1998, 280:1378-1383.

Another possible therapeutic effect associated with modulation of HSDs is that which is related to various pancreatic aliments. It is reported that inhibition of 11β-HSD1 in murine pancreatic β-cells results in increased insulin secretion. Davani et al., J. Biol. Chem. 2000, 275:34841-34844. This follows from the discovery that glucocorticoids were previously found to be responsible for reduced pancreatic insulin release in vivo, Billaudel et al., Horm. Metab. Res. 1979, 11:555-560. Thus, it is suggested that inhibition of 11β-HSD1 would yield other beneficial effects in the treatment of diabetes other than the predicted effects on the liver and fat reduction.

11β-HSD1 also regulates glucocorticoid activity in the brain and thus contributes to neurotoxicity. Rajan et al., Neuroscience 1996, 16:65-70; and Seckl et al., Neuroendocrinol. 2000, 18:49-99. Stress and/or glucocorticoids are known to influence cognitive function (de Quervain et al., Nature 1998, 394:787-790), and unpublished results indicate significant memory improvement in rats treated with a non-specific 11β-HSD inhibitor. These reports, in addition to the known effects of glucocorticoids in the brain, suggest that inhibiting HSDs in the brain may have a positive therapeutic effect against anxiety and related conditions. Tronche et al., Nature Genetics 1999, 23:99-103. 11β-HSD1 reactivates 11-DHC to corticosterone in hippocampal cells and can potentiate kinase neurotoxicity, resulting in age-related learning impairments. Therefore, selective inhibitors of 11β-HSD1 are believed to protect against hippocampal function decline with age. Yau et al., Proc Natl. Acad. Sci. USA 2001, 98:4716-4721. Thus, it has been hypothesized that inhibition of 11β-HSD1 in the human brain would protect against deleterious glucocorticoid-mediated effects on neuronal function, such as cognitive impairment, depression, and increased appetite.

HSDs are believed to play a role in immunomodulation based on the general perception that glucocorticoids suppress the immune system. There is known to be a dynamic interaction between the immune system and the HPA (hypothalamo-pituitary-adrenal) axis (Rook, Baillier's Clin. Endocrinol. Metab. 2000, 13: 576-581), and glucocorticoids help balance between cell-mediated responses and humoral responses.

Increased glucocorticoid activity, which may be induced by stress, is associated with a humoral response and as such, the inhibition of 11β-HSD1 may result in shifting the response towards a cell-based reaction. In certain disease states, such as tuberculosis, leprosy, and psoriasis, the immune reaction is typically biased towards a humoral response when a cell-based response might be more appropriate Inhibition of 11β-HSD1 is being studied for use to direct a cell-based response in these instances. Mason, Immunology Today 1991, 12:57-60. It follows then, that an alternative utility of 11β-HSD1 inhibition would be to bolster a temporal immune response in association with immunization to ensure that a cell based response would be obtained.

Recent reports suggest that the levels of glucocorticoid target receptors and of HSDs are connected with the risks of developing glaucoma. Stokes et al., Invest. Opthalmol. 2000, 41:1629-1638. Further, a connection between inhibition of 11β-HSD1 and a lowering of the intraocular pressure was reported. Walker et al., poster P3-698 at the Endocrine society meeting Jun. 12-15, 1999, San Diego. It was shown that administration of the nonspecific 11β-HSD1 inhibitor, carbenoxolone, resulted in the reduction of the intraocular pressure by 20% in normal patients. In the eye, 11β-HSD1 is expressed exclusively in the basal cells of the corneal epithelium, the non-pigmented epithelialium of the cornea (the site of aqueous production), ciliary muscle, and the sphincter and dilator muscles of the iris. In contrast, the distant isoenzyme 11β-hydroxysteroid dehydrogenase type 2 ("11β-HSD2") is highly expressed in the non-pigmented ciliary epithelium and corneal endothelium. No HSDs have been found at the trabecular meshwork, which is the site of drainage. Therefore, 11β-HSD1 is suggested to have a role in aqueous production.

Glucocorticoids also play an essential role in skeletal development and function but are detrimental to such development and function when present in excess. Glucocorticoid-induced bone loss is partially derived from suppression of osteoblast proliferation and collagen synthesis, as reported in Kim et al., J. Endocrinol. 1999, 162:371 379. It has been reported that the detrimental effects of glucocorticoids on bone nodule formation can be lessened by administration of carbenoxolone, which is a non-specific 11β-HSD1 inhibitor. Bellows et al., Bone 1998, 23:119-125. Additional reports suggest that 11β-HSD1 may be responsible for providing increased levels of active glucocorticoid in osteoclasts, and thus in augmenting bone resorption. Cooper et al., Bone 2000, 27:375-381. This data suggests that inhibition of 11β-HSD1 may have beneficial effects against osteoporosis via one or more mechanisms which may act in parallel.

It is known that bile acids inhibit 11β-HSD2 and that such inhibition results in a shift in the cortisol/cortisone equilibrium in the favor of cortisol. Quattropani et al., J. Clin. Invest. November 2001, 108:1299-305. A reduction in the hepatic activity of 11β-HSD2 is therefore predicted to reverse the cortisol/cortisone equilibrium to favor cortisone, which could provide therapeutic benefit in diseases such as hypertension.

The various isozymes of the 17-beta-hydroxysteroid dehydrogenases (17β-HSDs) bind to androgen receptors or estrogen receptors and catalyze the interconversion of various sex hormones including estradiol/estrone and testosterone/androstenedione. To date, six isozymes have been identified in humans and are expressed in various human tissues including endometrial tissue, breast tissue, colon tissue, and in the testes. 17-beta-Hydroxysteroid dehydrogenase type 2 (17β-HSD2) is expressed in human endometrium and its activity has been reported to be linked to cervical cancer. Kitawaki et al., J. Clin. Endocrin. Metab., 2000, 85:1371-3292-3296. 17-beta-Hydroxysteroid dehydrogenase type 3 (17β-HSD3) is expressed in the testes and its modulation may be useful for the treatment of androgen-related disorders.

Androgens and estrogens are active in their 17β-hydroxy configurations, whereas their 17-keto derivatives do not bind to androgen and estrogen receptors and are thus inactive. The conversion between the active and inactive forms (estradiol/estrone and testosterone/androstenedione) of sex hormones is catalyzed by members of the 17β-HSD family. 17β-HSD1 catalyzes the formation of estradiol in breast tissue, which is important for the growth of malignant breast tumors. Labrie et al., Mol. Cell. Endocrinol. 1991, 78:C113-C118. A similar role has been suggested for 17β-HSD4 in colon cancer. English et al., J. Clin. Endocrinol. Metab. 1999, 84:2080-2085. 17β-HSD3 is almost exclusively expressed in the testes and converts androstenedione into testosterone. Deficiency of this enzyme during fetal development leads to male pseudohermaphroditism. Geissler et al., Nat. Genet. 1994, 7:34-39. Both 17β-HSD3 and various 3α-HSD isozymes are involved in complex metabolic pathways which lead to androgen shuffles between inactive and active forms. Penning et al., Biochem. J. 2000, 351:67-77. Thus, modulation of certain HSDs can have potentially beneficial effects in the treatment of androgen- and estrogen-related disorders.

The 20-alpha-hydroxysteroid dehydrogenases (20α-HSDs) catalyze the interconversion of progestins (such as between progesterone and 20α-hydroxy progesterone). Other substrates for 20α-HSDs include 17α-hydroxypregnenolone or 17α-hydroxyprogesterone, leading to 20α-OH steroids. Several 20α-HSD isoforms have been identified and 20α-HSDs are expressed in various tissues, including the placenta, ovaries, testes and adrenals. Peltoketo, et al., J. Mol. Endocrinol. 1999, 23:1-11.

The 3-alpha-hydroxysteroid dehydrogenases (3α-HSDs) catalyze the interconversion of the androgens dihydrotestosterone (DHT) and 5α-androstane-3α,17β-diol and the interconversion of the androgens DHEA and androstenedione and therefore play an important role in androgen metabolism. Ge et al., Biology of Reproduction 1999, 60:855-860.

International Publications Nos. WO 2004/089896 and WO 2004/065351 disclose benzamide derivatives and their use as 11β-HSD1 modulators.

Despite the previous research done in the field of HSD inhibition, there remains a need for novel compounds that are potent inhibitors of the various families of HSDs and efficacious for the treatment of HSD-mediated conditions such as diabetes, obesity, glaucoma, osteoporosis, cognitive disorders, immune disorders, depression, hypertension, and others.

BRIEF SUMMARY OF THE INVENTION

In brief, the present invention relates to novel compounds, compositions thereof and methods for modulating the activity of hydroxysteroid dehydrogenases (HSDs), such as 11β-hydroxysteroid dehydrogenases, 17β-hydroxysteroid dehydrogenases, 20α-hydroxysteroid dehydrogenases, and 3α-hydroxysteroid dehydrogenases, including all isoforms thereof, including but not limited to 11β-hydroxysteroid dehydrogenase type 1 (hereinafter "11β-HSD1"), 11β-hydroxysteroid dehydrogenase type 2 (hereinafter "11β-HSD2"), and 17β-hydroxysteroid dehydrogenase type 3 (hereinafter "17β-HSD3"). In one embodiment, the compounds of the invention inhibit HSD activity.

The present invention also relates to methods for treating or preventing diseases or disorders associated with the action of hydroxysteroid dehydrogenases, comprising administering to a patient in need thereof a therapeutically effective amount of a benzamide derivative or a pharmaceutically acceptable salt, solvate, stereoisomer, or prodrug, or a mixture thereof. The invention encompasses both selective and non-selective inhibitors of hydroxysteroid dehydrogenases.

It should be understood that selective and non-selective inhibitors of hydroxysteroid dehydrogenases each have benefits in the treatment or prevention of diseases associated with, for example, abnormal glucose levels or hypothalmic function. The invention also encompasses selective inhibitors of HSDs. Two types of selectivity are contemplated, that with respect to selectivity for HSDs as a class over other types of receptors or gene targets related to glucose metabolism, or those which are selective for various HSDs or specific isoforms thereof compared to other HSDs or specific isoforms thereof.

In one embodiment, the benzamide derivatives can act as selective or non-selective 11β-HSD inhibitors. The compounds may inhibit the interconversion of inactive 11-keto steroids with their active hydroxy equivalents. The present invention provides methods by which the conversion of the inactive to the active form may be controlled, and to useful therapeutic effects which may be obtained as a result of such control. More specifically, but not exclusively, the invention is concerned with interconversion between cortisone and cortisol in humans.

In another embodiment, the benzamide derivatives of the present invention are orally active.

The benzamide derivatives are also useful for modulation of numerous metabolic functions including, but not limited to, one or more of: (i) regulation of carbohydrate metabolism, (ii) regulation of protein metabolism, (iii) regulation of lipid metabolism, (iv) regulation of normal growth and/or development, (v) influence on cognitive function, (vi) resistance to stress and mineralocorticoid activity.

The benzamide derivatives may also be useful for inhibiting hepatic gluconeogenesis, and may also be effective to relieve the effects of endogenous glucocorticoids in diabetes mellitus, obesity (including entripetal obesity), neuronal loss and/or the cognitive impairment of old age. Thus, in a further embodiment, the invention provides the use of an inhibitor of HSDs in methods directed to producing one or more therapeutic effects in a patient to whom the benzamide derivative is administered, said therapeutic effects selected from the group consisting of inhibition of hepatic gluconeogenesis, an increase in insulin sensitivity in adipose tissue and muscle, and the prevention of or reduction in neuronal loss/cognitive impairment due to glucocorticoid-potentiated neurotoxicity or neural dysfunction or damage.

The invention further provides methods for treating a condition selected from the group consisting of: hepatic insulin resistance, adipose tissue insulin resistance, muscle insulin resistance, neuronal loss or dysfunction due to glucocorticoid potentiated neurotoxicity, and any combination of the aforementioned conditions, the methods comprising administering to a patient in need thereof a therapeutically effective amount of a benzamide derivative.

The benzamide derivatives of the invention are compounds having Formula (II)

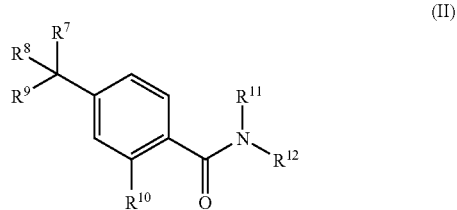

(II)

or pharmaceutically acceptable salts, solvates, stereoisomers or prodrugs thereof.

In one embodiment, $R^7$ is a member selected from the group consisting of —OH, halogen and $(C_1-C_6)$haloalkyl.

$R^8$ and $R^9$ are members independently selected from the group consisting of halogen, $(C_1-C_8)$alkyl, $(C_2-C_8)$alkenyl, $(C_2-C_8)$alkynyl, $(C_1-C_8)$alkoxy, $(C_1-C_6)$haloalkyl, $(C_2-C_8)$hydroxyalkyl and $(C_3-C_8)$cycloalkyl, wherein no more than two of $R^7$, $R^8$ and $R^9$ are halogen.

$R^{10}$ is a member selected from the group consisting of hydrogen, halogen, $(C_1-C_8)$alkyl and $(C_3-C_8)$cycloalkyl.

$R^{11}$ and $R^{12}$ are each members independently selected from the group consisting of $(C_1-C_8)$alkyl, $(C_2-C_8)$alkenyl, $(C_2-C_8)$alkynyl, $(C_1-C_6)$haloalkyl, $(C_2-C_8)$hydroxyalkyl, $(C_3-C_8)$cycloalkyl, $(C_3-C_8)$heterocycloalkyl, $(C_3-C_8)$cycloalkyl$(C_1-C_6)$alkyl, $(C_3-C_8)$cycloalkyl$(C_1-C_6)$alkoxy, $(C_3-C_8)$heterocycloalkyl$(C_1-C_6)$alkyl, aryl, heteroaryl$(C_1-C_6)$alkyl, aryl$(C_1-C_6)$alkyl, $R^{11}$ and $R^{12}$, together with the nitrogen to which they are attached may combine to form a five to eight-membered ring heterocycloalkyl.

Any cycloalkyl portion, heterocycloalkyl portion, aryl portion or heteroaryl portion is optionally substituted with from one to four members selected from the group consisting of halogen, —CN, —NO$_2$, $(C_1-C_8)$alkyl, $(C_2-C_8)$alkenyl, $(C_2-C_8)$alkynyl, $(C_1-C_8)$alkoxy, $(C_1-C_6)$haloalkyl, $(C_2-C_8)$hydroxyalkyl, aryl, heteroaryl, $(C_3-C_8)$cycloalkyl, $(C_3-C_8)$heterocycloalkyl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, —C(O)R', —C(O)OR', —NR'C(O)OR", —OR', —SR', —OC(O)R', —C(O)N(R')$_2$, —S(O)R", —SO$_2$R", —SO$_2$N(R')$_2$, —N(R')$_2$, —NR'C(O)R', —NR'SO$_2$R", —X—C(O)R', —X—C(O)OR', —X—NR'C(O)OR", —X—OR", —X—OC(O)R', —X—C(O)N(R')$_2$, —X—S(O)R", —X—SO$_2$R", —X—SO$_2$N(R')$_2$, —X—N(R')$_2$ and —X—NR'C(O)R'.

X is a branched or straight chain $(C_1-C_8)$alkylene group.

Each occurrence of R' is independently H or an unsubstituted member selected from the group consisting of $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_6)$haloalkyl, $(C_2-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, or two R' groups, when attached to the same nitrogen atom, can be combined with the nitrogen atom to which they are attached to form a heterocycle or heteroaryl group.

Each occurrence of R" is independently an unsubstituted member selected from the group consisting of $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_6)$haloalkyl, $(C_2-C_8)$hydroxyalkyl, $(C_3-C_8)$cycloalkyl, $(C_3-C_8)$heterocyclo alkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl or aryl$(C_1-C_6)$alkyl.

It should be understood that a compound where $R^7$ is —OH and $R^8$ and $R^9$ are both CF$_3$ is excluded from the scope of the present invention.

It should also be understood that Formula (II) does not include the following compounds:
4-(1-ethyl-1-hydroxypropyl)-N,N-bis(1-methylethyl)-benzamide.
4-(1-hydroxy-1-methylphenyl)-N-[1-[3-[6-[1-methyl-1-(methylsulfonyl)ethyl]-8-quinolinyl]phenyl]ethyl]-N-[(4-methylsulfonyl)phenyl]-benzamide.

The benzamide derivatives of the invention are also compounds having Formula (I),

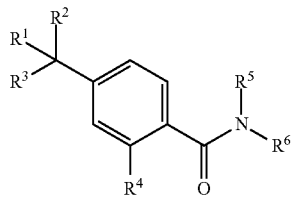

as well as pharmaceutically acceptable salts, solvates, stereoisomers, or prodrugs thereof.

In one embodiment, $R^1$ is a member selected from the group consisting of —OH, halogen and $(C_1\text{-}C_6)$haloalkyl;

$R^2$ and $R^3$ are members independently selected from the group consisting of halogen, $(C_1\text{-}C_8)$alkyl, $(C_2\text{-}C_8)$alkenyl, $(C_2\text{-}C_8)$alkynyl, $(C_1\text{-}C_8)$alkoxy, $(C_1\text{-}C_6)$haloalkyl, $(C_2\text{-}C_8)$hydroxyalkyl and $(C_3\text{-}C_8)$cycloalkyl, wherein no more than two of $R^1$, $R^2$ and $R^3$ are halogen;

$R^4$ is a member selected from the group consisting of hydrogen, halogen, $(C_1\text{-}C_8)$alkyl and $(C_3\text{-}C_8)$cycloalkyl;

$R^5$ is selected from the group consisting of halogen, —CN, —NO$_2$, $(C_1\text{-}C_8)$alkyl, $(C_2\text{-}C_8)$alkenyl, $(C_2\text{-}C_8)$alkynyl, $(C_1\text{-}C_6)$haloalkyl, $(C_2\text{-}C_8)$hydroxyalkyl, $(C_3\text{-}C_8)$cycloalkyl, $(C_3\text{-}C_8)$heterocycloalkyl, $(C_3\text{-}C_8)$cycloalkyl$(C_1\text{-}C_6)$alkyl, $(C_3\text{-}C_8)$cycloalkyl(C1-C$_6$)alkoxy, $(C_3\text{-}C_8)$heterocycloalkyl$(C_1\text{-}C_6)$alkyl, heteroaryl$(C_1\text{-}C_6)$alkyl, aryl, aryl$(C_1\text{-}C_6)$alkyl, —C(O)R', —C(O)OR', —NR'C(O)OR", —OR", —OC(O)R', —C(O)N(R')$_2$, —S(O)R", —SO$_2$R", —SO$_2$N(R')$_2$, —N(R')$_2$, —NR'C(O)R', —NR'SO$_2$R", —X—C(O)R', —X—C(O)OR', —X—NR'C(O)OR", —X—OR", —X—OC(O)R', —X—C(O)N(R')$_2$, —X—S(O)R", —X—SO$_2$R", —X—SO$_2$N(R')$_2$, —X—N(R')$_2$ and —X—NR'C(O)R';

$R^6$ is selected from the group consisting of halogen, —CN, —NO$_2$, methyl, ethyl, straight or branched butyl, straight or branched pentyl, straight or branched hexyl, straight or branched heptyl, straight or branched octyl, $(C_2\text{-}C_8)$alkenyl, $(C_2\text{-}C_8)$alkynyl, $(C_1\text{-}C_6)$haloalkyl, $(C_2\text{-}C_8)$hydroxyalkyl, $(C_3\text{-}C_8)$cycloalkyl, $(C_3\text{-}C_8)$heterocycloalkyl, $(C_3\text{-}C_8)$cycloalkyl(C1-C$_6$)alkyl, $(C_3\text{-}C_8)$cycloalkyl$(C_1\text{-}C_6)$alkoxy, $(C_3\text{-}C_8)$heterocycloalkyl$(C_1\text{-}C_6)$alkyl, aryl, heteroaryl$(C_1\text{-}C_6)$alkyl, aryl$(C_1\text{-}C_6)$alkyl, —C(O)R', —C(O)OR', —NR'C(O)OR", —OR", —OC(O)R', —C(O)N(R')$_2$, —S(O)R", —SO$_2$R", —SO$_2$N(R')$_2$, —N(R')$_2$, —NR'C(O)R', —NR'SO$_2$R", —X—C(O)R', —X—C(O)OR', —X—NR'C(O)OR", —X—OR", —X—OC(O)R', —X—C(O)N(R')$_2$, —X—S(O)R", —X—SO$_2$R", —X—SO$_2$N(R')$_2$, —X—N(R')$_2$ and —X—NR'C(O)R';

any cycloalkyl portion, heterocycloalkyl portion, aryl or heteroaryl portion is optionally substituted with from one to four members selected from the group consisting of halogen, —CN, —NO$_2$, $(C_1\text{-}C_8)$alkyl, $(C_2\text{-}C_8)$alkenyl, $(C_2\text{-}C_8)$alkynyl, $(C_1\text{-}C_8)$alkoxy, $(C_1\text{-}C_6)$haloalkyl, $(C_2\text{-}C_8)$hydroxyalkyl, —C(O)R', —C(O)OR', —NR'C(O)OR", —OR', —SR', —OC(O)R', —C(O)N(R')$_2$, —S(O)R", —SO$_2$R", —SO$_2$N(R')$_2$, —N(R')$_2$ and —NR'C(O)R';

X is a branched or straight chain $(C_1\text{-}C_8)$alkylene group;

each occurrence of R' is independently H or an unsubstituted member selected from the group consisting of $(C_1\text{-}C_8)$alkyl, $(C_2\text{-}C_8)$alkenyl, $(C_2\text{-}C_8)$alkynyl, $(C_1\text{-}C_4)$alkoxy$(C_1\text{-}C_4)$alkyl, $(C_1\text{-}C_6)$haloalkyl, $(C_2\text{-}C_8)$hydroxyalkyl, $(C_3\text{-}C_8)$cycloalkyl, $(C_3\text{-}C_8)$heterocycloalkyl, heteroaryl, aryl, $(C_3\text{-}C_8)$cycloalkyl$(C_1\text{-}C_6)$alkyl, $(C_3\text{-}C_8)$heterocycloalkyl$(C_1\text{-}C_6)$ alkyl, heteroaryl$(C_1\text{-}C_6)$alkyl, aryl$(C_1\text{-}C_6)$alkyl, or two R' groups, when attached to the same nitrogen atom, can be combined with the nitrogen atom to which they are attached to form a heterocycle or heteroaryl group; and each occurrence of R" is independently an unsubstituted member selected from the group consisting of $(C_1\text{-}C_8)$alkyl, $(C_2\text{-}C_8)$alkenyl, $(C_2\text{-}C_8)$alkynyl, $(C_1\text{-}C_4)$alkoxy$(C_1\text{-}C_4)$alkyl, $(C_1\text{-}C_6)$haloalkyl, $(C_2\text{-}C_8)$hydroxyalkyl, $(C_3\text{-}C_8)$cycloalkyl, $(C_3\text{-}C_8)$heterocycloalkyl, heteroaryl, aryl, $(C_3\text{-}C_8)$cycloalkyl$(C_1\text{-}C_6)$alkyl, heterocyclyl$(C_1\text{-}C_6)$alkyl, heteroaryl$(C_1\text{-}C_6)$alkyl or aryl$(C_1\text{-}C_6)$alkyl;

with the proviso that:

when $R^1$ is —OH, then $R^2$ and $R^3$ are not both CF$_3$.

In one embodiment, the invention provides pharmaceutical compositions comprising a benzamide derivative and a pharmaceutically acceptable vehicle, carrier, excipient or diluent.

In another embodiment, the invention provides methods for treating insulin-dependent diabetes mellitus comprising administering to a patient in need thereof a therapeutically effective amount of a benzamide derivative of Formula (I) or (II).

In another embodiment, the invention provides methods for treating non-insulin-dependent diabetes mellitus comprising administering to a patient in need thereof a therapeutically effective amount of a benzamide derivative of Formula (I) or (II).

In another embodiment, the invention provides methods for treating insulin resistance comprising administering to a patient in need thereof a therapeutically effective amount of a benzamide derivative of Formula (I) or (II).

In another embodiment, the invention provides methods for treating obesity comprising administering to a patient in need thereof a therapeutically effective amount of a benzamide derivative of Formula (I) or (II).

In another embodiment, the invention provides methods for modulating cortisol production comprising administering to a patient in need thereof a therapeutically effective amount of a benzamide derivative of Formula (I) or (II).

In another embodiment, the invention provides methods for modulating hepatic glucose production comprising administering to a patient in need thereof a therapeutically effective amount of a benzamide derivative of Formula (I) or (II).

In another embodiment, the invention provides methods for modulating hypothalamic function comprising administering to a patient in need thereof a therapeutically effective amount of a benzamide derivative of Formula (I) or (II).

In one embodiment, the invention provides methods for treating a hydroxysteroid dehydrogenase-mediated condition or disorder comprising administering to a patient in need thereof a therapeutically effective amount of a benzamide derivative of Formula (I) or (II).

In a further embodiment, the invention provides methods for modulating a hydroxysteroid dehydrogenase, comprising administering to a patient in need thereof a therapeutically effective amount of a benzamide derivative of Formula (I) or (II).

In still another embodiment, the invention provides methods for treating an 11β-HSD1-mediated condition or disorder comprising administering to a patient in need thereof a therapeutically effective amount of a benzamide derivative of Formula (I) or (II).

In yet another embodiment, the invention provides method for modulating the function of 11β-HSD1 in a cell comprising administering to a patient in need thereof a therapeutically effective amount of a benzamide derivative of Formula (I) or (II).

In a further embodiment, the invention provides methods for modulating 11β-HSD1, comprising administering to a patient in need thereof a therapeutically effective amount of a benzamide derivative of Formula (I) or (II).

In one embodiment, the invention provides methods for treating an 11β-HSD2-mediated condition or disorder comprising administering to a patient in need thereof a therapeutically effective amount of a benzamide derivative of Formula (I) or (II).

In another embodiment, the invention provides method for modulating the function of 11β-HSD2 in a cell comprising administering to a patient in need thereof a therapeutically effective amount of a benzamide derivative of Formula (I) or (II).

In a further embodiment, the invention provides methods for modulating 11β-HSD2, comprising administering to a patient in need thereof a therapeutically effective amount of a benzamide derivative of Formula (I) or (II).

In one embodiment, the invention provides methods for treating an 17β-HSD3-mediated condition or disorder comprising administering to a patient in need thereof a therapeutically effective amount of a benzamide derivative of Formula (I) or (II).

In another embodiment, the invention provides method for modulating the function of 17β-HSD3 in a cell comprising administering to a patient in need thereof a therapeutically effective amount of a benzamide derivative of Formula (I) or (II).

In a further embodiment, the invention provides methods for modulating 17β-HSD3, comprising administering to a patient in need thereof a therapeutically effective amount of a benzamide derivative of Formula (I) or (II).

These and other embodiments of this invention will be evident upon reference to the following detailed description. To that end, certain patent and other documents are cited herein to more specifically set forth various embodiments of this invention. Each of these documents are hereby incorporated by reference in their entirety.

DETAILED DESCRIPTION OF THE INVENTION

As used herein, the terms have the following meanings:

The term "alkyl" as used herein refers to a straight or branched chain, saturated hydrocarbon having the indicated number of carbon atoms. For example, ($C_1$-$C_6$)alkyl is meant to include, but is not limited to methyl, ethyl, propyl, isopropyl, butyl, sec-butyl, tent-butyl, pentyl, isopentyl, neopentyl, hexyl, isohexyl, and neohexyl. An alkyl group can be unsubstituted or optionally substituted with one or more substituents as described herein below.

The term "alkenyl" as used herein refers to a straight or branched chain unsaturated hydrocarbon having the indicated number of carbon atoms and at least one double bond. Examples of a ($C_2$-$C_8$)alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein below.

The term "alkynyl" as used herein refers to a straight or branched chain unsaturated hydrocarbon having the indicated number of carbon atoms and at least one triple bond. Examples of a ($C_2$-$C_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

The term "alkylene" refers to a divalent alkyl group (e.g., an alkyl group attached to two other moieties, typically as a linking group). Examples of a ($C_1$-$C_7$)alkylene include —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, and —$CH_2CH_2CH_2CH_2CH_2CH_2CH_2$—, as well as branched versions thereof. An alkylene group can be unsubstituted or optionally substituted with one or more substituents as described herein below.

The term "alkoxy" as used herein refers to an —O-alkyl group having the indicated number of carbon atoms. For example, a ($C_1$-$C_6$)alkoxy group includes —O-methyl, —O-ethyl, —O-propyl, —O-isopropyl, —O-butyl, —O-sec-butyl, —O-tent-butyl, —O-pentyl, —O-isopentyl, —O-neopentyl, —O-hexyl, —O-isohexyl, and —O-neohexyl.

The term "aminoalkyl," as used herein, refers to an alkyl group (typically one to six carbon atoms) wherein from one or more of the $C_1$-$C_6$ alkyl group's hydrogen atoms is replaced with an amine of formula —$N(R^a)_2$, wherein each occurrence of $R^a$ is independently —H or ($C_1$-$C_6$)alkyl. Examples of aminoalkyl groups include, but are not limited to, —$CH_2NH_2$, —$CH_2CH_2NH_2$—, —$CH_2CH_2CH_2NH_2$, —$CH_2CH_2CH_2CH_2NH_2$, —$CH_2CH_2CH_2CH_2CH_2NH_2$, —$CH_2CH_2CH_2CH_2CH_2CH_2NH_2$, —$CH_2CH_2CH_2N(CH_3)_2$, t-butylaminomethyl, isopropylaminomethyl and the like.

The term "aryl" as used herein refers to a 6- to 14-membered monocyclic, bicyclic or tricyclic aromatic hydrocarbon ring system. Examples of an aryl group include phenyl and naphthyl. An aryl group can be unsubstituted or optionally substituted with one or more substituents as described herein below.

The term "cycloalkyl" as used herein refers to a 3- to 14-membered saturated or unsaturated non-aromatic monocyclic, bicyclic or tricyclic hydrocarbon ring system. The bicyclic or tricyclic hydrocarbon ring systems may be spiro-fused. Included in this class are cycloalkyl groups which are fused to a benzene ring. Representative cycloalkyl groups include, but are not limited to, cyclopropyl, cyclobutyl, cyclobutenyl, cyclopentyl, cyclopentenyl, cyclopentadienyl, cyclohexyl, cyclohexenyl, 1,3-cyclohexadienyl, cycloheptyl, cycloheptenyl, 1,3-cycloheptadienyl, 1,4-cycloheptadienyl, -1,3,5-cycloheptatrienyl, cyclooctyl, cyclooctenyl, 1,3-cyclooctadienyl, 1,4-cyclooctadienyl, -1,3,5-cyclooctatrienyl, spiro[5,4]decane, decahydronaphthalene, octahydronaphthalene, hexahydronaphthalene, octahydroindene, hexahydroindene, tetrahydroinden, decahydrobenzocycloheptene, octahydrobenzocycloheptene, hexahydrobenzocycloheptene, tetrahydrobenzocycloheptene, dodecahydroheptalene, decahydroheptalene, octahydroheptalene, hexahydroheptalene, and tetrahydroheptalene. A cycloalkyl group can be unsubstituted or optionally substituted with one or more substituents as described herein below.

The term "halo" as used herein refers to —F, —Cl, —Br or —I.

The term "haloalkyl," as used herein, refers to a $C_1$-$C_6$ alkyl group wherein from one or more of the $C_1$-$C_6$ alkyl group's hydrogen atom is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "heteroaryl" as used herein refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, quinoxalinyl. A heteroaryl group can be unsubstituted or optionally substituted with one or more substituents as described herein below.

As used herein, the term "heteroatom" is meant to include oxygen (O), nitrogen (N), and sulfur (S).

As used herein, the term "heterocycle" or "heterocycloalkyl" as used herein refers to 5- to 14-membered ring systems which are either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including monocyclic, bicyclic, and tricyclic ring systems. The bicyclic or tricyclic ring systems may be spiro-fused. The bicyclic and tricyclic ring systems may encompass a heterocycle or heteroaryl fused to a benzene ring. The heterocycle may be attached via any heteroatom or carbon atom. Heterocycles include heteroaryls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, dioxanyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thiophenyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl, and quinazolinyl. A heterocycle group can be unsubstituted or optionally substituted with one or more substituents as described herein below.

The term "hydroxyalkyl," as used herein, refers to an alkyl group having the indicated number of carbon atoms wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof.

Substituents for the groups referred to as alkyl, heteroalkyl, alkylene, alkenyl, alkynyl, cycloalkyl, heterocycloalkyl, cycloalkenyl and heterocycloalkenyl can be a variety of groups selected from: —OR', =O, =NR', =N—OR', —NR'R", —SR', -halo, —SiR'R"R'", —OC(O)R', —C(O)R', —CO$_2$R', —CONR'R", —OC(O)NR'R", —NR"C(O)R', —NR'"C(O)NR'R", —NR'"SO$_2$NR'R", —NR"CO$_2$R', —NHC(NH$_2$)=NH, —NR'C(NH$_2$)=NH, —NHC(NH$_2$)=NR', —S(O)R', —SO$_2$R', —SO$_2$NR'R", —NR"SO$_2$R', —CN and —NO$_2$, in a number ranging from zero to three, with those groups having zero, one or two substituents being exemplary. R', R" and R'" each independently refer to hydrogen, unsubstituted (C$_1$-C$_8$)alkyl, unsubstituted hetero(C$_1$-C$_8$) alkyl, unsubstituted aryl and aryl substituted with one to three substituents selected from -halo, unsubstituted alkyl, unsubstituted alkoxy, unsubstituted thioalkoxy and unsubstituted aryl(C$_1$-C$_4$)alkyl. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. An alkyl or heteroalkyl group will have from zero to three substituents, with those groups having two or fewer substituents being exemplary in the present invention. In some embodiments, an alkyl or heteroalkyl radical will be unsubstituted or monosubstituted. An alkyl or heteroalkyl radical can be unsubstituted. From the above discussion of substituents, one of skill in the art will understand that the term "alkyl" is meant to include groups such as trihaloalkyl (e.g., —CF$_3$ and —CH$_2$CF$_3$).

Exemplary substituents for the alkyl and heteroalkyl radicals are selected from: —OR', =O, —NR'R", —SR', -halo, —SiR'R"R'", —OC(O)R', —C(O)R', —CO$_2$R', —C(O) NR'R", —OC(O)NR'R", —NR"C(O)R', —NR"CO$_2$R', —NR'"SO$_2$NR'R", —S(O)R', —SO$_2$R', —SO$_2$NR'R", —NR"SO$_2$R', —CN and —NO$_2$, where R', R" and R'" are as defined above. Typically, substituents are selected from: —OR', =O, —NR'R", -halo, —OC(O)R', —CO$_2$R', —C(O) NR'R", —OC(O)NR'R", —NR"C(O)R', —NR"CO$_2$R', —NR'"SO$_2$NR'R", —SO$_2$R', —SO$_2$NR'R", —NR"SO$_2$R'— CN and —NO$_2$.

Similarly, substituents for the aryl and heteroaryl groups are varied and selected from: -halo, —OR', —OC(O)R', —NR'R", —SR', —R', —CN, —NO$_2$, —CO$_2$R', —C(O) NR'R", —C(O)R', —OC(O)NR'R", —NR"C(O)R', —NR"CO$_2$R', —NR'"C(O)NR'R", —NR'"SO$_2$NR'R", —NHC(NH$_2$)=NH, —NR'C(NH$_2$)=NH, —NH—C(NH$_2$) =NR', —S(O)R', —SO$_2$R', —SO$_2$NR'R", —NR"SO$_2$R', —N$_3$, —CH(Ph)$_2$, perfluoroalkoxy and perfluoro(C$_1$-C$_4$) alkyl, in a number ranging from zero to the total number of open valences on the aromatic ring system; and where R', R" and R'" are independently selected from hydrogen, unsubstituted (C$_1$-C$_8$)alkyl, unsubstituted hetero(C$_1$-C$_8$)alkyl, unsubstituted aryl, unsubstituted heteroaryl, unsubstituted aryl(C$_1$-C$_4$)alkyl and unsubstituted aryloxy(C$_1$-C$_4$)alkyl. Typically, an aryl or heteroaryl group will have from zero to three substituents, with those groups having two or fewer substituents being exemplary in the present invention. In one embodiment of the invention, an aryl or heteroaryl group will be unsubstituted or monosubstituted. In another embodiment, an aryl or heteroaryl group will be unsubstituted.

Exemplary substituents for aryl and heteroaryl groups are selected from: -halo, —OR', —OC(O)R', —NR'R", —SR', —R', —CN, —NO$_2$, —CO$_2$R', —CONR'R", —C(O)R', —OC(O)NR'R", —NR"C(O)R', —S(O)R', —SO$_2$R', —SO$_2$NR'R", —NR"SO$_2$R', —N$_3$, —CH(Ph)$_2$, perfluoroalkoxy and perfluoro(C$_1$-C$_4$)alkyl, where R'and R" are as defined above. Typically, substituents are selected from: -halo, —OR', —OC(O)R', —NR'R", —R', —CN, —NO$_2$, —CO$_2$R', —CONR'R", —NR"C(O)R', —SO$_2$R', —SO$_2$NR'R", —NR"SO$_2$R', perfluoroalkoxy and perfluoro (C$_1$-C$_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —$(CH_2)_s$—X—$(CH_2)_t$—, where s and t are independently integers of from 0 to 3, and X is —O—, —NR'—, —S—, —S(O)—, —$S(O)_2$—, or —$S(O)_2NR'$—. The substituent R' in —NR'— and —$S(O)_2NR'$— is selected from hydrogen or unsubstituted ($C_1$-$C_6$)alkyl.

It is to be understood that the substituent —$CO_2H$, as used herein, may be optionally replaced with bioisosteric replacements such as:

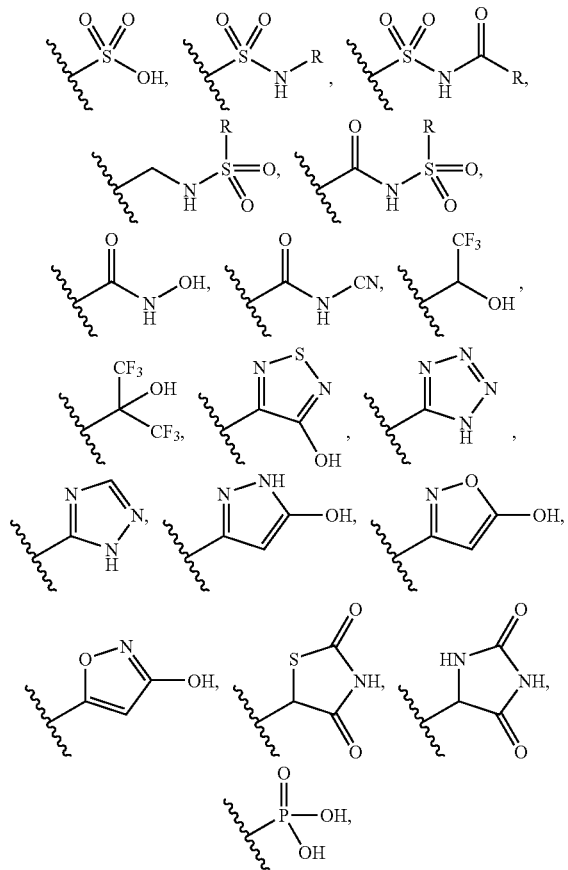

and the like. See, e.g., *The Practice of Medicinal Chemistry*; Wermuth, C. G., Ed.; Academic Press: New York, 1996; p. 203.

The benzamide derivative can also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of a benzamide derivative, including tautomeric forms of the compound.

Certain benzamide derivatives may have asymmetric centers and therefore exist in different enantiomeric and diastereomeric forms. A benzamide derivative can be in the form of an optical isomer or a diastereomer. Accordingly, the invention encompasses benzamide derivatives and their uses as described herein in the form of their optical isomers, diasteriomers and mixtures thereof, including a racemic mixture. Optical isomers of the benzamide derivatives can be obtained by known techniques such as asymmetric synthesis, chiral chromatography, simulated moving bed technology or via chemical separation of stereoisomers through the employment of optically active resolving agents.

As used herein and unless otherwise indicated, the term "stereoisomer" or means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, even or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

It should be noted that if there is a discrepancy between a depicted structure and a name given that structure, the depicted structure controls. In addition, if the stereochemistry of a structure or a portion of a structure is not indicated with, for example, bold or dashed lines, the structure or portion of the structure is to be interpreted as encompassing all stereoisomers of it.

A benzamide derivative can be in the form of a pharmaceutically acceptable salt. Depending on the its structure, the phrase "pharmaceutically acceptable salt," as used herein, refers to a pharmaceutically acceptable organic or inorganic acid or base salt of a benzamide derivative. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. Furthermore, a pharmaceutically acceptable salt can have more than one charged atom in its structure. In this instance the pharmaceutically acceptable salt can have multiple counterions. Hence, a pharmaceutically acceptable salt can have one or more charged atoms and/or one or more counterions.

As used herein, the term "isolated and purified form" means that when isolated (e.g., from other components of a synthetic organic chemical reaction mixture), the isolate contains at least 30%, at least 35%, at least 40%, at least 45%, at least 50%, at least 55%, at least 60%, at least 65%, at least 70%, at least 75%, at least 80%, at least 85%, at least 90%, at least 95% or at least 98% of a benzamide derivative by weight of the isolate. In one embodiment, the isolate contains at least 95% of a benzamide derivative by weight of the isolate.

As used herein, the term "prodrug" means a derivative of a compound that can hydrolyze, oxidize, or otherwise react under biological conditions (in vitro or in vivo) to provide an active compound, particularly a benzamide derivative. Examples of prodrugs include, but are not limited to, derivatives and metabolites of a benzamide derivative that include biohydrolyzable groups such as biohydrolyzable amides, biohydrolyzable esters, biohydrolyzable carbamates, biohydrolyzable carbonates, biohydrolyzable ureides, and biohydrolyzable phosphate analogues (e.g., monophosphate, diphosphate or triphosphate). For instance, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6$^{th}$ ed. (Donald J. Abraham ed., 2001, Wiley) and *Design and Application of Prodrugs* (H. Bundgaard ed., 1985, Harwood Academic Publishers Gmfh).

As used herein, the terms "treat", "treating" and "treatment" refer to the eradication or amelioration of a disease or symptoms associated with a disease. In certain embodiments, such terms refer to minimizing the spread or worsening of the disease resulting from the administration of one or more prophylactic or therapeutic agents to a patient with such a disease.

As used herein, the terms "prevent", "preventing" and "prevention" refer to the prevention of the onset, recurrence or spread of the disease in a patient resulting from the administration of a prophylactic or therapeutic agent.

The term "effective amount" as used herein refers to an amount of a benzamide derivative or other active ingredient sufficient to provide a therapeutic or prophylactic benefit in the treatment or prevention of a disease or to delay or minimize symptoms associated with a disease. Further, a therapeutically effective amount with respect to a benzamide derivative means that amount of therapeutic agent alone, or in combination with other therapies, that provides a therapeutic benefit in the treatment or prevention of a disease. Used in connection with a benzamide derivative, the term can encompass an amount that improves overall therapy, reduces or avoids symptoms or causes of disease, or enhances the therapeutic efficacy of or synergies with another therapeutic agent.

As used herein, "syndrome X" refers to a collection of abnormalities including hyperinsulinemia, obesity, elevated levels of triglycerides, uric acid, fibrinogen, small dense LDL particles and plasminogen activator inhibitor 1 (PAI-1), and decreased levels of HDL cholesterol. Syndrome X is further meant to include metabolic syndrome.

The terms "modulate", "modulation" and the like refer to the ability of a compound to increase or decrease the function, or activity of, for example, 11β-HSD1. "Modulation", as used herein in its various forms, is intended to encompass inhibition, antagonism, partial antagonism, activation, agonism and/or partial agonism of the activity associated with 11β-HSD1. 11β-HSD1 inhibitors are compounds that, e.g., bind to, partially or totally block stimulation, decrease, prevent, delay activation, inactivate, desensitize, or down regulate signal transduction. 11β-HSD1 activators are compounds that, e.g., bind to, stimulate, increase, open, activate, facilitate, enhance activation, sensitize or up regulate signal transduction. The ability of a compound to modulate 11β-HSD1 can be demonstrated in an enzymatic assay or a cell-based assay.

For example, the inhibition of 11β-HSD1 may decrease cortisol levels in a patient and/or increase cortisone levels in a patient by blocking the conversion of cortisone to cortisol. Alternatively, the inhibition of 11β-HSD2 can increase cortisol levels in a patient and/or decrease cortisone levels in a patient by blocking the conversion of cortisol to cortisone.

A "patient" includes an animal (e.g., cow, horse, sheep, pig, chicken, turkey, quail, cat, dog, mouse, rat, rabbit or guinea pig), in one embodiment a mammal such as a non-primate and a primate (e.g., monkey and human), and in another embodiment a human. In one embodiment, a patient is a human. In specific embodiments, the patient is a human infant, child, adolescent or adult.

The term "HSD" as used herein, refers to hydroxysteroid dehydrogenase enzymes in general, including, but not limited to, 11-beta-hydroxysteroid dehydrogenases (11β-HSDs), 17-beta-hydroxysteroid dehydrogenases (17β-HSDs), 20-alpha-hydroxysteroid dehydrogenases (20α-HSDs), 3-alpha-hydroxysteroid dehydrogenases (3α-HSDs), and all isoforms thereof.

The term "11β-HSD1" as used herein, refers to the 11-beta-hydroxysteroid dehydrogenase type 1 enzyme, variant, or isoform thereof. 11β-HSD1 variants include proteins substantially homologous to native 11β-HSD1, i.e., proteins having one or more naturally or non-naturally occurring amino acid deletions, insertions or substitutions (e.g., 11β-HSD1 derivatives, homologs and fragments). The amino acid sequence of a 11β-HSD1 variant is, for example, at least about 80% identical to a native 11β-HSD1, or at least about 90% identical, or at least about 95% identical.

The term "11β-HSD2" as used herein, refers to the 11-beta-hydroxysteroid dehydrogenase type 2 enzyme, variant, or isoform thereof. 11β-HSD2 variants include proteins substantially homologous to native 11β-HSD2, i.e., proteins having one or more naturally or non-naturally occurring amino acid deletions, insertions or substitutions (e.g., 11β-HSD2 derivatives, homologs and fragments). The amino acid sequence of a 11β-HSD2 variant is, for example, at least about 80% identical to a native 11β-HSD2, or at least about 90% identical, or at least about 95% identical. (see Bart et al., *J. Med. Chem.*, 2002, 45:3813-3815).

The term "17β-HSD3" as used herein, refers to the 17-beta-hydroxysteroid dehydrogenase type 3 enzyme, variant, or isoform thereof. 17β-HSD3 variants include proteins substantially homologous to native 17β-HSD3, i.e., proteins having one or more naturally or non-naturally occurring amino acid deletions, insertions or substitutions (e.g., 17β-HSD3 derivatives, homologs and fragments). The amino acid sequence of a 17β-HSD3 variant is, for example, at least about 80% identical to a native 17β-HSD3, or at least about 90% identical, or at least about 95% identical.

As used herein, the term "HSD-responsive condition or disorder" and related terms and phrases refer to a condition or disorder that responds favorably to modulation of a hydroxysteroid dehydrogenase enzyme (HSD). Favorable responses to HSD modulation include alleviation or abrogation of the disease and/or its attendant symptoms, inhibition of the disease, i.e., arrest or reduction of the development of the disease, or its clinical symptoms, and regression of the disease or its clinical symptoms. An HSD-responsive condition or disease may be completely or partially responsive to HSD modulation. An HSD-responsive condition or disorder may be associated with inappropriate, e.g., less than or greater than normal, HSD activity and at least partially responsive to or affected by HSD modulation (e.g., an HSD inhibitor results in some improvement in patient well-being in at least some patients). Inappropriate HSD functional activity might arise as the result of HSD expression in cells which normally do not express HSD, decreased HSD expression or increased HSD expression. An HSD-responsive condition or disorder may include condition or disorder mediated by any HSD or isoform thereof.

As used herein, the term "11β-HSD1-responsive condition or disorder" and related terms and phrases refer to a condition or disorder that responds favorably to modulation of 11β-HSD1 activity. Favorable responses to 11β-HSD1 modulation include alleviation or abrogation of the disease and/or its attendant symptoms, inhibition of the disease, i.e., arrest or reduction of the development of the disease, or its clinical symptoms, and regression of the disease or its clinical symptoms. An 11β-HSD1-responsive condition or disease may be completely or partially responsive to 11β-HSD1 modulation. An 11β-HSD1-responsive condition or disorder may be associated with inappropriate, e.g., less than or greater than normal, 11β-HSD1 activity and at least partially responsive to or affected by 11β-HSD1 modulation (e.g., a 11β-HSD1 inhibitor results in some improvement in patient well-being in at least some patients). Inappropriate 11β-HSD1 functional activity might arise as the result of 11β-HSD1 expression in cells which normally do not express 11β-HSD1, decreased 11β-HSD1 expression or increased 11β-HSD1 expression. A 11β-HSD1-responsive condition or disorder may include a 11β-HSD1-mediated condition or disorder.

As used herein, the term "11β-HSD2-responsive condition or disorder" and related terms and phrases refer to a condition or disorder that responds favorably to modulation of 11β-HSD2 activity. Favorable responses to 11β-HSD2 modulation include alleviation or abrogation of the disease and/or its attendant symptoms, inhibition of the disease, i.e., arrest or reduction of the development of the disease, or its clinical symptoms, and regression of the disease or its clinical symptoms. An 11β-HSD2-responsive condition or disease may be completely or partially responsive to 11β-HSD2 modulation. An 11β-HSD2-responsive condition or disorder may be associated with inappropriate, e.g., less than or greater than normal, 11β-HSD2 activity and at least partially responsive to or affected by 11β-HSD2 modulation (e.g., a 11β-HSD2 inhibitor results in some improvement in patient well-being in at least some patients).

As used herein, the term "17β-HSD3-responsive condition or disorder" and related terms and phrases refer to a condition or disorder that responds favorably to modulation of 17β-HSD3 activity. Favorable responses to 17β-HSD3 modulation include alleviation or abrogation of the disease and/or its attendant symptoms, inhibition of the disease, i.e., arrest or reduction of the development of the disease, or its clinical symptoms, and regression of the disease or its clinical symptoms. An 17β-HSD3-responsive condition or disease may be completely or partially responsive to 17β-HSD3 modulation. An 17β-HSD3-responsive condition or disorder may be associated with inappropriate, e.g., less than or greater than normal, 17β-HSD3 activity and at least partially responsive to or affected by 17β-HSD3 modulation (e.g., a 17β-HSD3 inhibitor results in some improvement in patient well-being in at least some patients). Inappropriate 17β-HSD3 functional activity might arise as the result of 17β-HSD3 expression in cells which normally do not express 17β-HSD3, decreased 17β-HSD3 expression or increased 17β-HSD3 expression. A 17β-HSD3-responsive condition or disorder may include a 17β-HSD3-mediated condition or disorder.

As used herein, the term "HSD-mediated condition or disorder" and related terms and phrases refer to a condition or disorder characterized by inappropriate, e.g., less than or greater than normal, activity of a hydroxysteroid dehydrogenase (HSD). An HSD-mediated condition or disorder may be completely or partially characterized by inappropriate HSD activity. However, an HSD-mediated condition or disorder is one in which modulation of an HSD results in some effect on the underlying condition or disease (e.g., an HSD inhibitor results in some improvement in patient well-being in at least some patients).

As used herein, the term "11β-HSD1-mediated condition or disorder" and related terms and phrases refer to a condition or disorder characterized by inappropriate, e.g., less than or greater than normal, 11β-HSD1 activity. A 11β-HSD1-mediated condition or disorder may be completely or partially characterized by inappropriate 11β-HSD1 activity. However, a 11β-HSD1-mediated condition or disorder is one in which modulation of 11β-HSD1 results in some effect on the underlying condition or disease (e.g., a 11β-HSD1 inhibitor results in some improvement in patient well-being in at least some patients).

As used herein, the term "11β-HSD2-mediated condition or disorder" and related terms and phrases refer to a condition or disorder characterized by inappropriate, e.g., less than or greater than normal, 11β-HSD2 activity. A 11β-HSD2-mediated condition or disorder may be completely or partially characterized by inappropriate 11β-HSD2 activity. However, a 11β-HSD2-mediated condition or disorder is one in which modulation of 11β-HSD2 results in some effect on the underlying condition or disease (e.g., a 11β-HSD2 inhibitor results in some improvement in patient well-being in at least some patients).

As used herein, the term "17β-HSD3-mediated condition or disorder" and related terms and phrases refer to a condition or disorder characterized by inappropriate, e.g., less than or greater than normal, 17β-HSD3 activity. A 17β-HSD3-mediated condition or disorder may be completely or partially characterized by inappropriate 17β-HSD3 activity. However, a 17β-HSD3-mediated condition or disorder is one in which modulation of 17β-HSD3 results in some effect on the underlying condition or disease (e.g., a 17β-HSD3 inhibitor results in some improvement in patient well-being in at least some patients).

The following abbreviations are used herein and have the indicated definitions: DMEM is Dulbecco's Modified Eagle Medium; Et$_3$N is triethylamine; EtOAc is ethyl acetate; MeOH is methanol; MS is mass spectrometry; NMR is nuclear magnetic resonance; PBS is phosphate-buffered saline; SPA is scintillation proximity assay; THF is tetrahydrofuran; and TMS is trimethylsilyl.

Compounds of the Invention

The present invention provides compounds of Formula (I) and (II) as well as their pharmaceutically acceptable salts, solvates, stereoisomers, or prodrugs thereof, or mixtures thereof collectively referred to as the "The Benzamide Derivatives":

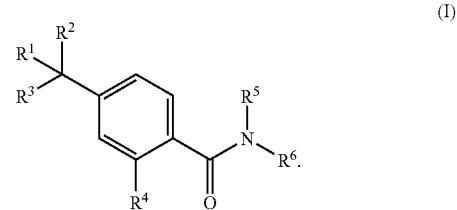

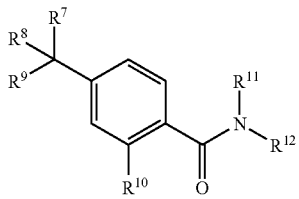

wherein $R^1$, $R^2$, $R^3$, $R^4$, $R^5$, $R^6$, $R^7$, $R^8$, $R^9$, $R^{10}$, $R^{11}$, and $R^{12}$ are defined above.

In one embodiment, $R^5$ is $(C_1-C_8)$alkyl, in particular, $(C_1-C_3)$alkyl. In some embodiments, $R^5$ is selected from methyl, ethyl and isopropyl.

In another embodiment, $R^5$ is $(C_3-C_8)$cycloalkyl, in particular, $R^5$ is cyclopropyl or cyclohexyl.

In another embodiment, $R^6$ is an aryl, in particular, phenyl. In some embodiments, wherein $R^6$ is aryl optionally substituted with one to four substituents. In some embodiments, $R^6$ is selected from dichloro-substituted phenyl, 2-chloro-5-cyano-phenyl, 2-chloro-phenyl and 2-chloro-5-trifluoromethyl-phenyl.

In another embodiment, $R^6$ is aryl$(C_1-C_6)$ alkyl, in particular, $R^6$ is benzyl.

In another embodiment, $R^6$ is cycloalkyl, in particular, $R^6$ is cyclopropyl or cyclohexyl.

In another embodiment, $R^5$ or $R^6$ is selected from $CH_2-CF_3$, $-CH_2-CHF_2$ and $-CH_2-CH_2F$.

In one embodiment, $R^5$ and $R^6$ are each members independently selected from the group consisting of $(C_1-C_8)$alkyl, $(C_2-C_8)$alkenyl, $(C_2-C_8)$alkynyl, $(C_1-C_8)$haloalkyl, $(C_2-C_8)$hydroxyalkyl, $(C_3-C_8)$cycloalkyl, $(C_3-C_8)$heterocycloalkyl, $(C_3-C_8)$cycloalkyl$(C_1-C_6)$alkyl, $(C_3-C_8)$cycloalkyl$(C_1-C_6)$alkoxy, $(C_3-C_8)$heterocycloalkyl$(C_1-C_6)$alkyl, aryl, heteroaryl$(C_1-C_6)$alkyl, aryl$(C_1-C_6)$alkyl; or $R^5$ and $R^6$, together with the nitrogen to which they are attached may combine to form a five to eight-membered ring heterocycloalkyl.

In one embodiment, $R^7$ is $-OH$, $R^8$ is $(C_1-C_3)$alkyl, and $R^9$ is $(C_1-C_3)$haloalkyl, and $R^{11}$ is selected from the group consisting of $(C_3-C_6)$cycloalkyl, in particular cyclopropyl, $(C_1-C_3)$haloalkyl, and $(C_1-C_3)$alkyl.

In another embodiment, $R^{12}$ is aryl$(C_1-C_6)$alkyl, in particular $R^{12}$ is benzyl. In still another embodiment, $R^{12}$ is $(C_3-C_8)$ alkyl, in particular, cyclohexyl monosubstituted in the 4-position. In some embodiments, the 4-position substituent on the cyclohexyl is aryl or heteroaryl.

In yet another embodiment, $R^{11}$ and $R^{12}$ together with the nitrogen to which they are attached form a five to eight-membered ring heterocycloalkyl.

In another embodiment, the $R^7$-$R^9$ moiety is:

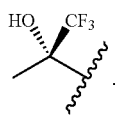

In another embodiment, the $R^7$-$R^9$ moiety is:

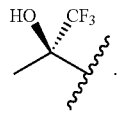

The benzamide derivatives can have asymmetric centers and therefore exist in different enantiomeric and diastereomeric forms. This invention relates to the use of all optical isomers and stereoisomers of the benzamide derivatives, and mixtures thereof, and to all pharmaceutical compositions and methods of treatment that may employ or contain them.

It should be noted that racemates, racemic mixtures, and stereoisomers, particularly diastereomeric mixtures or diastereomerically pure compounds and enantiomers or enantiomerically pure compounds of the above are all encompassed.

Specific examples of compounds of Formula (I) are provided below:

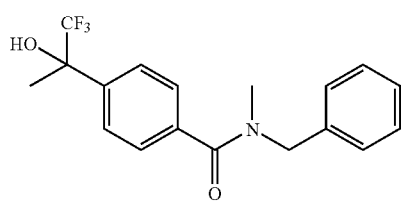

1

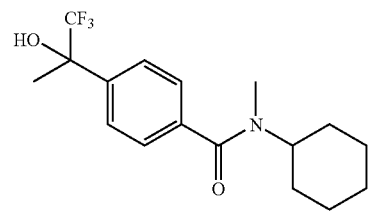

2

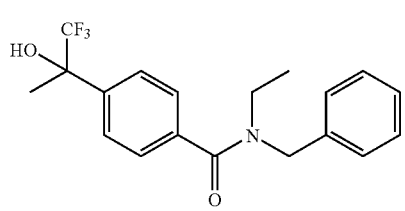

3

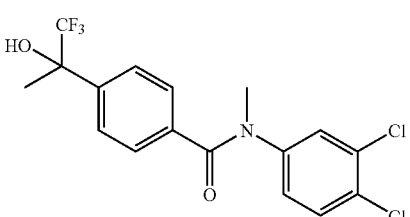

4

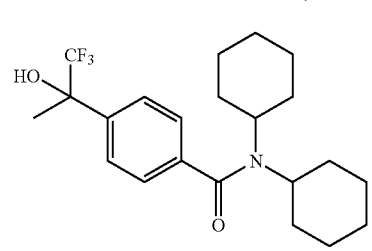

5

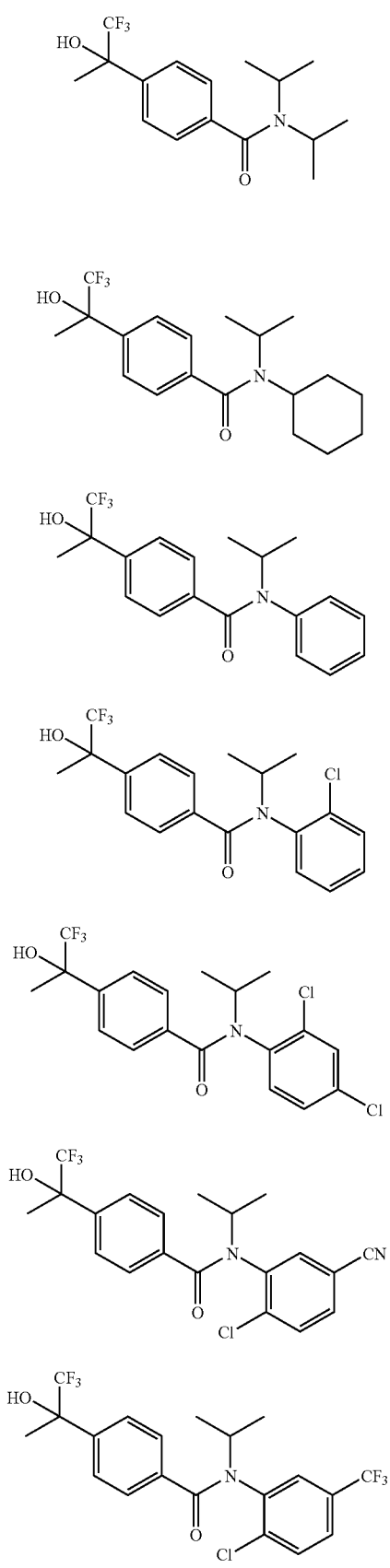
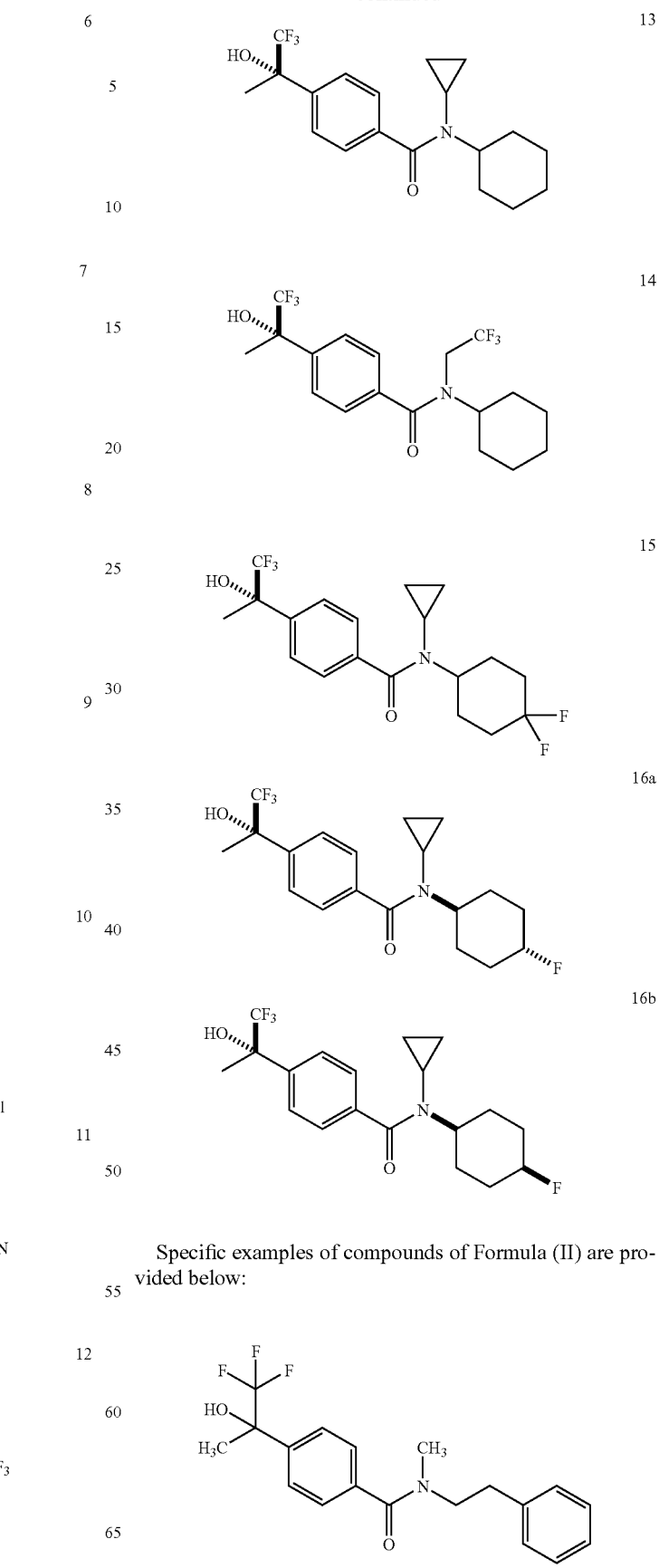
Specific examples of compounds of Formula (II) are provided below:
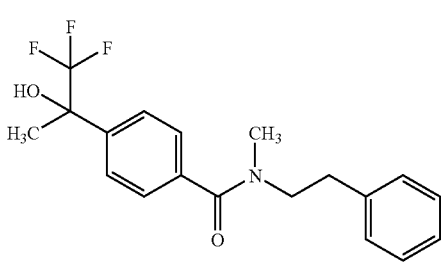

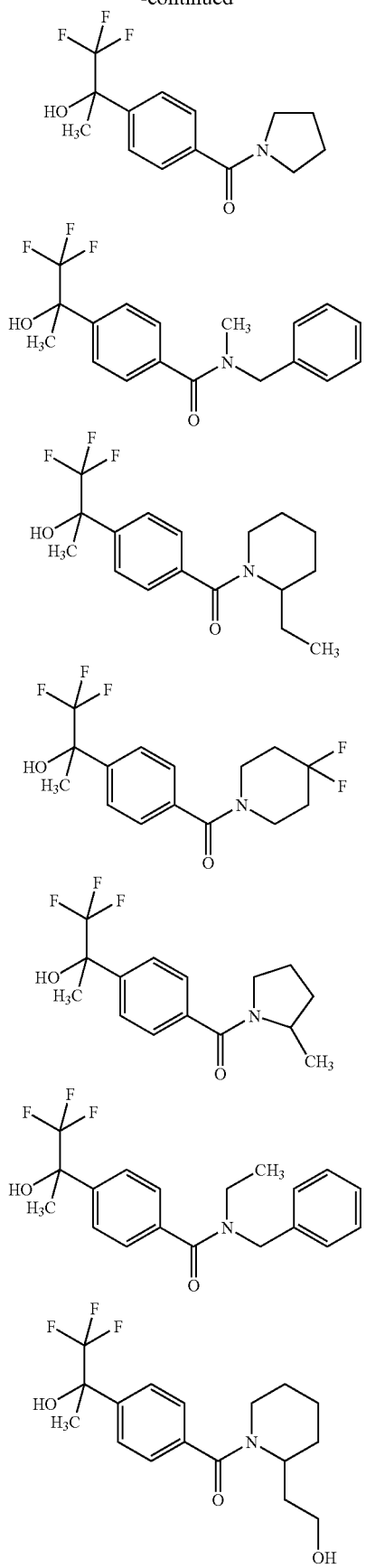
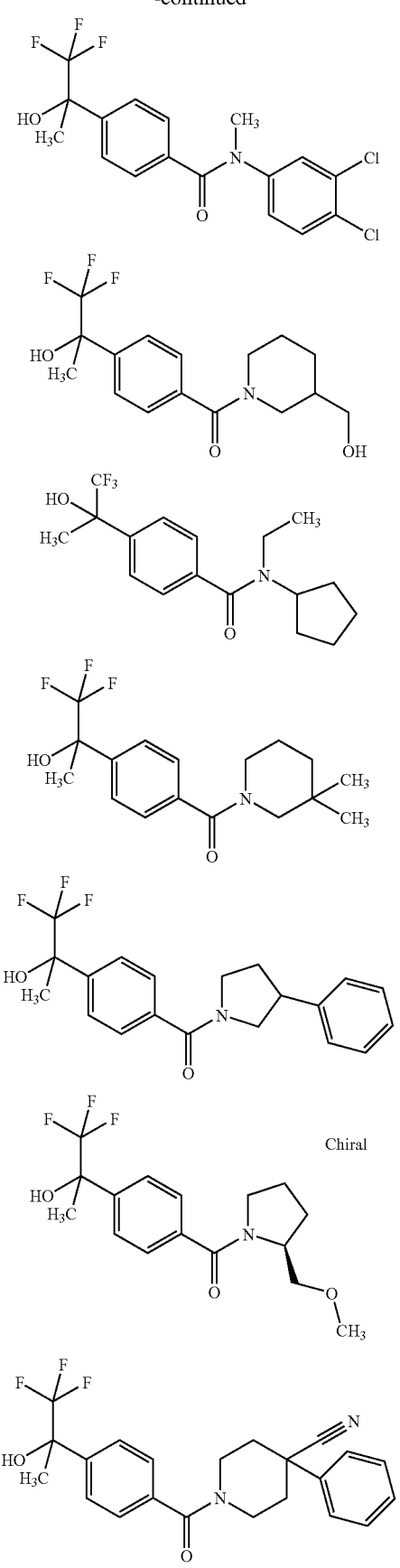

25
-continued
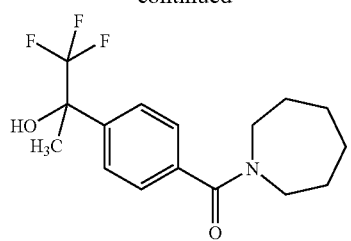
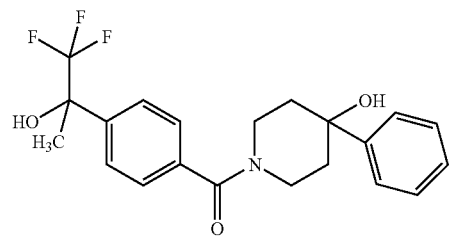
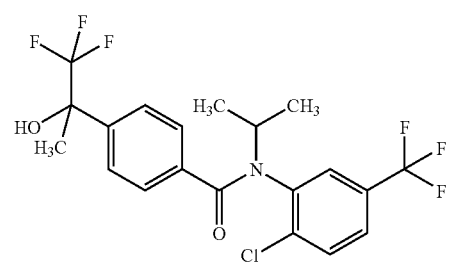
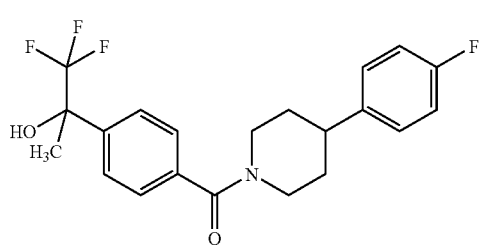
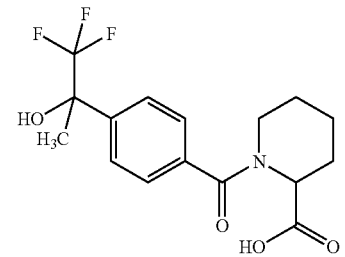
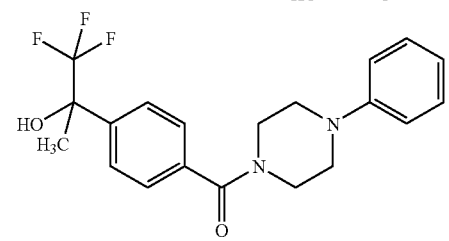
26
-continued
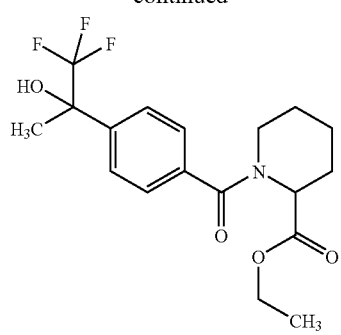
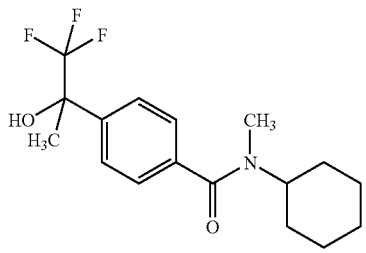
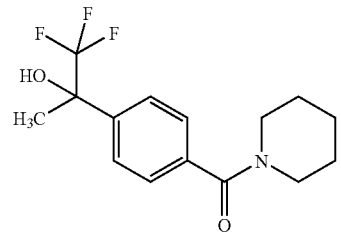
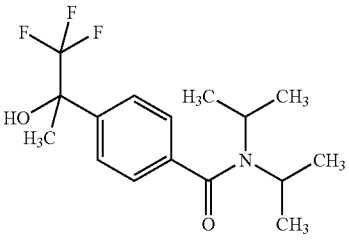
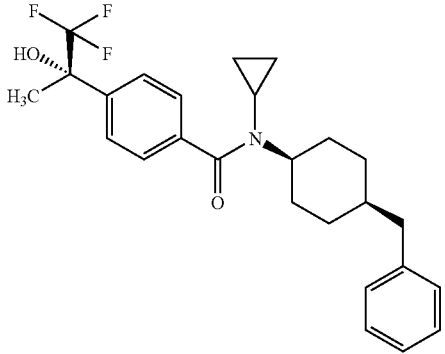

-continued
27
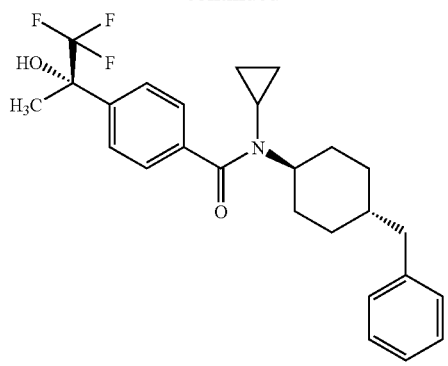
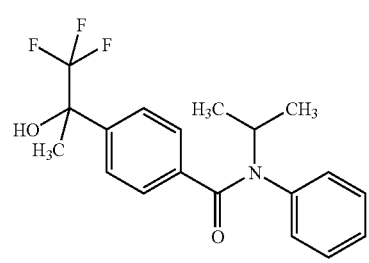
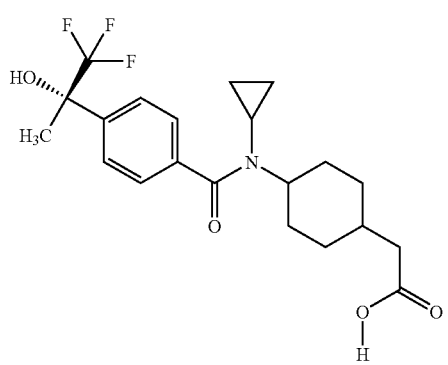
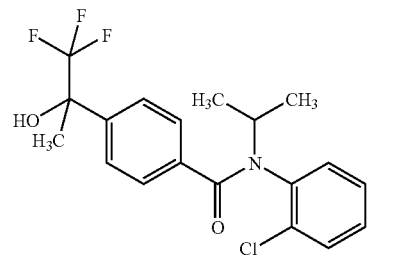
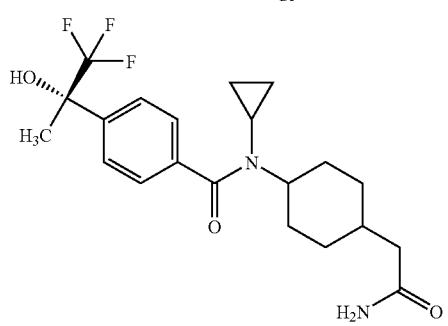
28
-continued
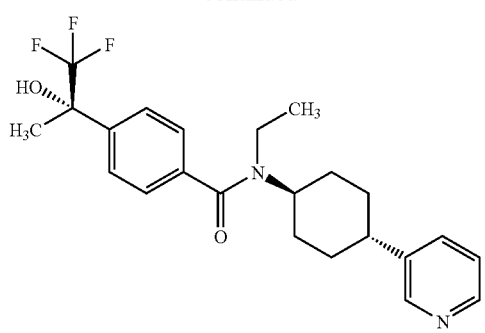
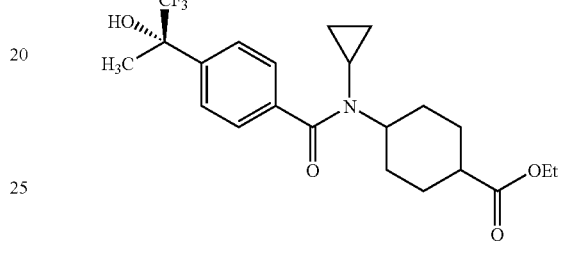
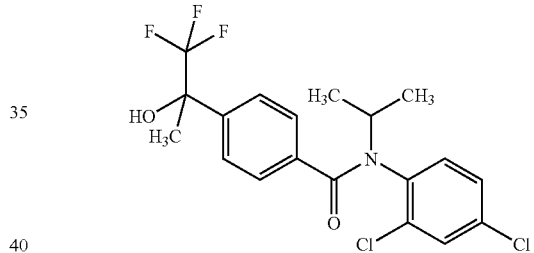
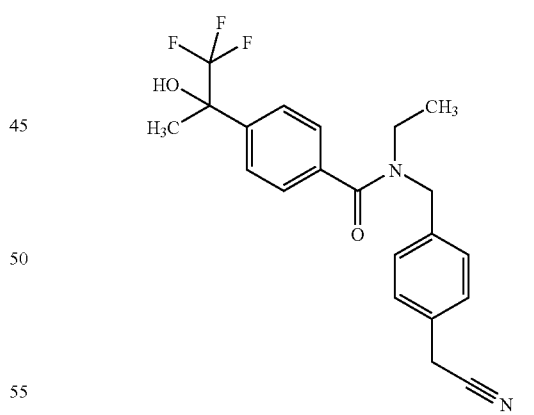
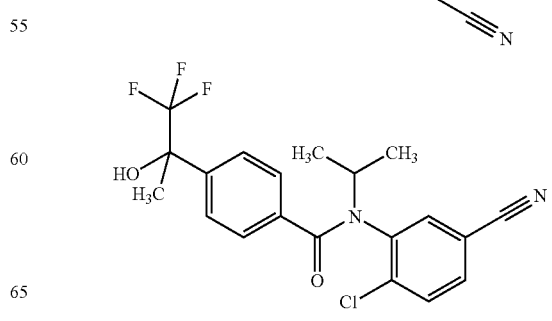

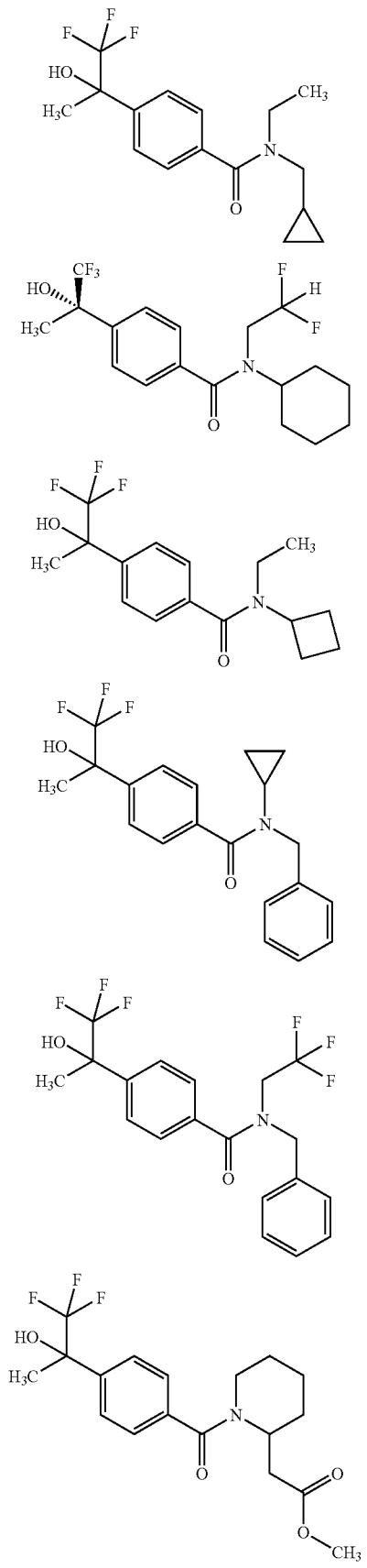
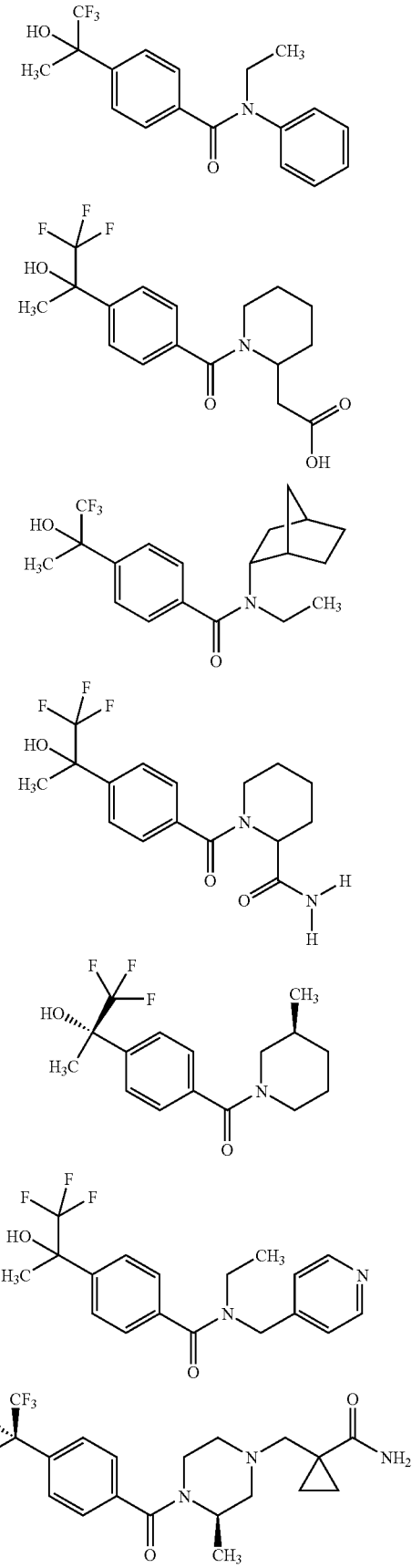

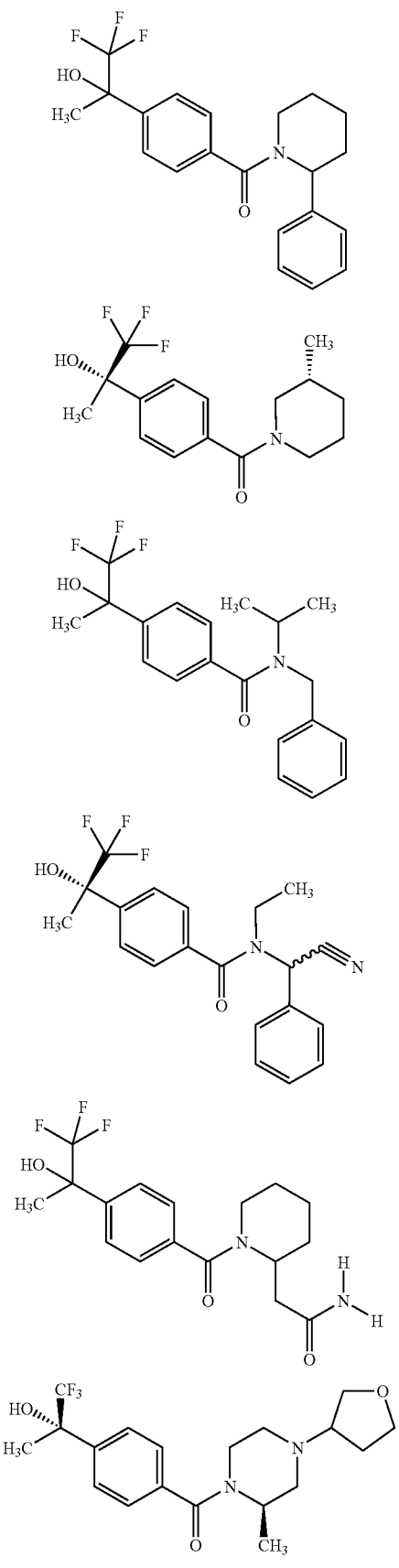
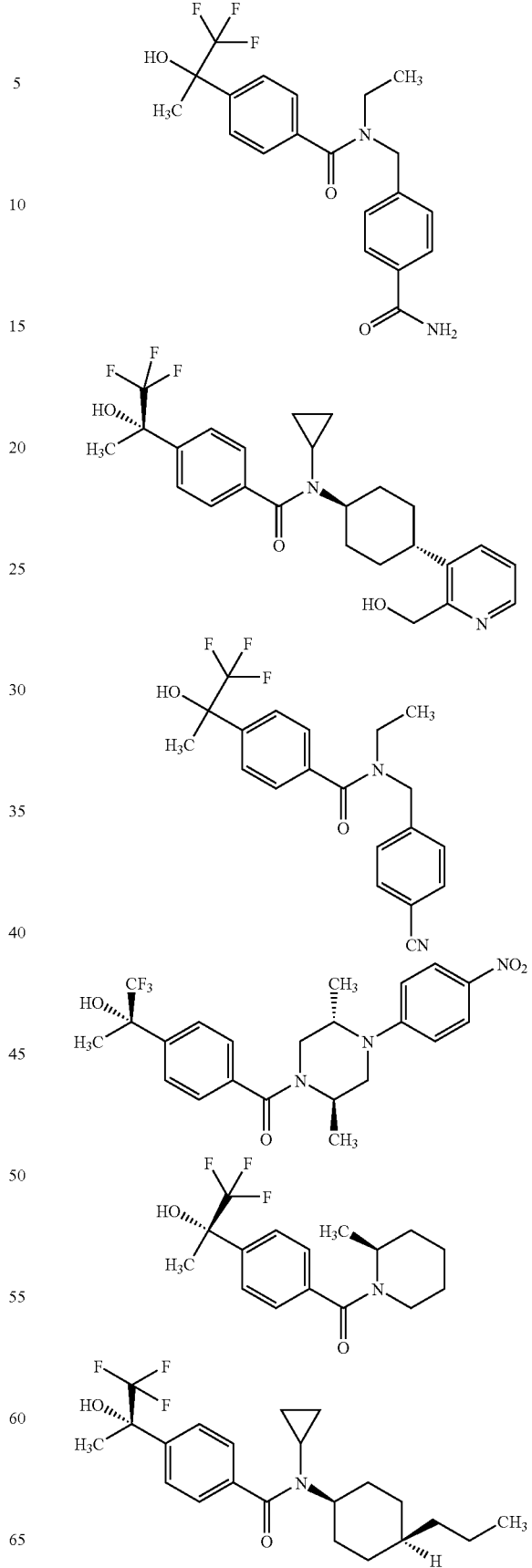

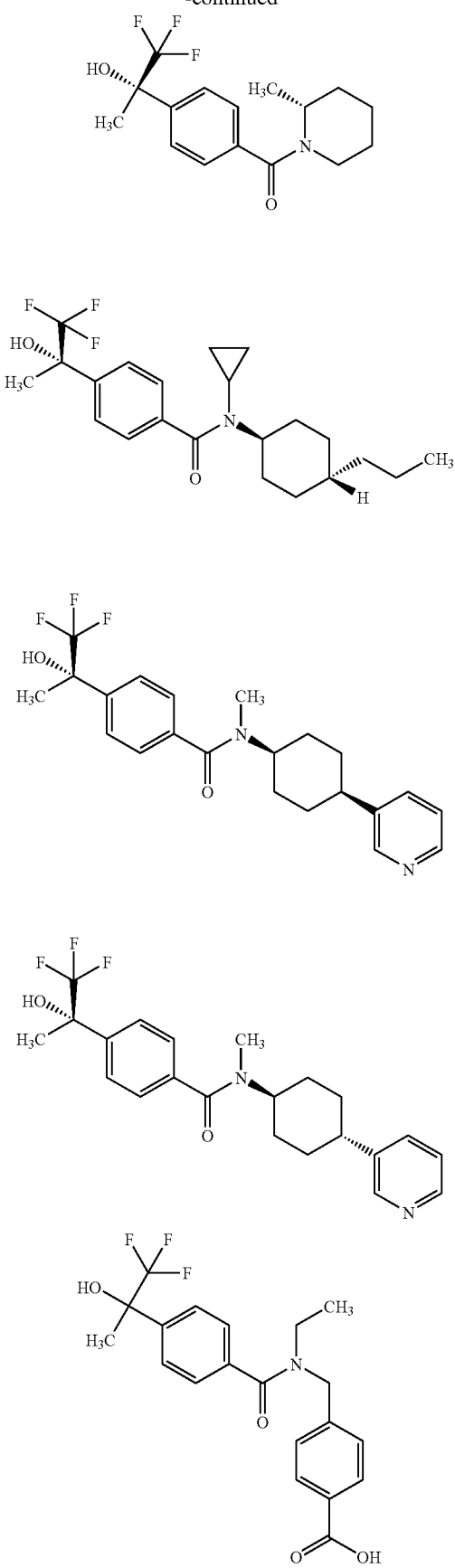

35
-continued
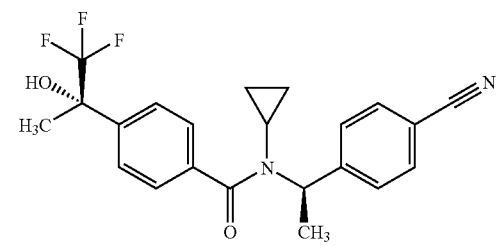
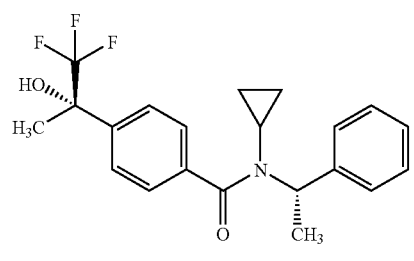
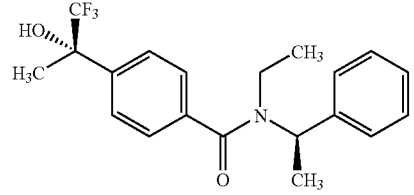
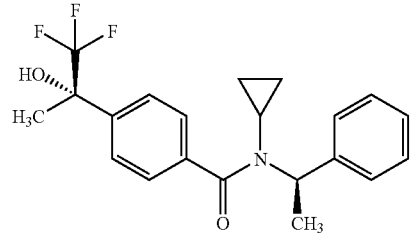
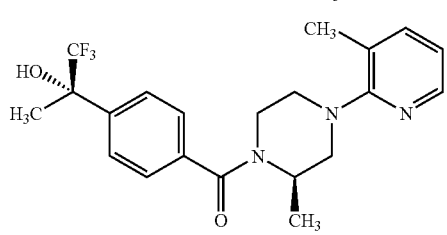
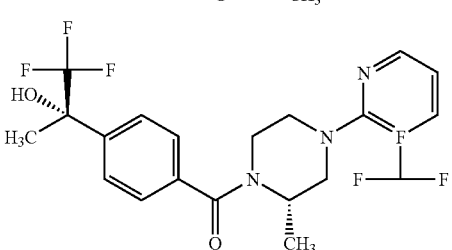
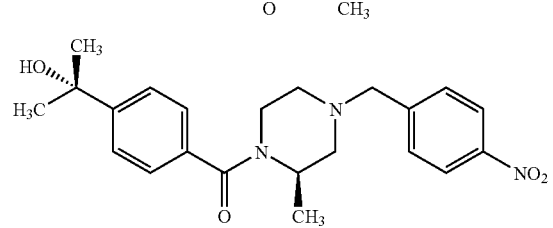
36
-continued
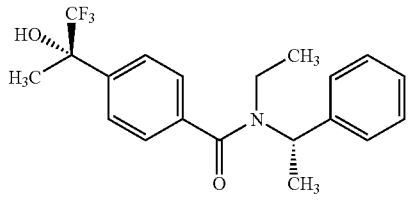
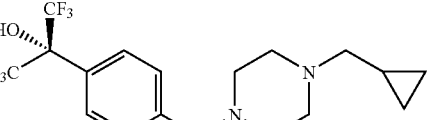
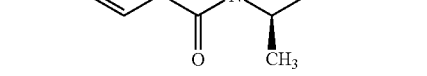
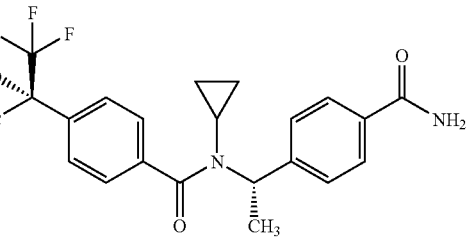
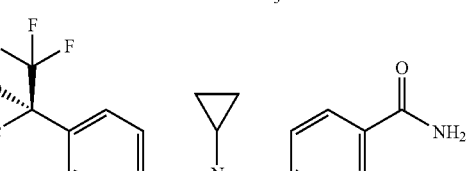
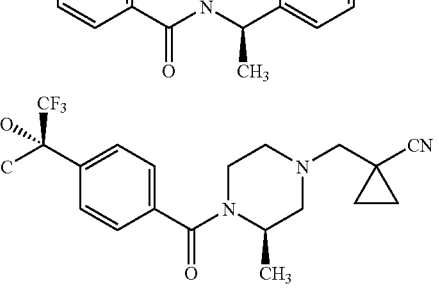
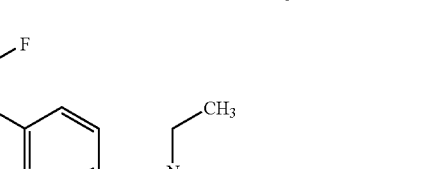
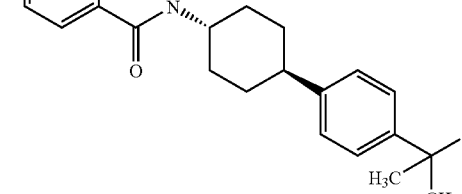
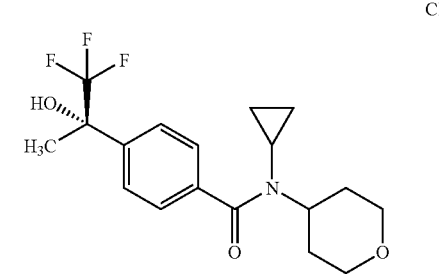

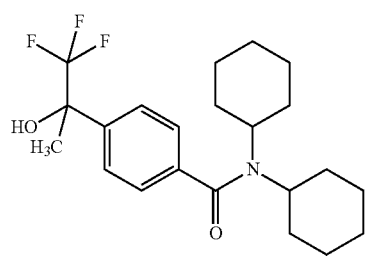
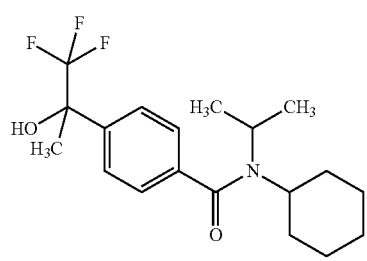
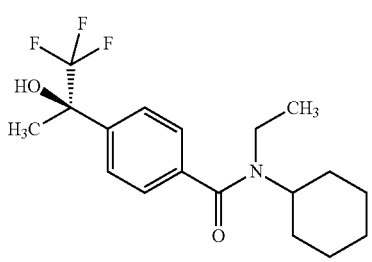
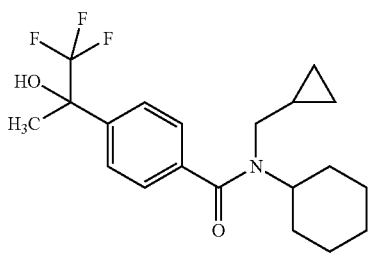
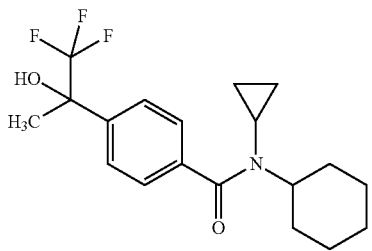
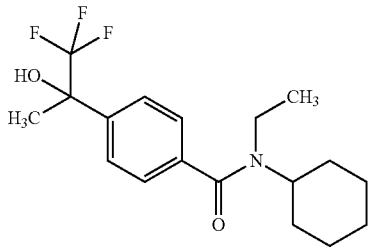
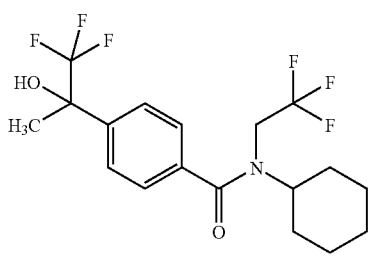
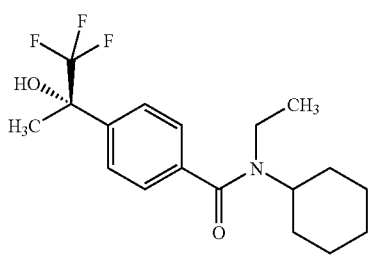
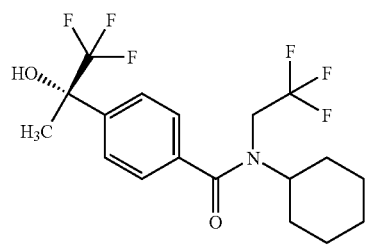
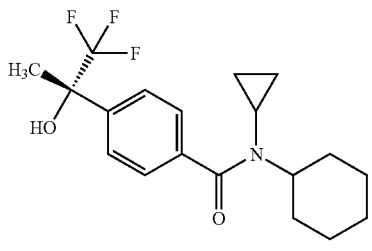
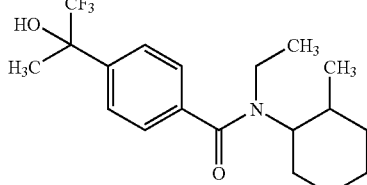
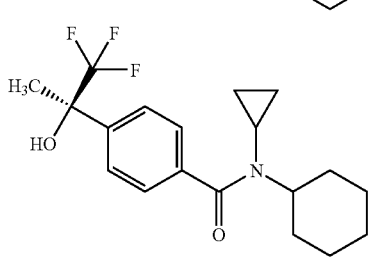

39
-continued
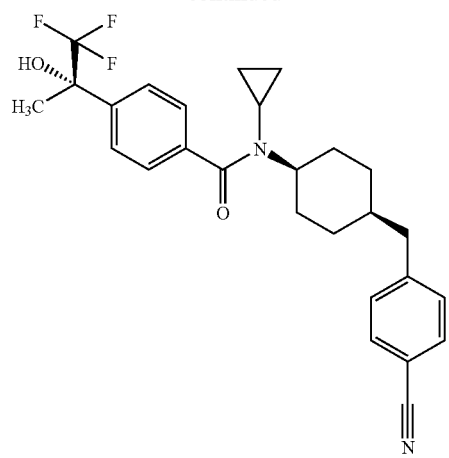
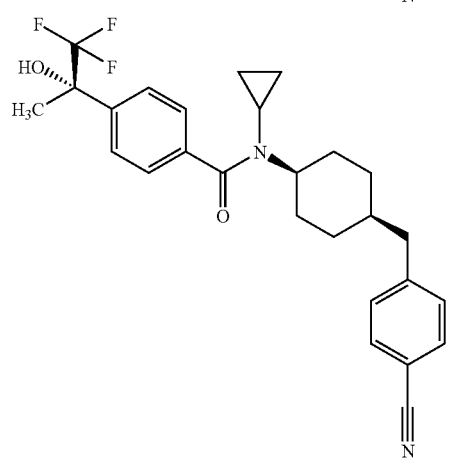
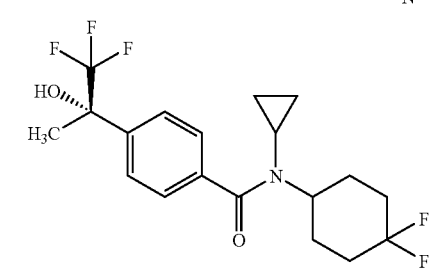
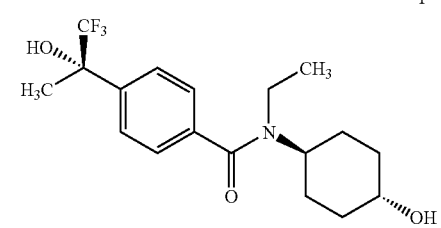
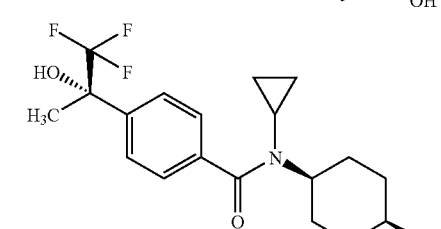
40
-continued
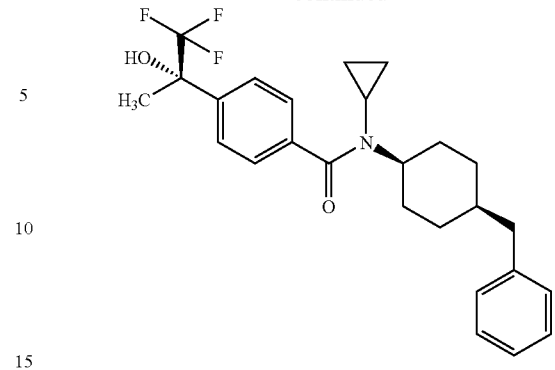
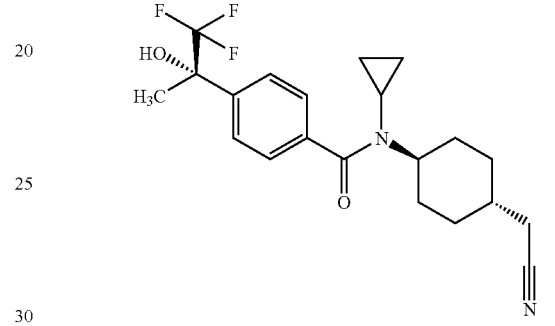
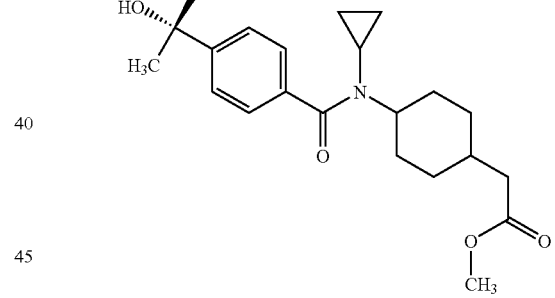
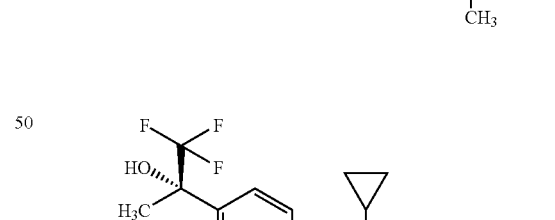
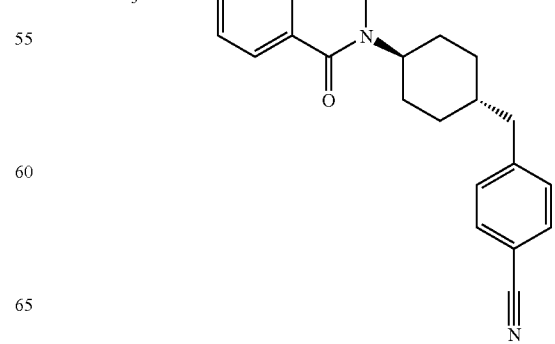

41
-continued
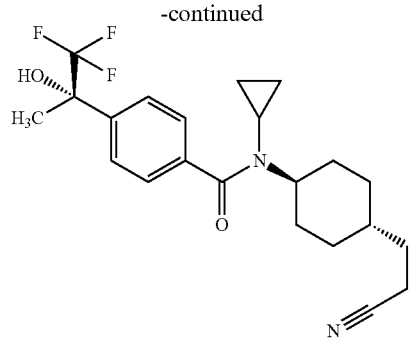
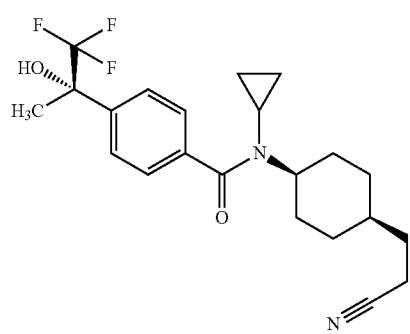
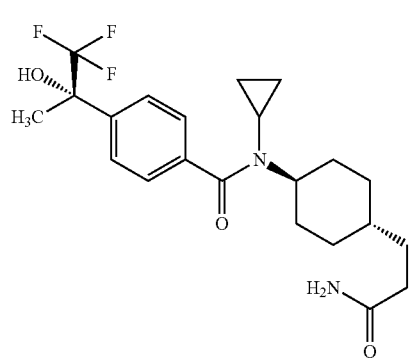
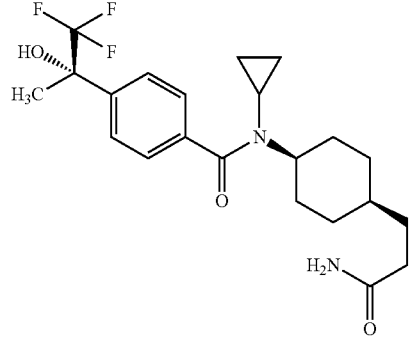
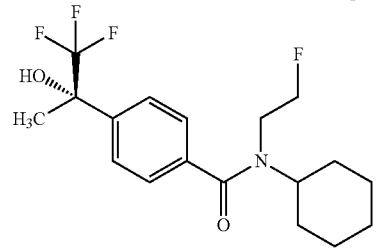
42
-continued
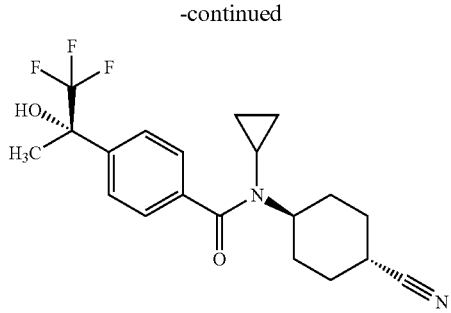
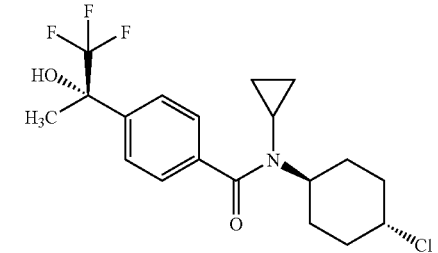
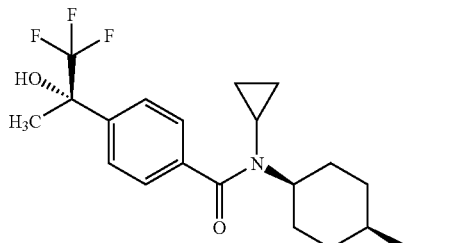
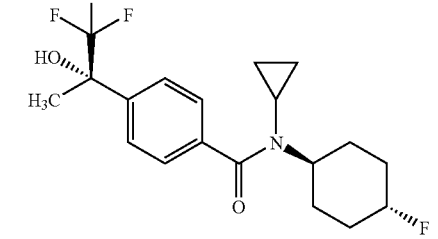
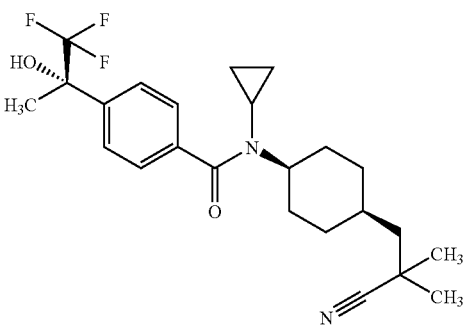
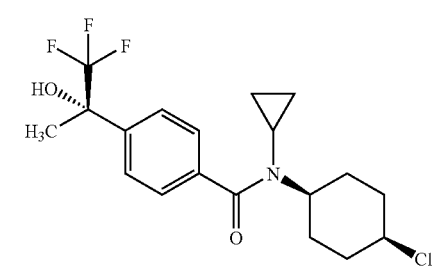

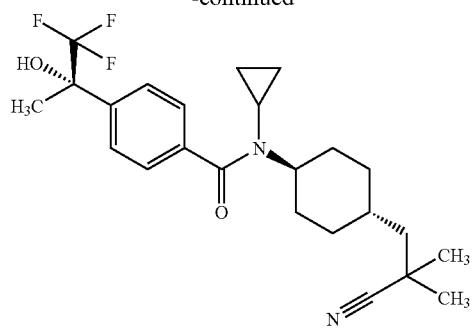
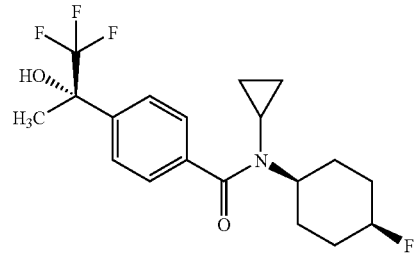
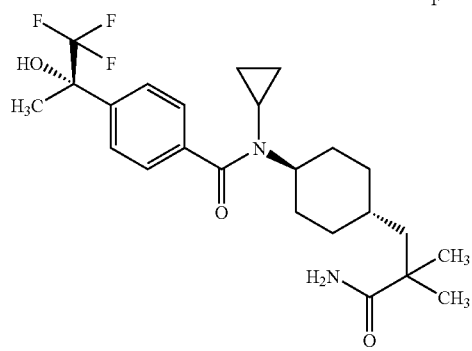
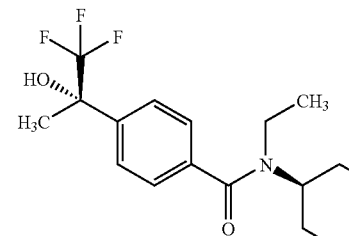
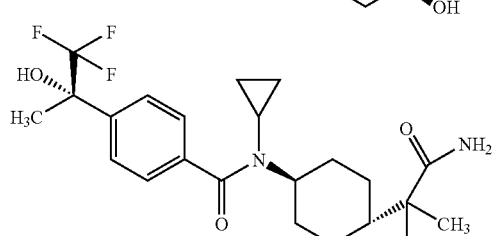
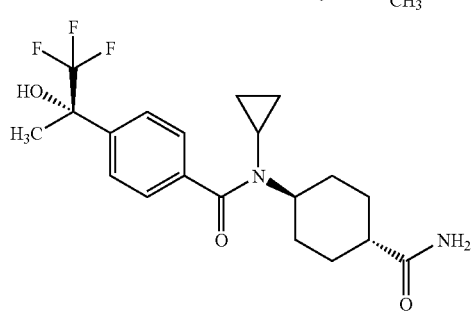
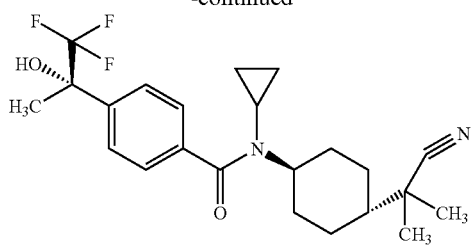
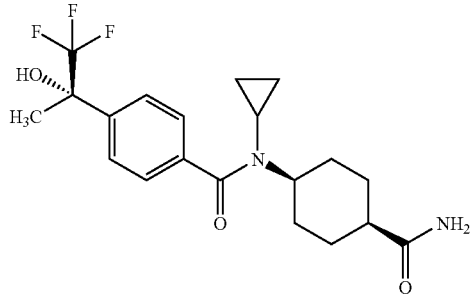
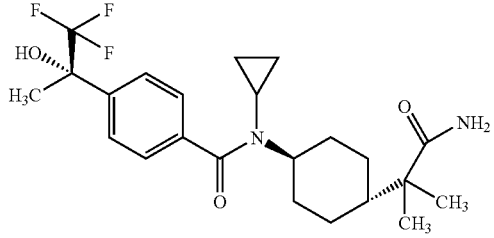
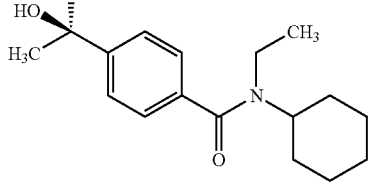
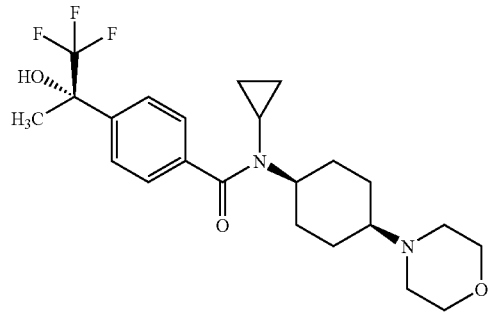
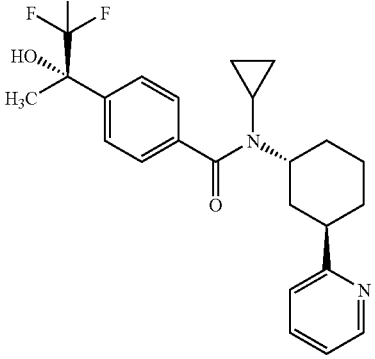

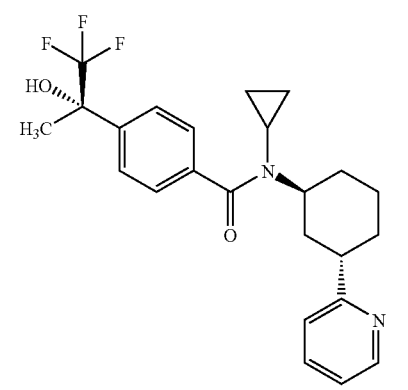
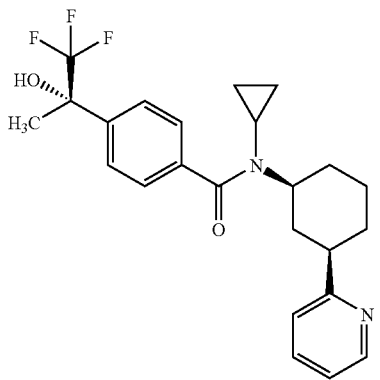
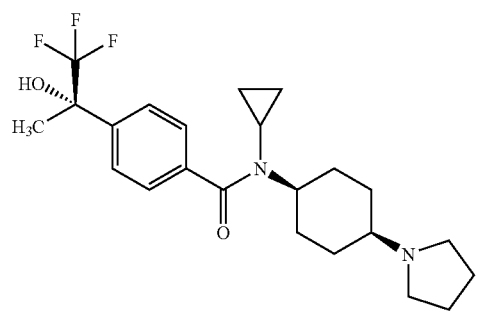
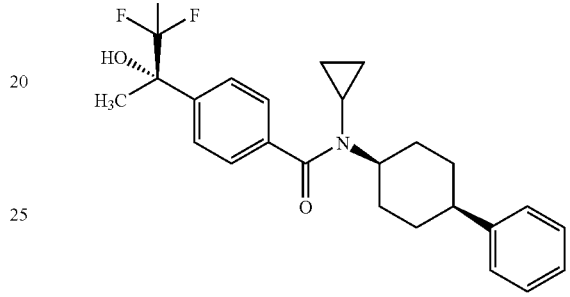
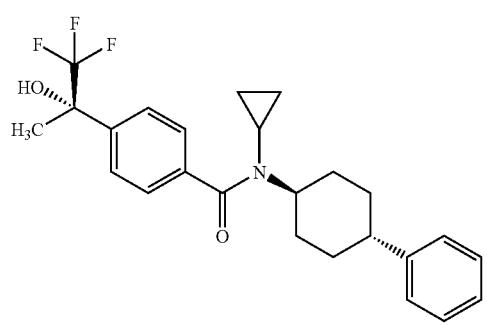
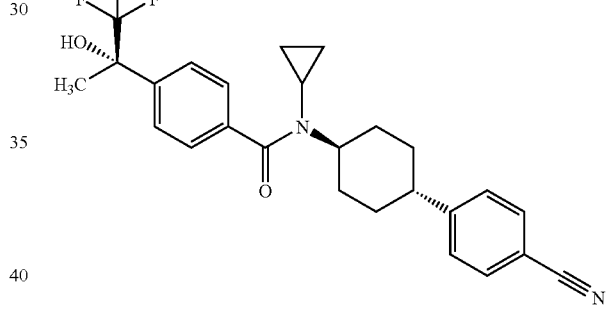
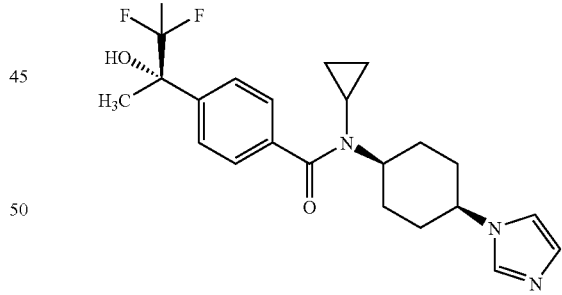
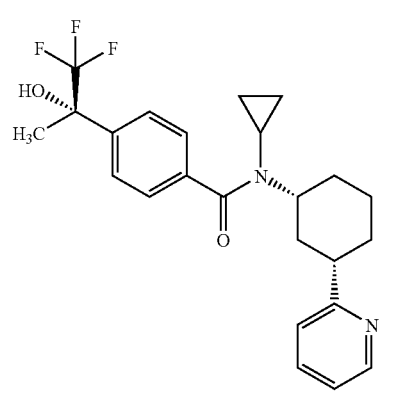
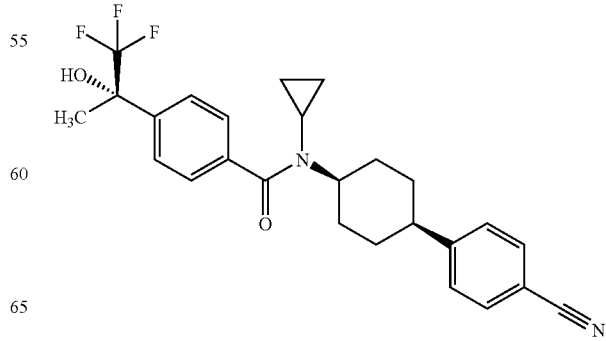

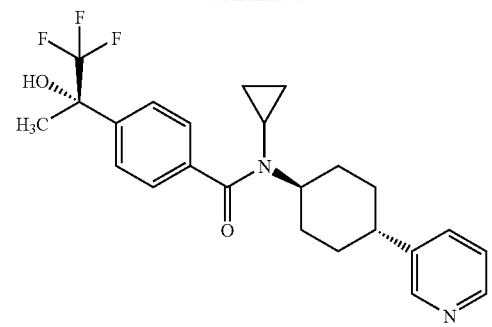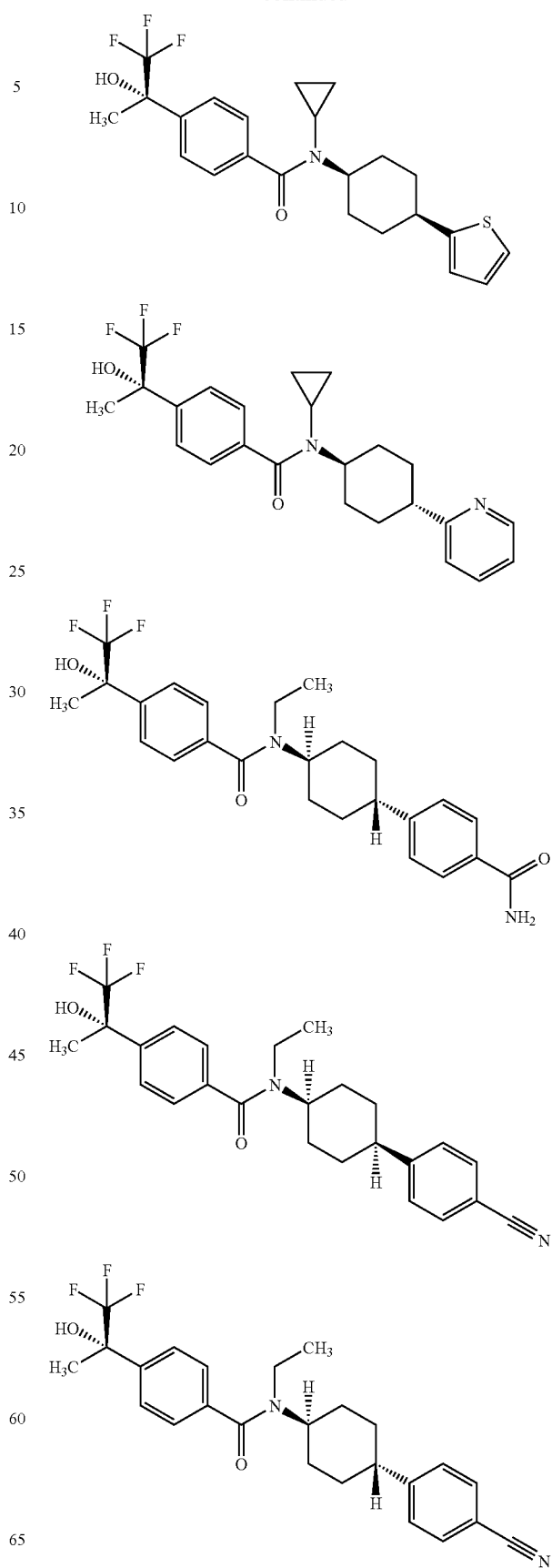

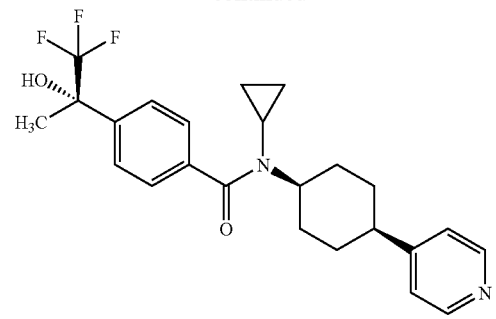
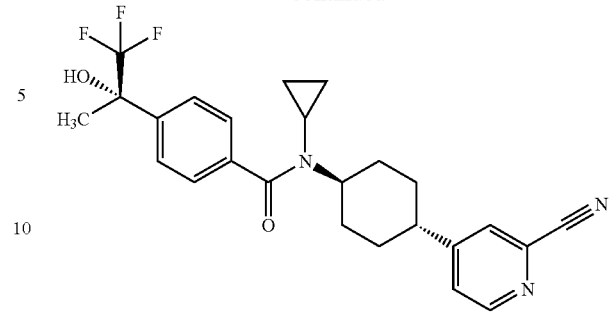
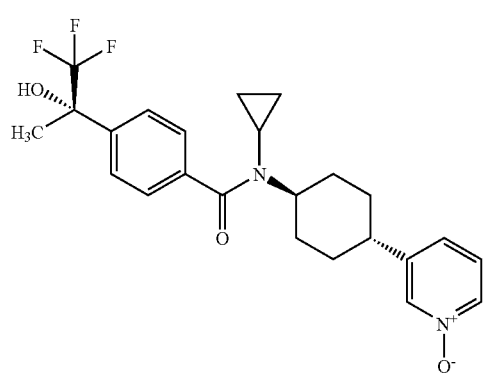
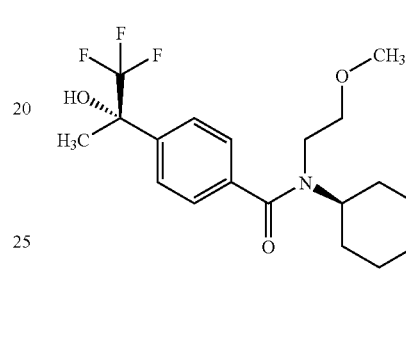
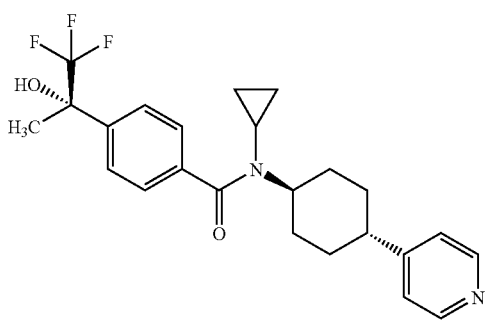
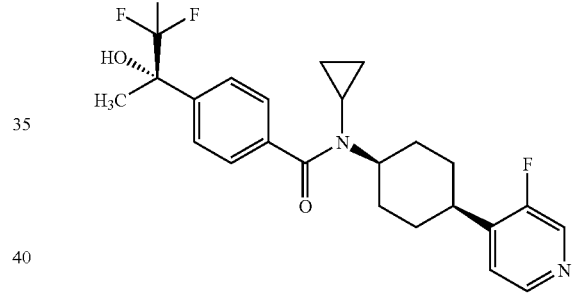
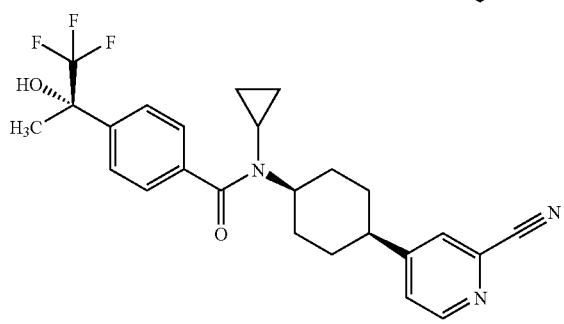
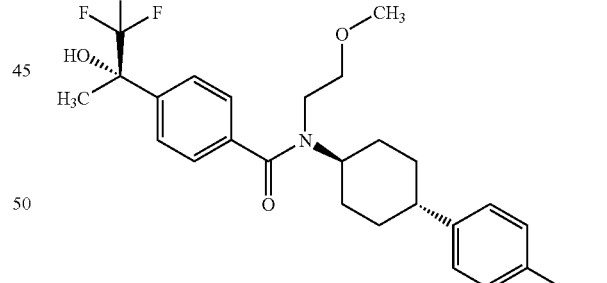
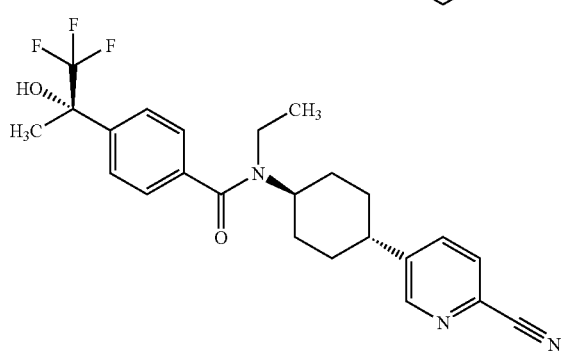
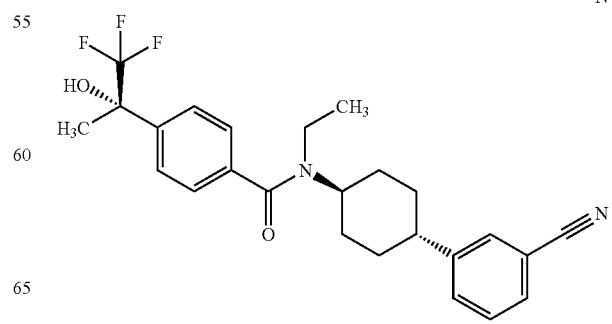

51
-continued
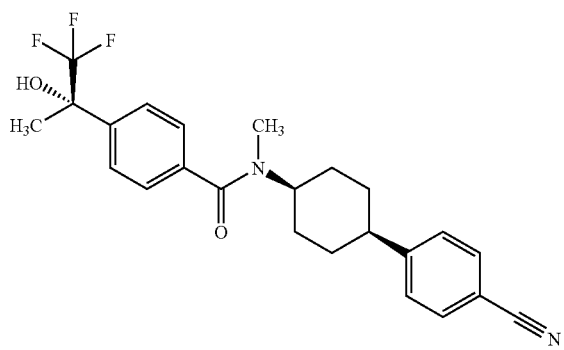
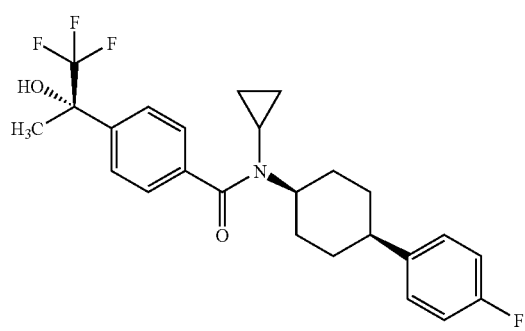
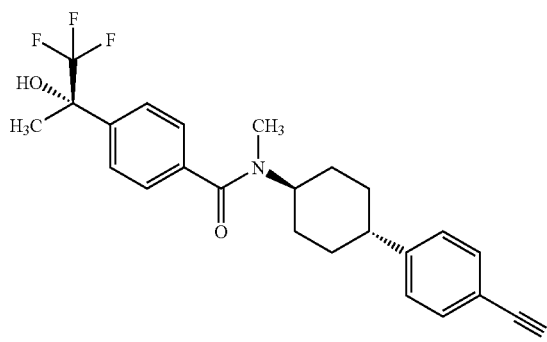
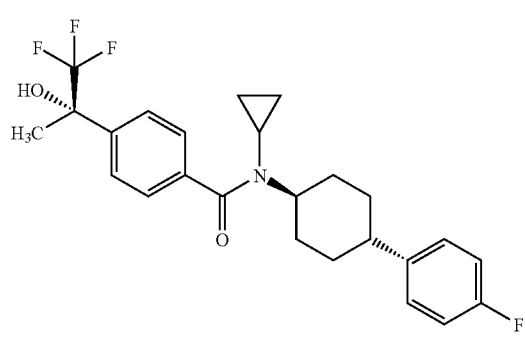
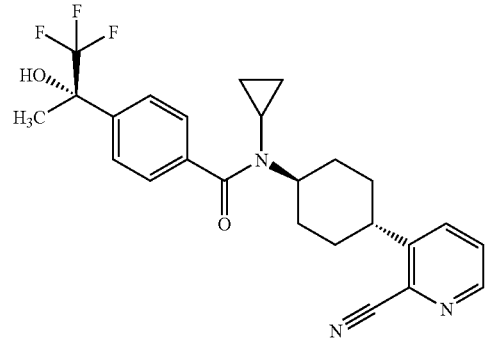
52
-continued
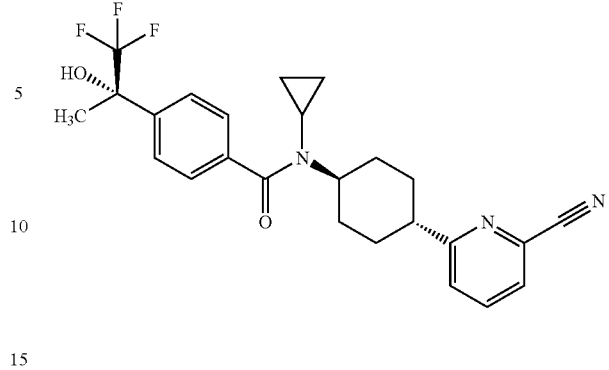
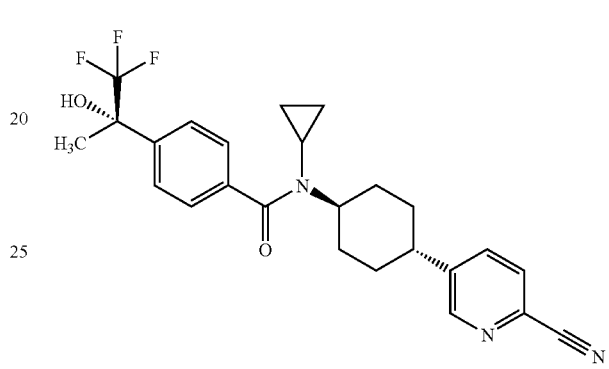
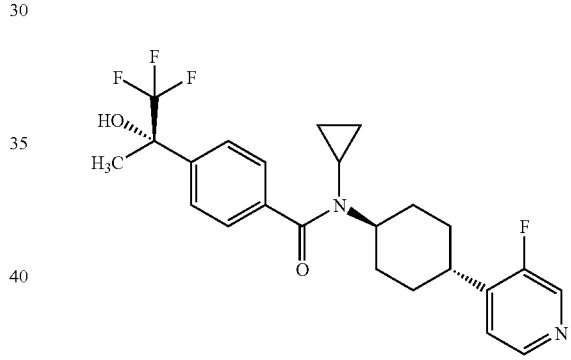
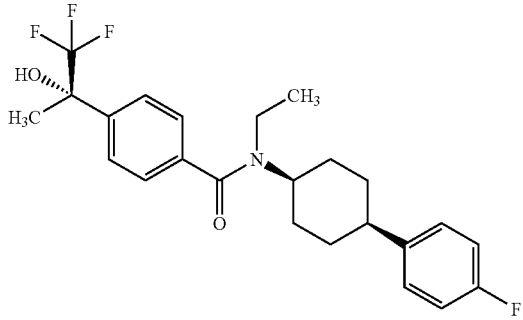
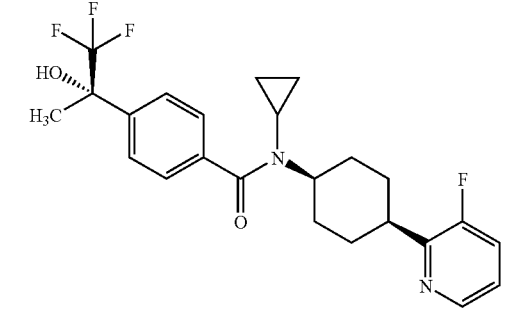

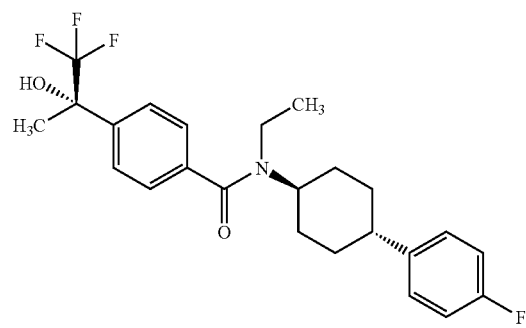
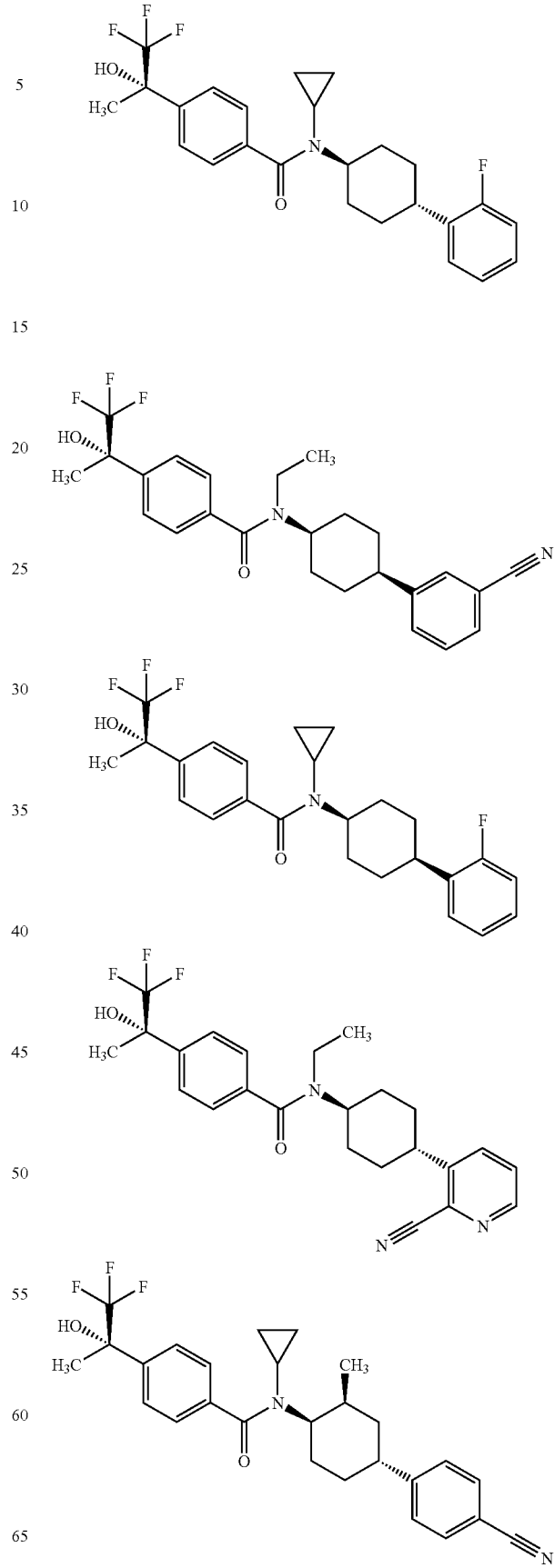

55
-continued
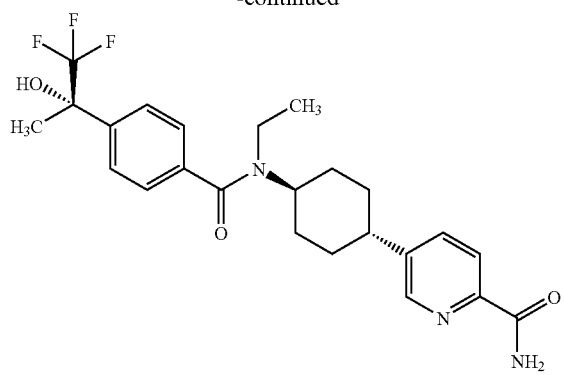
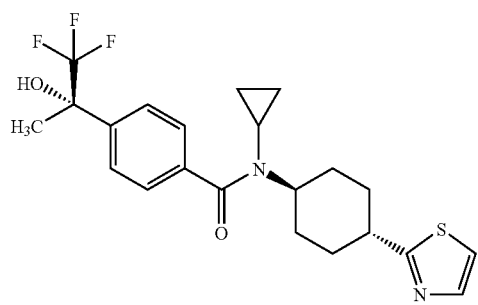
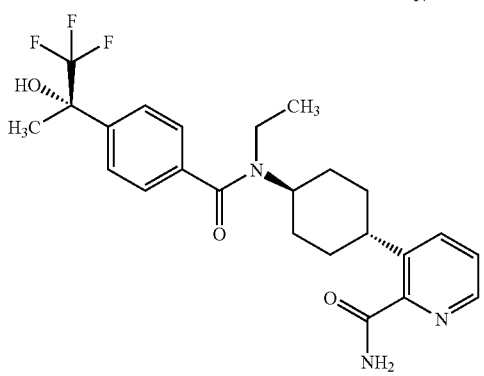
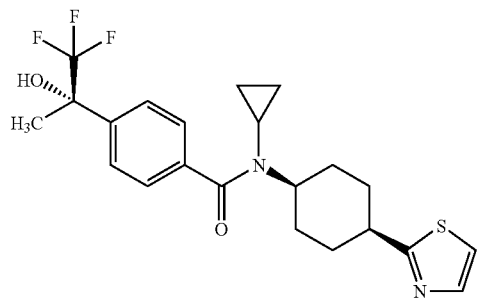
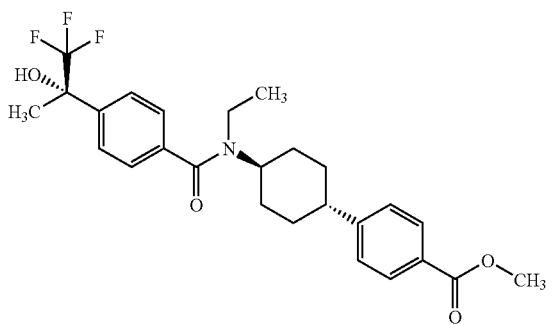
56
-continued
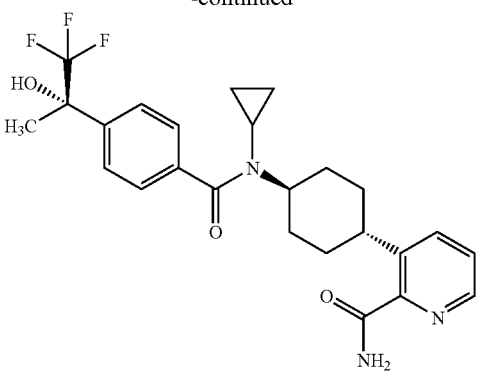
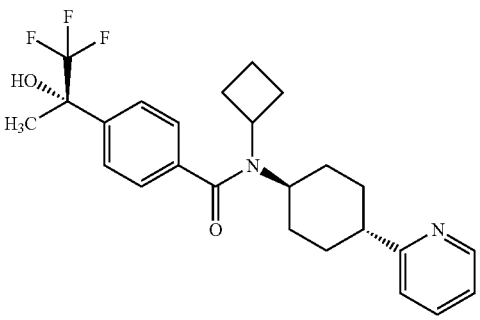
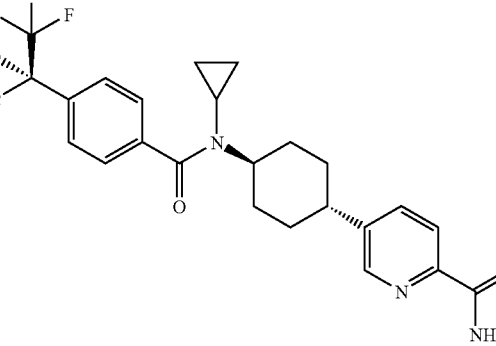
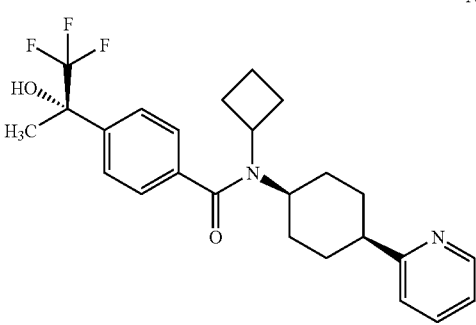

-continued

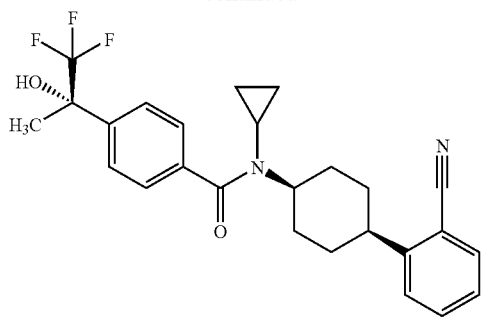

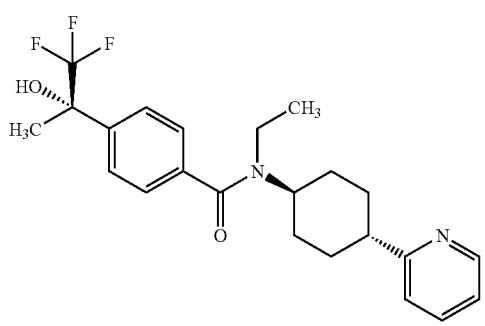

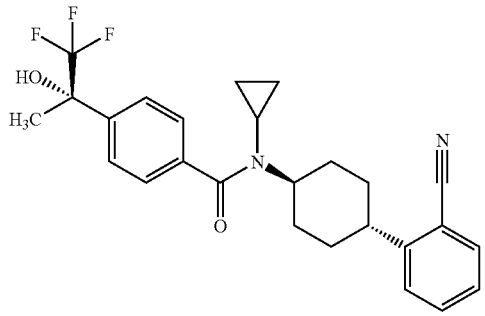

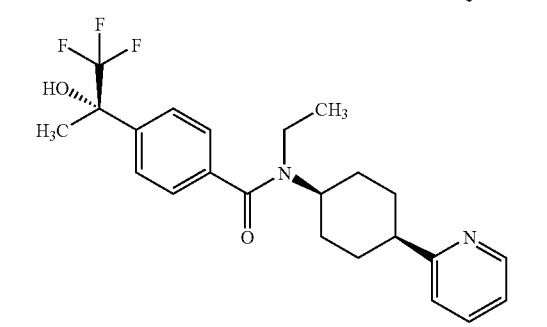

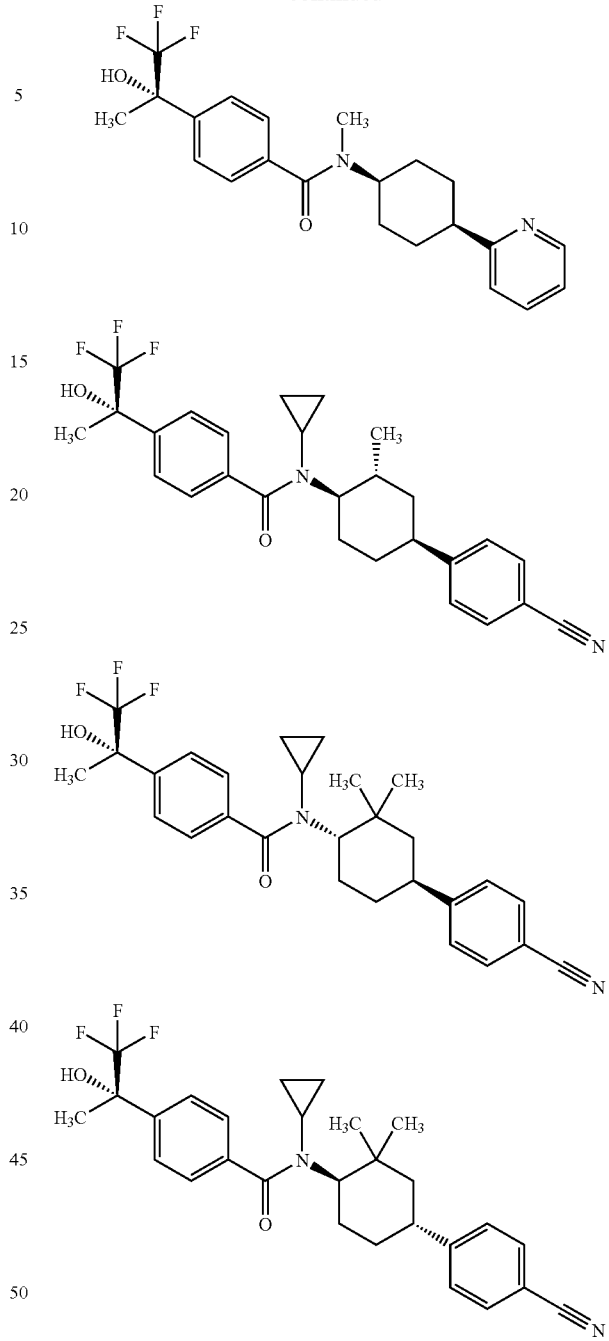

The present invention also provides compositions comprising a therapeutically effective amount of a benzamide derivative of Formula (I) and a pharmaceutically acceptable vehicle, carrier, diluent or excipient.

The invention further provides benzamide derivatives of Formula (I) or (II) that are in isolated and purified form.

The invention provides methods for treating diabetes comprising administering to a patient in need thereof a therapeutically effective amount of a benzamide derivative of Formula (I) or (II).

The invention also provides methods for treating obesity comprising administering to a patient in need thereof a therapeutically effective amount of a benzamide derivative of Formula (I) or (II).

The invention further provides methods for treating an HSD-mediated condition or disorder comprising administering to a patient in need thereof a therapeutically effective amount of a benzamide derivative of Formula (I) or (II).

The invention further provides methods for treating an 11β-HSD1-mediated condition or disorder comprising administering to a patient in need thereof a therapeutically effective amount of a benzamide derivative of Formula (I) or (II).

The invention further provides methods for treating an 11β-HSD2-mediated condition or disorder comprising administering to a patient in need thereof a therapeutically effective amount of a benzamide derivative of Formula (I) or (II).

The invention further provides methods for treating an 17β-HSD3-mediated condition or disorder comprising administering to a patient in need thereof a therapeutically effective amount of a benzamide derivative of Formula (I) or (II).

The invention further provides methods for treating an HSD-responsive condition or disorder comprising administering to a patient in need thereof a therapeutically effective amount of a benzamide derivative of Formula (I) or (II).

The invention further provides methods for treating an 11β-HSD1-responsive condition or disorder comprising administering to a patient in need thereof a therapeutically effective amount of a benzamide derivative of Formula (I) or (II).

The invention further provides methods for treating an 11β-HSD2-responsive condition or disorder comprising administering to a patient in need thereof a therapeutically effective amount of a benzamide derivative of Formula (I) or (II).

The invention further provides methods for treating an 17β-HSD3-responsive condition or disorder comprising administering to a patient in need thereof a therapeutically effective amount of a benzamide derivative of Formula (I) or (II).

For example, and in another embodiment, the invention relates to the manufacture of a medicament comprising a compound according to any one of the above embodiments.

Another embodiment of the invention relates to a method of manufacturing a medicament for the treatment of diabetes, syndrome X, obesity, polycystic ovarian disease, an eating disorder, craniopharyngioma, Prader-Willi syndrome, Frohlich's syndrome, hyperlipidemia, dyslipidemia, hypercholesterolemia, hypertriglyceridemia, low HDL levels, high HDL levels, hyperglycemia, insulin resistance, hyperinsulinemia, Cushing's syndrome, hypertension, atherosclerosis, vascular restenosis, retinopathy, nephropathy, neurodegenerative disease, neuropathy, muscle wasting, cognitive disorders, dementia, depression, psoriasis, glaucoma, osteoporosis, a viral infection, an inflammatory disorder or an immune disorder, the method comprising combining a compound according to any one of the above embodiments with a pharmaceutical carrier to form the medicament.

Another embodiment of the invention relates to a method of manufacturing a medicament for the treatment of diabetes or obesity, the method comprising combining a compound according to any one of the above embodiments with a pharmaceutical carrier to form the medicament.

Another embodiment of the invention relates to a method of manufacturing a medicament for the treatment of insulin-dependent diabetes mellitus, the method comprising combining a compound according to any one of the above embodiments with a pharmaceutical carrier to form the medicament.

Another embodiment of the invention relates to a method of manufacturing a medicament for the treatment of non-insulin-dependent diabetes mellitus, the method comprising combining a compound according to any one of the above embodiments with a pharmaceutical carrier to form the medicament.

Another embodiment of the invention relates to a method of manufacturing a medicament for the treatment of insulin resistance, the method comprising combining a compound according to any one of the above embodiments with a pharmaceutical carrier to form the medicament.

Another embodiment of the invention relates to a method of manufacturing a medicament for modulating cortisol production, the method comprising combining a compound according to any one of the above embodiments with a pharmaceutical carrier to form the medicament.

Another embodiment of the invention relates to a method of manufacturing a medicament for modulating hepatic glucose production, the method comprising combining a compound according to any one of the above embodiments with a pharmaceutical carrier to form the medicament.

Another embodiment of the invention relates to a method of manufacturing a medicament for modulating hepatic glucose production, the method comprising combining a compound according to any one of the above embodiments with a pharmaceutical carrier to form the medicament.

Another embodiment of the invention relates to a method of manufacturing a medicament for modulating hypothalamic function, the method comprising combining a compound according to any one of the above embodiments with a pharmaceutical carrier to form the medicament.

Another embodiment of the invention relates to a method of manufacturing a medicament for the inhibition of a hydroxysteroid dehydrogenase, the method comprising combining a compound according to any one of the above embodiments with a pharmaceutical carrier to form the medicament.

Another embodiment of the invention relates to a method of manufacturing a medicament for the inhibition of 11β-HSD1, 11β-HSD2 or 17β-HSD3, the method comprising combining a compound according to any one of the above embodiments with a pharmaceutical carrier to form the medicament.

Another embodiment of the invention relates to a method of manufacturing a medicament for the modulation of the function of a hydroxysteroid dehydrogenase, the method comprising combining a compound according to any one of the above embodiments with a pharmaceutical carrier to form the medicament.

Another embodiment of the invention relates to a method of manufacturing a medicament for the modulation of the function of 11β-HSD1, 11β-HSD2 or 17β-HSD3, the method comprising combining a compound according to any one of the above embodiments with a pharmaceutical carrier to form the medicament.

Another embodiment of the invention is the use of a compound according to any one of the above embodiments in a method of manufacture of a medicament for the treatment of diabetes, syndrome X, obesity, polycystic ovarian disease, an eating disorder, craniopharyngioma, Prader-Willi syndrome, Frohlich's syndrome, hyperlipidemia, dyslipidemia, hypercholesterolemia, hypertriglyceridemia, low HDL levels, high HDL levels, hyperglycemia, insulin resistance, hyperinsulinemia, Cushing's syndrome, hypertension, atherosclerosis, vascular restenosis, retinopathy, nephropathy, neurodegenerative disease, neuropathy, muscle wasting, cognitive disorders, dementia, depression, psoriasis, glaucoma, osteoporosis, a viral infection, an inflammatory disorder or an immune disorder.

Another embodiment of the invention is the use of a compound according to any one of the above embodiments in a method of manufacture of a medicament for the treatment of diabetes or obesity.

Another embodiment of the invention is the use of a compound according to any one of the above embodiments in a method of manufacture of a medicament for the modulating the function of a hydroxysteroid dehydrogenase.

Another embodiment of the invention is the use of a compound according to any one of the above embodiments in a method of manufacture of a medicament for the modulating the function of 11β-HSD1, 11β-HSD2, or 17β-HSD3.

Another embodiment of the invention is the use of a compound according to any one of the above embodiments in a method of manufacture of a medicament for the inhibition of a hydroxysteroid dehydrogenase.

Another embodiment of the invention is the use of a compound according to any one of the above embodiments in a method of manufacture of a medicament for the inhibition of 11β-HSD1, 11β-HSD2, or 17β-HSD3.

Preparation of the Benzamide Derivatives of Formula I and II

Those skilled in the art will recognize that there are a variety of methods available to synthesize molecules represented in the claims. In general, useful methods for synthesizing compounds represented in the claims consist of three parts, which may be done in any order: formation of an amide bond, installation of a —CR$^1$R$^2$R$^3$ group, and installation or modification of functional groups appended to the —NR$^5$R$^6$ group and the R$^4$-substituted aryl ring. Retrosynthetic disconnection of the compounds of the invention into fragments a-c useful for construction of the compounds, is shown below:

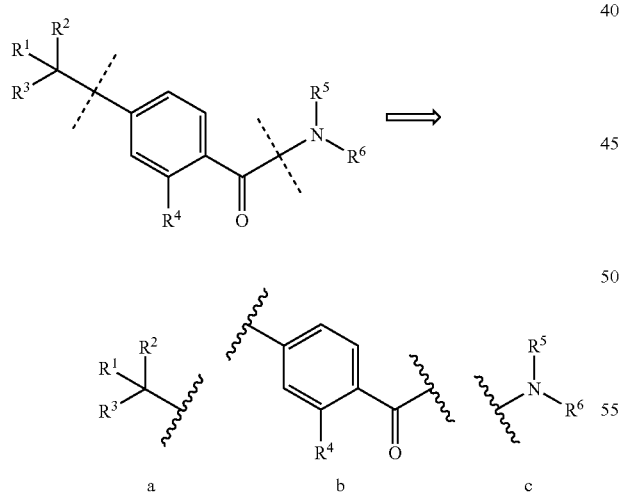

Several methods for the preparation of claimed compounds are illustrated below (eq. 1-3). Equation one demonstrates one method of forming the amide linkage. In the case of eq. 1, X may be chosen from an appropriate group such as OH, Cl and F, or from any group capable of activating a carbonyl group for displacement by an amine (e.g., OSu, imidazole, etc.).

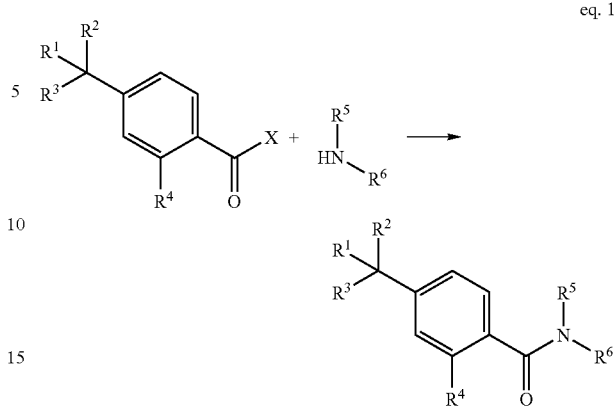

eq. 1

The coupling referred to in eq. 1 may be assisted by the use of organic or inorganic bases, activating agents such as HBTU, and also by catalysts, in particular by those catalysts known in the art which assist in the formation of amide bonds, such as DMAP, HOBT, etc. Suitable coupling partners include a carboxylic acid and an amine, an acyl chloride and an amine, an acyl fluoride and an amine, COOSu and an amine and so forth. Those skilled in the art will recognize that there are other possible combinations which will also result in the desired product.

Installation of the —CR$^1$R$^2$R$^3$ group may occur before or after the central coupling reaction, and the group may be further modified at various times during the preparation of the claimed molecules. Equation 2 demonstrates one method, in which the —CR$^1$R$^2$R$^3$ group may be installed in the form of a ketone before the central coupling reaction, followed by further modification to reach compounds of the invention. Following the central coupling, addition of a nucleophile ("Nu") such as CF$_3^-$ or CH$_3^-$ via addition of, e.g., CF$_3$TMS, MeLi, MeMgBr or similar reagent completes the installation of the —CR$^1$R$^2$R$^3$ group. This may be followed by further modification of substituents to complete the preparation.

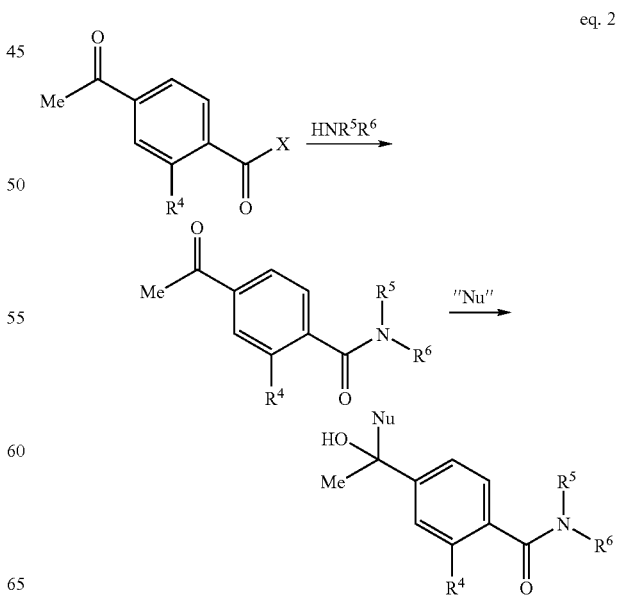

eq. 2

Alternatively, the —CR¹R²R³ group may be installed following the central coupling via Friedel-Crafts acylation, as shown in eq. 3. Those skilled in the art will understand that this may or may not be advantageous depending on the substituent pattern. Further modification as in eqs. 1 and 2 provides the compounds of the invention.

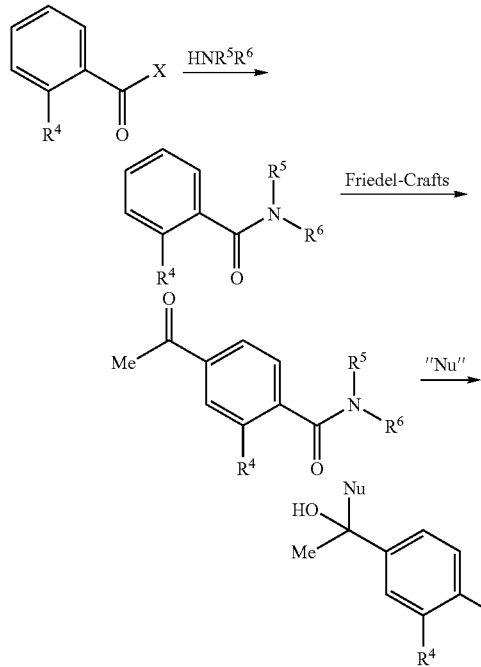

eq. 3

Introduction of a trifluoromethyl carbinol moiety may be achieved via a variety of methods, some of which are exemplified in eq. 4-6. One may introduce the CF₃ group by addition to a ketone using CF₃TMS and TBAF, or the quaternary ammonium base of TBAF may be substituted with a chiral quaternary base, such as in eq. 4, to preferentially produce one enantiomer in excess (for an example see Caron et al. (2003) *Synthesis* 1693-1698). Another useful method is the chiral addition of a nucleophile such as MeLi or MeMgBr mediated via an amine or aminoalcohol additive (eq. 5) to a trifluoromethylketone (for an example see Thompson et al. (1995) *Tetrahedron Lett.* 49:8937-8940). Yet another useful method is Friedel-Crafts alkylation (eq. 6), which may be done in a fashion to give optically active products via the use of chiral catalysts such as binaphthol derived titanium catalysts (Ishii et al. (2000) *J. Org. Chem.* 65:1597-1599), and chiral copper catalysts (Zhuang et al. (2001) *J. Org. Chem.* 66:1009-1013). Asymmetric dihydroxylation of trifluoromethyl styrene can be a highly selective method to synthesize this type of chiral carbinol. Sharpless dihydroxylation is well established and usually highly enantioselective. As shown the diol is transferred to the corresponding cyclic sulfate. The sulfate can then be reduced, subsequent hydrolysis gives the desired carbinol (eq. 7). One skilled in the art will understand that a variety of methods are available for this transformation. For the most efficient preparation of any particular compound in the claims, one skilled in the art will recognize that the timing of the introduction of the —CR¹R²R³ group can vary, and may be the first, last, or intermediate transformation in the preparation of a given compound.

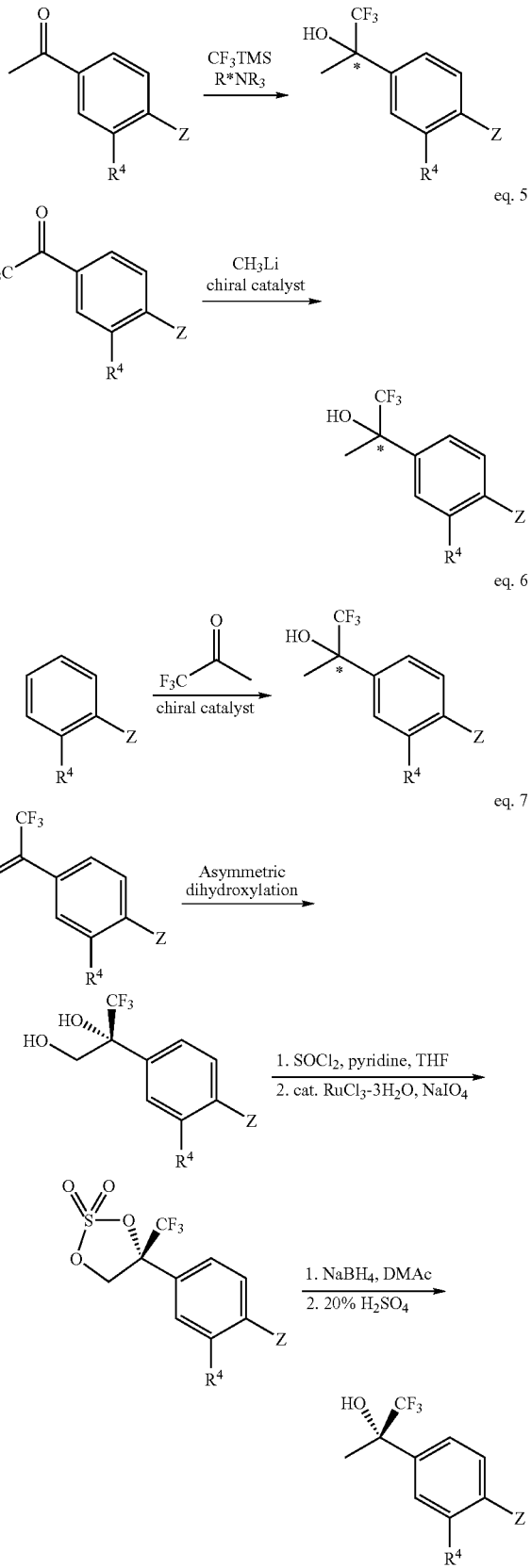

A variety of the methods described above have been used to prepare compounds of the invention, some of which are exemplified in the examples.
Pharmaceutical Compositions Pharmaceutical compositions and single unit dosage forms comprising a benzamide derivative, or a pharmaceutically acceptable stereoisomer, prodrug, salt, solvate, hydrate, or clathrate thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of inflammation or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous (e.g., <1% water) pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The benzamide derivatives can be administered to a mammal (human, mouse, rat, rabbit, dog, cat, bovine, pig, monkey etc.) as an 11β-HSD1 modulator, a prophylactic or therapeutic drug of diabetes, a prophylactic or therapeutic drug of diabetic complication (retinopathy, nephropathy, neuropathy, cardiac infarction and cerebral infarction based on arteriosclerosis etc.), a prophylactic or therapeutic drug of hyperlipemia, a prophylactic or therapeutic drug of obesity, neurodegenerative disease and the like, or a prophylactic or therapeutic drug of diseases mediated by 11β-HSD1.

The benzamide derivatives can be administered to a mammal concurrently with an additional therapeutic agent for the treatment of a disease, such as diabetes or obesity, with the aim of the prophylaxis or treatment of a disease. As such, the benzamide derivatives of the present invention can be administered in combination with other therapeutic agents for the treatment or prevention of numerous diseases, including, but not limited to, diabetes and obesity.

Depending on the disease to be treated and the patient's condition, the compounds of the invention may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration and may be formulated, alone or together, in suitable dosage unit formulations containing conventional non-toxic pharmaceutically acceptable carriers, adjuvants and vehicles appropriate for each route of administration. The invention also contemplates administration of the compounds of the invention in a depot formulation, in which the active ingredient is released over a defined time period.

In the case of a combined administration, the benzamide derivatives may be administered simultaneously with other another therapeutic agent that is useful for the treatment or prevention of diabetes, obesity or other disease or may be administered at a time prior to or subsequent to another therapeutic agent. In the case of combined administration, a pharmaceutical composition containing the benzamide derivative and an additional therapeutic agent can be administered.

Alternatively, a pharmaceutical composition containing the benzamide derivative and a pharmaceutical composition containing an additional therapeutic agent may be administered separately. The administration routes of respective pharmaceutical compositions may be the same or different.

In the case of a combined administration, the benzamide derivatives may be administered at a dose of 50 mg to 800 mg per administration, which is given once to several times a day is contemplated (e.g., once-weekly). In addition, the compound may be administered at a smaller dose. The combined pharmaceutical agent can be administered at a dose generally employed for the prophylaxis or treatment of diabetes or obesity or at a smaller dose than that.

Like the amounts and types of excipients, the amounts and specific types of active ingredients in a dosage form may differ depending on factors such as, but not limited to, the route by which it is to be administered to patients. However, typical dosage forms of the invention comprise a benzamide derivative, or a pharmaceutically acceptable salt, solvate, clathrate, hydrate, polymorph or prodrug thereof. In the treatment or prevention of diabetes, obesity, glaucoma, osteoporosis, cognitive disorders, immune disorders, depression or other conditions or disorders associated with the modulation of an hydroxysteroid dehydrogenase, an appropriate dosage level will generally be from about 0.001 to about 100 mg per kg patient body weight per day which can be administered in single or multiple doses. An exemplary dosage level will be from about 0.01 to about 25 mg/kg per day or about 0.05 to about 10 mg/kg per day. In other embodiments, a suitable dosage level may be from about 0.01 to about 25 mg/kg per day, about 0.05 to about 10 mg/kg per day, or about 0.1 to about 5 mg/kg per day. Within this range the dosage may be from about 0.005 to about 0.05, about 0.05 to about 0.5 or about 0.5 to about 5.0 mg/kg per day lie within the range of from about 0.1 mg to about 2000 mg per day, given as a single once-a-day dose in the morning but typically as divided doses throughout the day taken with food. In one embodiment, the daily dose is administered twice daily in equally divided doses. A daily dose range can be from about 5 mg to about 500 mg per day, or between about 10 mg and about 300 mg per day. In managing the patient, the therapy can be initiated at a lower dose, perhaps from about 1 mg to about 25 mg, and increased if necessary up to from about 200 mg to about 2000 mg per day as either a single dose or divided doses, depending on the patient's global response.

For multidrug therapy, the weight ratio of the compound of the invention to the second active ingredient may be varied and will depend upon the effective dose of each ingredient. Generally, an effective dose of each will be used. Thus, for example, when a compound of the invention is combined with an NSAID, the weight ratio of the compound of the invention to the NSAID will generally range from about 1000:1 to about 1:1000, such as about 200:1 to about 1:200. Combinations of a compound of the invention and other active ingredients will generally also be within the aforementioned range, but in each case, an effective dose of each active ingredient should be used.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

For oral administration, the compositions can be provided in the form of tablets containing about 1 to about 1000 milligrams of the active ingredient. In other embodiments, the compositions are provided in provided in the form of tablets containing about 1.0, about 5.0, about 10.0, about 15.0. about 20.0, about 25.0, about 50.0, about 75.0, about 100.0, about 150.0, about 200.0, about 250.0, about 300.0, about 400.0, about 500.0, about 600.0, about 750.0, about 800.0, about 900.0, or about 1000.0 milligrams of the active ingredient for the symptomatic adjustment of the dosage to the patient to be treated. The compounds may be administered on a regimen of 1 to 4 times per day, such as, for example, once or twice per day.

Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

Controlled-release pharmaceutical products can improve drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intra-arterial. Because their administration typically bypasses patients' natural defenses against contaminants, parenteral dosage forms can be sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. For example, lyophilized sterile compositions suitable for reconstitution into particulate-free dosage forms suitable for administration to humans.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Parenteral dosage forms are exemplary for the methods of preventing, treating or managing disease in a cancer patient.

Transdermal and Topical Dosage Forms

Transdermal and topical dosage forms of the invention include, but are not limited to, creams, lotions, ointments, gels, solutions, emulsions, suspensions, or other forms known to one of skill in the art. See, e.g., Remington's Pharmaceutical Sciences, 18th eds., Mack Publishing, Easton Pa. (1990); and Introduction to Pharmaceutical Dosage Forms, 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants also can be added to pharmaceutical compositions and dosage forms if desired. Examples of such additional ingredients are well known in the art. See, e.g., Remington's Pharmaceutical Sciences, 18th eds., Mack Publishing, Easton Pa. (1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Mucosal Dosage Forms and Lung Delivery

Mucosal dosage forms of the invention include, but are not limited to, ophthalmic solutions, sprays and aerosols, or other forms known to one of skill in the art. See, e.g., Remington's Pharmaceutical Sciences, 18th eds., Mack Publishing, Easton Pa. (1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

A compound of the invention can also be administered directly to the lung by inhalation (see e.g., Tong et al., International Publication No. WO 97/39745; Clark et al, International Publication No. WO 99/47196, which are herein incorporated by reference). For administration by inhalation, a benzamide derivative can be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver a benzamide derivative directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device can be used to administer a benzamide derivative to the lung (See, e.g., Raleigh et al., Proc. Amer. Assoc. Cancer Research Annual Meeting, 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver a benzamide derivative to the lung is a liquid spray device supplied, for example, by Aradigm Corporation. Liquid spray systems use extremely small nozzle holes to aerosolize liquid drug formulations that can then be directly inhaled into the lung.

In one embodiment, a nebulizer device is used to deliver a benzamide derivative to the lung. Nebulizers create aerosols from liquid drug formulations by using, for example, ultrasonic energy to form fine particles that can be readily inhaled (See e.g., Verschoyle et al., British J Cancer, 1999, 80, Suppl 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics Inhaled compounds, delivered by nebulizer devices, are currently under investigation as treatments for aerodigestive cancer (Engelke et al., Poster 342 at American Association of Cancer Research, San Francisco, Calif., Apr. 1-5, 2000) and lung cancer (Dahl et al., Poster 524 at American Association of Cancer Research, San Francisco, Calif., Apr. 1-5, 2000).

In one embodiment, an electrohydrodynamic ("EHD") aerosol device is used to deliver a benzamide derivative to the lung. EHD aerosol devices use electrical energy to aerosolize liquid drug solutions or suspensions (see e.g., Noakes et al., U.S. Pat. No. 4,765,539; Coffee, U.S. Pat. No. 4,962,885; Coffee, International Publication No. WO 94/12285; Coffee, International Publication No. WO 94/14543; Coffee, International Publication No. WO 95/26234, Coffee, International Publication No. WO 95/26235, Coffee, International Publication No. WO 95/32807, which are herein incorporated by reference). The electrochemical properties of the compound of the invention formulation may be important parameters to optimize when delivering this drug to the lung with an EHD aerosol device and such optimization is routinely performed by one of skill in the art. EHD aerosol devices may more efficiently delivery drugs to the lung than existing pulmonary delivery technologies. Other methods of intra-pulmonary delivery of a benzamide derivative will be known to the skilled artisan and are within the scope of the invention.

Liquid drug formulations suitable for use with nebulizers and liquid spray devices and EHD aerosol devices will typically include a benzamide derivative with a pharmaceutically acceptable carrier. For instance, the pharmaceutically acceptable carrier is a liquid such as alcohol, water, polyethylene glycol or a perfluorocarbon. Optionally, another material can be added to alter the aerosol properties of the solution or suspension of a benzamide derivative. In some embodiments, this material is liquid such as an alcohol, glycol, polyglycol or a fatty acid. Other methods of formulating liquid drug solutions or suspension suitable for use in aerosol devices are known to those of skill in the art (See, e.g., Biesalski, U.S. Pat. No. 5,112,598; Biesalski, U.S. Pat. No. 5,556,611, which are herein incorporated by reference). A compound of the invention can also be formulated in rectal or vaginal compositions such as suppositories or retention enemas, e.g., containing conventional suppository bases such as cocoa butter or other glycerides.

In addition to the formulations described previously, a benzamide derivative can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Other Delivery Systems

Alternatively, other pharmaceutical delivery systems can be employed. Liposomes and emulsions are well known examples of delivery vehicles that can be used to deliver a benzamide derivative. Certain organic solvents such as dimethylsulfoxide can also be employed, although usually at the cost of greater toxicity. A compound of the invention can also be delivered in a controlled release system. In one embodiment, a pump can be used (Sefton, CRC Crit. Ref Biomed Eng., 1987, 14, 201; Buchwald et al., Surgery, 1980, 88, 507; Saudek et al., N. Engl. J. Med, 1989, 321, 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J Macromol. Sci. Rev. Macromol. Chem., 1983, 23, 61; see also Levy et al., Science 1985, 228, 190; During et al., Ann. Neurol., 1989, 25,351; Howard et al., 1989, J. Neurosurg. 71, 105). In yet another embodiment, a controlled-release system can be placed in proximity of the target of the compounds of the invention, e.g., the lung, thus requiring only a fraction of the systemic dose (see, e.g., Goodson, in Medical Applications of Controlled Release, supra, vol. 2, pp. 115 (1984)). Other controlled-release system can be used (see e.g., Langer, Science, 1990, 249, 1527).

Suitable excipients (e.g., carriers and diluents) and other materials that can be used to provide mucosal dosage forms encompassed by this invention are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., Remington's Pharmaceutical Sciences, 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Therapeutic Uses of the Benzamide Derivatives

In one embodiment, the invention provides methods of treating or preventing a condition or disorder associated with the modulation of hydroxysteroid dehydrogenases by administering to a patient having such a condition or disorder a therapeutically effective amount of a compound or composition of the invention. In one group of embodiments, conditions and disorders, including chronic diseases of humans or other species, can be treated with modulators, stimulators, or inhibitors of hydroxysteroid dehydrogenases, such as 11β-HSD1.

Treatment or Prevention of Diabetes

Diabetes and diabetic conditions can be treated or prevented by administration of a therapeutically effective amount of a benzamide derivative.

Types of diabetes that can be treated or prevented by administering a therapeutically effective amount of a benzamide derivative include type I diabetes mellitus (juvenile onset diabetes, insulin dependent-diabetes mellitus or IDDM), type II diabetes mellitus (non-insulin-dependent diabetes mellitus or NIDDM), insulinopathies, diabetes associated with pancreatic disorders, diabetes associated with other disorders (such as Cushing's Syndrome, acromegaly, pheochromocytoma, glucagonoma, primary aldosteronism, and somatostatinoma), type A and type B insulin resistance syndromes, lipatrophic diabetes, and diabetes induced by β-cell toxins.

In one embodiment, the type of diabetes being treated is type II diabetes.

Treatment or Prevention of Obesity

Obesity can be treated or prevented by administration of a therapeutically effective amount of a benzamide derivative.

Obesity may have genetic, environmental (e.g., expending less energy than is consumed) and regulatory determinants. Obesity includes exogenous, hyperinsulinar, hyperplasmic, hypothyroid, hypothalamic, symptomatic, infantile, upper body, alimentary, hypogonadal, simple and central obesity, hypophyseal adiposity and hyperphagia. Metabolic disorders, such as hyperlidemia and diabetes, and cardiovascular disorders, such as hypertension and coronary artery disease, are commonly associated with obesity.

Complications due to obesity may also be treated or prevented by administering a therapeutically effective amount of a benzamide derivative. Such complications include, but are not limited to, sleep apnea, Pickwickian syndrome, orthopedic disturbances of weight-bearing and non-weight-bearing joints, and skin disorders resulting from increased sweat or skin secretions.

Treatment or Prevention of Other Conditions

Other conditions that can be treated or prevented by administering a therapeutically effective amount of a benzamide derivative include, but are not limited to any condition which is responsive to the modulation, such as inhibition, of hydroxysteroid dehydrogenases or specific isoforms thereof, and thereby benefit from administration of such a modulator. Representative conditions in this regard include, but are not limited to, metabolic disorders and related cardiovascular risk factors such as syndrome X, polycystic ovarian disease, eating disorders (e.g., anorexia and bulimia), craniopharyngioma, Prader-Willi syndrome, Frohlich's syndrome, hyperlipidemia, dyslipidemia, hypercholesterolemia, hypertriglyceridemia, low HDL levels, high HDL levels, hyperglycemia, insulin resistance, hyperinsulinemia and Cushing's syndrome; diseases associated therewith such as hypertension, atherosclerosis, vascular restenosis, retinopathy and nephropathy; neurologic disorders such as neurodegenerative disease, neuropathy and muscle wasting; cognitive disorders, such as age-related learning disorders, dementia, neurodegeneration, as well as for improvement of cognitive function in subjects ranging from the severely impaired (e.g., Parkinsons's or Alzheimer's associated dementia) to mildly impaired (e.g., age-associated memory impairment, drug-induced cognitive impairment) to unimpaired subjects (e.g., cognitive enhancers for the general population) (see, Sandeep, et al., PNAS, electronically available at www.pnas.org/cgi/doi/10.1073/pnas.0306996101); androgen and/or estrogen-related disorders such as prostate cancer, colon cancer, breast cancer, benign prostatic hyperplasia, ovarian cancer, uterine cancer, and male pseudohermaphrodism; endometriosis, dementia, depression, psoriasis, glaucoma, osteoporosis, viral infections, inflammatory disorders, and immune disorders.

Additional Therapeutic Agents

In one embodiment, the present methods for treating or preventing further comprise the administration of a therapeutically effective amount of another therapeutic agent useful for treating or preventing the diseases or disorders disclosed herein. In this embodiment, the time in which the therapeutic effect of the other therapeutic agent is exerted overlaps with the time in which the therapeutic effect of the benzamide derivative is exerted.

The compounds of the invention can be combined or used in combination with other agents useful in the treatment, prevention, suppression or amelioration of the conditions or disorders for which compounds of the invention are useful, including diabetes, obesity, glaucoma, osteoporosis, cognitive disorders, immune disorders, depression and those pathologies noted above.

Such other agents, or drugs, may be administered, by a route and in an amount commonly used therefor, simultaneously or sequentially with a benzamide derivative. In one embodiment, a pharmaceutical composition contains such other drugs in addition to the compound of the invention when a benzamide derivative is used contemporaneously with one or more other drugs. Accordingly, the pharmaceutical compositions of the invention include those that also contain one or more other active ingredients or therapeutic agents, in addition to a benzamide derivative.

In one embodiment, for the treatment or prevention of diabetes, a benzamide derivative can be administered with another therapeutic agent, including, but not limited to, antidiabetic agents such as insulin, inhaled insulin (Exubera®), insulin mimetics, insulin secretogues, sulfonylureas (e.g., glyburide, meglinatide, glimepiride, gliclazide, glipizide, gliquidone, chloropropresponsivemide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide), biguanides (e.g., metformin (Glucophage®)), α-glucosidase inhibitors (e.g., acarbose, voglibose and miglitol), thiazolidinone compounds (e.g., rosiglitazone (Avandia®), troglitazone (Rezulin®), ciglitazone, pioglitazone (Actos®) and englitazone), prandial glucose regulators (e.g., repaglinide and nateglinide) and glucagon receptor antagonists.

In another embodiment, for the treatment or prevention of obesity, a benzamide derivative can be administered with another therapeutic agent, including, but not limited to, β3 adrenergic receptor agonists, leptin or derivatives thereof, neuropeptide Y (e.g., NPY5) antagonists, and mazindol.

Examples of other therapeutic agents that may be combined with a benzamide derivative, either administered separately or in the same pharmaceutical compositions, include, but are not limited to: (i) cholesterol lowering agents such as HMG-CoA reductase inhibitors (e.g., lovastatin, simvastatin (Zocor®), pravastatin, fluvastatin, atorvastatin (Lipitor®) and other statins), bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fibric acid derivatives (e.g., gemfibrozil, clofibrate, fenofibrate and benzafibrate), probucol, nitroglycerin, and inhibitors of cholesterol absorption (e.g., beta-sitosterol and acylCoA-cholesterol acyltransferase (ACAT) inhibitors such as melinamide), HMG-CoA synthase inhibitors, squalene epoxidase inhibitors and squalene synthetase inhibitors; (ii) antithrombotic agents, such as thrombolytic agents (e.g., streptokinase, alteplase, anistreplase and reteplase), heparin, hirudin and warfarin derivatives, β-blockers (e.g., atenolol), β adrenergic agonists (e.g., isoproterenol), angiotensin II antagonists, ACE inhibitors and vasodilators (e.g., sodium nitroprusside, nicardipine hydrochloride, nitroglycerin and enalopril at); (iii) PPAR agonists, e.g., PPARγ and PPAR$_δ$ agonists; (iv) DP antagonists; (v) lubricants or emollients such as petrolatum and lanolin, keratolytic agents, vitamin $D_3$ derivatives (e.g., calcipotriene and calcipotriol (Dovonex®)), PUVA, anthralin (Drithrocreme®), etretinate (Tegison®) and isotretinoin; (vi) glaucoma therapies such as cholinergic agonists (e.g., pilocarpine and carbachol), cholinesterase inhibitors (e.g., physostigmine, neostigmine, demacarium, echothiophate iodide and isofluorophate), carbonic anhydrase inhibitors (e.g., acetazolamide, dichlorphenamide, methazolamide, ethoxzolamide and dorzolamide), non-selective adrenergic agonists (e.g., epinephrine and dipivefrin), $α_2$-selective adrenergic agonists (e.g., apraclonidine and brimonidine), β-blockers (e.g., timolol, betazolol, levobunolol, carteolol and metipranolol), prostaglandin analogs (e.g., latanoprost) and osmotic diuretics (e.g., glycerin, mannitol and isosorbide); corticosteroids, such as beclomethasone, methylprednisolone, betamethasone, prednisone, prenisolone, dexamethasone, fluticasone and hydrocortisone, and corticosteroid analogs such as budesonide; (vii) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (viii) non-steroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetylsalicylic acid and sulfasalazine) and the pyrazolones (e.g., apazone, bezpiperylon, feprazone, mofebutazone, oxyphenbutazone and phenylbutazone); (ix) cyclooxygenase-2 (COX-2) inhibitors such as celecoxib (Celebrex®) and rofecoxib (Vioxx®); (xi) inhibitors of phosphodiesterase type IV (PDE-IV); (xii) opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine; (xiii) a hepatoprotective agent; and (xiv) other compounds such as 5-aminosalicylic acid and prodrugs thereof.

The weight ratio of the compound of the invention to the second active ingredient may be varied and will depend upon the effective dose of each ingredient. Generally, an effective dose of each will be used. Thus, for example, when a benzamide derivative is combined with an NSAID, the weight ratio of the compound of the invention to the NSAID will generally range from about 1000:1 to about 1:1000, such as, for example, about 200:1 to about 1:200. Combinations of a benzamide derivative and other active ingredients will generally also be within the aforementioned range, but in each case, an effective dose of each active ingredient should be used.

Kits

The invention encompasses kits that can simplify the administration of the benzamide derivatives or composition of the invention to a patient.

A typical kit of the invention comprises a unit dosage of a benzamide derivative. In one embodiment, the unit dosage form is in a container, which can be sterile, containing a therapeutically effective amount of a benzamide derivative and a pharmaceutically acceptable vehicle. In another embodiment, the unit dosage form is in a container containing a therapeutically effective amount of a benzamide derivative as a lyophilate or pharmaceutically acceptable salt. In this instance, the kit can further comprise another container that contains a solution useful for the reconstitution of the lyophilate or dissolution of the salt. The kit can also comprise a label or printed instructions for use of the benzamide derivatives.

In a further embodiment, the kit comprises a unit dosage form of a composition of the invention.

Kits of the invention can further comprise one or more devices that are useful for administering the unit dosage forms of the benzamide derivatives or a composition of the invention. Examples of such devices include, but are not limited to, a syringe, a drip bag, a patch or an enema, which optionally contain the unit dosage forms.

The present invention is not to be limited in scope by the specific embodiments disclosed in the examples which are intended as illustrations of a few embodiments of the invention and any embodiments that are functionally equivalent are within the scope of this invention. Indeed, various modifications of the invention in addition to those shown and described herein will become apparent to those skilled in the art and are intended to fall within the scope of the appended claims. To this end, it should be noted that one or more hydrogen atoms or methyl groups may be omitted from the drawn structures consistent with accepted shorthand notation of such organic compounds, and that one skilled in the art of organic chemistry would readily appreciate their presence.

EXAMPLES

Preparation of 4-(1,1,1-Trifluoro-2-hydroxypropan-2-yl)benzoic Acid

Methyl 4-(1,1,1-trifluoro-2-hydroxypropan-2-yl)benzoate

To a mixture of methyl 4-acetylbenzoate (5.0 g, 28.1 mmol) and $CF_3SiMe_3$ (12.5 mL, 84.2 mmol) in THF (150 mL) was added TBAF (1.0 M, 78.6 mL, 78.6 mmol) dropwise at 0° C. The mixture was stirred for 2.5 h at room temperature, diluted with $Et_2O$ (100 mL). The solution was washed with saturated aqueous $NaHCO_3$ and brine, dried and concentrated. Flash chromatography of the residue, using 2:8 EtOAc-Hexane, gave methyl 4-(1,1,1-trifluoro-2-hydroxypropan-2-yl)benzoate (6.0 g). $^1H$ NMR ($CDCl_3$) δ 8.07(d, J=8.5 Hz, 2 H), δ 7.67(d, J=8.5 Hz, 2 H), 3.93(s, 3 H), 2.70(br, 1H), 1.80(s, 3H). MS 249.1 (M+H$^+$).

4-(1,1,1-Trifluoro-2-hydroxypropan-2-yl)benzoic acid

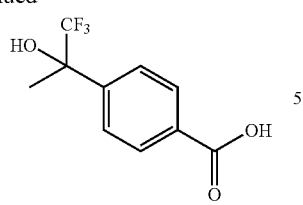

A mixture of methyl 4-(1,1,1-trifluoro-2-hydroxypropan-2-yl)benzoate (6.0 g, 24.2 mmol) and KOH (2.72 g, 48.4 mmol) in 1,4-dioxane (100 mL) and H$_2$O (50 mL) was refluxed for 2 h. The reaction mixture was cooled to room temperature, and 1,4-dioxane evaporated in vacuo. The aqueous residue was acidified with 2N HCl and extracted with CH$_2$Cl$_2$. The extracts were washed with brine and dried. Flash chromatography of the residue, using 3:7 EtOAc-Hexane, gave 4-(1,1,1-trifluoro-2-hydroxypropan-2-yl)benzoic acid (4.93 g). $^1$H NMR (CDCl$_3$) δ 11.0(br, 1H), 7.95(d, J=6.8 Hz, 2 H), 7.71(d, J=6.8 Hz, 2 H), 6.73 (s, 1 H), 1.71(s, 3H). MS 235.0 (M+H$^+$).

Example 1

Preparation of N-Benzyl-N-methyl-4-(1,1,1-trifluoro-2-hydroxypropan-2-yl)benzamide (1)

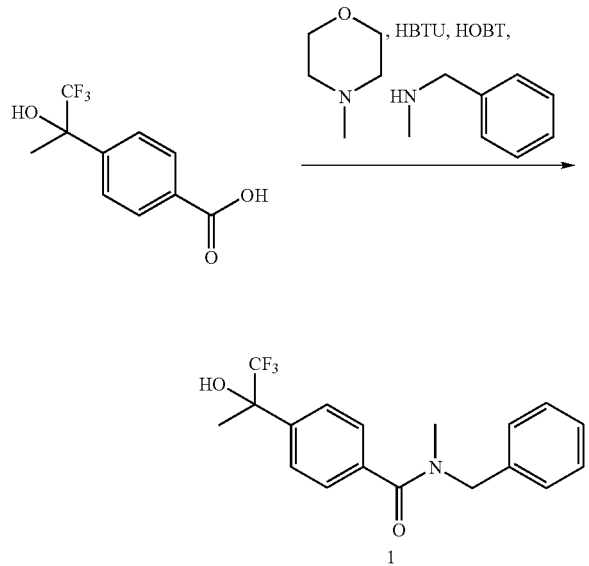

A mixture of 4-(1,1,1-trifluoro-2-hydroxypropan-2-yl)benzoic acid (30.0 mg, 0.128 mmol), HBTU (73 mg, 0.192 mmol), HOBT (26 mg, 0.192 mmol), 4-methylmorpholine (0.03 mL, 0.218 mmol) and N-methyl(phenyl)methanamine (0.14 mL, 1.28 mmol) in DMF (1.5 mL) was stirred at room temperature for 3 h. The reaction mixture was diluted with Et$_2$O (10 mL). The solution was washed with water and brine, dried and concentrated. Flash chromatography of the residue, using 3:7 EtOAc-Hexane, gave the amide N-benzyl-N-methyl-4-(1,1,1-trifluoro-2-hydroxypropan-2-yl)benzamide (42.4 mg). $^1$H NMR (CD$_3$OD) δ 7.70 (br, 2 H), 7.51 (br, 2 H), δ 7.40-7.30(m, 4 H), 7.22(br, 1 H), 4.80(s, 1.32 H), 4.51(s, 0.68 H), 3.05(s, 0.96 H), 2.93(s, 1.94 H), 1.80(br, 3H). MS 338.0 (M+H$^+$).

Example 2

Preparation of N-Cyclohexyl-N-methyl-4-(1,1,1-trifluoro-2-hydroxypropan-2-yl)benzamide (2)

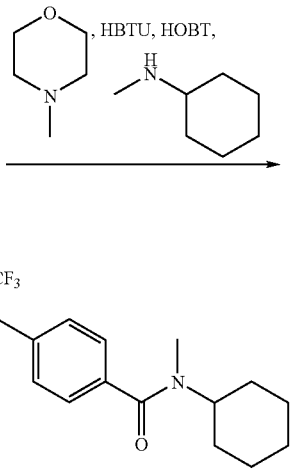

A mixture of 4-(1,1,1-trifluoro-2-hydroxypropan-2-yl)benzoic acid (30.0 mg, 0.128 mmol), HBTU (73 mg, 0.192 mmol), HOBT (26 mg, 0.192 mmol), 4-methylmorpholine (0.03 mL, 0.218 mmol) and N-methylcyclohexanamine (0.17 mL, 1.28 mmol) in DMF (1.5 mL) was stirred at room temperature for 3 h. The reaction mixture was diluted with Et$_2$O (10 mL). The solution was washed with water and brine, dried and concentrated. Flash chromatography of the residue, using 3:7 EtOAc-Hexane, gave the amide N-cyclohexyl-N-methyl-4-(1,1,1-trifluoro-2-hydroxypropan-2-yl)benzamide (41.1 mg). $^1$H NMR (CD$_3$OD) δ 7.71 (br, 2 H), 7.38 (br, 2 H), 4.41(br, 0.45 H), 3.45 (br, 0.55 H), 2.98(br, 1.65 H), 2.85 (br, 1.35 H), 1.90-1.40 (m, including a singlet at δ 1.75, 11 H), 1.20-0.76 (m, 2H). MS 330.1 (M+H$^+$).

Example 3

Preparation of N-Benzyl-N-ethyl-4-(1,1,1-trifluoro-2-hydroxypropan-2-yl)benzamide (3)

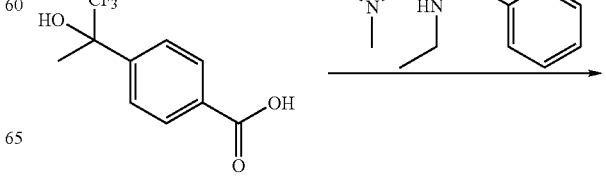

-continued

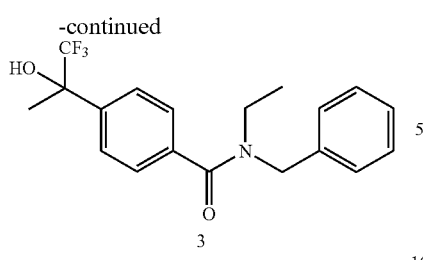

3

A mixture of 4-(1,1,1-trifluoro-2-hydroxypropan-2-yl) benzoic acid (30.0 mg, 0.128 mmol), HBTU (73 mg, 0.192 mmol), HOBT (26 mg, 0.192 mmol), 4-methylmorpholine (0.03 mL, 0.218 mmol) and N-benzylethanamine (0.18 mL, 1.28 mmol) in DMF (1.5 mL) was stirred at room temperature for 3 h. The reaction mixture was diluted with Et$_2$O (10 mL). The solution was washed with water and brine, dried and concentrated. Flash chromatography of the residue, using 3:7 EtOAc-Hexane, gave the amide N-benzyl-N-ethyl-4-(1,1,1-trifluoro-2-hydroxypropan-2-yl)benzamide (26.8 mg). $^1$H NMR (CD$_3$OD) δ 7.60 (br, 2 H), 7.46 (d, J=8.0 Hz, 2 H), δ 7.38-7.32(m, 3 H), 7.30 (d, J=8.1 Hz, 1 H), 7.20(br, 1 H), 4.82 (br, 1.10 H), 4.50 (br, 0.90 H), 3.51 (br, 0.90 H), 3.22 (br, 1.10 H), 2.50(br, 1H), 1.77 (br, 3H), 1.35-1.05 (m, 3 H). MS 352.1(M+H$^+$).

Example 4

Preparation of N-(3,4-Dichlorophenyl)-N-methyl-4-(1,1,1-trifluoro-2-hydroxypropan-2-yl)benzamide

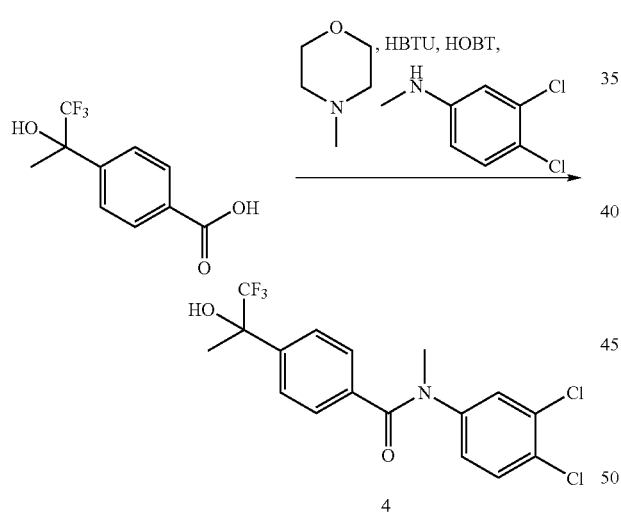

4

A mixture of 4-(1,1,1-trifluoro-2-hydroxypropan-2-yl) benzoic acid (30.0 mg, 0.128 mmol), HBTU (73 mg, 0.192 mmol), HOBT (26 mg, 0.192 mmol), 4-methylmorpholine (0.03 mL, 0.218 mmol) and 3,4-dichloro-N-methylbenzenamine (0.20 mL, 1.28 mmol) in DMF (1.5 mL) was stirred at 110° C. for 18 h. The reaction mixture was cooled to room temperature and diluted with Et$_2$O (10 mL). The solution was washed with water and brine, dried and concentrated. Flash chromatography of the residue, using 3:7 EtOAc-Hexane, gave the amide N-(3,4-dichlorophenyl)-N-methyl-4-(1,1,1-trifluoro-2-hydroxypropan-2-yl)benzamide (6.6 mg). $^1$H NMR (CD$_3$OD) δ 7.57(d, J=8.5 Hz, 2 H), 7.44(d, J=2.5 Hz, 1 H), 7.43 (d, J=8.5 Hz, 1 H), 7.38(d, J=8.5 Hz, 2 H), 7.13(dd, J=8.5, 2.5 Hz, 1 H), 5.52 (s, 1 H), 3.48 (s, 3H), 1.70 (s, 3H). MS 392.0 (M+H$^+$).

Example 5

Preparation of N,N-Dicyclohexyl-4-(1,1,1-trifluoro-2-hydroxypropan-2-yl)benzamide (5)

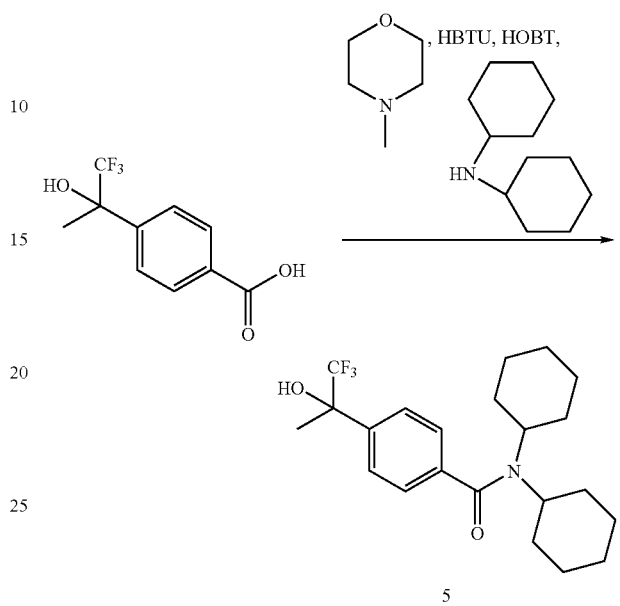

5

A mixture of 4-(1,1,1-trifluoro-2-hydroxypropan-2-yl) benzoic acid (46.2 mg, 0.197 mmol), HBTU (112 mg, 0.296 mmol), HOBT (40.0 mg, 0.296 mmol), 4-methylmorpholine (0.04 mL, 0.335 mmol) and dicyclohexylamine (0.40 mL, 1.97 mmol) in DMF (1.5 mL) was stirred at room temperature for 3 h. The reaction mixture was diluted with Et$_2$O (10 mL). The solution was washed with water and brine, dried and concentrated. Flash chromatography of the residue, using 3:7 EtOAc-Hexane, gave the amide N,N-dicyclohexyl-4-(1,1,1-trifluoro-2-hydroxypropan-2-yl)benzamide (45.3 mg). $^1$H NMR (CDCl$_3$) δ 7.57 (d, J=8.0 Hz, 2 H), 7.30 (d, J=8.0 Hz, 2 H), 3.40-3.00 (m, 2 H), 2.68 (br, 1H), 1.85-1.72 (m, including a singlet at δ 1.78, 7 H), 1.72-1.40 (m, 8 H), 1.35-0.95(m, 8 H). MS 398.2 (M+H$^+$).

Example 6

Preparation of N,N-Diisopropyl-4-(1,1,1-trifluoro-2-hydroxypropan-2-yl)benzamide (6)

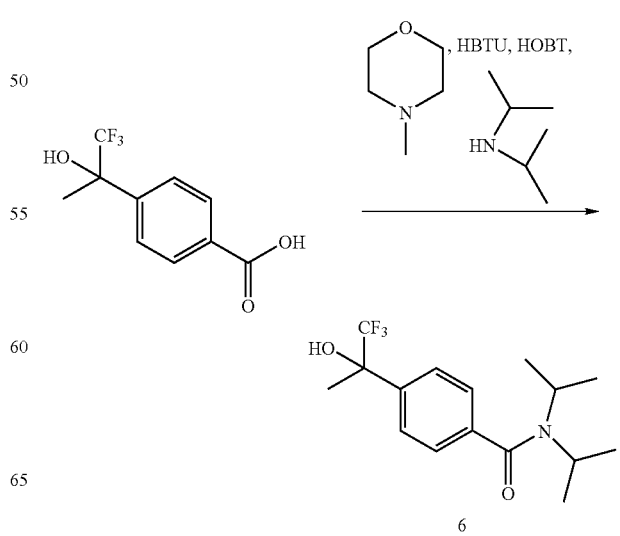

6

A mixture of 4-(1,1,1-trifluoro-2-hydroxypropan-2-yl)benzoic acid (46.2 mg, 0.197 mmol), HBTU (112 mg, 0.296 mmol), HOBT (40.0 mg, 0.296 mmol), 4-methylmorpholine (0.04 mL, 0.335 mmol) and diisopropylamine (0.28 mL, 1.97 mmol) in DMF (1.5 mL) was stirred at room temperature for 3 h. The reaction mixture was diluted with Et$_2$O (10 mL). The solution was washed with water and brine, dried and concentrated. Flash chromatography of the residue, using 3:7 EtOAc-Hexane, gave the amide N,N-diisopropyl-4-(1,1,1-trifluoro-2-hydroxypropan-2-yl)benzamide (14.1 mg). $^1$H NMR (CD$_3$OD) δ 7.70 (d, J=8.8 Hz, 2 H), 7.33 (d, J=8.8 Hz, 2 H), 3.82 (br, 1 H), 3.64 (br, 1 H), 1.73 (s, 3 H), 1.52(br, 6 H), 1.16 (br, 6 H). MS 318.1 (M+H$^+$).

Example 7

Preparation of N-Cyclohexyl-N-isopropyl-4-(1,1,1-trifluoro-2-hydroxypropan-2-yl)benzamide (7)

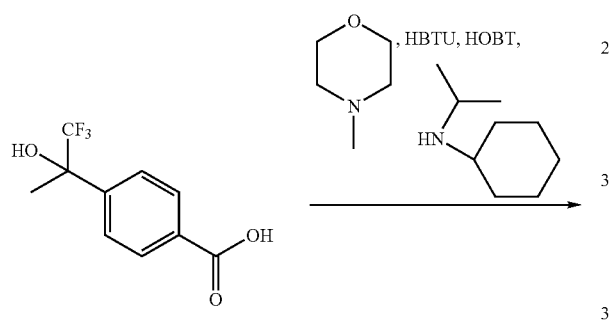

A mixture of 4-(1,1,1-trifluoro-2-hydroxypropan-2-yl)benzoic acid (46.2 mg, 0.197 mmol), HBTU (112 mg, 0.296 mmol), HOBT (40.0 mg, 0.296 mmol), 4-methylmorpholine (0.04 mL, 0.335 mmol) and N-isopropylcyclohexanamine (0.32 mL, 1.97 mmol) in DMF (1.5 mL) was stirred at room temperature for 3 h. The reaction mixture was diluted with Et$_2$O (10 mL). The solution was washed with water and brine, dried and concentrated. Flash chromatography of the residue, using 3:7 EtOAc-Hexane, gave the amide N-cyclohexyl-N-isopropyl-4-(1,1,1-trifluoro-2-hydroxypropan-2-yl)benzamide (52.7 mg). $^1$H NMR (CDCl$_3$) δ 7.57 (d, J=8.4 Hz, 2 H), 7.31 (d, J=8.4 Hz, 2 H), 4.00-3.00 (m, 2 H), 2.65 (br, 1 H), 1.90-1.72 (m, including a singlet at δ 1.78, 5 H), 1.78-1.40 (m, 7 H), 1.40-0.95(m, 7 H). MS 358.1 (M+H$^+$).

Example 8

Preparation of N-Isopropyl-N-phenyl-4-(1,1,1-trifluoro-2-hydroxypropan-2-yl)benzamide (8)

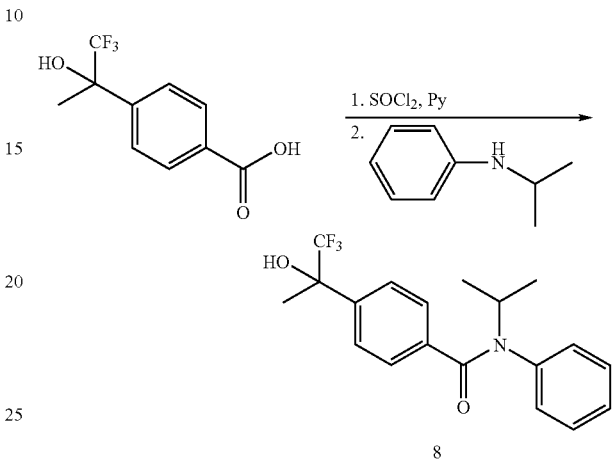

To 4-(1,1,1-trifluoro-2-hydroxypropan-2-yl)benzoic acid (50.0 mg, 0.21 mmol) in THF (3 mL) SOCl$_2$ (0.02 mL, 0.32 mmol) and Pyridine (0.03 mL, 0.42 mmol) were added. The reaction mixture was stirred at 80° C. for 2 h and cooled to room temperature. To the reaction mixture N-isopropylbenzenamine (0.04 mL, 0.315 mmol) was added. The resulting reaction mixture was stirred at room temperature for 18 h. The reaction mixture was diluted with CH$_2$Cl$_2$ (10 mL). The solution was washed with saturated aqueous CuSO$_4$, water and brine, dried and concentrated. Flash chromatography of the residue, using 3:7 EtOAc-Hexane, gave the amide N-isopropyl-N-phenyl-4-(1,1,1-trifluoro-2-hydroxypropan-2-yl)benzamide (62.5 mg). $^1$H NMR (CD$_3$OD) δ 7.42 (br, 2 H), 7.31-7.18 (m, 5 H), 7.12 (d, J=7.2 Hz, 2 H), 5.00(br, 1 H), 1.61(s, 3 H), 1.22(m, 6 H). MS 352.1 (M+H$^+$).

Example 9

Preparation of N-(2-Chlorophenyl)-N-isopropyl-4-(1,1,1-trifluoro-2-hydroxypropan-2-yl)benzamide (9)

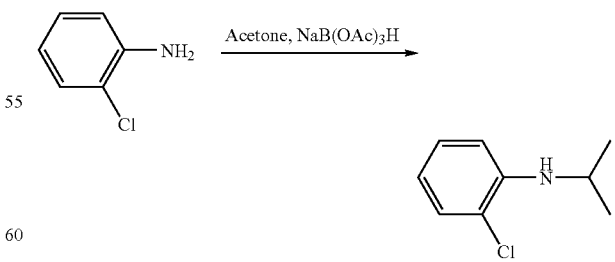

2-Chloro-N-isopropylbenzenamine

To 2-chlorobenzenamine (500 mg, 3.23 mmol) and acetone (1.2 mL, 16.1 mmol) in ClCH$_2$CH$_2$Cl (10 mL) was added NaB(OAc)₃H (2.74 g, 12.9 mmol). The reaction mixture was stirred at room temperature for 18 h. The reaction mixture was diluted with saturated aqueous solution of NaHCO₃, extracted with CH₂Cl₂, washed with brine, dried and concentrated. Flash chromatography of the residue, using 1:9 MeOH—CH₂Cl₂, gave the amine 2-chloro-N-isopropylbenzenamine (0.40 g). ¹H NMR (CDCl₃) δ 7.27 (d, J=7.5 Hz, 1H), 7.16 (dd, J=7.5, 7.5 Hz, 1 H), 6.71 (d, J=7.5 Hz, 1H), 6.64 (dd, J=7.5, 7.5 Hz, 1 H), 4.35(br, 1 H), 3.70(m, 1 H), 1.30(br, 6 H).

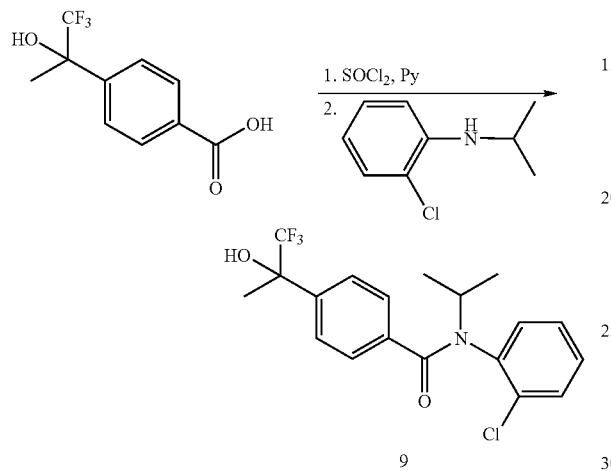

To 4-(1,1,1-trifluoro-2-hydroxypropan-2-yl)benzoic acid (50.0 mg, 0.21 mmol) in THF (3 mL) were added SOCl₂ (0.02 mL, 0.32 mmol) and pyridine (0.03 mL, 0.42 mmol). The reaction mixture was stirred at 80° C. for 2 h and cooled to room temperature. 2-Chloro-N-isopropylbenzenamine (70 mg, 0.42 mmol) was added, and the resulting reaction mixture was stirred at room temperature for 18 h. The mixture was diluted with CH₂Cl₂ (10 mL). The solution was washed with saturated aqueous CuSO₄, water and brine, dried and concentrated. Flash chromatography of the residue, using 3:7 EtOAc-Hexane, gave the amide N-(2-chlorophenyl)-N-isopropyl-4-(1,1,1-trifluoro-2-hydroxypropan-2-yl)benzamide (69.2 mg). ¹H NMR (CD₃OD) δ 7.50-7.20 (m, 8 H), 3.31(m, 1H), 1.62(s, 3 H), 1.44(d, J=6.4 Hz, 3 H), 1.13(d, J=6.4 Hz, 3 H). MS 386.0 (M+H⁺).

Example 10

Preparation of N-(2,4-Dichlorophenyl)-N-isopropyl-4-(1,1,1-trifluoro-2-hydroxypropan-2-yl)benzamide (10)

2,4-Dichloro-N-isopropylbenzenamine

To 2,4-dichlorobenzenamine (500 mg, 3.09 mmol) and acetone (1.2 mL, 16.1 mmol) in ClCH₂CH₂Cl (10 mL) was added NaB(OAc)₃H (2.62 g, 12.3 mmol). The reaction mixture was stirred at room temperature for 18 h. The reaction mixture was diluted with saturated aqueous solution of NaHCO₃, extracted with CH₂Cl₂, washed with brine, dried and concentrated. Flash chromatography of the residue, using 1:9 MeOH—CH₂Cl₂, gave the amine 2,4-dichloro-N-isopropylbenzenamine (0.38 g). ¹H NMR (CDCl₃) δ 7.27(s, 1H), 7.11 (d, J=9.0 Hz, 1 H), 6.61 (d, J=9.0 Hz, 1 H), 4.18(br, 1 H), 3.66(m, 1 H), 1.28(br, 6 H). MS 204.1 (M+H⁺).

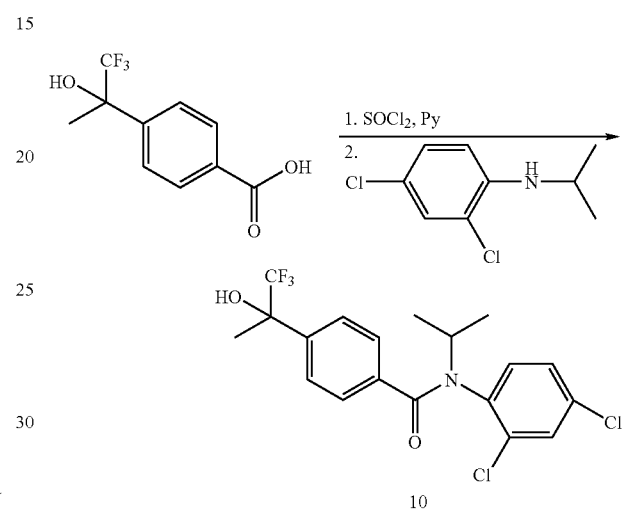

To 4-(1,1,1-trifluoro-2-hydroxypropan-2-yl)benzoic acid (50.0 mg, 0.21 mmol) in THF (3 mL) were added SOCl₂ (0.02 mL, 0.32 mmol) and pyridine (0.03 mL, 0.42 mmol). The reaction mixture was stirred at 80° C. for 2 h and cooled to room temperature. 2,4-Dichloro-N-isopropylbenzenamine (85 mg, 0.42 mmol) was added, and the resulting reaction mixture was stirred at room temperature for 18 h. The mixture was diluted with CH₂Cl₂ (10 mL). The solution was washed with saturated aqueous CuSO₄, water and brine, dried and concentrated. Flash chromatography of the residue, using 3:7 EtOAc-Hexane, gave the amide N-(2,4-dichlorophenyl)-N-isopropyl-4-(1,1,1-trifluoro-2-hydroxypropan-2-yl)benzamide (68.1 mg). ¹H NMR (CDCl₃) δ 7.50-7.15 (m, including a singlet at δ 7.20, 7H), 4.18(br, 0.5 H), 3.65 (br, 0.5 H), 2.41(br, 1H), 1.71(s, 3 H), 1.40(br, 3 H), 1.13(d, J=6.8 Hz, 3 H). MS 420.1 (M+H⁺).

Example 11

Preparation of N-(2-Chloro-5-cyanophenyl)-N-isopropyl-4-(1,1,1-trifluoro-2-hydroxypropan-2-yl)benzamide (11)

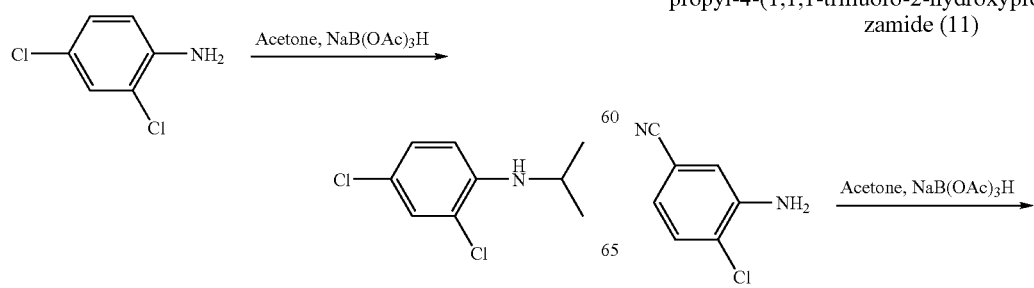

4-Chloro-3-(isoropylamino)benzonitrile

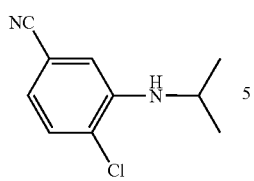

To 3-amino-4-chlorobenzonitrile (470 mg, 3.09 mmol) and acetone (1.2 mL, 16.1 mmol) in ClCH$_2$CH$_2$Cl (10 mL) was added NaB(OAc)$_3$H (2.62 g, 12.3 mmol). The reaction mixture was stirred at room temperature for 18 h. The reaction mixture was diluted with saturated aqueous solution of NaHCO$_3$, extracted with CH$_2$Cl$_2$, washed with brine, dried and concentrated. Flash chromatography of the residue, using 1:9 MeOH—CH$_2$Cl$_2$, gave the amine 4-chloro-3-(isopropylamino)benzonitrile (0.35 g). $^1$H NMR (CDCl$_3$) δ 7.33 (d, J=9.0 Hz, 1 H), 6.90 (d, J=9.0 Hz, 1 H), 6.88(s, 1H), 4.35(br, 1 H), 3.67(m, 1 H), 1.31 (br, 6 H).

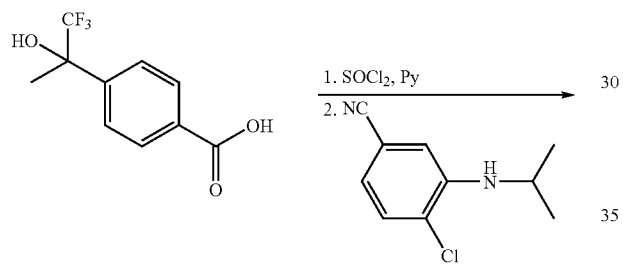

To 4-(1,1,1-trifluoro-2-hydroxypropan-2-yl)benzoic acid (50.0 mg, 0.21 mmol) in THF (3 mL) were added SOCl$_2$ (0.02 mL, 0.32 mmol) and pyridine (0.03 mL, 0.42 mmol). The reaction mixture was stirred at 80° C. for 2 h and cooled to room temperature. 4-Chloro-3-(isopropylamino)benzonitrile (81 mg, 0.42 mmol) was added, and the resulting reaction mixture was stirred at room temperature for 18 h. The mixture was diluted with CH$_2$Cl$_2$ (10 mL). The solution was washed with saturated aqueous CuSO$_4$, water and brine, dried and concentrated. Flash chromatography of the residue, using 3:7 EtOAc-Hexane, gave the amide N-(2-chloro-5-cyanophenyl)-N-isopropyl-4-(1,1,1-trifluoro-2-hydroxypropan-2-yl) benzamide (5.5 mg). $^1$H NMR (CDCl$_3$) δ 7.99(s, 1H), 7.75- 7.15 (m, 6 H), 4.55(s, 1 H), 1.64(s, 3 H), 1.44(br, 3 H), 1.24(d, J=4.4 Hz, 3 H). MS 411.1 (M+H$^+$).

Example 12

Preparation of N-(2-Chloro-5-(trifluoromethyl)phenyl)-N-isopropyl-4-(1,1,1-trifluoro-2-hydroxypropan-2-yl)benzamide (12)

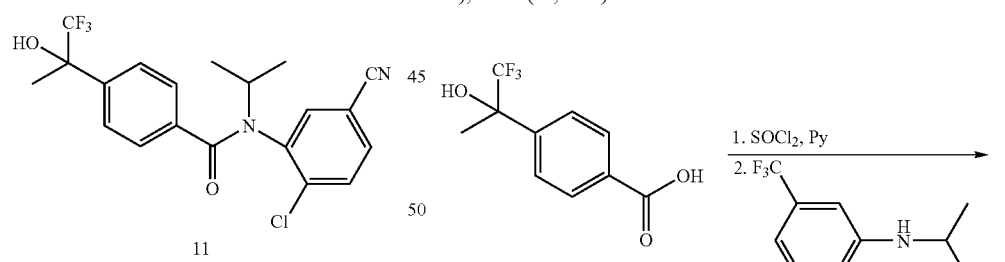

2-Chloro-N-isopropyl-5-(trifluoromethyl)benzenamine

To 2-chloro-5-(trifluoromethyl)benzenamine (430 mg, 3.09 mmol) and acetone (1.2 mL, 16.1 mmol) in ClCH$_2$CH$_2$Cl (10 mL) was added NaB(OAc)$_3$H (2.62 g, 12.3 mmol). The reaction mixture was stirred at room temperature for 18 h. The reaction mixture was diluted with saturated aqueous solution of NaHCO$_3$, extracted with CH$_2$Cl$_2$, washed with brine, dried and concentrated. Flash chromatography of the residue, using 1:9 MeOH—CH$_2$Cl$_2$, gave the amine 2-chloro-N-isopropyl-5-(trifluoromethyl)benzenamine (0.35 g). $^1$H NMR (CDCl$_3$) δ 7.35 (d, J=9.0 Hz, 1 H), 6.87 (s, 1H), 6.86 (d, J=9.0 Hz, 1 H), 4.48 (br, 1H), 3.73(m, 1 H), 1.32 (br, 6 H).

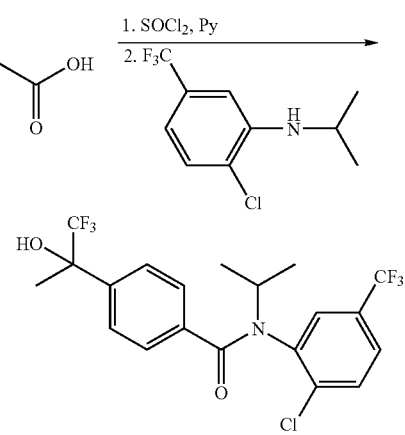

To 4-(1,1,1-trifluoro-2-hydroxypropan-2-yl)benzoic acid (50.0 mg, 0.21 mmol) in THF (3 mL) were added SOCl$_2$ (0.02 mL, 0.32 mmol) and pyridine (0.03 mL, 0.42 mmol). The reaction mixture was stirred at 80° C. for 2 h and cooled to room temperature. 2-Chloro-N-isopropyl-5-(trifluoromethyl)benzenamine (100 mg, 0.42 mmol) was added, and the resulting reaction mixture was stirred at room temperature for 18 h. The mixture was diluted with $CH_2Cl_2$ (10 mL). The solution was washed with saturated aqueous $CuSO_4$, water and brine, dried and concentrated. Flash chromatography of the residue, using 3:7 EtOAc-Hexane, gave the amide N-(2-chloro-5-(trifluoromethyl)phenyl)-N-isopropyl-4-(1,1,1-trifluoro-2-hydroxypropan-2-yl)benzamide (43.8 mg). $^1$H NMR ($CD_3OD$) δ 7.90-7.10 (m, 7H), 3.75(br, 1H), 1.73(s, 3 H), 1.43(br, 3 H), 1.16(br, 3 H). MS 454.1 (M+H$^+$).

Example 13

Preparation of (S)-N-Cyclohexyl-N-cyclopropyl-4-(1,1,1-trifluoro-2-hydroxypropan-2-yl)benzamide (13)

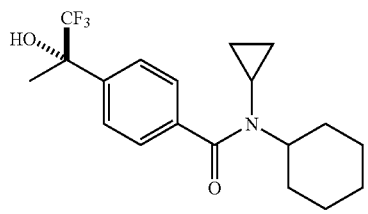

Preparation of optically active (S)-4-(1,1,1-Trifluoro-2-hydroxypropan-2-yl)benzoic acid

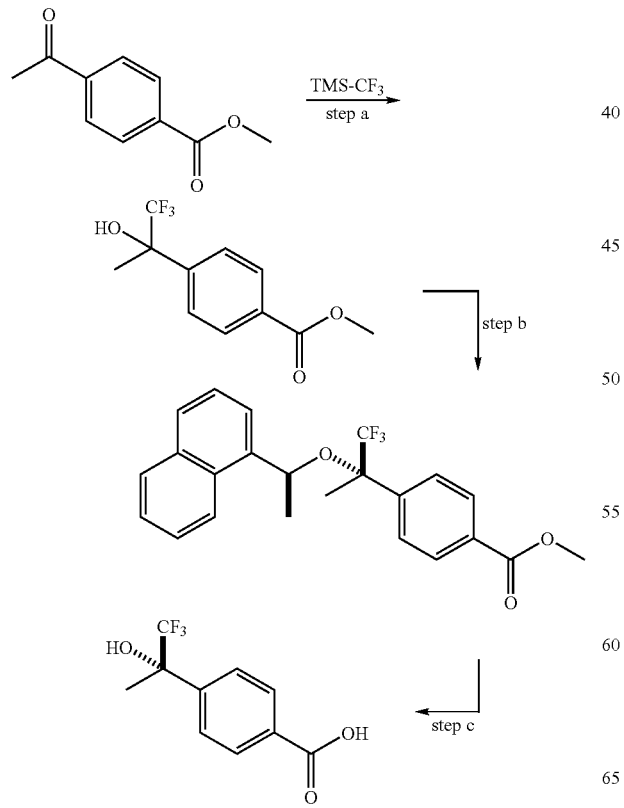

Methyl 4-(1,1,1-trifluoro-2-hydroxypropan-2-yl)benzoate

A 3 L flask containing methyl 4-acetylbenzoate (60 g, 0.34 mol, 1.0 equiv.) in 1.0 L THF was charged with 96.6 g TMS-$CF_3$ (0.68 mol, 2.0 equiv.) at 0° C. The solution was allowed to stir for 30 min. Tetrabutylammonium fluoride (680 mL, 1.0M in THF, 0.68 mol, 2.0 equiv.) was added dropwise via addition funnel over a period of 3 h. After addition, the solution was allowed to stir for an additional 30 min. and warm to room temperature. The solution was concentrated under reduced pressure. The mixture was diluted with saturated $NaHCO_3$, extracted (4×10% MeOH/$CH_2Cl_2$). The organic extracts were combined, dried ($MgSO_4$) and concentrated under reduced pressure. Flash chromatography ($SiO_2$, 15% EtOAc/Hexanes) gave 67 g of the product as orange oil (0.27 mol).

Methyl 4-(S)-1,1,1-trifluoro-2-(((S)-1-(naphthalen-1-yl)ethyl)carbamoyloxy)-propan-2-yl)benzoate A 500 mL flask containing a portion of product obtained above (25 g, 0.1 mol, 1.0 equiv.) in 150 mL $CH_2Cl_2$ was charged with 19.7 g DMAP (0.16 mol, 1.6 equiv.) at 0° C. 4-Nitrophenyl chloroformate (28.5 g, 0.14 mol, 1.4 equiv.) was added in portions. The resulting mixture was allowed to stir for 15 min at 0° C. and 3.0 h at room temperature. The mixture was cooled to 0° C. (S)-1-(1-Naphthalenyl)ethanamine (34.2 g, 0.2 mol, 2.0 equiv.) was added in portions. After addition, the solution was allowed to stir at room temperature for 1 h. The mixture was diluted with EtOAc, washed with 6×1 M NaOH, 1 N HCl and brine. The organic extracts was dried and concentrated under reduced pressure. The two diastereomers were separated by flash chromatography ($SiO_2$, 15% methyl-t-butyl ether/Hexanes). The first portion of the two close spots was collected and concentrated under reduced pressure to give 14 g of the (S,S) diastereomer as colorless oil (31.4 mmol).

(S)-4-(1,1,1-Trifluoro-2-hydroxypropan-2-yl)benzoic acid

A 250 mL flask containing product obtained above (13.5 g, 30 mmol, 1.0 equiv.) was charged with 70 mL THF, 30 mL $H_2O$, 30 mL MeOH and 0.73 g LiOH (0.3 mol, 10.0 equiv.). The resulting mixture was stirred at 45° C. overnight. The mixture was extracted with $CH_2Cl_2$. The aqueous layer was the acidified with 2 N HCl to pH ~4 and extracted (5×10% MeOH/$CH_2Cl_2$). The organic extracts were dried ($MgSO_4$), concentrated under reduced pressure to give 7.5 g of the product as white solid (32.0 mmol).

Preparation of N-Cyclopropylcyclohexylamine

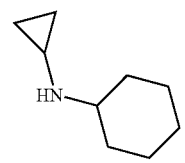

To cyclohexanone (1.0 mL, 10 mmol) in dichloroethane (30 mL) was added cyclopropylamine (0.70 mL, 10 mmol), NaBH(OAc)$_3$ (3.18 g, 15 mmol) and AcOH (0.57 mL, 10 mmol). The reaction was stirred at room temperature for 10 h.

The reaction mixture was poured into water (60 mL) and acidified to pH 2 with 5 N HCl followed by removal of the organic portion. The aqueous portion was brought to pH>12 with 5 N NaOH and extracted with $CH_2Cl_2$ (3×30 mL). The collected organic extracts were dried with $Na_2SO_4$ and the volatile organics were removed in vacuo to afford the desired intermediate.

(S)-N-Cyclohexyl-N-cyclopropyl-4-(1,1,1-trifluoro-2-hydroxypropan-2-yl)benzamide (13)

To 4-(1,1,1-trifluoro-2-hydroxypropan-2-yl)benzoic acid (0.10 g, 0.43 mmol), HBTU (0.19 g, 0.51 mmol), and HOBt (0.072 g, 0.53 mmol) was added DMF (1 mL) and Hünig's base (0.18 mL, 1.0 mmol). The acid was activated by stirring at room temperature for 5 min. To the activated ester was added N-cyclopropylcyclohexylamine (0.13 g, 0.86 mmol). The reaction mixture was stirred for 1 h, poured into $H_2O$ (7 mL), acidified with 5 N HCl and extracted with $CH_2Cl_2$ (2 mL). The organic extracts were washed with 1 N NaOH (4 mL), dried with $Na_2SO_4$, and removed in vacuo. Silica gel chromatography (gradient 20 to 30% ethyl acetate in hexanes) afforded racemic N-cyclohexyl-N-cyclopropyl-4-(1,1,1-trifluoro-2-hydroxypropan-2-yl)benzamide. Chiral HPLC (Chiracel AD-H, isocratic 10% IPA in hexanes) afforded the early eluting R— and late eluting S-isomers, 35 mg and 37 mg, respectively. S-isomer: $^1H$ NMR (500 MHz, $CDCl_3$) δ 0.40-0.50 (m, 2H), 0.51-0.61 (m, 2H), 1.12-1.25 (m, 1H), 1.33-1.45 (m, 2H), 1.67-1.75 (m, 2H), 1.79-1.90 (m, 7H), 1.91-2.00 (m, 1H), 2.53-2.6 (m, 1 H), 2.83 (s, 1H), 4.03-4.15 (bs, 1H), 7.47 (d, J=9 Hz, 2H), 7.58 (d, J=9 Hz, 2H).

Example 14

Preparation of (S)-N-Cyclohexyl-4-(1,1,1-trifluoro-2-hydroxypropan-2-yl)-N-(2,2,2-trifluoroethyl)benzamide

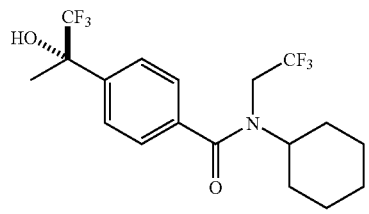

14

Preparation of N-cyclohexyl-2,2,2-trifluoroacetamide

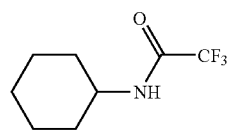 [SMILES: O=C(NC1CCCCC1)C(F)(F)F]

To an ice cooled solution of cyclohexylamine (1.0 mL, 8.8 mmol), $CH_2Cl_2$ (18 mL), and pyridine (0.74 mL, 9.2 mmol) was added dropwise trifluoroacetic anhydride. The ice bath was removed, and the reaction was stirred at room temperature overnight. The reaction mixture was poured into water (50 mL) and extracted with $CH_2Cl_2$ (2×20 mL). The combined organic extracts were dried with $Na_2SO_4$ and the solvent removed in vacuo to yield 1.6 g of the desired acetamide.

Preparation of N-(2,2,2-trifluoroethyl)cyclohexylamine

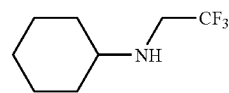

Directly to ice cooled solid N-cyclohexyl-2,2,2-trifluoroacetamide under nitrogen atmosphere was added slowly 1 M $BH_3$ in THF (23 mL). The ice bath was removed from the system, and the reaction mixture refluxed overnight. The mixture was cooled to 0° C., treated with MeOH (6.7 mL), and returned to reflux for 5 h. After cooling to room temperature, the reaction mixture was poured into water (100 mL) and acidified to pH 2 with 5 N HCl. Following extraction with $CH_2Cl_2$ (3×40 mL), the aqueous layer was brought to pH 10 with 5 N NaOH and extracted with $CH_2Cl_2$ (2×50 mL). The combined organic extracts were dried with $Na_2SO_4$ and the solvent carefully removed in vacuo to obtain 1.36 g of volatile N-(2,2,2-trifluoroethyl)cyclohexylamine.

(S)-N-Cyclohexyl-4-(1,1,1-trifluoro-2-hydroxypropan-2-yl)-N-(2,2,2-trifluoroethyl)benzamide (14)

To a solution of (S)-4-(1,1,1-trifluoro-2-hydroxypropan-2-yl)benzoic acid (0.10 g, 0.43 mmol), pyridine (0.069, 0.86 mmol), and THF (1 mL) was added $SOCl_2$ (0.046 mL, 0.64 mmol). The reaction was stirred at 80° C. for 2 h. After cooling to room temperature, half of the acid chloride was sequestered for reaction. To this material was added 2 equiv. of N-(2,2,2-trifluoroethyl)cyclohexylamine (0.077 mg, 0.43 mmol). The amide forming reaction was stirred at room temperature overnight. The reaction mixture was poured into water (5 mL), acidified with 5 N HCl and extracted with $CH_2Cl_2$ (2 mL). The organic extracts were washed with 1 N NaOH (4 mL), dried with $Na_2SO_4$, and removed in vacuo. Silica gel chromatography (gradient 20 to 30% ethyl acetate in hexanes) afforded 21 mg of (S)-N-cyclohexyl-4-(1,1,1-trifluoro-2-hydroxypropan-2-yl)-N-(2,2,2-trifluoroethyl)benzamide. $^1H$ NMR (400 MHz, $CDCl_3$) δ 1.10-1.20 (m, 3H), 1.42-1.65 (m, 3H), 1.74-1.85 (m, 7H), 2.68 (bs, 1H), 3.68 (bs, 1H), 4.02-4.19 (m, 2 H), 7.44 (d, J=8 Hz, 2H), 7.66 (d, J=8 Hz, 2H).

Example 15

Preparation of (S)-N-cyclopropyl-N-(4,4-difluorocyclohexyl)-4-(1,1,1-trifluoro-2-hydroxypropan-2-yl)benzamide (15)

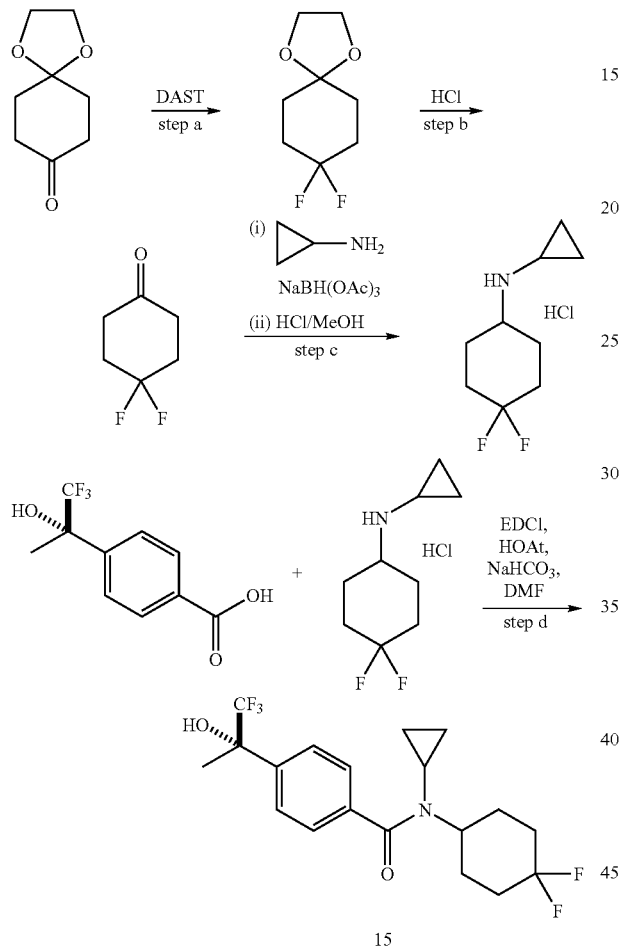

(S)-N-cyclopropyl-N-(4,4-difluorocyclohexyl)-4-(1,1,1-trifluoro-2-hydroxypropan-2-yl)benzamide (15)

Step a. A solution of 1,4-cyclohexanedione monoethylene acetal (2.00 g, 12.8 mmol, 1.0 equiv.) in $CH_2Cl_2$ (60 mL) was treated at 0° C. with DAST (2.00 mL, 15.4 mmol, 1.2 equiv.). After being stirred at 0° C. for 30 min and at 25° C. h for 12 h, the reaction mixture was diluted ($CH_2Cl_2$), washed (1× saturated aqueous $NaHCO_3$, and 1× brine), dried ($Na_2SO_4$), and concentrated under reduced pressure. Flash chromatography of the residue ($SiO_2$, 10% EtOAc/Hexanes) provided 0.89 g of the product as a yellow solid (4.96 mmol).

Step b. A solution of 4,4-difluorocyclohexanone ethylene acetal prepared above in step a (250 mg, 1.40 mmol) in THF (12 mL) was treated with 3 N aqueous hydrochloric acid (8 mL). After being stirred at 25° C. for 3 days, THF was removed under the reduced pressure and the reaction was extracted (4×10% $MeOH/CH_2Cl_2$). The combined organic layer was dried ($Na_2SO_4$) and concentrated under reduced pressure to provide 60 mg of the product as a yellow liquid (0.45 mmol).

Step c. A solution of 4,4-difluorocyclohexanone prepared above in step b (60 mg, 0.45 mmol, 1.0 equiv.), cyclopropylamine (47 μL, 0.68 mmol, 1.5 equiv.), and AcOH (77 μL, 1.35 mmol, 3.0 equiv.) in $ClCH_2CH_2Cl$ (2.5 mL) was treated at 0° C. with $NaBH(OAc)_3$ (190 mg, 0.90 mmol, 2.0 equiv.). After being stirred for 12 h at 25° C., the reaction was quenched (1 N aqueous NaOH), extracted (5×10% $MeOH/CH_2Cl_2$), dried ($Na_2SO_4$) and concentrated under reduced pressure. The resulting residue was treated with 1.25 N methanolic HCl solution (1 mL) and concentrated under reduced pressure to provide 46 mg of the product as a yellow solid (0.22 mmol).

Step d. A solution of N-cyclopropyl-4,4-difluorocyclohexanamine hydrochloride prepared above in step c (46 mg, 0.22 mmol, 1.0 equiv.) and (S)-4-(1,1,1-trifluoro-2-hydroxypropan-2-yl)benzoic acid (60 mg, 0.24 mmol, 1.1 equiv.) in DMF (0.8 mL) was treated at 0° C. with EDCI (64 mg, 0.33 mmol, 1.5 equiv.), HOAt (45 mg, 0.33 mmol, 1.5 equiv.) and $NaHCO_3$ (56 mg, 0.66 mmol, 3.0 equiv.) successively. After being stirred at 25° C. for 12 h, the reaction was diluted (EtOAc) and washed (1×10% aqueous citric acid, 1× saturated $NaHCO_3$, and 1× brine). The organic layer was dried ($Na_2SO_4$) and concentrated under reduced pressure. Flash chromatography of the residue ($SiO_2$, 35% EtOAc/Hexanes) gave 37 mg of the product as a white solid (0.095 mmol). $^1H$ NMR ($CDCl_3$, 500 MHz) δ 7.59 (d, J=8.2 Hz, 2H), 7.47 (d, J=8.5 Hz, 2H), 4.33-4.28 (m, 1H), 2.59-2.54 (m, 2H), 2.28-2.05 (m, 4H) 2.02-1.80 (m, 4H), 1.79 (s, 3H), 0.60-0.52 (m, 2H), 0.48-0.40 (m, 2H). MS (ESI) 392 $[M+H]^+$.

Example 16

Preparation of N-cyclopropyl-N-[(1r,4r)-4-fluorocyclohexyl]-4-[(S)-1,1,1-trifluoro-2-hydroxypropan-2-yl]benzamide (16a) and N-cyclopropyl-N-[(1s,4s)-4-fluorocyclohexyl]-4-[(S)-1,1,1-trifluoro-2-hydroxypropan-2-yl]benzamide (16b)

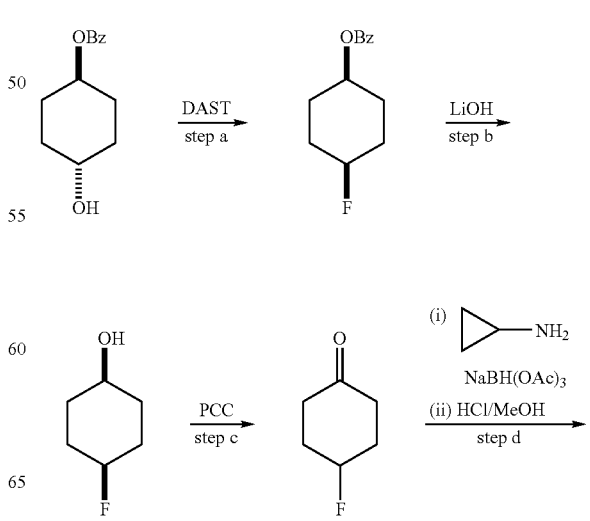

-continued

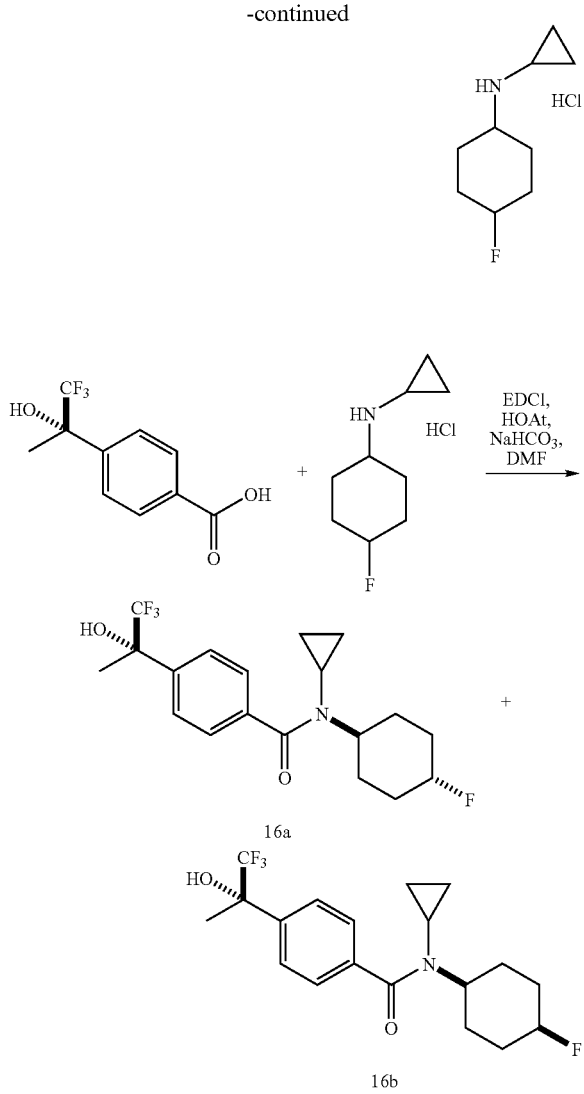

N-cyclopropyl-N-[(1r,4r)-4-fluorocyclohexyl]-4-[(S)-1,1,1-trifluoro-2-hydroxypropan-2-yl]benzamide (16a) and N-cyclopropyl-N-[(1s,4s)-4-fluorocyclohexyl]-4-[(S)-1,1,1-trifluoro-2-hydroxypropan-2-yl]benzamide (16b)

Step a. A solution of (1r,4r)-4-hydroxycyclohexyl benzoate (5.26 g, 23.9 mmol, 1.0 equiv.) in $CH_2Cl_2$ (120 mL) was treated at −78° C. with a solution of DAST (2.00 mL, 15.4 mmol, 1.2 equiv.) in $CH_2Cl_2$ (120 mL). After being stirred at −78° C. for 10 min, 0° C. for 1 h, and at 25° C. h for 2 h, the reaction was diluted ($CH_2Cl_2$), washed (1×$H_2O$, and 1× brine), dried ($Na_2SO_4$), and concentrated under reduced pressure. Flash chromatography of the residue ($SiO_2$, 5% MTBE/Hexanes) provided 1.01 g of the product as a white solid (4.54 mmol).

Step b. A solution of (1s,4s)-4-fluorocyclohexyl benzoate prepared above in step a (300 mg, 1.35 mmol) in THF/MeOH (v/v, 1/1, 5.4 mL) was treated with 1.2 N aqueous LiOH (1.4 mL). After being stirred at 25° C. for 5 h, the reaction mixturewas diluted ($H_2O$) and extracted (5×10% MeOH/$CH_2Cl_2$).

The combined organic layer was dried ($Na_2SO_4$) and concentrated under reduced pressure to provide 150 mg of the product as a yellow solid (1.26 mmol).

Step c. A solution of PCC (437 mg, 2.03 mmol, 1.6 equiv.) and molecular sieve, 4 Å (powder, 4.37 g) in $CH_2Cl_2$ (10 mL) was treated at 0° C. with a solution of (1s,4s)-4-fluorocyclohexanol prepared above in step b (150 mg, 1.26 mmol). After being stirred for 1 h at 25° C., the reaction was diluted ($Et_2O$), filtered ($SiO_2$), washed ($Et_2O$), and concentrated under reduced pressure to provide 103 mg of the product as a yellow liquid (0.89 mmol).

Step d. A solution of 4-fluorocyclohexanone prepared above in step c (103 mg, 0.89 mmol, 1.0 equiv.), cyclopropylamine (140 μL, 2.02 mmol, 2.3 equiv.), and AcOH (230 μL, 4.02 mmol, 4.5 equiv.) in $ClCH_2CH_2Cl$ (7.5 mL) was treated at 0° C. with $NaBH(OAc)_3$ (573 mg, 2.70 mmol, 3.0 equiv.). After being stirred for 12 h at 25° C., the reaction was quenched (1 N aqueous NaOH), extracted (5×10% MeOH/$CH_2Cl_2$), dried ($Na_2SO_4$) and concentrated under reduced pressure. The resulting residue was treated with 1.25 N methanolic HCl solution (3 mL) and concentrated under reduced pressure to provide 170 mg of the product as a yellow solid (0.88 mmol).

Step e. N-cyclopropyl-N-[(1r,4r)-4-fluorocyclohexyl]-4-[(S)-1,1,1-trifluoro-2-hydroxypropan-2-yl]benzamide (16a) and N-cyclopropyl-N-[(1s,4s)-4-fluorocyclohexyl]-4-[(S)-1,1,1-trifluoro-2-hydroxypropan-2-yl]benzamide (16b). A solution of N-cyclopropyl-4-fluorocyclohexanamine hydrochloride prepared above in step d (170 mg, 0.88 mmol, 1.0 equiv.) and (S)-4-(1,1,1-trifluoro-2-hydroxypropan-2-yl)benzoic acid (226 mg, 0.97 mmol, 1.1 equiv.) in DMF (2.9 mL) was treated at 0° C. with EDCI (252 mg, 1.32 mmol, 1.5 equiv.), HOAt (179 mg, 1.32 mmol, 1.5 equiv.) and $NaHCO_3$ (222 mg, 2.63 mmol, 3.0 equiv.) successively. After being stirred at 25° C. for 12 h, the reaction was diluted (EtOAc) and washed (1×10% aqueous citric acid, 1× saturated $NaHCO_3$, and 1× brine). The organic layer was dried ($Na_2SO_4$) and concentrated under reduced pressure. Flash chromatography of the residue ($SiO_2$, 20%-35% EtOAc/Hexanes, gradient elution) gave 33 mg of 16a as a white solid (0.087 mmol, 10%) and 47 mg of 16b as a white solid (0.12 mmol).

16a: $R_f$=0.30 (40% EtOAc/hexanes). $^1$H NMR ($CDCl_3$, 500 MHz) δ 7.57 (d, J=8.2 Hz, 2H), 7.45 (d, J=8.5 Hz, 2H), 4.60-4.45 (m, 1H), 4.12-4.05 (m, 1H), 2.77-2.74 (m, 1H), 2.59-2.54 (m, 1H), 2.23-2.18 (m, 2H), 2.00-1.90 (m, 4H), 1.79 (s, 3H), 1.68-1.61 (m, 2H), 0.58-0.53 (m, 2H), 0.46-0.40 (m, 2H). MS (ESI) 374 [M+H]$^+$.

16b: $R_f$=0.25 (40% EtOAc/hexanes). $^1$H NMR ($CDCl_3$, 500 MHz) δ 7.56 (d, J=8.1 Hz, 2H), 7.45 (d, J=8.5 Hz, 2H), 4.74 (d, J=48 Hz, 1H), 4.32-4.24 (m, 1H), 2.93-2.89 (m, 1H) 2.57-2.52 (m, 1H), 2.21-2.10 (m, 4H) 1.85-1.78 (m, 1H), 1.73-1.56 (m, 3H), 0.58-0.53 (m, 2H), 0.48-0.44 (m, 2H). MS (ESI) 374 [M+H]$^+$.

Example 17

Preparation of N-cyclopropyl-N-[trans-4-phenylcyclohexyl]-4-[(S)-1,1,1-trifluoro-2-hydroxypropan-2-yl]benzamide and N-cyclopropyl-N-[cis-4-phenylcyclohexyl]-4-[(S)-1,1,1-trifluoro-2-hydroxypropan-2-yl]benzamide

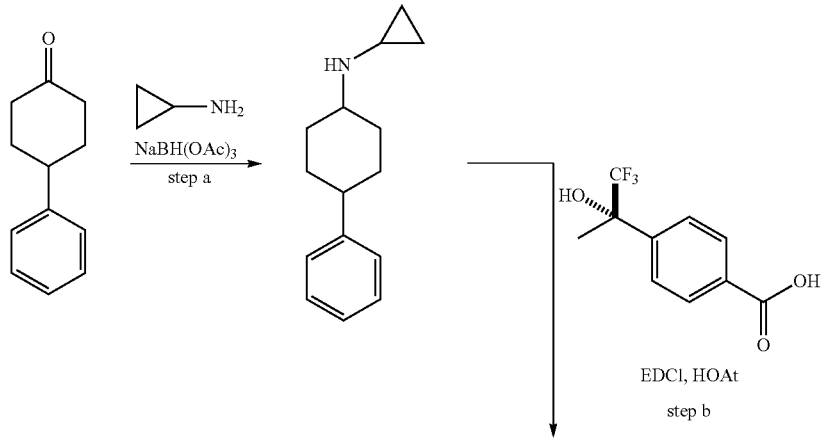

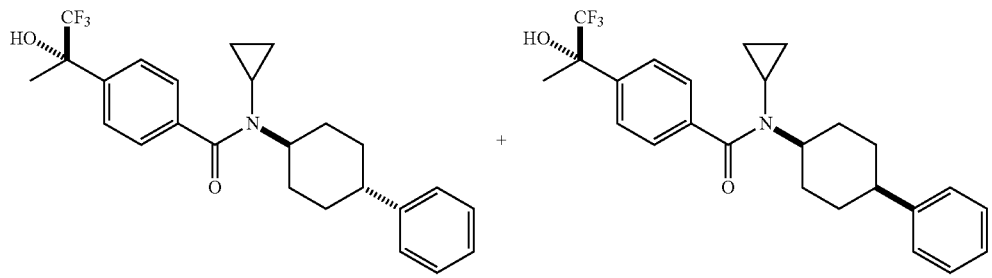

a). A solution of 4-phenylcyclohexanone (500 mg, 2.87 mmol) in 1,2-dichloroethane (16 mL) was treated at 0° C. with cyclopropylamine (298 μL, 4.31 mmol, 1.5 equiv.), acetic acid (329 μL, 5.74 mmol, 2.0 equiv.), and NaBH(OAc)$_3$ (1.22 g, 5.74 mmol, 2.0 equiv) successively. After being stirred at 25° C. for 12 h, the reaction mixture was diluted (EtOAc), washed (1×1 N aqueous NaOH and 2× brine). The organics were dried (Na$_2$SO$_4$) and concentrated under reduced pressure provide the product as a colorless liquid. The product was used for next step without further purification.

b). A solution of N-cyclopropyl-4-phenylcyclohexanamine prepared above in step a (81 mg, 0.38 mmol, 1.1 equiv.) and (S)-4-(1,1,1-trifluoro-2-hydroxypropan-2-yl)benzoic acid (80 mg, 0.34 mmol, 1.0 equiv.) in DMF (1.7 mL) was treated at 0° C. with EDCI (85 mg, 0.44 mmol, 1.3 equiv.), HOAt (60 mg, 0.44 mmol, 1.3 equiv), and NaHCO$_3$ (57 mg, 0.68 mmol, 2.0 equiv.) successively. After being stirred at 25° C. for 12 h, the reaction was diluted (EtOAc), washed (1×10% aqueous citric acid, 1× saturated aqueous NaHCO$_3$, and 1× brine). The organics were dried (Na$_2$SO$_4$), and concentrated under reduced pressure. Flash chromatography (SiO$_2$, 20% EtOAc/Hexanes) gave the trans product as a white solid (R$_f$=0.22 in 25% EtOAc/Hexanes): $^1$H NMR (CDCl$_3$, 500 MHz, trans isomer) δ 7.59 (d, J=8.1 Hz, 2H), 7.49 (d, J=8.0 Hz, 2H), 7.32-7.18 (m, 5H), 4.28-4.18 (m, 1H), 2.66-2.57 (m, 3H), 2.08-1.99 (m, 6H), 1.79 (s, 3H), 1.69-1.59 (m, 2H), 0.61-0.57 (m, 2H), 0.54-0.48 (m, 2H); MS(ESI) 432 [M+H]$^+$. Further elution using more polar solvent (SiO$_2$, 25% EtOAc/Hexane) afforded the cis isomer as a white solid (R$_f$=0.20 in 25% EtOAc/Hexanes).

Example 18

Preparation of N-[trans-4-(4-cyanophenyl)cyclohexyl]-N-cyclopropyl-4-[(S)-1,1,1-trifluoro-2-hydroxypropan-2-yl]benzamide

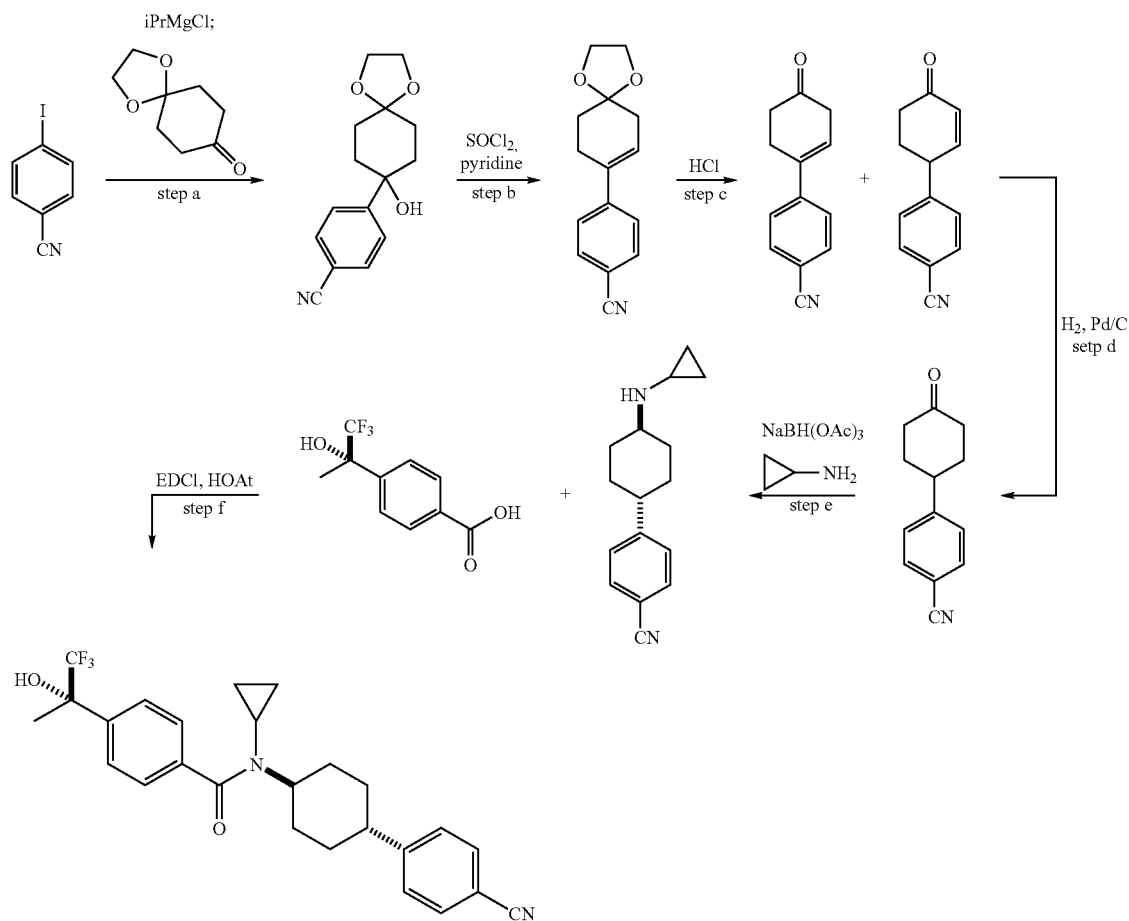

a). To a solution of 4-iodobenzonitrile (15.0 g, 65.5 mmol) in THF (135 mL) was added a solution of iso-PrMgCl in THF (2.0 M, 36.0 mL, 72.1 mmol, 1.1 equiv.) at −20° C. dropwise over 10 min and the reaction was stirred at −20° C. for 1 h. Then a solution of 1,4-cyclohexanedione monoethylene acetal (11.3 g, 72.1 mmol, 1.1 equiv.) in THF (100 mL) was added dropwise at −20° C. over 20 min. After being stirred at 25° C. for 1 h, the resulting reaction was diluted (EtOAc) and washed (1× saturated aqueous NH$_4$Cl and 1×brine). The organics were dried (Na$_2$SO$_4$) and concentrated under reduced pressure. Purification of the residue by recrystallization (EtOAc/n-Hexane, v/v=1/2) afforded the product as a white solid.

b). To a solution of 4-(8-hydroxy-1,4-dioxa-spiro[4.5]dec-8-yl)-benzonitrile prepared above in step a (9.50 g, 36.6 mmol) in pyridine (73 mL) was added thionyl chloride (15.0 mL, 5.6 equiv.) at −10° C. dropwise over 10 min. After being stirred for 2 h at 0° C., the reaction was diluted (EtOAc) and washed (3× ice-cold 1 N HCl and 1× brine). The organics were dried (Na$_2$SO$_4$) and concentrated under reduced pressure to provide the product as a pale yellow solid. The product was used for the next step without further purification.

c). To a solution of crude 4-(1,4-dioxa-spiro[4.5]dec-7-en-8-yl)-benzonitrile prepared above in step b (36.6 mmol) in THF (150 mL) was added 3 N HCl (100 mL). After being stirred for 16 h, the reaction was diluted (EtOAc) and washed (1× brine, 1× saturated aqueous NaHCO$_3$, and 1× brine). The organics were dried (Na$_2$SO$_4$) and concentrated under reduced pressure to provide the product as a yellow solid. The product was used for next step without further purification.

d). To a solution of the crude mixture of 4-(4-oxo-cyclohex-1-enyl)-benzonitrile and 4-(4-oxo-cyclohex-1-enyl)-benzonitrile prepared above in step c (36.6 mmol) in EtOAc (120 mL) was added 10% Pd—C (900 mg) and the reaction was degassed (3×vacuum and H$_2$). After being stirred 7 hours under H$_2$ atmosphere, additional 10% Pd—C (500 mg) was added and the resulting reaction was stirred for an additional 12 h under H$_2$ atmosphere. The catalyst was removed by filtration through Celite and the filtrate was concentrated under reduced pressure to give 4-(4-oxo-cyclohexyl)-benzonitrile as a white solid. The product was used for next step without further purification.

e). A solution of crude 4-(4-oxo-cyclohexyl)-benzonitrile prepared above in step d (36.6 mmol) in 1,2-dichloroethane (170 mL) was treated at 0° C. with cyclopropylamine (3.80 mL, 54.7 mmol, 1.5 equiv.), acetic acid (4.19 mL, 73.2 mmol, 2.0 equiv.), and NaBH(OAc)$_3$ (15.5 g, 73.2 mmol, 2.0 equiv) successively. After being stirred at 25° C. for 12 h, the reaction mixture was diluted (EtOAc), washed (1×1 N aqueous NaOH and 2× brine), dried (Na$_2$SO$_4$) and concentrated under reduced pressure. Flash chromatography (SiO$_2$, 20-30% EtOAc/n-Hexane containing 2.5% of TEA, gradient elution) gave the cis amine (R$_f$=0.50 in 40% EtOAc/n-Hexane containing 2.5% TEA). Further elution using more polar solvent (30-50% EtOAc/n-Hexane containing 2.5% of TEA, gradient elution) afforded the trans amine as a pale yellow solid (R$_f$=0.25 in 40% EtOAc/n-Hexane containing 2.5% TEA).

f). A solution of 4-[trans-4-(cyclopropylamino)cyclohexyl]benzonitrile (6.30 g, 26.2 mmol) and (S)-4-(1,1,1-trifluoro-2-hydroxypropan-2-yl)benzoic acid (6.14 g, 26.2 mmol, 1.0 equiv.) in DMF (66 mL) was treated at 0° C. with EDCI (6.53 g, 34.1 mmol, 1.3 equiv.), HOAt (4.64 g, 34.1 mmol, 1.3 equiv), and NaHCO$_3$ (4.40 g, 52.4 mmol, 2.0 equiv.) successively. After being stirred at 25° C. for 12 h, the reaction was diluted (EtOAc), washed (2×1 N aqueous HCl, 2×1 N NaOH, and 1× brine), dried (Na$_2$SO$_4$), and concentrated under reduced pressure. Purification of the residue by recrystallization (3×50% EtOAc/n-Hexane) afforded the product amide as a white solid: $^1$H NMR (CDCl$_3$, 500 MHz) δ 7.59 (d, J=8.1 Hz, 2H), 7.59 (d, J=8.1 Hz, 2H), 7.49 (d, J=8.2 Hz, 2H), 7.32 (d, J=8.1 Hz, 2H), 4.25-4.15 (m, 1H), 2.75-2.57 (m, 3H), 2.20-1.92 (m, 6H), 1.80 (s, 3H), 1.69-1.59 (m, 2H), 0.61-0.57 (m, 2H), 0.54-0.48 (m, 2H); MS(ESI) 457 [M+H]$^+$.

Example 19

Preparation of N-ethyl-N-[trans-4-(4-fluorophenyl)cyclohexyl]-4-[(S)-1,1,1-trifluoro-2-hydroxypropan-2-yl]benzamide and N-ethyl-N-[cis-4-(4-fluorophenyl)cyclohexyl]-4-[(S)-1,1,1-trifluoro-2-hydroxypropan-2-yl]benzamide

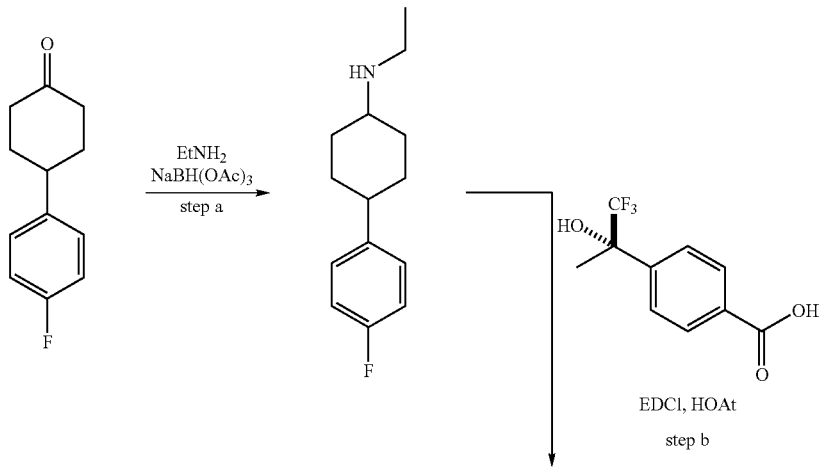

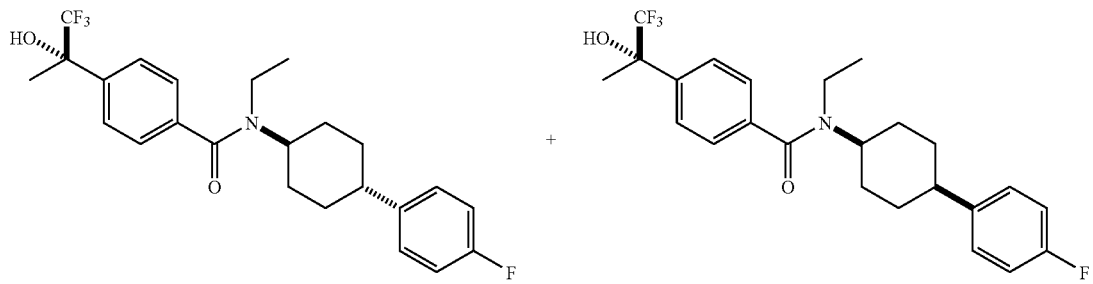

a). Using step a, b, c, and d described above in example B, but substituting 1-fluoro-4-iodobenzene for 4-iodobenzonitrile, 4-(4-fluorophenyl)cyclohexanone was prepared. Then, a solution of 4-(4-fluorophenyl)cyclohexanone (70 mg, 0.37 mmol) in 1,2-dichloroethane (4 mL) was treated at 0° C. with ethylamine (2 M solution in THF, 550 μL, 1.10 mmol, 3.0 equiv.), acetic acid (64 μL, 1.10 mmol, 3.0 equiv.), and NaBH(OAc)$_3$ (235 mg, 1.10 mmol, 3.0 equiv) successively. After being stirred at 25° C. for 12 h, the reaction mixture was diluted (EtOAc), and washed (1×1 N aqueous NaOH and 2× brine). The organics were dried (Na$_2$SO$_4$) and concentrated under reduced pressure provide the product as a yellow liquid. The product was used in the next step without further purification.

b). A solution of N-ethyl-4-(4-fluorophenyl)cyclohexanamine prepared above in step a (78 mg, 0.35 mmol, 1.0 equiv.) and (S)-4-(1,1,1-trifluoro-2-hydroxypropan-2-yl)benzoic acid (81 mg, 0.35 mmol, 1.0 equiv.) in DMF (0.72 mL) was treated at 0° C. with EDCI (87 mg, 0.46 mmol, 1.3 equiv.), HOAt (61 mg, 0.46 mmol, 1.3 equiv), and NaHCO$_3$ (59 mg, 0.70 mmol, 2.0 equiv.) successively. After being stirred at 25° C. for 3 days, the reaction was diluted (EtOAc), washed (1×10% aqueous citric acid, 1× saturated aqueous NaHCO$_3$, and 1× brine). The organics were dried (Na$_2$SO$_4$), and concentrated under reduced pressure. A mixture of two geometric isomers was resolved by chiral HPLC to give the cis isomer ($t_R$=14.1 min) and the trans isomer as a colorless solid ($t_R$=18.6 min): $^1$H NMR (CDCl$_3$, 400 MHz, trans isomer) δ 7.62 (d, J=8.0 Hz, 2H), 7.38 (d, J=8.4 Hz, 2H), 7.19-7.00 (m, 2H), 6.98-6.90 (m, 2H), 4.48-4.30 (m, 1H), 3.70-3.40 (m, 2H), 3.40-3.30 (m, 1H), 2.65-2.40 (m, 2H), 2.00-1.75 (m, 5H), 1.80 (s, 3H), 1.70-1.50 (m, 2H), 1.40-1.20 (m, 3H); MS(ESI) 438 [M+H]$^+$. The flow rate was 18 mL/min on a Chiralpak OD-H 20 mm I.D.×250 mm, 5 mic column (Daicel Chemical Industries LTD), using 12% isopropyl alcohol/hexanes as an eluent.

Example 20

Preparation of N-cyclopropyl-N-((trans-4-(pyridin-4-yl)cyclohexyl)-4-((S)-1,1,1-trifluoro-2-hydroxypropan-2-yl)benzamide and N-cyclopropyl-N-((cis-4-(pyridin-4-yl)cyclohexyl)-4-((S)-1,1,1-trifluoro-2-hydroxypropan-2-yl)benzamide

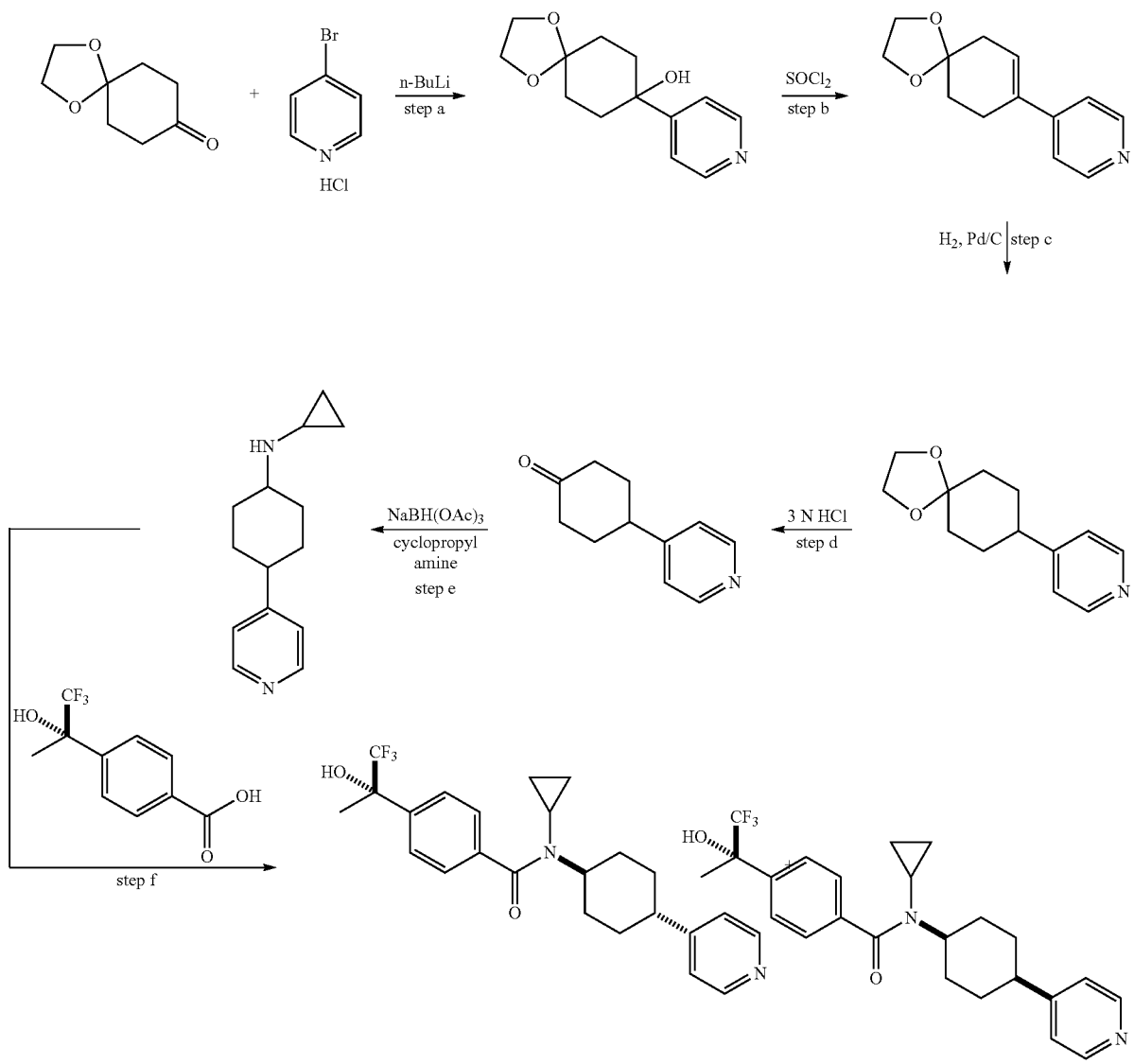

a). To a solution of n-butyllithium (2.5 M in hexane, 12.8 mL) in dry ether (35 mL) was added 30 mL of 4-bromopyridine (5.1 g, 32 mmol) in ether (ethereal solution was prepared from 4-bromopyridine hydrochloride and 2 N aqueous NaOH) dropwise at −78° C. After stirring at the same temperature, a solution of cyclohexane-1,4-dione monoethylene ketal (5.0 g, 32 mmol) in dry THF (30 mL) was added over a period of 10 min. Stirring was continued for 1 h at −78° C. and then the reaction mixture was slowly warmed to −20° C. over 1 h. The reaction mixture was then poured into saturated aqueous NH$_4$Cl and the layers were separated. The aqueous layer was extracted (3× CHCl$_3$), and the combined organics were dried and concentrated under reduced pressure. The resulting oil was purified by flash chromatography (SiO$_2$, 50% EtOAc/Hexane) to give the product as a light yellow solid.

b). Thionyl chloride (3.5 mL) was added to a solution of 4-hydroxy-4-(4-pyridyl)cyclohexanone ethylene ketal (2.0 g, 8.5 mmol, prepared in step a) in pyridine (16 mL) over 10 min at −10° C. After stirring at 0° C. for 2 h the reaction mixture was carefully diluted (sat. NaHCO$_3$) and extracted with CH$_2$Cl$_2$. The extracts were combined, dried and concentrated in vacuo to give the product as a colorless liquid.

c). A solution of 4-(4-pyridyl)cyclohex-3-en-1-one ethylene ketal (1.8 g, 8.3 mmol, prepared in step b) in ethyl acetate (30 mL) and ethanol (3 mL) containing 10% Pd/C (500 mg) was hydrogenated under atmospheric pressure at room temperature for 24 h. After filtration of the catalyst, the solution was concentrated under reduced pressure to give the product as a colorless liquid.

d). 3 N HCl (3 mL) was added to a solution of 4-(4-pyridyl)cyclohexanone ethylene ketal prepared in step c (1.6 g, 7.3 mmol) in THF (3 mL). The mixture was stirred at room temperature for 12 h and then diluted (sat. NaHCO$_3$). The resulting solution was extracted (10% MeOH/CH$_2$Cl$_2$), dried and concentrated. The residue was purified by flash chromatography (SiO$_2$, 60% EtOAc/Hexane) to give the product as a white solid.

e). A solution of 4-(pyridin-4-yl)cyclohexanone prepared above (264 mg, 1.5 mmol, 1.0 equiv) in 1,2-dichloroethane (10 mL) was treated at 0° C. with cyclopropylamine (175 mg, 2.0 equiv), acetic acid (0.09 mL, 1.0 equiv.) and NaBH(OAc)$_3$ (636 mg, 2.0 equiv) successively. After being stirred at 25° C. for 12 h, the reaction mixture was carefully diluted (sat. NaHCO$_3$) and extracted (10% MeOH/CH$_2$Cl$_2$). The combined organics were washed (brine), dried (Na$_2$SO$_4$) and concentrated under reduced pressure to provide the crude product.

f). N-cyclopropyl-N-((trans-4-(pyridin-4-yl)cyclohexyl)-4-((S)-1,1,1-trifluoro-2-hydroxypropan-2-yl)benzamide and N-cyclopropyl-N-((cis-4-(pyridin-4-yl) cyclohexyl)-4-((S)-1,1,1-trifluoro-2-hydroxypropan-2-yl)benzamide. A solution of the crude material from step e and (S)-4-(1,1,1-trifluoro-2-hydroxypropan-2-yl)benzoic acid (351 mg, 1.0 equiv) in DMF (10 mL) was treated at 0° C. with EDCI (372 mg, 1.3 equiv), HOAt (265 mg, 1.3 equiv) and NaHCO$_3$ (252 mg, 2.0 equiv) successively. After being stirred at 25° C. for 12 h, the reaction was diluted (EtOAc), washed (2 N NaOH and brine), dried (Na$_2$SO$_4$) and concentrated under reduced pressure. The residue was purified by flash chromatography (SiO$_2$, 100% EtOAc) to provide the product as a mixture of cis and trans isomers. The separation of the mixture by chiral HPLC gave both trans and cis products as white solids: $^1$H NMR (DMSO, 400 MHz, trans isomer) δ 8.48 (brs, 2 H), 7.62 (d, J=7.0 Hz, 2H), 7.52 (d, J=7.0 Hz, 2H), 7.32 (brs, 2 H), 6.67 (s, 1 H), 4.07 (m, 1H), 2.76-2.50 (m, 2 H), 2.00 (m, 6 H), 1.73 (s, 3 H), 1.62 (m, 2 H), 0.52-0.40 (m, 4 H). The flow rate was 18 ml/min on a Chiralpak OD-H 20 mm I.D.×250 mm, 5 mic column (Daicel Chemical Industries LTD), using 20% isopropyl alcohol/hexane as the eluent.

Example 21

Preparation of N-ethyl-N-[trans-4-(4-cyanophenyl)cyclohexyl]-4-[(S)-1,1,1-trifluoro-2-hydroxypropan-2-yl]benzamide

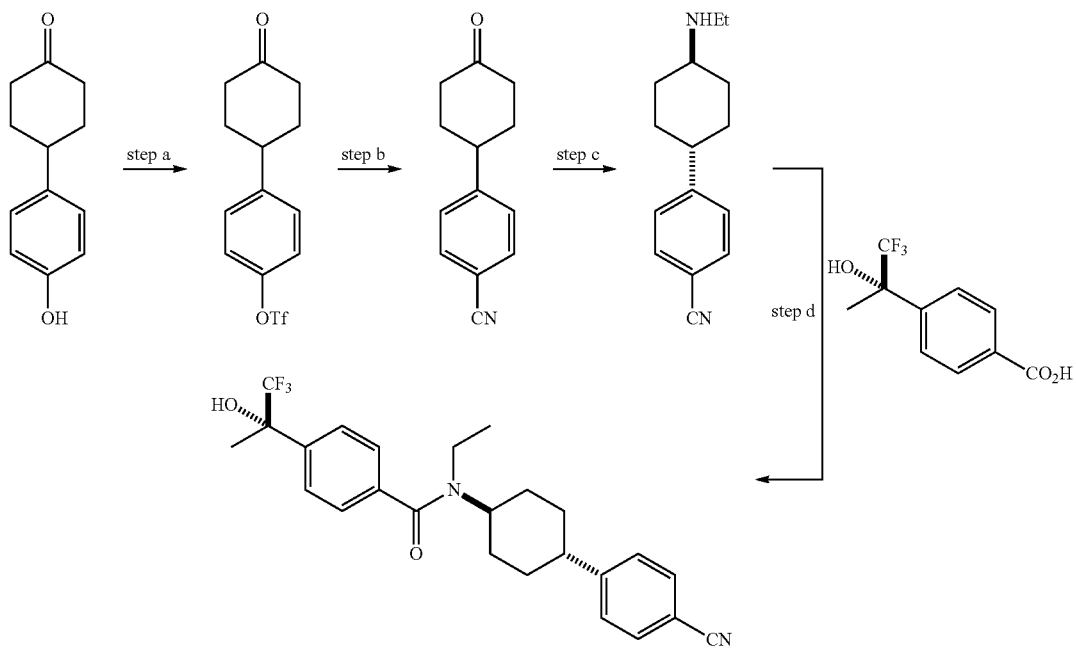

a). To a stirred solution of the 4-(4-hydroxyphenyl)cyclohexanone (2 g, 10.5 mmol, 1 equiv) in 15 mL $CH_2Cl_2$ was added triethylamine (2 mL, 13.6 mmol, 1.3 equiv) and the mixture cooled to −25° C. under N2 in a dry ice bath. Trifluoromethylsulfonic acid anhydride (2.12 mL, 12.6 mmol, 1.2 equiv) was added to the solution dropwise. The mixture was stirred and allowed to warm to ambient temperature overnight. The mixture was then diluted with sat. $NaHCO_3$ solution, extracted (3×$CH_2Cl_2$), washed (1× brine), dried over $Na_2SO_4$, filtered, and concentrated under reduced pressure. Purification by flash chromatography ($SiO_2$, 100% $CH_2Cl_2$) gave the product triflate.

b). $Zn(CN)_2$ (1.17 g, 10 mmol, 1 equiv), dppf (166 mg, 0.3 mmol, 0.03 equiv) and $Pd_2(dba)_3$ (137 mg, 0.15 mmol, 0.015 equiv) were combined in a 25 ml flask and held under high vacuum for 10 minutes. The mixture was then taken up in 5 mL DMF and the triflate generated in step a (5 g, 15.5 mmol, 1.5 equiv) was added, and the mixture stirred with a nitrogen sparge for 5 minutes. The reaction mixture was then heated to 120° C. over night and then allowed to cool to ambient temperature. The mixture was diluted with sat. $NaHCO_3$, filtered to remove insolubles, the filtrate diluted (EtOAc), washed (1× sat. $NaHCO_3$, 1× brine), dried ($Na_2SO_4$), filtered and concentrated. The mixture was purified by flash chromatography to give the product nitrile.

c). To a stirred solution of the ketonitrile prepared above (2 g, 10 mmol, 1 equiv) in 50 mL 2:2:1 THF:1,2-dichloroethane:MeOH was added ethylamine hydrochloride (4.12 g, 50 mmol, 5 equiv) followed by sodium cyanoborohydride (6.36 g, 30 mmol, 3 equiv) and the mixture was stirred under nitrogen for 2.5 hours. The mixture was diluted (10% citric acid (aq)), the aqueous layer was reserved and made basic with 33% KOH (aq), and then extracted (2× EtOAc). The organics were dried over $MgSO_4$, filtered, concentrated and purified over silica (7.5% MeOH in $CH_2Cl_2$ with 1% $NH_4OH$) to isolate the trans isomer.

d). (S)-4-(1,1,1-Trifluoro-2-hydroxypropan-2-yl)benzoic acid (761 mg, 3.25 mmol, 1 equiv) was combined with the ethylamine species generated as in step c (675 mg, 2.96 mmol, 1 equiv) in 10 mL dry DMF, along with HOAt (600 mg, 4.4 mmol, 1.5 equiv), EDC hydrochloride (852 mg, 2.1 mmol, 1.5 equiv) and $NaHCO_3$ (500 mg, 6 mmol, 2 equiv) and the reaction stirred overnight under nitrogen. The reaction was diluted (10% HCl (aq)), extracted (2×$CH_2Cl_2$), washed (1×1 N NaOH) dried over $MgSO_4$, filtered and concentrated. The mixture was purified by HPLC 60-70% acetonitrile-water 18 min. $^1$H NMR (DMSO-d6, 400 MHz, temperature 75 C) δ 7.67 (dd, J=8, 8 Hz, 4H), 7.39 (dd, J=8, 15.6 Hz, 4H), 6.35 (s, 1 Hz), 3.9-3.4 (broad M, 1 H), 3.35 (m, 2H), 2.67 (m, 1H), 1.19-1.60 (broad m, 6H), 1.74 (s, 3H), 1.5-1.34 (broad m, 2H), 1.14-0.9 (dd, J=6.8, 6.8 Hz, 3H); MS(ESI) 445.5 $[M+H]^+$.

Example 22

Preparation of N-ethyl-N-[trans-4-(4-carboxyamidephenyl)cyclohexyl]-4-[(S)-1,1,1-trifluoro-2-hydroxypropan-2-yl]benzamide

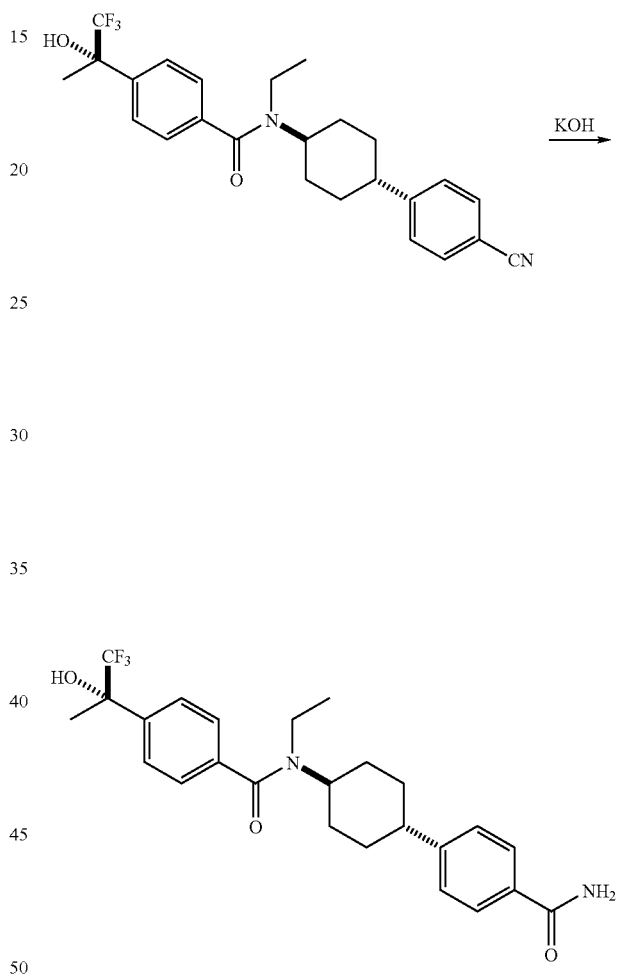

N-ethyl-N4-[trans-4-(4-cyanophenyl)cyclohexyl]-4-[(S)-1,1,1-trifluoro-2-hydroxypropan-2-yl]benzamide prepared in the above example (50 mg, 0.11 mmol, 1 equiv) was hydrolyzed in 1 mL tent-butanol in the presence of KOH (100 mg) at 100° C. overnight. The mixture was allowed to cool to ambient temperature, diluted with water, extracted (3×5% MeOH in $CH_2Cl_2$), dried ($Na_2SO_4$), filtered and concentrated. The resulting oil was purified by HPLC (45-60% acetonitrile/water, 45 minute gradient) to yield the product carboxyamide as a white solid. $^1$H NMR (DMSO-d6, 400 MHz) δ 7.87 (s, 1H), 7.84-7.71 (broad m, 2H), 7.66 (d, J=7.6 Hz, 2H), 7.38 (d, J=8 Hz, 2H), 7.35-7.1 (broad m, 3H), 6.69 (s, 1H), 4.4-4.0 (broad m, 1H), 3.3-3.1 (broad m, 1H), 2.0-1.5 (broad m, 10H), 1.4-0.9 (broad m, 5H); MS(ESI) 463.5 $[M+H]^+$.

Example 23

Preparation of N-cyclopropyl-N-(trans-4-(pyridin-3-yl)cyclohexyl)-4-((S)-1,1,1-trifluoro-2-hydroxypropan-2-yl)benzamide

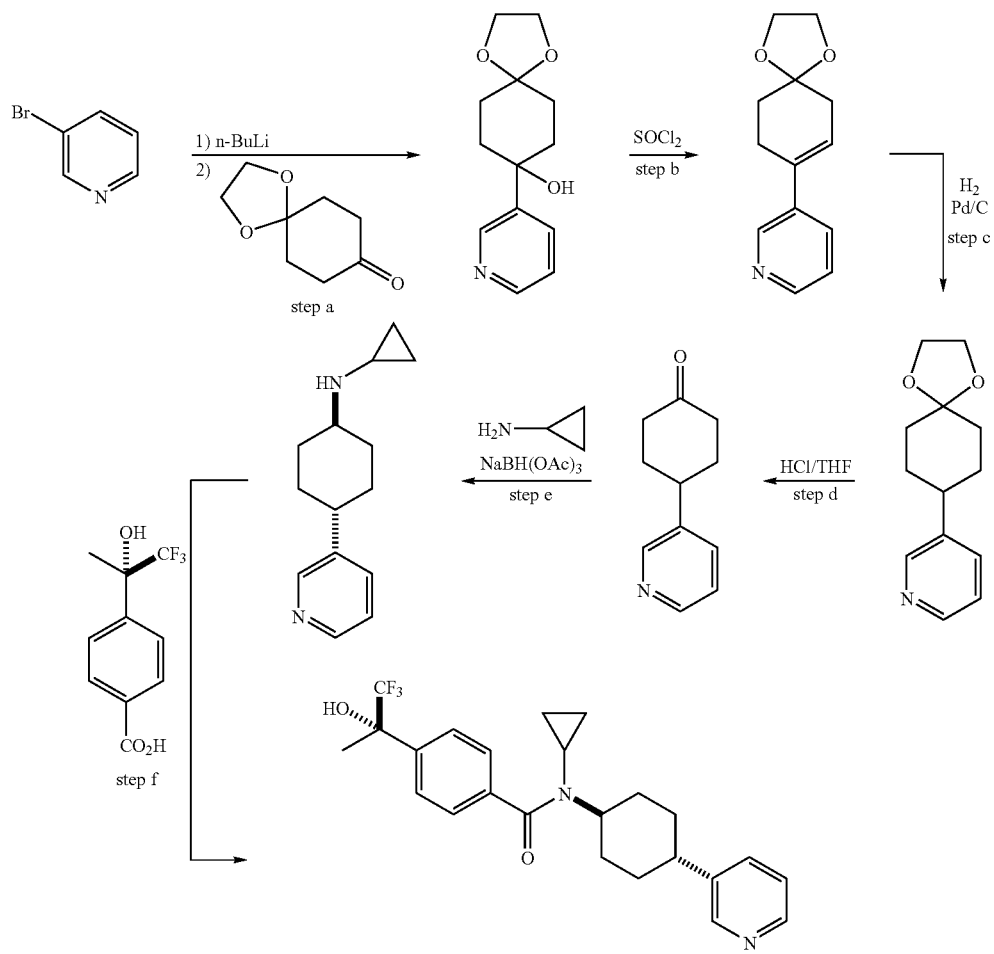

a). To a solution of n-BuLi (2.5 M in hexanes, 88.4 mL, 221.0 mmol) in Et$_2$O (250 mL) at −78° C. was added a chilled solution (−78° C.) of 3-bromopyridine (35 g, 221.0 mmol) in Et$_2$O (125 mL) via cannula. After being stirred for 10 min, a solution of 1,4-cyclohexanedione monoethylene ketal (34.5 g, 221.0 mmol) in THF (125 mL) was added via cannula The reaction mixture was stirred for 1 h at −78° C., then slowly warmed to −20° C. over 1 h. The reaction was quenched by pouring into saturated aqueous NH$_4$Cl, and the layers were separated. The aqueous layer was extracted with CH$_2$Cl$_2$ (100 mL×3) and the combined organic layers were washed with brine (200 mL), dried with MgSO$_4$ and concentrated in vacuo. The crude product was triturated with Et$_2$O to afford 4-hydroxy-4-(3-pyridyl)cyclohexanone ethylene ketal as a white solid.

b). Thionyl chloride (45 mL, 622.5 mmol) was slowly added to a solution of 4-hydroxy-4-(3-pyridyl)cyclohexanone ethylene ketal (prepared as in step a, 29.3 g, 124.5 mmol) in pyridine (250 mL) at −10° C. After stirring at 0° C. for 2.5 h, the reaction mixture was poured onto ice and adjusted to pH 8 with 2 N NaOH. The aqueous layer was extracted with CH$_2$Cl$_2$ (100 mL×3) and the combined organic layers were washed with brine (200 mL), dried with MgSO$_4$, and concentrated in vacuo to afford crude 4-(3-pyridyl)cyclohex-3-en-1-one ethylene ketal, which was used without further purification.

c). A mixture of 4-(3-pyridyl)cyclohex-3-en-1-one ethylene ketal prepared above (26 g, 120.0 mmol) in EtOAc (240 mL), containing 10% Pd/C (3.9 g), was hydrogenated under atmospheric pressure for 24 h. At this time, an additional 1.3 g of 10% Pd/C was added and the mixture allowed to stir an additional 2.5 d under an atmosphere of hydrogen gas. The reaction mixture was filtered through a pad of celite and concentrated in vacuo to afford crude 4-(3-pyridyl)cyclohexanone ethylene ketal, which was used without further purification.

d). A solution of 4-(3-pyridyl)cyclohexanone ethylene ketal prepared above (27 g, 120.0 mmol) in THF (200 mL) and 2 N HCl (100 mL) was stirred at 23° C. for 23 h. The reaction was quenched by adding saturated aqueous NaHCO$_3$ and diluted with EtOAc (200 mL). The aqueous layer was extracted with CH$_2$Cl$_2$ (100 mL×4) and the combined organic layers were washed with brine (200 mL), dried with MgSO$_4$ and concentrated in vacuo. The crude product was filtered through a plug of silica gel, washing with 5% MeOH in CH$_2$Cl$_2$, which afforded 4-(3-pyridyl)cyclohexanone.

e). Cyclopropyl amine (11.4 mL, 165 mmol) was added to a solution of 4-(3-pyridyl)cyclohexanone (19.2 g, 110 mmol)

in DCE (360 mL) and acetic acid (12.6 mL, 220 mmol). The reaction mixture was cooled to 0° C. and NaBH(OAc)$_3$ (46 g, 220 mmol) was added protionwise. After being stirred for 21 h at 23° C., the reaction was re-cooled to 0° C. and quenched with 1 M NaOH (200 mL). The aqueous layer was extracted with CH$_2$Cl$_2$ (2×200 mL) and the combined organic layers were washed with brine (300 mL), dried with MgSO$_4$, filtered, and concentrated in vacuo. The crude mixture of cis and trans amines was purified by flash column chromatography (gradient elution, 40% EtOAc/hexanes (2.5% TEA)→70% EtOAc/hexanes (2.5% TEA)) to provide trans-N-cyclopropyl-4-(pyridine-3-yl)cyclohexylamine.

f). trans-N-cyclopropyl-4-(pyridine-3-yl)cyclohexylamine (7.3 g, 34.0 mmol, prepared as described above), (S)-4-(1,1,1-trifluoro-2-hydroxypropan-2-yl)benzoic acid (8.7 g, 37.3 mmol), EDCI (9.1 g, 47.6 mmol), HOAt (6.5 g, 47.6 mmol), and NaHCO$_3$ (5.7 g, 68.0 mmol) were combined and dissolved in DMF (125 mL). After being stirred for 16 h at 23° C., the reaction was quenched with 1 M NaOH (150 mL) and diluted with EtOAc (300 mL). The aqueous layer was extracted with EtOAc (100 mL) and 10% MeOH/CH$_2$Cl$_2$ (5×100 mL) and the combined organic layers were washed with H$_2$O (400 mL) and brine (400 mL), dried with MgSO$_4$, filtered, and concentrated in vacuo. The crude material was purified by flash column chromatography (gradient elution, 3%→10% MeOH/CH$_2$Cl$_2$) to afford the product: $^1$H NMR (CDCl$_3$, 500 MHz) δ 8.49 (s, 1H), 8.46 (d, J=3.6 Hz, 1H), 7.61 (d, J=8.1 Hz, 2H), 7.58 (d, J=7.7 Hz, 1H), 7.50 (d, J=8.3 Hz, 2H), 7.24 (dd, 1H-overlapping with CDCl$_3$), 4.23 (m, 1H), 2.80 (m, 1H), 2.62 (m, 2H), 2.05 (m, 6H), 1.80 (s, 3H), 1.65 (m, 2H), 0.60 (d, J=4.8 Hz, 2H), 0.49 (m, 2H); MS(ESI) 433.3 [M+H]$^+$; Anal. (C$_{24}$H$_{27}$F$_3$N$_2$O$_2$) C, H, N.

Example 24

Preparation of N-(trans-4-(6-cyanopyridin-3-yl)cyclohexyl)-N-ethyl-4-((S)-1,1,1-trifluoro-2-hydroxypropan-2-yl)benzamide a) To a solution of 4-(3-pyridyl)cyclohexanone ethylene ketal (3.6 g, 16.5 mmol) in CH$_2$Cl$_2$ (65 mL) was added m-CPBA (4.3 g, 24.8 mmol). After being stirred for 2 hr at 23° C., the reaction mixture was diluted with CH$_2$Cl$_2$ and washed with 1 M NH$_4$OH (2×50 ml), then H$_2$O (5×50 mL). The aqueous layer was extracted with CH$_2$Cl$_2$ (4×50 mL), washed with brine (2×20 mL), dried with MgSO$_4$, filtered, and concentrated in vacuo to afford the N-oxide product. The crude material was used in the subsequent reaction without further purification.

b) A solution of the N-oxide prepared above (2.7 g, 11.5 mmol), Et$_3$N (8.0 mL, 57.5 mmol), TMSCN (4.5 mL, 34.4 mmol) and CH$_3$CN (40 mL) was heated to 85° C. After being stirred for 14 h, the reaction mixture was cooled to 23° C. and concentrated in vacuo. This material was diluted with EtOAc (100 mL), washed with NaHCO$_3$ (2×50 mL) and brine (100 mL), and the combined aqueous layers were extracted with 10% MeOH/CH$_2$Cl$_2$ (5×50 mL), dried with MgSO$_4$, filtered, and concentrated in vacuo. The crude material was purified by flash column chromatography (gradient elution, 0%→5%→10% MeOH/CH$_2$Cl$_2$) to afford a 1.4:1 mixture of 6-cyano (desired) and 2-cyano pyridines.

c) To a solution of 5-(4-oxocyclohexyl)picolinonitrile (prepared by ketal hydrolysis of the material prepared in step b, as in step d of the previous example) mixed with ~40% of 3-(4-oxocyclohexyl)picolinonitrile (395 mg, 1.97 mmol), ethylamine hydrochloride (322 mg, 3.95 mmol), DCE (4 mL), MeOH (4 mL), and THF (4 mL) was added sodium triacetoxyborohydride (837 mg). After being stirred for 15 h at 23° C., the reaction mixture was quenched with 1 M NaOH (20 mL), diluted with EtOAc, and washed with brine (20 mL). The aqueous layer was extracted with 10% MeOH/CH$_2$Cl$_2$, dried with MgSO$_4$, filtered, and concentrated in vacuo. The crude material was purified by flash column chromatography (gradient elution, 40% EtOAc/hexanes (2.5% TEA)→100% EtOAc/hexanes (2.5% TEA) →10% MeOH/CH$_2$Cl$_2$ (2.5% TEA)) to provide a 2.8:1 mixture of 5-(trans-4-(ethylamino)cyclohexyl)picolinonitrile and 3-(trans-4-(ethylamino)cyclohexyl)picolinonitrile.

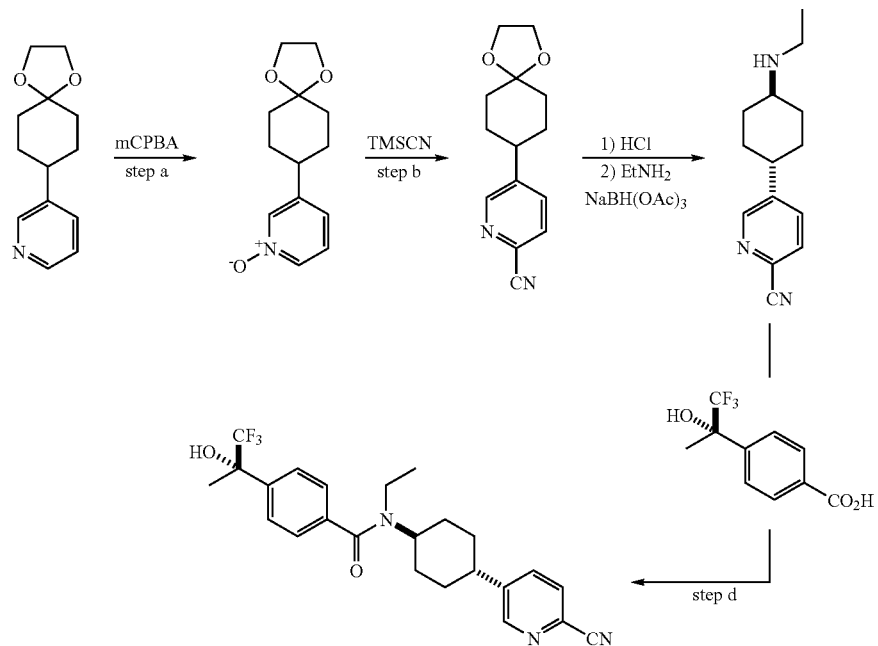

d) Using the conditions from step f described in the previous example, the following compound was prepared: N-(trans-4-(6-cyanopyridin-3-yl)cyclohexyl)-N-ethyl-4-((S)-1,1,1-trifluoro-2-hydroxypropan-2-yl)benzamide: $^1$H NMR (MeOD, 400 MHz, mixture of rotamers) δ 8.66 (m, 0.5H), 8.55 (m, 1H), 7.94 (m, 0.5 H), 7.75 (d, J=7.0 Hz, 5H), 7.43 (d, J=7.7 Hz, 3H), 4.31 (m, 0.5 H), 3.67 (m, 1H), 3.56 (m, 2H), 2.71 (m, 1.5 H), 1.99 (m, 9.5 H), 1.78 (s, 5H), 1.32 (m, 5H), 1.11 (m, 1.5 H); MS(ESI) 446.2 [M+H]$^+$; Anal. ($C_{24}H_{26}F_3N_3O_2$) C, H, N; C: calcd 64.71; found, 64.12, H: calcd 5.88; found, 5.89, N: calcd 9.43; found, 9.08.

Example 25

Preparation of 4-(3-fluoropyridin-2-yl)-4-hydroxycyclohexanone ethylene ketal and 4-(3-fluoropyridin-4-yl)-4-hydroxycyclohexanone ethylene ketal

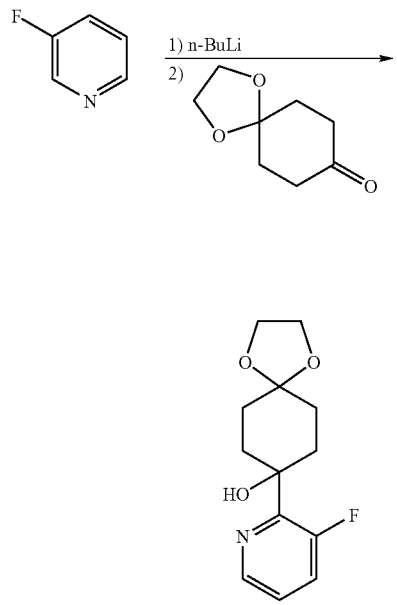

To a solution of n-BuLi (2.5 M in hexanes, 8.4 mL, 21.1 mmol) in Et$_2$O (30 mL) at −78° C. was added 3-fluopyridine (2 g, 20.1 mmol) in Et$_2$O (7 mL) via syringe. After being stirred for 30 min at −40° C., the reaction mixture was cooled to −78° C. and a solution of 1,4-cyclohexanedione monoethylene ketal (3.1 g, 20.0 mmol) in Et$_2$O:THF (7:3, 7 mL) was added via syringe. The reaction mixture was stirred for 2 h at −78° C., then warmed to −10° C. over 1 h. The reaction was quenched by pouring into saturated aqueous NH$_4$Cl, and the layers were separated. The aqueous layer was extracted with CH$_2$Cl$_2$ (50 mL×3) and the combined organic layers were washed with brine (100 mL), dried with MgSO$_4$, and concentrated in vacuo. The crude product was purified by flash column chromatography (gradient elution, 3%→5%→10% MeOH/CH$_2$Cl$_2$) to provide 4-(3-fluoropyridin-2-yl)-4-hydroxycyclohexanone ethylene ketal (contaminated with ~30% of 1,4-cyclohexanedione monoethylene ketal) and 4-(3-fluoropyridin-4-yl)-4-hydroxycyclo-hexanone ethylene ketal.

Example 26

Preparation of N-cyclopropyl N-(trans-4-(3-fluoropyridin-2-yl)-cyclohexyl)-4-((S)-1,1,1-trifluoro-2-hydroxypropan-2-yl)benzamide

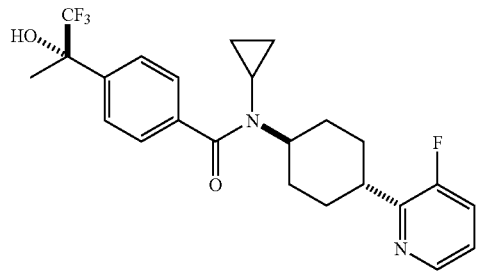

Using the steps described in the previous examples and starting with 4-(3-fluoropyridin-2-yl)-4-hydroxycyclohexanone ethylene ketal, the following compound was prepared: N-cyclopropyl N-(trans-4-(3-fluoropyridin-2-yl)-cyclohexyl)-4-((S)-1,1,1-trifluoro-2-hydroxypropan-2-yl)benzamide: $^1$H NMR (CDCl$_3$, 500 MHz) δ 8.37 (br s, 1H), 7.60 (d, J=7.4 Hz, 2H), 7.50 (d, J=7.9 Hz, 2H), 7.35 (t, J=8.4 Hz, 1H), 7.17 (br s, 1H), 4.22 (m, 1H), 3.13 (m, 1H), 2.64 (m, 1H), 2.10 (m, 4H), 2.01 (m, 2H), 1.92 (m, 2H), 1.81 (s, 3H), 0.64 (m, 2H), 0.54 (m, 2H); MS(ESI) 451.1 [M+H]$^+$; Anal. ($C_{24}H_{26}F_4N_2O_2$) C, H, N; C: calcd 63.99; found, 63.42, H: calcd 5.82; found, 5.77, N: calcd 6.22; found, 6.00.

Example 27

Preparation of N-cyclopropyl N-(trans-4-(3-fluoropyridin-4-yl)-cyclohexyl)-4-((S)-1,1,1-trifluoro-2-hydroxypropan-2-yl)benzamide

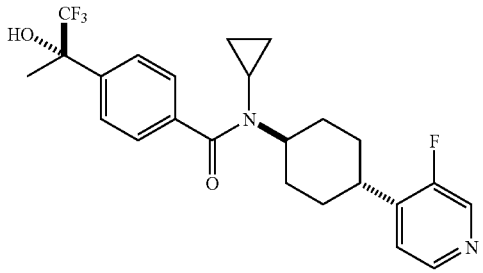

Using the steps described in the previous examples and starting with 4-(3-fluoropyridin-4-yl)-4-hydroxycyclohexanone ethylene ketal, the following compound was prepared: N-cyclopropyl N-(trans-4-(3-fluoropyridin-4-yl)-cyclohexyl)-4-((S)-1,1,1-trifluoro-2-hydroxypropan-2-yl)benzamide: $^1$H NMR (CDCl$_3$, 500 MHz) δ 8.45 (s, 1H), 8.41 (d, J=5.0 Hz, 1H), 7.64 (d, J=8.3 Hz, 2H), 7.54 (d, J=8.2 Hz, 2H), 7.30 (d, overlapping with CDCl$_3$, 1H), 4.29 (m, 1H), 3.02 (m, 1H), 2.65 (m, 1H), 2.13 (m, 4H), 2.06 (m, 2H), 1.83 (s, 3H), 1.70 (m, 2H), 0.63 (m, 2H), 0.52 (m, 2H); Anal. ($C_{24}H_{26}F_4N_2O_2$) C, H, N.

Example 28

Preparation of (S)-N-(4-(2-cyanoethyl)cyclohexyl)-N-cyclopropyl-4-(1,1,1-trifluoro-2-hydroxypropan-2-yl)benzamide

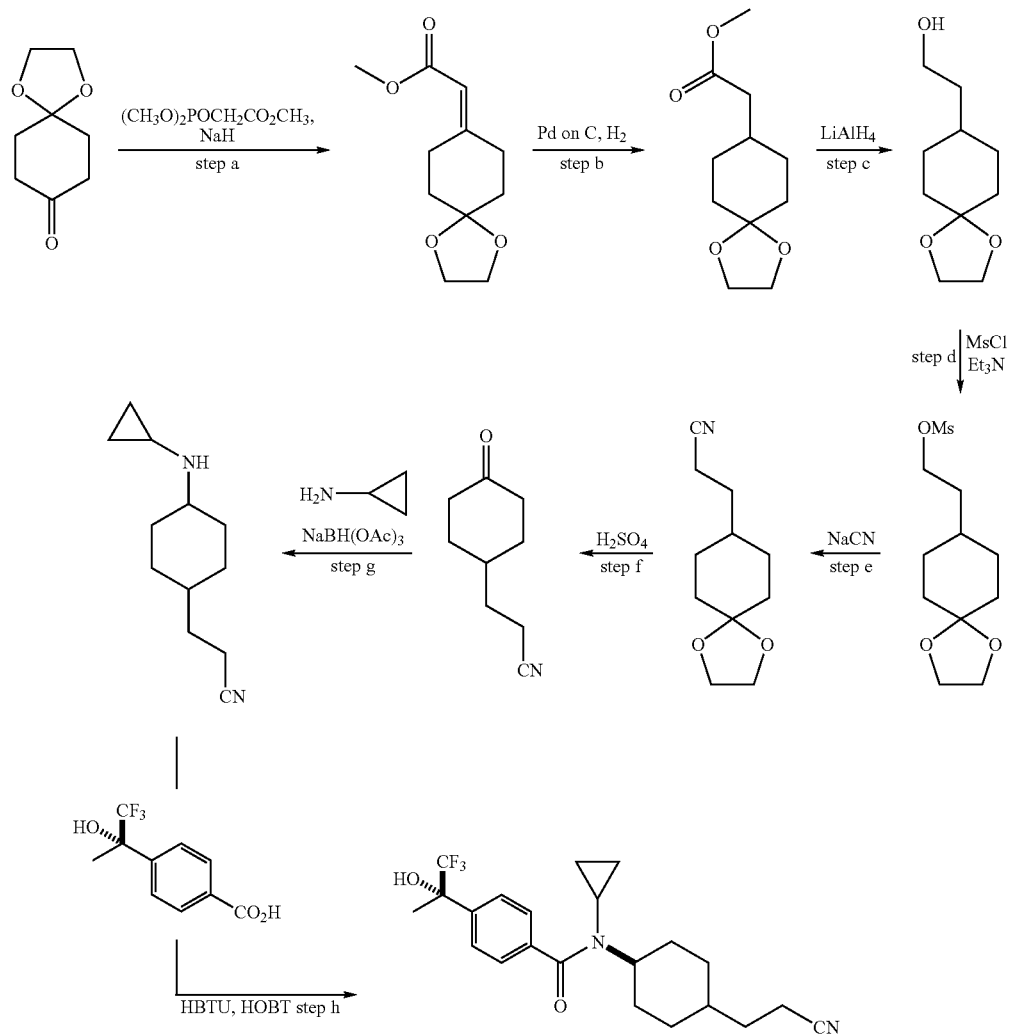

a). To a 0° C. solution of trimethyl phosphonoacetate (4.8 mL, 34 mmol) in DMPU (12 mL) and THF (30 mL) was added a suspension of NaH (0.74 g, 31 mmol) in THF (45 mL). To the resulting mixture was added a solution 1,4-dioxaspiro[4.5]decane-8-one (4.7 g, 30 mL) in THF (30 mL). After stirring at 0° C. for 5 min the suspension was allowed to reach room temperature and stirred for 12 h. The resulting solution was poured into water (900 mL) and extracted with Et$_2$O (2×200 mL). The combined organics were washed with brine and dried over MgSO$_4$, and organics were removed in vacuo. Silica gel chromatography (gradient of 5 to 7% ethyl acetate in hexanes) afforded the product.

b). To the ketal protected methyl 2-(4-oxocyclohexylidene)acetate prepared in step a (5.4 g, 25 mmol) and 10% Pd on C (1 mmol) was added under a nitrogen atmosphere EtOH (150 mL). The vessel was evacuated and purged to a H$_2$ balloon, and the contents were stirred overnight under H$_2$ balloon atmosphere. Following evacuation and purging to nitrogen, the contents were filtered through Celite. The pad was washed successively with EtOH and CH$_2$Cl$_2$. Organics were removed in vacou to afford the product.

c). To a suspension of LiAlH$_4$ (1.4 g, 37 mmol) in THF (40 mL) was added a solution of the ketal protected methyl 2-(4-oxocyclohexyl)acetate (5.3 g, 25 mmol) prepared in step b in THF (40 mL). The reaction was brought to reflux and stirred for 17.5 h. To the reaction was added EtOAc (2.25 mL) followed by water (1.5 mL), 10% NaOH (1.5 mL), and water (6 mL). The suspension was dried with MgSO$_4$ and filtered. Organics were removed in vacuo to afford the product.

d). To solution of the ketal protected 4-(2-hydroxyethyl)cyclohexanone prepared in step c (4.6 g, 25 mmol) and TEA (7 mL, 50 mmol) in THF (65 mL) cooled to 0° C. was added a solution of methanesulfonyl chloride (2.9 mL, 37 mmol) in THF (16 mL). The reaction was warmed to room temperature and stirred for 23 h. The solution was poured into saturated NaHCO$_3$ (80 mL) and Et$_2$O (160 mL). The sequestered organics were dried with MgSO$_4$ and removed in vacuo to afford the product.

e). A suspension of the ketal protected 2-(4-oxocyclohexyl)ethyl methanesulfonate produced in step d (6.6 g, 25 mmol) and NaCN (3.7 g, 75 mmol) in DMSO (100 mL) was heated to 120° C. and stirred for 24 h. To the cooled suspension was added Et₂O (200 mL) and water (200 mL). The organics were further washed with water (3×200 mL) and brine (200 mL), and were dried over MgSO₄. Removal of solvent in vacuo afforded the product.

f). To a solution of the ketal protected 3-(4-oxocyclohexyl) propanenitrile produced in step e (1.1 g, 5.7 mmol) in EtOH (20 mL) was added 20% H₂SO₄ (aq) (20 mL). The reaction was stirred for 8 h. Following neutralization with 5 N NaOH, the solution was exctracted with E₂O (3×100 mL). The combined organics were dried over MgSO₄ and removed in vacuo to afford the product.

g). To a solution of 3-(4-oxocyclohexyl)propanenitrile prepared in step f (0.81 g, 5.4 mmol) in dichloroethane (16 mL) was added cyclopropyl amine (0.38 mL, 5.4 mmol) and NaBH(OAc)₃ (1.7 g, 8.1 mmol). The reaction was cooled to 0° C. and AcOH (0.31 mL, 5.4 mmol) was added. After 5 min, the reaction was allowed to warm to room temperature and was stirred for 4 h. To the suspension was added water (15 mL). The aqueous acidity was brought to pH 2 with 5 N HCl and the organics were removed following extraction. The aqueous layer was brought to pH 13 with 5 N NaOH and was extracted with 10% MeOH in CH₂Cl₂ (3×30 mL). The combined organics were dried over Na₂SO₄ and removed in vacuo to afford the product.

h) To a solution of (S)-4-(1,1,1-trifluoro-2-hydroxypropan-2-yl)benzoic acid (0.33 g, 1.4 mmol), HBTU (0.64, 1.7 mmol), and HOBt (0.24 g, 1.8 mmol) in DMF (3.3 mL) was added Hünig's base (0.58 mL, 3.4 mmol). The solution was stirred for 5 minutes prior to the addition of 3-(4-(cyclopropylamino)cyclohexyl)propanenitrile prepared in step g (0.32 g, 1.7 mmol). The reaction was stirred at room temperature for 5 h followed by quenching with 3-(dimethylamino)-propylamine (0.1 mL). The reaction contents were poured into 1 N HCl (30 mL) and extracted with CH₂Cl₂ (2×10 mL). The organic layer was washed with 0.5 N NaOH (10 mL), dried with Na₂SO₄, and concentrated in vacuo. Silica gel chromatography (60% MTBE in hexanes) separated cis and trans isomers with the desired trans isomer eluting last to provide (S)-N-(4-(2-cyanoethyl)cyclohexyl)-N-cyclopropyl-4-(1,1,1-trifluoro-2-hydroxypropan-2-yl)benzamide. ¹H NMR (500 MHz, CDCl₃): δ 0.40-0.48 (bs, 2H), 0.58 (bd, J=6 Hz, 2H), 1.05-1.20 (m, 2 H), 1.42-1.56 (m, 1H), 1.60-1.64 (m, 3H), 1.81 (s, 3H), 1.85-1.92 (m, 4H), 1.97-2.00 (m, 2H), 2.41 (t, J=7 Hz, 2H), 2.56-3.00 (m, 1 H), 2.69 (bs, 1H), 4.13 (bs, 1H), 7.48 (d, J=8 Hz, 2H), 7.60 (d, J=8 Hz, 2H).

Example 29

Preparation of (S)-N-(4-(3-amino-3-oxopropyl)cyclohexyl)-N-cyclopropyl-4-(1,1,1-trifluoro-2-hydroxypropan-2-yl)benzamide

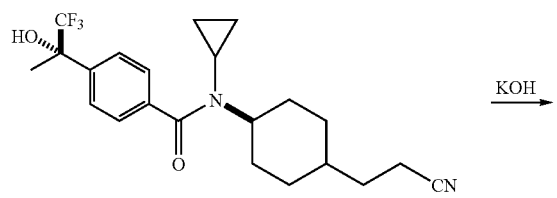

KOH

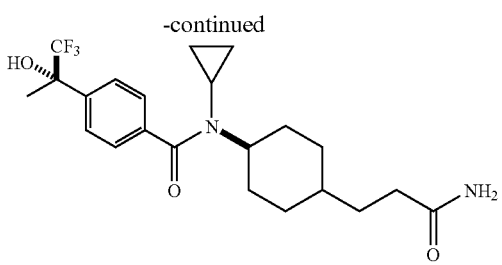

To (S)-N-(4-(2-cyanoethyl)cyclohexyl)-N-cyclopropyl-4-(1,1,1-trifluoro-2-hydroxypropan-2-yl)benzamide prepared above (0.040 g, 0.098 mmol) and KOH (0.55 g, 0.98 mmol) was added tent-butanol (3.75 mL). The mixture was heated to 85° C. and stirred for 15 h. The solution was diluted with water (10 mL) and extracted with 10% MeOH in CH₂Cl₂ (2×15 mL). The combined organics were dried over Na₂SO₄ and removed in vacuo. Silica gel chromatography (gradient of 0-10% MeOH in CH₂Cl₂) afforded (S)-N-(4-(3-amino-3-oxopropyl)cyclohexyl)-N-cyclopropyl-4-(1,1,1-trifluoro-2-hydroxypropan-2-yl)benzamide. ¹H NMR (500 MHz, CD₃OD): δ 0.45 (bs, 2H), 0.58 (bs, 2H), 1.05-1.15 (m, 2 H), 1.27-1.48 (m, 2H), 1.51-1.59 (m, 2H), 1.77 (s, 3H), 1.90-2.00 (m, 5H), 2.25-2.28 (m, 2H), 2.71 (bs, 1H), 4.00 (bs, 1H), 7.52 (d, J=8 Hz, 2H), 7.70 (d, J=8 Hz, 2H).

Biological Examples

Procedures Useful for the Biological Evaluation of the Benzamide Derivatives

In addition to the extensive literature disclosing the role of HSDs in various diseases and disorders, described herein are assays useful for testing the Benzamide Derivatives of the present invention.

Assays

In vitro 11β-HSD1 (Hydroxysteroid Dehydrogenase 1) Activity Inhibitory Action

The 11β-HSD1 inhibitory activity was examined by quantitative determination by an SPA (scintillation proximity assay) system of the suppressive action on the conversion from cortisone to cortisol using human 11β-HSD1 (hereinafter recombinant 11β-HSD1) expressed using a baculo-virus system as an enzyme source. For the reaction, a reagent was added to a 96 well plate (96 well Opti-plates™-96 (Packard)) to the following final concentration and a volume of 100 μl was reacted at room temperature for 90 min. The reaction solution used was 0.1 μg/ml recombinant 11β-HSD1, 500 μM NADPH, 16 nM ³H cortisone (Amersham Biosciences, 1.78 Tbq/mol) dissolved in 0.1% BSA (Sigma)-containing PBS and the test drug was 2 μl of a compound solution (dissolved in DMSO). After 90 min, the reaction was stopped by adding PBS (40 μl, containing 0.1% BSA (Sigma)) containing 0.08 μg of anti-cortisol mouse monoclonal antibody (East Coast Biologics), 365 μg SPA PVT mouse antibody-binding beads (Amersham Biosciences) and 175 μM carbenoxolone (Sigma) to the reaction solution. After the completion of the reaction, the plate was incubated overnight at room temperature and the radioactivity was measured by Topcount (Packard). For control, the value (0% inhibition) of the well containing 2 μl of DMSO instead of the test drug was used, and for positive control, the value (100% inhibition) of the well containing carbenoxolone instead of the test drug at the final concentration of 50 μM was used. The inhibition (%) of the test drug was calculated by ((value of control−value of test drug)/(value of control−value of positive control))×100(%).

The IC$_{50}$ value was analyzed using a computer-based curve fitting software.

This example provides assays that are useful in evaluating and selecting a compound that modulates 11β-HSD1.

Biochemical 11β-HSD1 assay by SPA

Recombinant human, mouse and rat 11β-HSD1 were expressed in baculovirus expression system, isolated by affinity purification and used as the enzyme sources for cortisone to cortisol conversion in vitro. $^3$H-Cortisone (Amersham Bioscience, 1.78 Tbq/mol. 49 Ci/mmol) was used as the substrate, and a monoclonal anti-cortisol antibody and the scintillation proximity assay (SPA) system were used to detect the product of the 11β-HSD1-catalyzed reaction, $^3$H-cortisol. Reactions took place at room temperature for 90 min. in 96-well Opti-plates™-96 (Packard) in 100 µL volume with 2 µL test compounds or control in DMSO, 0.1 µg/mL 11β-HSD1 protein, 500 µM NADPH and 16 nM radioactive cortisone, in PBS buffer supplemented with 0.1% BSA (Sigma). Reaction was stopped with the addition of 40 µL buffer containing 0.08 µg anti-cortisol monoclonal antibody (East Coast Biologics), 365 µg SPA PVT antibody-binding beads (Amersham Biosciences) and 175 µM carbenoxolone (Sigma).

Plates were incubated at room temperature overnight before being read on a Topcount (Packard). The point of 50% inhibition of 11β-HSD1 enzyme activity (IC$_{50}$) was determined by computer-based curve fitting.

Cell-Based 11β-HSD1 Assay by SPA

This cell-based assay measures the conversion of $^3$H-cortisone to $^3$H-cortisol in a HEK-293 cell line stably overexpressing human recombinant 11β-HSD1. HEK-293 cells were grown in DMEM/F12 supplemented with 10% fetal bovine serum, and plated onto poly-D-lysine-coated 96-well assay plates (Costar 3903), 100,000 cells per well in 50 µL assay media (phenol free DMEM/F12 (Invitrogen)+0.2% BSA+1% antibiotic-antimycotic solutions). The solution was incubated at 37° C. for 24 h, and the reaction was initiated by the addition of 25 µL of assay media containing compounds of desired concentration and 25 µL of assay media containing 40 nM of $^3$H-cortisone to each well. The reaction mixture was incubated at 37° C. for 90 min. and the reaction terminated by the addition of 25 µL of assay media containing 0.2 µg of anti-cortisol monoclonal antibody (East Coast Biologics), 500 µg SPA PVT antibody-binding beads (Amersham Biosciences) and 500 µM carbenoxolone (Sigma).

Plates were incubated at room temperature for at least 2 h before being read on Topcount (Packard). The point of 50% inhibition of 11β-HSD1 enzyme activity (IC$_{50}$) was determined by computer-based curve fitting.

Cell-Based 11β-HSD1 Assay by SPA

This cell-based assay measures the conversion of $^3$H-cortisone to $^3$H-cortisol in a HEK-293 cell line stably overexpressing human recombinant 11β-HSD1. HEK-293 cells were grown in DMEM/F12 supplemented with 10% fetal bovine serum, and plated onto poly-D-lysine-coated 96-well assay plates (Costar 3903), 100,000 cells per well in 50 µL assay media (phenol free DMEM/F12 (Invitrogen)+0.2% BSA+1% antibiotic-antimycotic solutions). The solution was incubated at 37° C. for 24 h, and the reaction was initiated by the addition of 25 µL of assay media containing compounds of desired concentration and 25 µL of assay media containing 40 nM of $^3$H-cortisone to each well. The reaction mixture was incubated at 37° C. for 90 min. and the reaction terminated by the addition of 25 µL of assay media containing 0.2 µg of anti-cortisol monoclonal antibody (East Coast Biologics), 500 µg SPA PVT antibody-binding beads (Amersham Biosciences) and 500 µM carbenoxolone (Sigma).

Plates were incubated at room temperature for at least 2 h before being read on Topcount (Packard). The point of 50% inhibition of 11β-HSD1 enzyme activity (IC$_{50}$) was determined by computer-based curve fitting.

Scintillation Proximity Assay

[1,2(n)-$^3$H]-cortisone was purchased from Amersham Pharmacia Biotech. Anti-cortisol monoclonal mouse antibody, clone 6D6.7 was obtained from Immunotech and Scintillation proximity assay (SPA) beads coated with monoclonal antimouse antibodies were from Amersham Pharmacia Biotech. NADPH, tetrasodium salt was from Calbiochem and glucose-6-phosphate (G-6-P) was supplied by Sigma. The human 11-β-hydroxysteroid dehydrogenase type-1 enzyme (11-β-HSD1) was expressed in *Pichia pastoris*. 18-β-glycyrrhetinic acid (GA) was obtained from Sigma. The serial dilutions of the compounds were performed on a Tecan Genesis RSP 150. Compounds to be tested were dissolved in DMSO (1 mM) and diluted in 50 mM Tris-HCl, pH 7.2 containing 1 mM EDTA.

The multiplication of plates was done on a WallacQuadra. The amount of the product [$^3$H]-cortisol, bound to the beads was determined in a Packard, Top Count microplate liquid scintillation counter.

The 11-β-HSD1 enzyme assay was carried out in 96 well microtiter plates (Packard, Optiplate) in a total well volume of 220 µL and contained 30 mM Tris-HCl, pH 7.2 with 1 mM EDTA, a substrate mixture tritiated Cortisone/NADPH (175 nM/181 µM), G-6-P (1 mM) and inhibitors in serial dilutions (9 to 0.15 µM). Reactions were initiated by the addition of human 11-β-HSD$_1$, either as *Pichia pastoris* cell homogenate or microsomes prepared from *Pichia pastoris* (the final amount of enzyme used was varied between 0.057 to 0.11 mg/mL). Following mixing, the plates were shaken for 30 to 45 minutes at room temperature. The reactions were terminated with 10 µL 1 mM GA stop solution. Monoclonal mouse antibody was then added (10 µL of 4 µM) followed by 100 µL of SPA beads (suspended according to the manufacturers instructions). Appropriate controls were set up by omitting the 11-β-HSD1 to obtain the non-specific binding (NSB) value.

The plates were covered with plastic film and incubated on a shaker for 30 minutes, at room temperature, before counting. The amount of [$^3$H]-cortisol, bound to the beads was determined in a microplate liquid scintillation counter. The calculation of the K$_i$ values for the inhibitors was performed by use of Activity Base. The K$_i$ value is calculated from IC$_{50}$ and the K$_m$ value is calculated using the Cheng Prushoff equation (with reversible inhibition that follows the Michaelis-Menten equation): K$_i$=IC$_{50}$(1+[S]/K$_m$) [Cheng, Y. C.; Prushoff, W. H. Biochem. Pharmacol. 1973, 22, 3099-3108]. The IC$_{50}$ is measured experimentally in an assay wherein the decrease of the turnover of cortisone to cortisol is dependent on the inhibition potential of each substance.

Cloning, Expression and Purification of 11β-HSD1

The expression and purification of the murine enzyme is described by J. Zhang, et al. Biochemistry, 44, 2005, pp 6948-57. The expression and purification of the human enzyme is similar to that of the murine sequence.

Enzyme Assay:

The 1050 and Ki of the compounds are determined by the following method:

1. Prepare an Assay Buffer, (pH 7.2, 50 mM Tris-HCL, 1 mM EDTA) fresh each week.
2. Prepare the following solutions:
   NADPH (Sigma, 200 µM)
   $^3$H-Cortisone (Amersham Biosciences, 45 Ci/mmol, 200 nM)

Enzyme Prep (20 nM for human, 10 nM for mouse)
Cortisol Antibody (East Coast Biologicals, (1:50 dilution)
Anti-mouse SPA beads (Amersham Biosciences, 15 mg/ml)
18β-Glycyrrhetinic acid ("GA") (Aldrich, 1 μM)
Compound Stock Solution (10 mM in DMSO), serially diluted in assay buffer. Each compound is tested at six different concentrations usually (10 μM to 0.1 nM). All of the solutions and dilutions are made in the Assay Buffer.

3. Assay is run using white/white, 96-well assay plates (Corning) in a total volume of 100 μL.

4. Into each well of a 96-well plate is added Assay Buffer (30 μL), compound (10 μL) NADPH (10 μL), and $^3$H-cortisone (10 μL).

5. Initiate reaction by adding 40 μL of HSD-1 enzyme prep to the wells.

6. The plate is covered with tape and incubated on an orbital shaker for 1 h at RT.

7. After 1 h, the tape is removed and anti-cortisol antibody (10 μL), GA solution (10 μL), and SPA bead preparation (100 μL) is added.

8. The plate is incubated (30 min) on an orbital shaker at RT.

9. The counts are read on a TopCount NXT reader.

10. A dose-reponse curve is first plotted using the Graphpad Prism software, to generate the IC50 values.

With this IC50 value and the known Km value for the substrate and HSD1 enzyme, an estimated Ki can be calculated with the Chen and Prusoff equation {Ki=IC50/[1+(substrate/Km)]}.

The compounds of the present invention all show 11β-HSD1 enzyme activity (IC$_{50}$) in the assays ranging from 1000 nM to <1 nM.

What is claimed is:

1. A method for treating age-related cognitive disorders comprising administering to a patient in need thereof a therapeutically effective amount of a compound of formula (II):

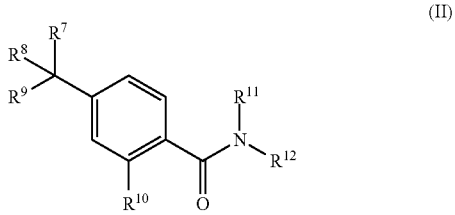

wherein
$R^7$ is —OH;
$R^8$ is $(C_1-C_8)$alkyl and $R^9$ is —$(C_1-C_6)$haloalkyl;
$R^{10}$ is a member selected from the group consisting of hydrogen, halogen, $(C_1-C_8)$alkyl and $(C_3-C_8)$cycloalkyl;
$R^{11}$ and $R^{12}$ are each members independently selected from the group consisting of $(C_1-C_8)$alkyl, $(C_2-C_8)$alkenyl, $(C_2-C_8)$alkynyl, $(C_1-C_6)$haloalkyl, $(C_2-C_8)$hydroxyalkyl, $(C_3-C_8)$cycloalkyl, $(C_3-C_8)$heterocycloalkyl, $(C_3-C_8)$cycloalkyl$(C_1-C_6)$alkyl, $(C_3-C_8)$cycloalkyl$(C_1-C_6)$alkoxy, $(C_3-C_8)$heterocycloalkyl$(C_1-C_6)$alkyl, aryl, heteroaryl$(C_1-C_6)$alkyl, aryl$(C_1-C_6)$alkyl;
wherein $R^{11}$ and $R^{12}$, together with the nitrogen to which they are attached may combine to form a five to fourteen-membered ring heterocycloalkyl containing from 1 to 4 heteroatoms independently selected from nitrogen and sulfur;
any cycloalkyl portion, heterocycloalkyl portion, aryl portion or heteroaryl portion is optionally substituted with from one to four members selected from the group consisting of halogen, —CN, —NO$_2$, $(C_1-C_8)$alkyl, $(C_2-C_8)$alkenyl, $(C_2-C_8)$alkynyl, $(C_1-C_8)$alkoxy, $(C_1-C_6)$haloalkyl, $(C_2-C_8)$hydroxyalkyl, aryl, heteroaryl, $(C_3-C_8)$cycloalkyl, $(C_3-C_8)$heterocycloalkyl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, —C(O)R', —C(O)OR', —NR'C(O)OR'', —OR', —SR', —OC(O)R', —C(O)N(R')$_2$, —S(O)R'', —SO$_2$R'', —SO$_2$N(R')$_2$, —N(R')$_2$, —NR'C(O)R', —NR'SO$_2$R'', —X—C(O)R', —X—C(O)OR', —X—NR'C(O)OR'', —X—OR'', —X—OC(O)R', —X—C(O)N(R')$_2$, —X—S(O)R'', —X—SO$_2$R'', —X—SO$_2$N(R')$_2$, —X—N(R')$_2$ and —X—NR'C(O)R',
wherein any alkyl or alkylene group is optionally substituted by up to three substituents selected from the group consisting of —OR', =O, —NR'R'', -halo, —OC(O)R', —CO$_2$R', —C(O)NR'R'', —OC(O)NR'R'', —NR''C(O)R', —NR''CO$_2$R', —NR'SO$_2$NR'R'', —SO$_2$R', —SO$_2$NR'R'', —NR''SO$_2$R'—CN and —NO$_2$;
X is a branched or straight chain $(C_1-C_8)$alkylene group;
each occurrence of R' is independently H or an unsubstituted member selected from the group consisting of $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_6)$haloalkyl, $(C_2-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, or two R' groups, when attached to the same nitrogen atom, can be combined with the nitrogen atom to which they are attached to form a heterocycle or heteroaryl group; and
each occurrence of R'' is independently an unsubstituted member selected from the group consisting of $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_6)$haloalkyl, $(C_2-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl or aryl$(C_1-C_6)$alkyl;
or a pharmaceutically acceptable salt or stereoisomer thereof.

2. The method according to claim 1, wherein the compound of formula (II) is selected from the group consisting of:
N-Benzyl-N-methyl-4-(1,1,1-trifluoro-2-hydroxypropan-2-yl)benzamide,
N-Cyclohexyl-N-methyl-4-(1,1,1-trifluoro-2-hydroxypropan-2-yl)benzamide,
N-Benzyl-N-ethyl-4-(1,1,1-trifluoro-2-hydroxypropan-2-yl)benzamide,
N-(3,4-Dichlorophenyl)-N-methyl-4-(1,1,1-trifluoro-2-hydroxypropan-2-yl)benzamide,
N,N-Dicyclohexyl-4-(1,1,1-trifluoro-2-hydroxypropan-2-yl)benzamide,
N,N-Diisopropyl-4-(1,1,1-trifluoro-2-hydroxypropan-2-yl)benzamide,
N-Cyclohexyl-N-isopropyl-4-(1,1,1-trifluoro-2-hydroxypropan-2-yl)benzamide,
N-Isopropyl-N-phenyl-4-(1,1,1-trifluoro-2-hydroxypropan-2-yl)benzamide, N-(2-Chlorophenyl)-N-isopropyl-4-(1,1,1-trifluoro-2-hydroxypropan-2-yl)benzamide, N-(2,4-Dichlorophenyl)-N-isopropyl-4-(1,1,1-trifluoro-2-hydroxypropan-2-yl)benzamide, N-(2-Chloro-5-cyanophenyl)-N-isopropyl-4-(1,1,1-trifluoro-2-hydroxypropan-2-yl)benzamide, N-(2-Chloro-5-(trifluoromethyl)phenyl)-N-isopropyl-4-(1,1,1-trifluoro-2-hydroxypropan-2-yl)benzamide, N-cyclohexyl-N-cyclopropyl-4((S)-1,1,1-trifluoro-2-hydroxypropan-2-yl)benzamide, N-cyclohexyl-4((S)-1,1,1-trifluoro-2-hydroxypropan-2-yl)-N-(2,2,2-trifluoroethyl)benzamide, N-cyclopropyl-4((S)-1,1,1-trifluoro-2-hydroxypropan-2-yl)-N-(4,4-difluorocyclohexyl)benzamide, N-cyclopropyl-4((S)-1,1,1-trifluoro-2-hydroxypropan-2-yl)-N-((1r,4r)-4-fluorocyclohexyl)benzamide, and N-cyclopropyl-4((S)-1,1,1-trifluoro-2-hydroxypropan-2-yl)-N-((1s,4s)-4-fluorocyclohexyl)benzamide, or a pharmaceutically acceptable salt or stereoisomer thereof.

3. The method according to claim 1, wherein the compound of formula (II) is selected from the following table:

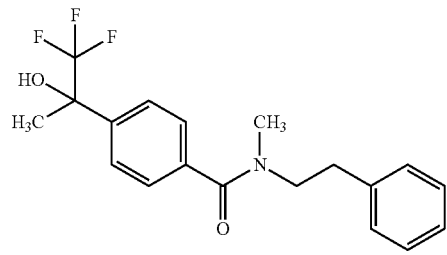

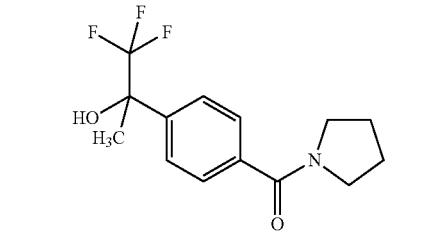

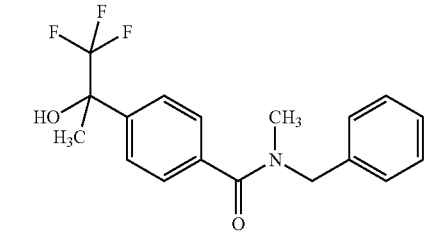

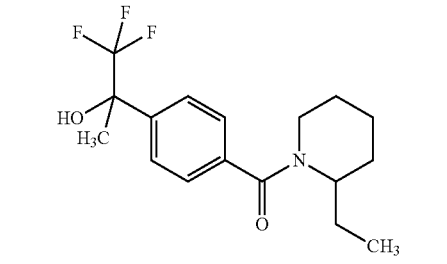

-continued

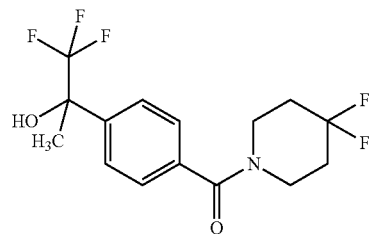

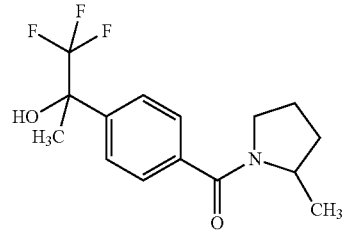

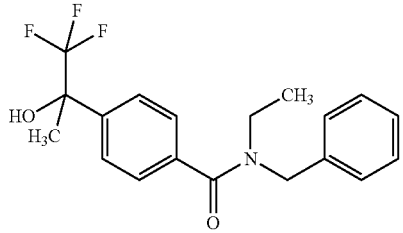

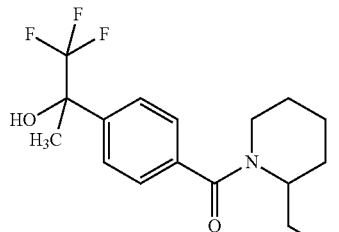

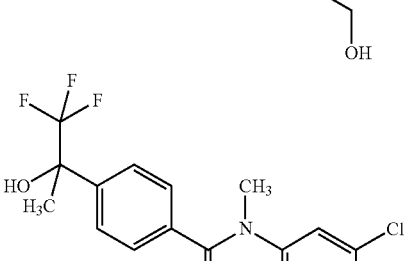

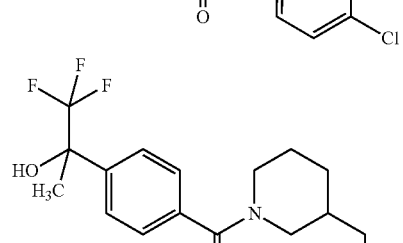

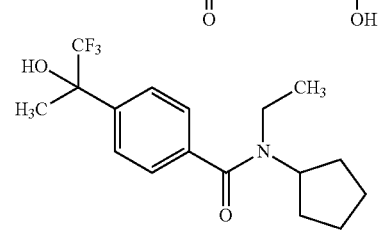

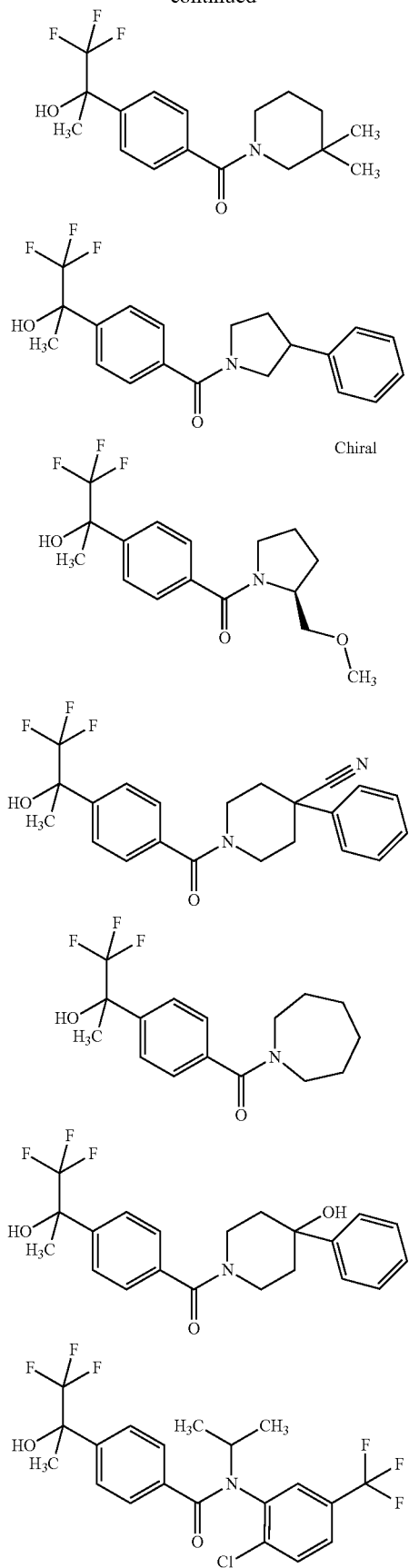
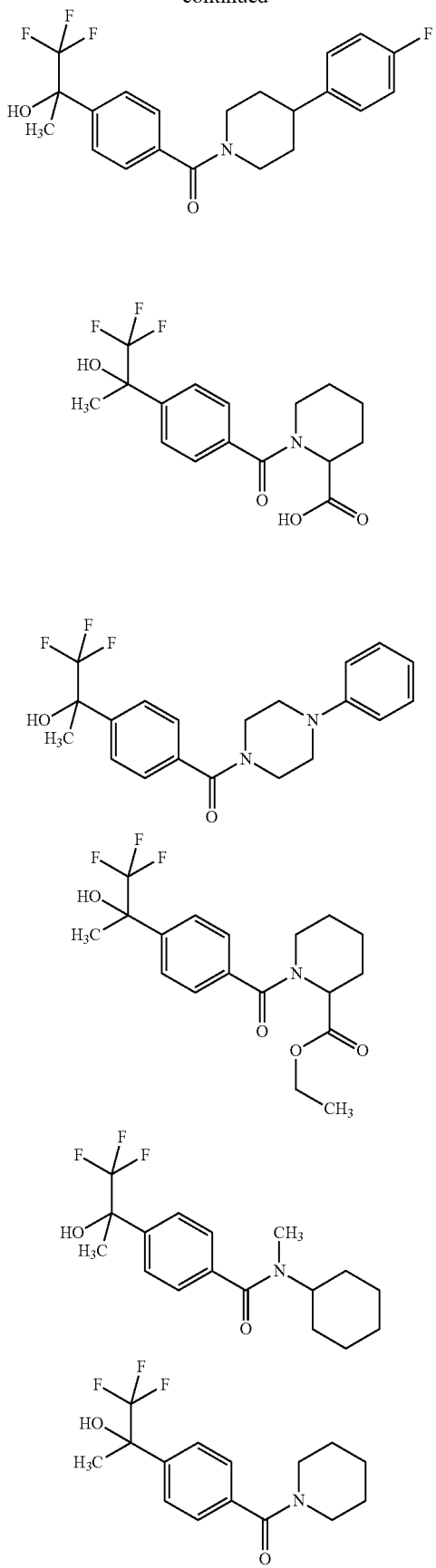

127
-continued
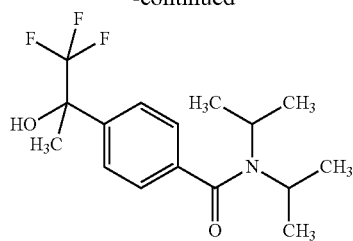
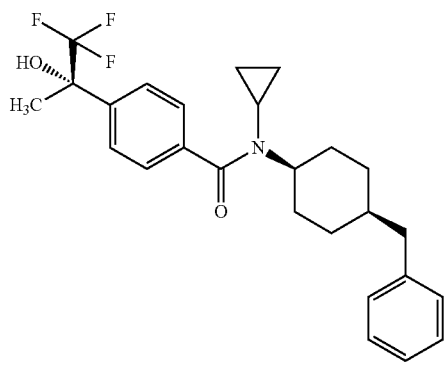
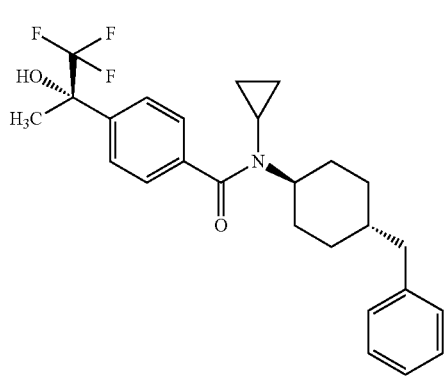
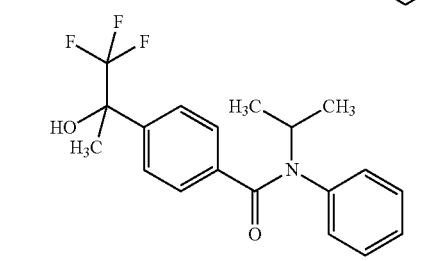
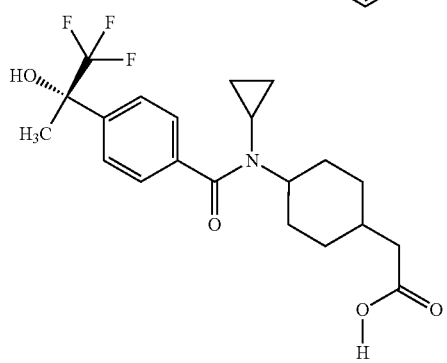
128
-continued
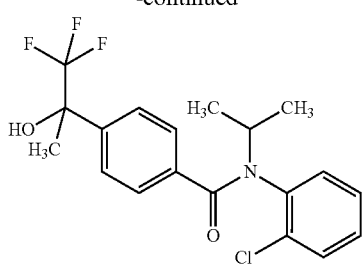
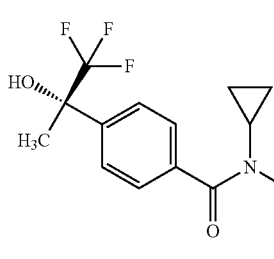
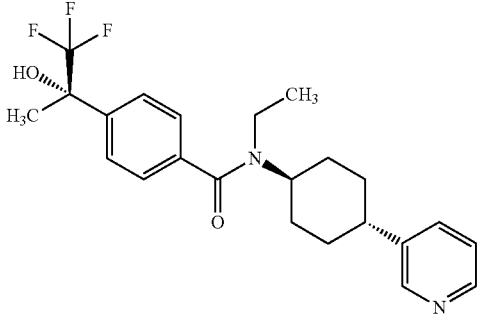
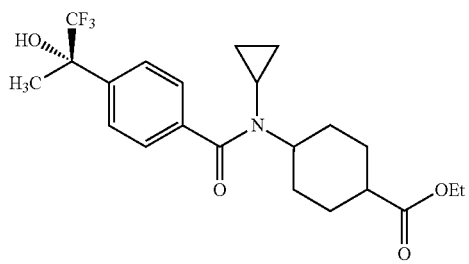
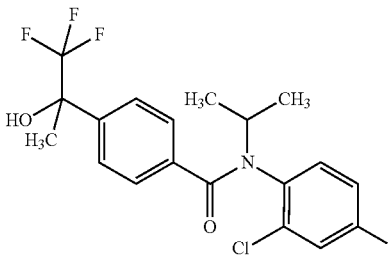

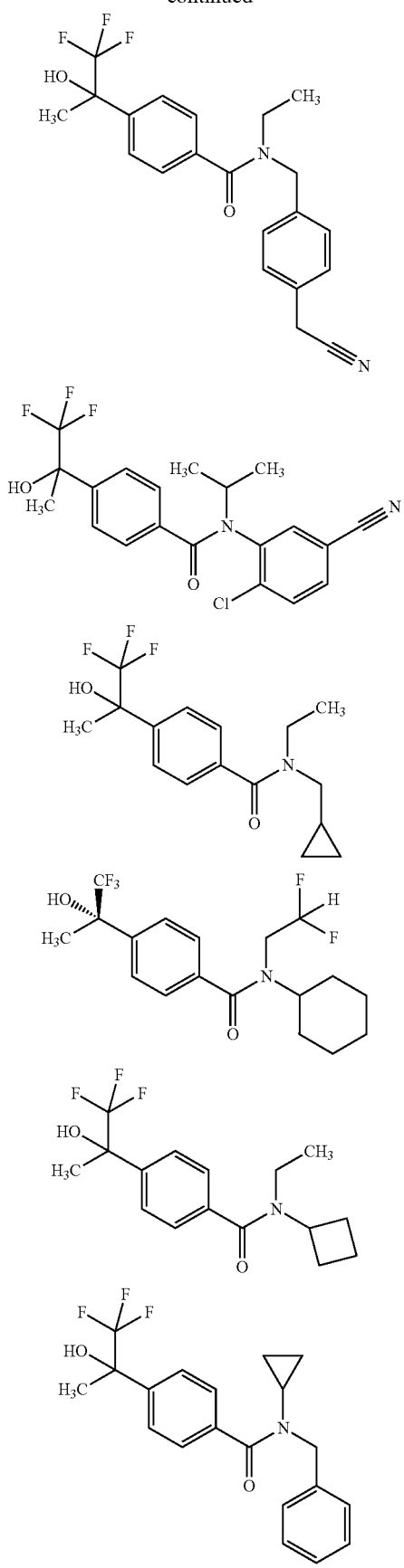
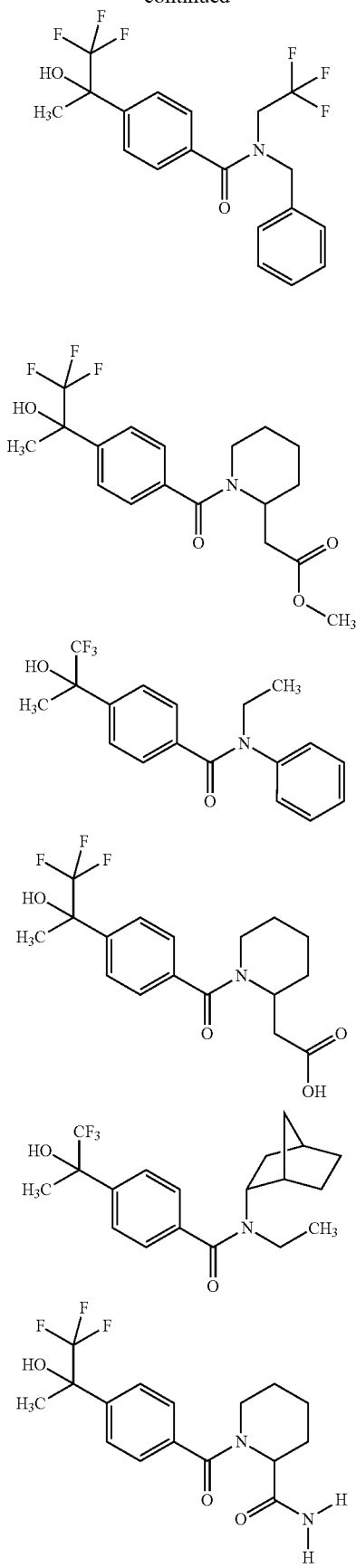

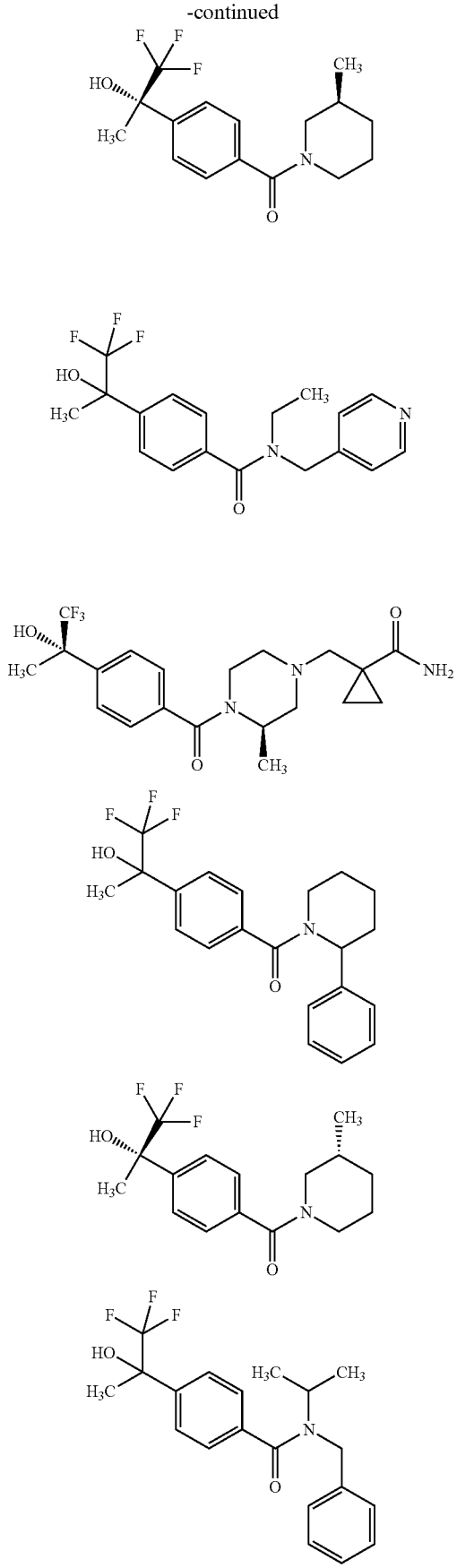
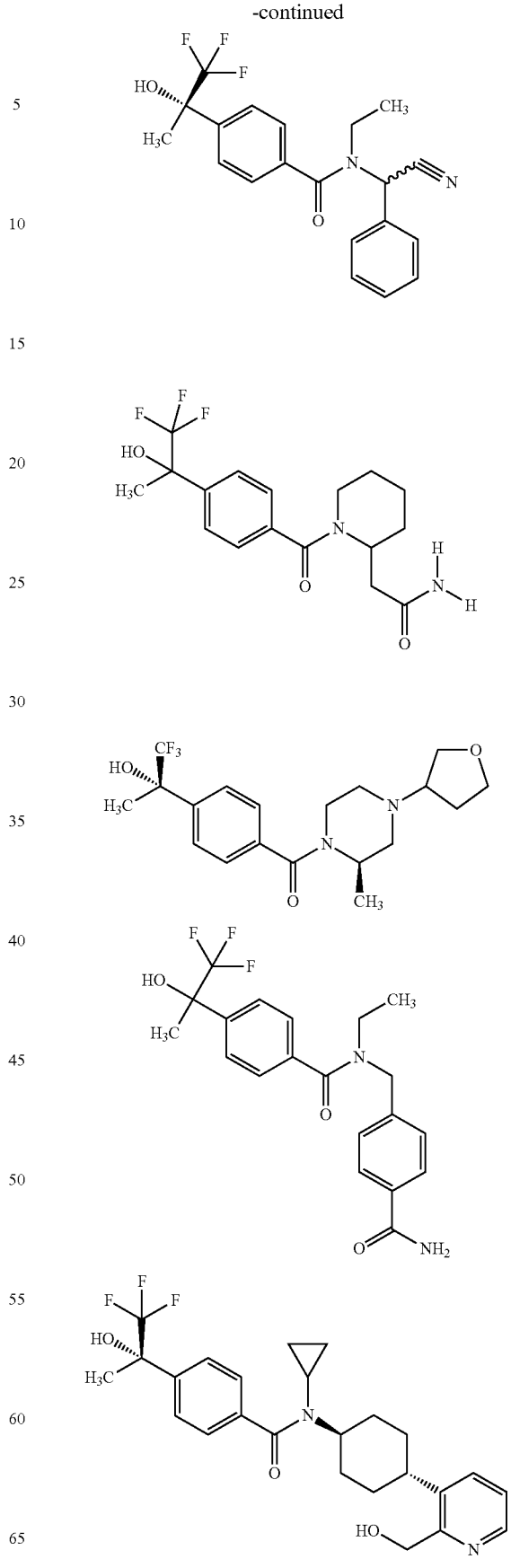

133
-continued
134
-continued
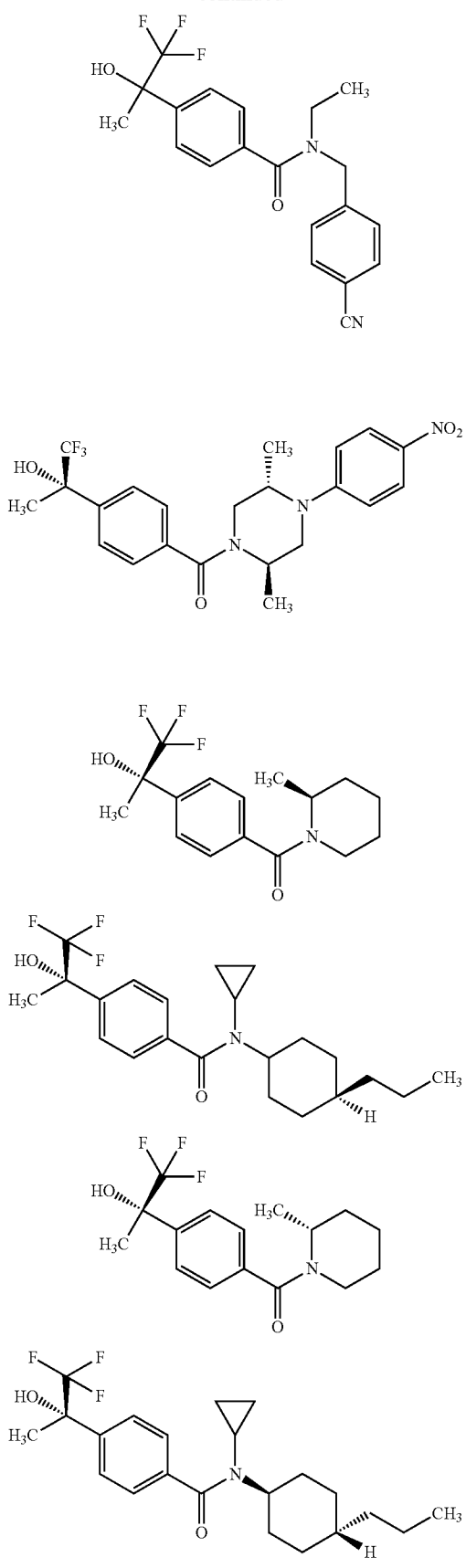
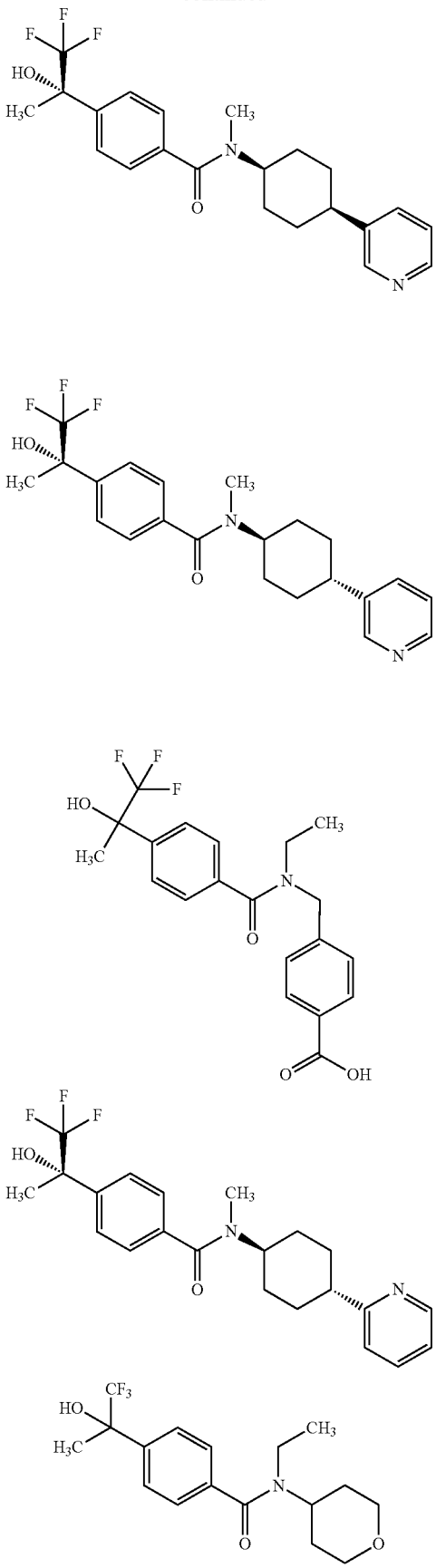

135
-continued
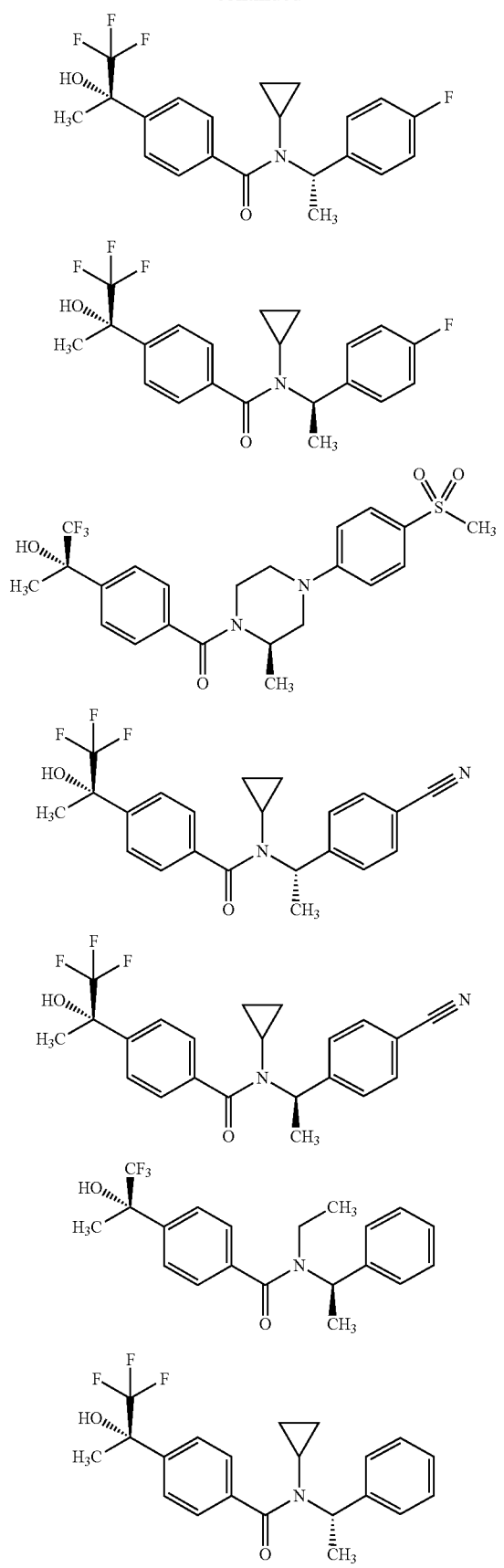
136
-continued
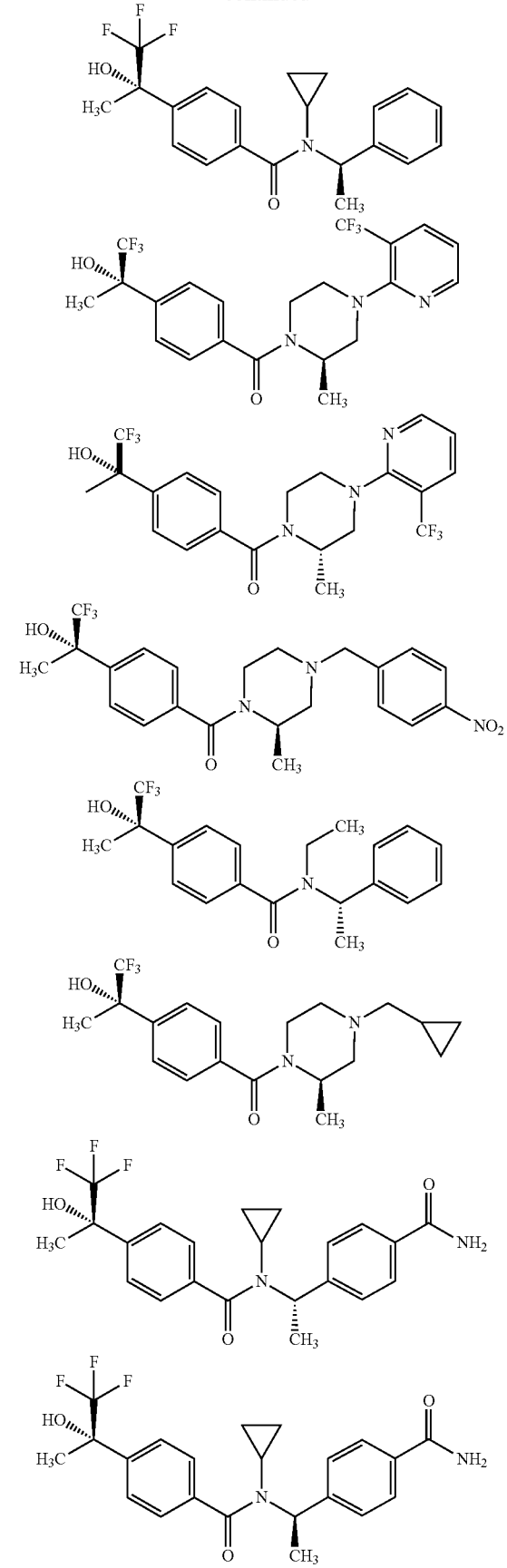

137
-continued
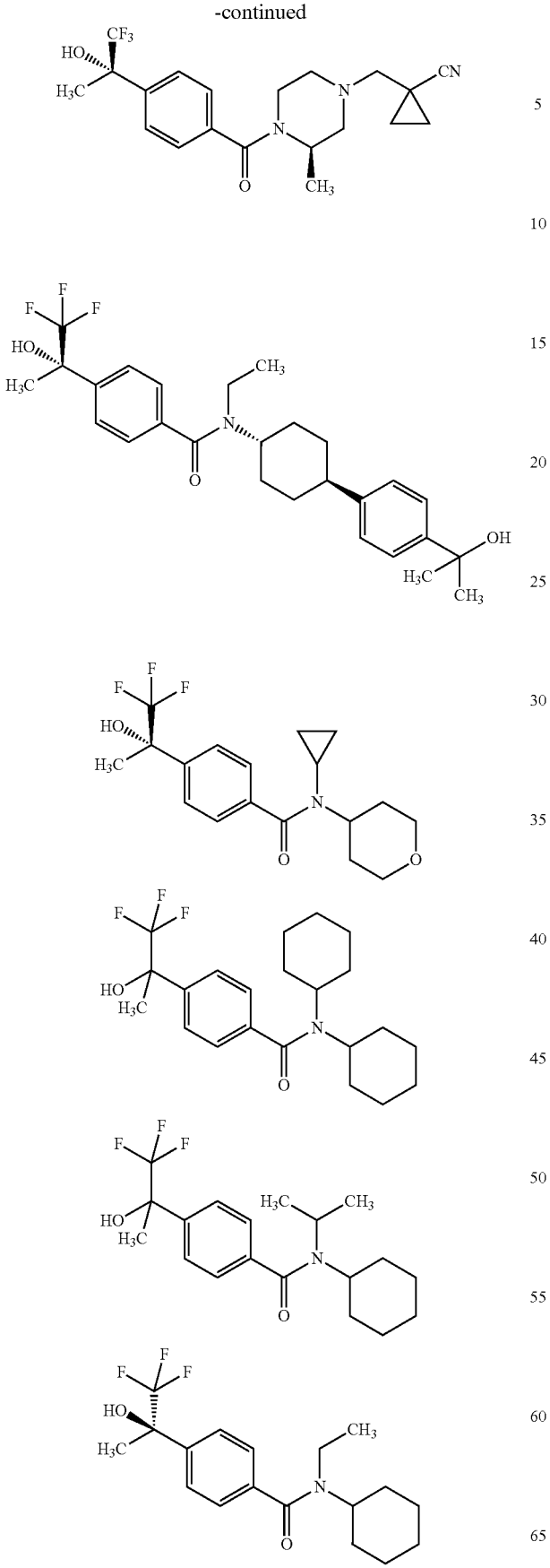
138
-continued
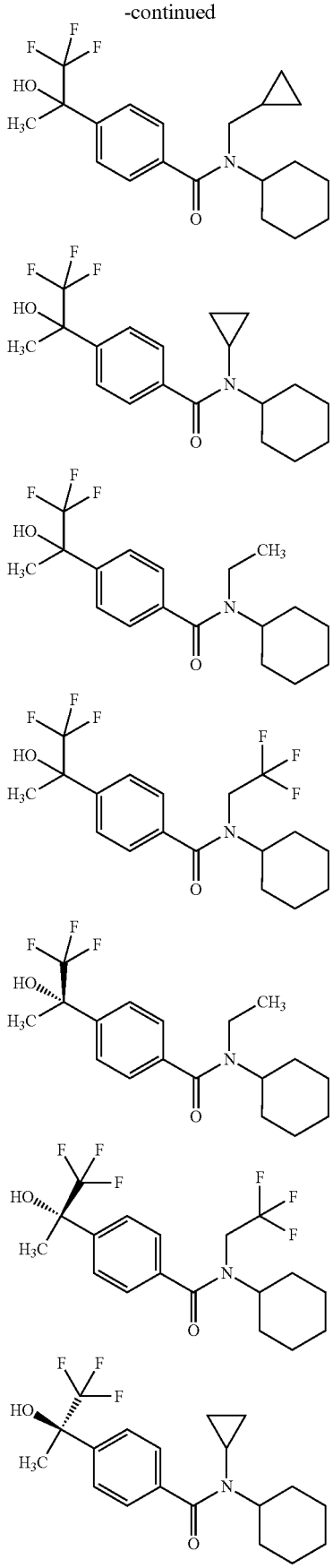

-continued
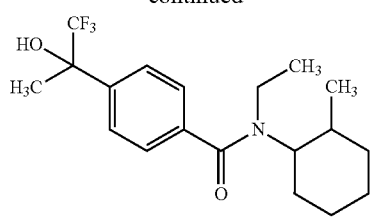
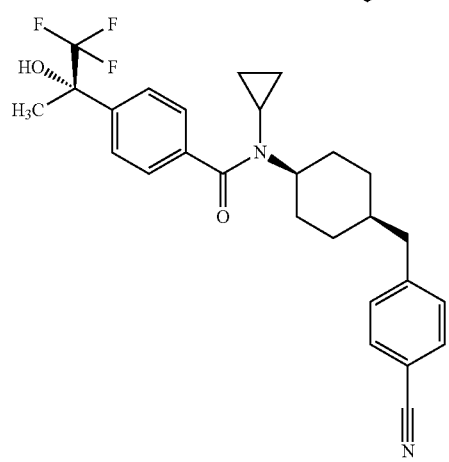
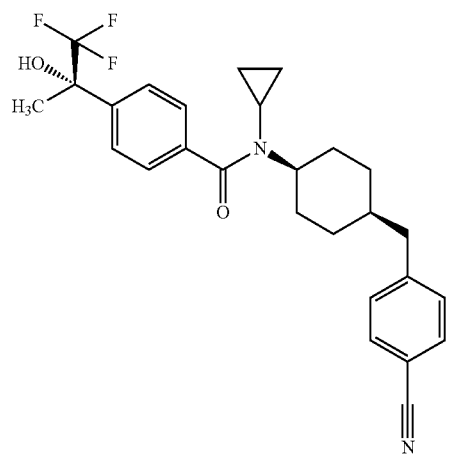
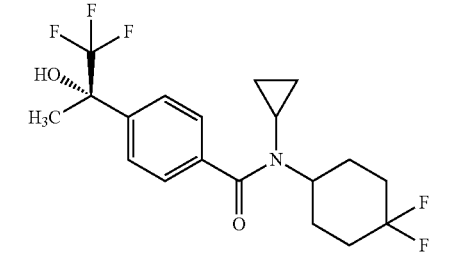
-continued
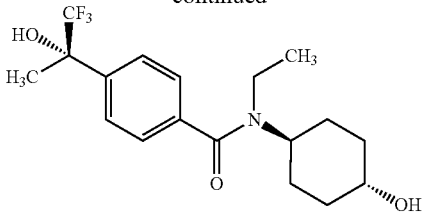
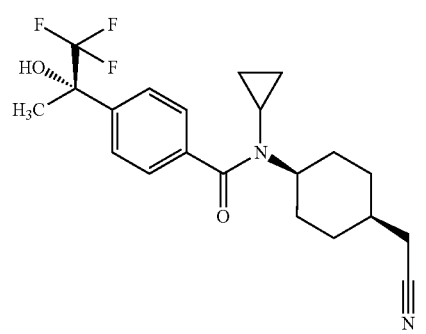
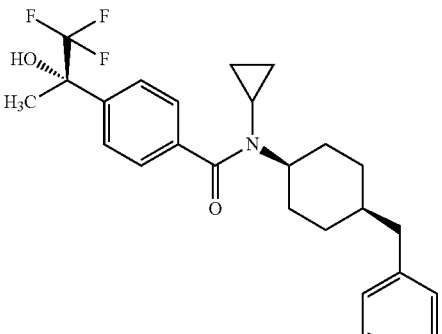
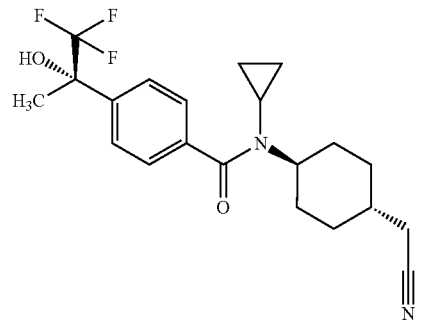
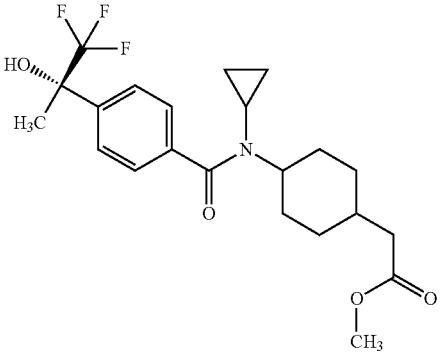

141
-continued
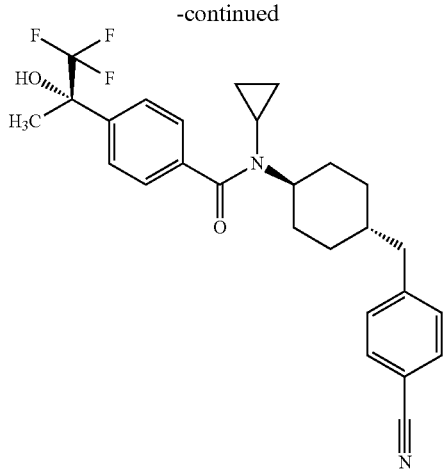
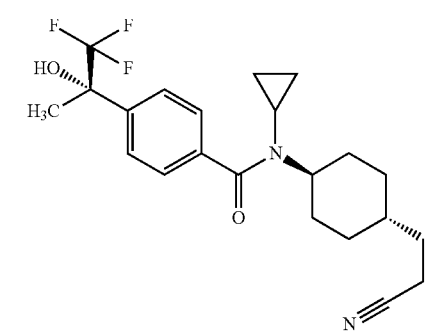
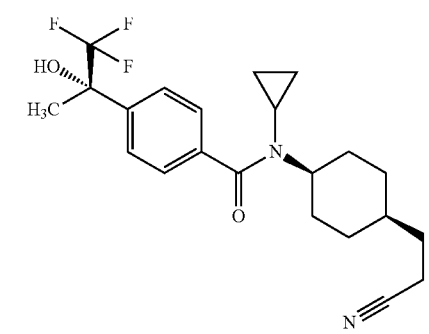
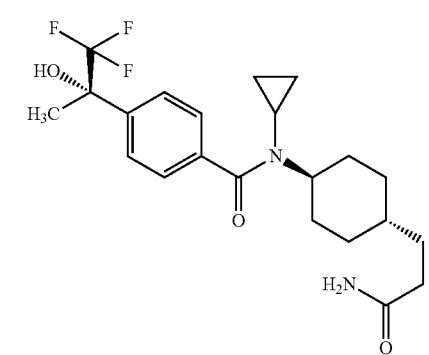
142
-continued
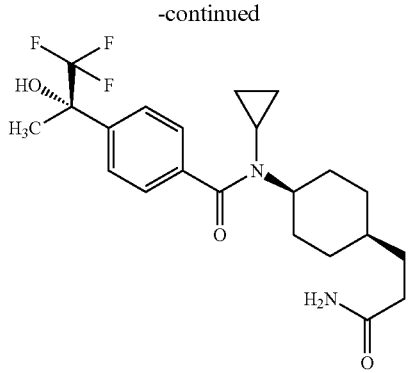
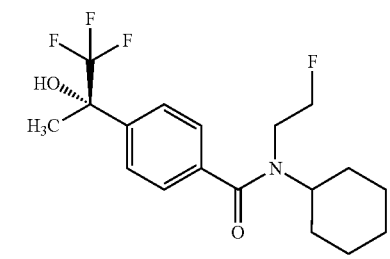
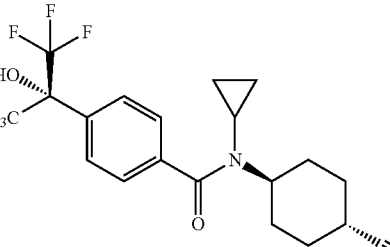
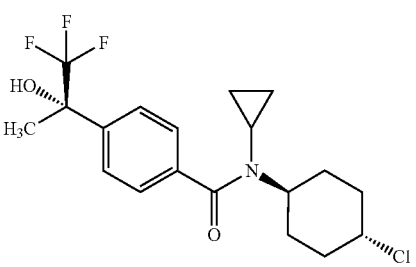
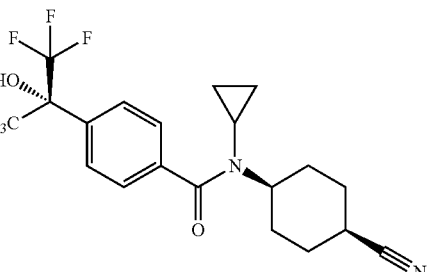
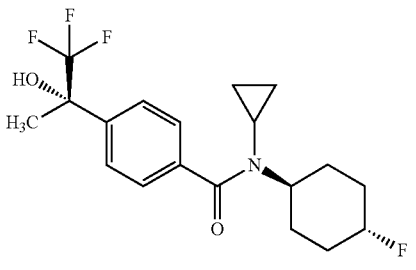

143
-continued
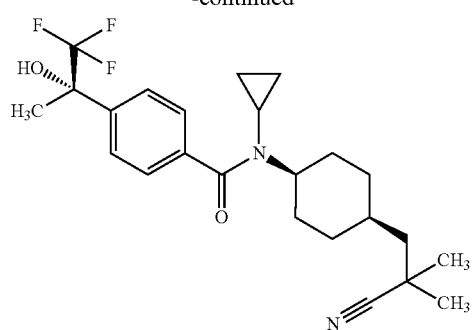
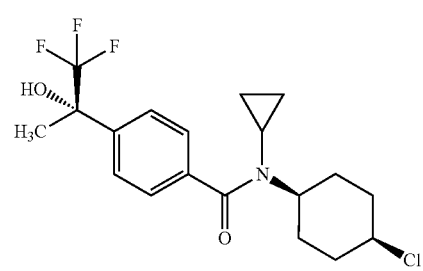
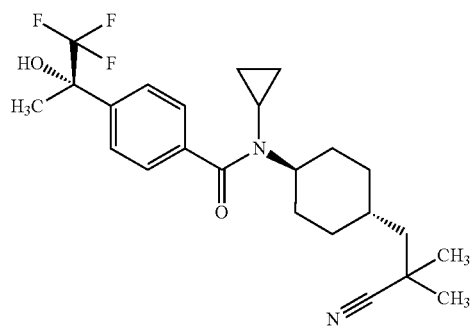
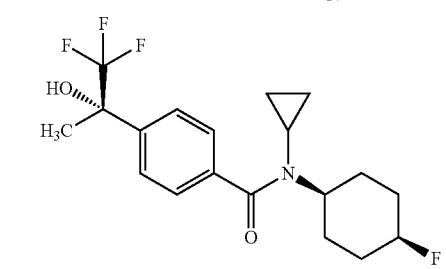
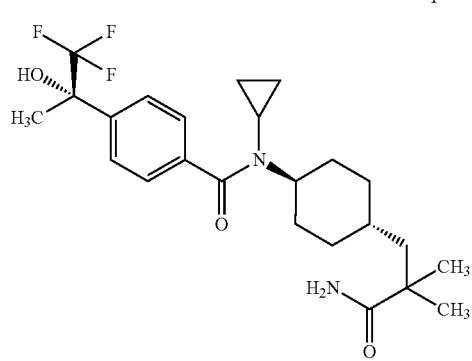
144
-continued
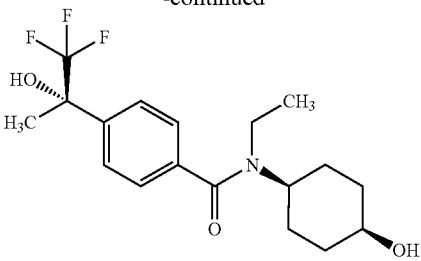
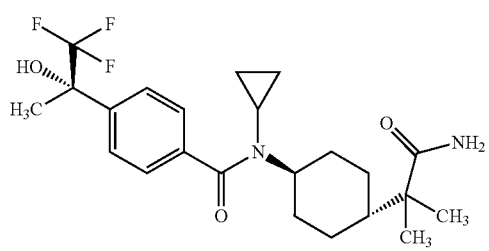
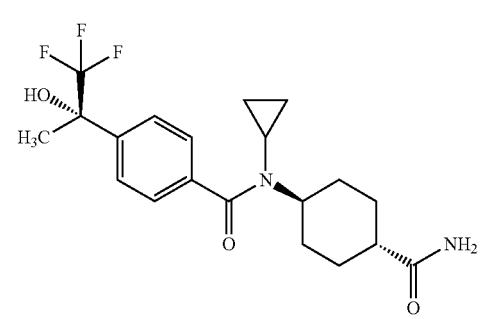
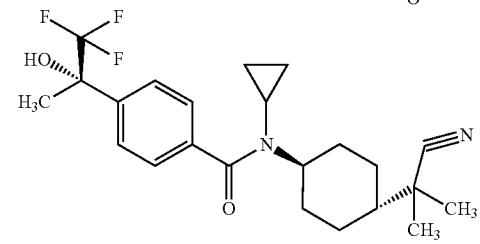
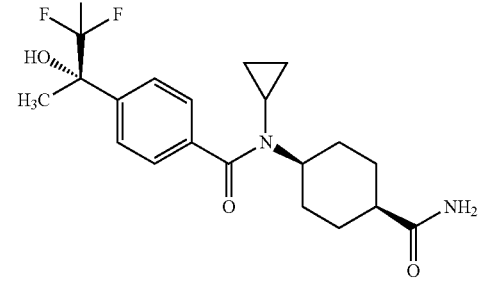
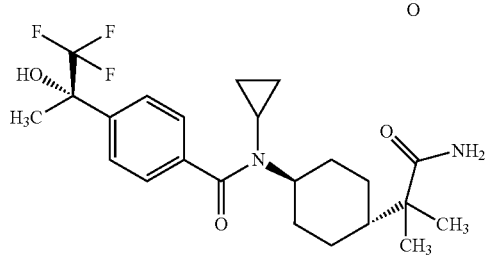

145
-continued
146
-continued
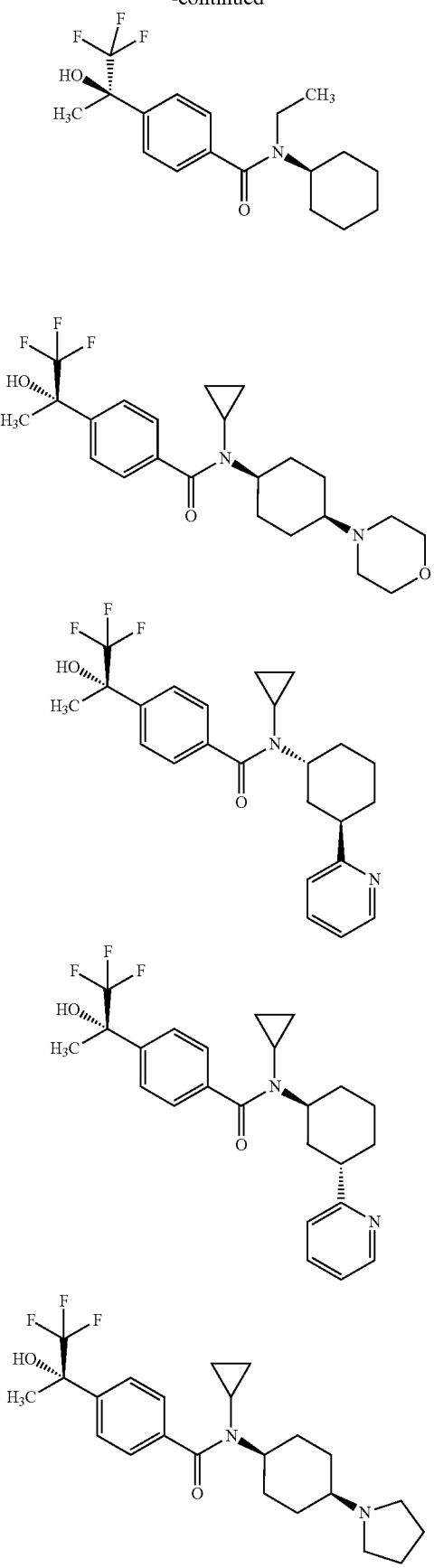
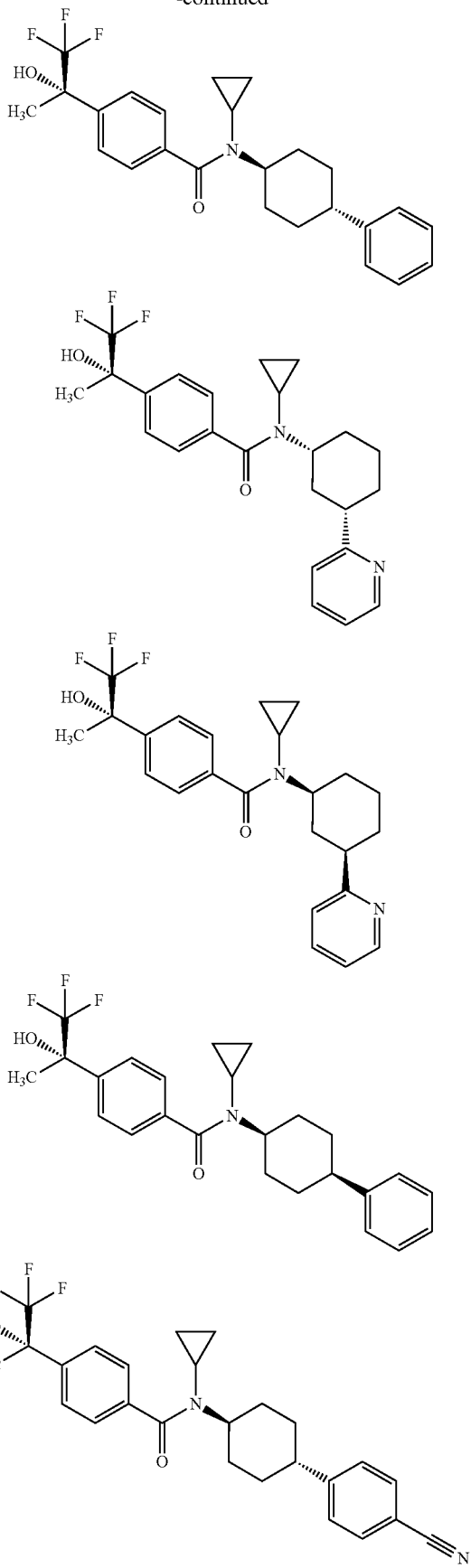

147
-continued
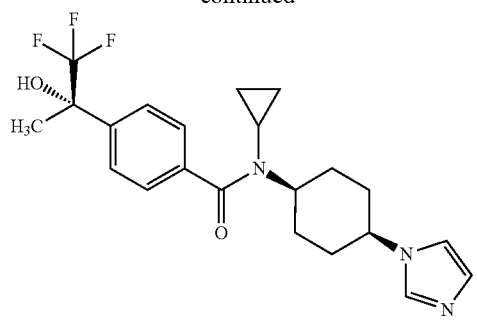
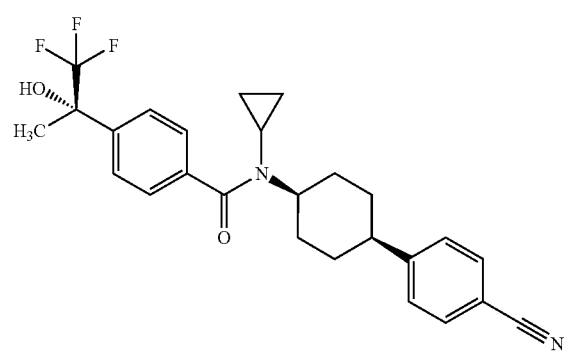
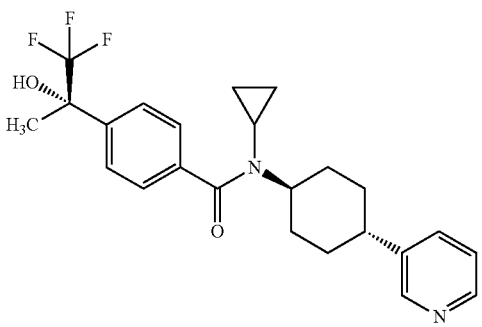
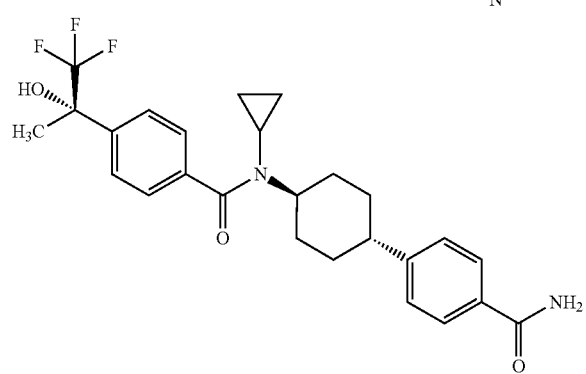
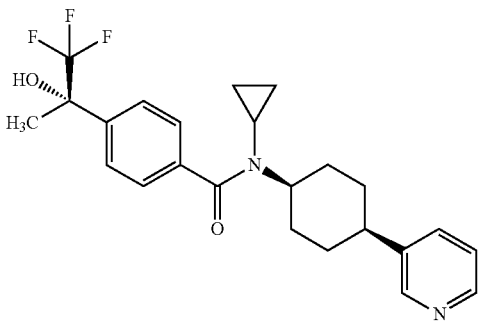
148
-continued
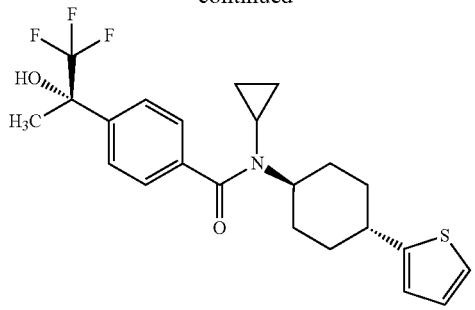
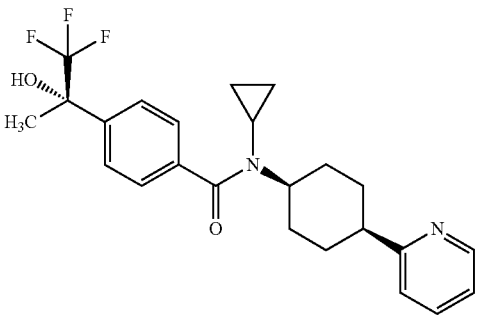
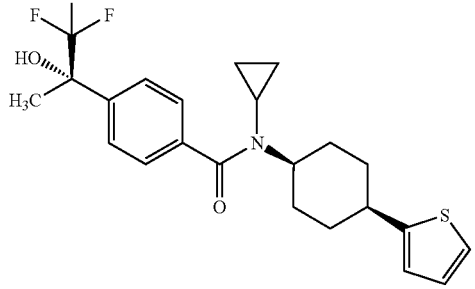
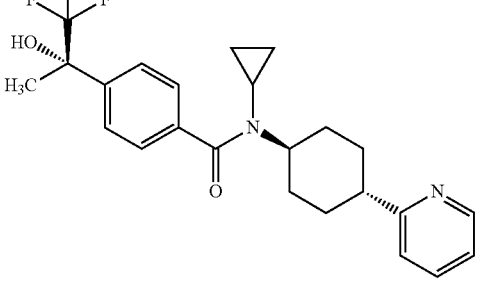
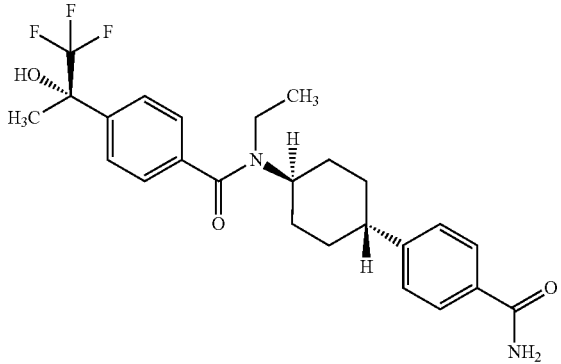

149
-continued
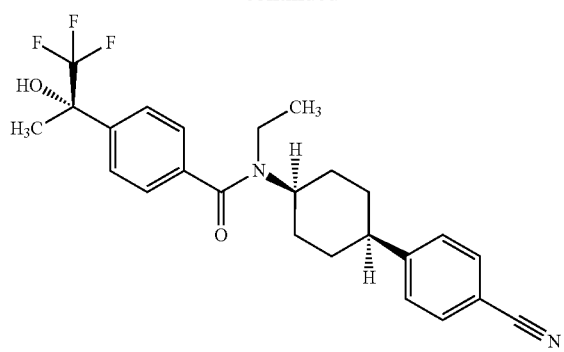
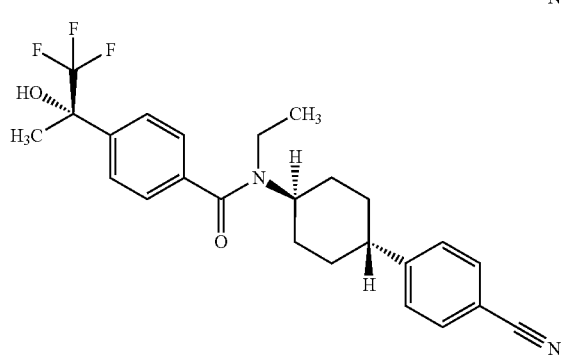
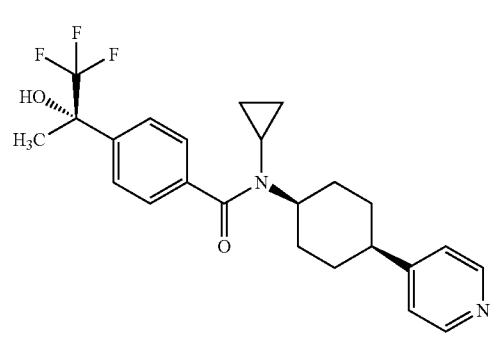
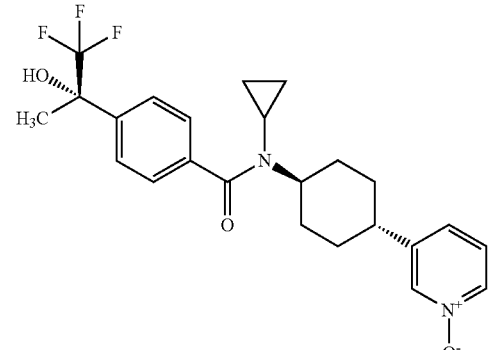
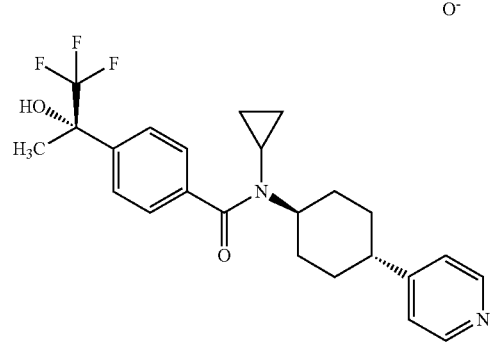
150
-continued
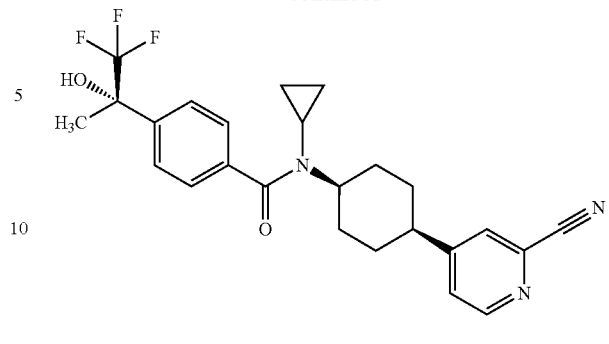
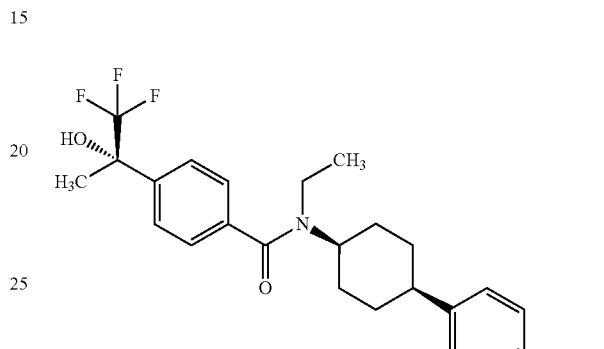
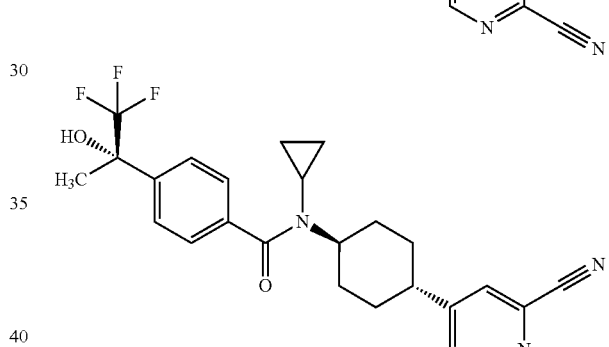
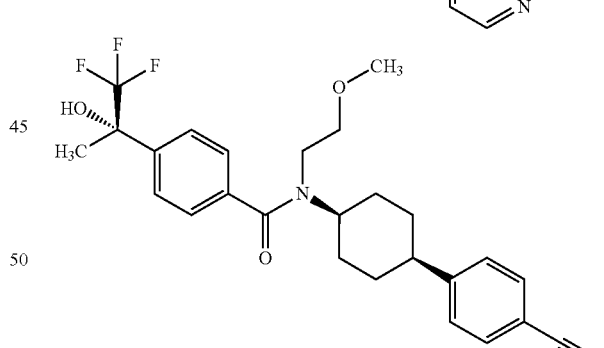
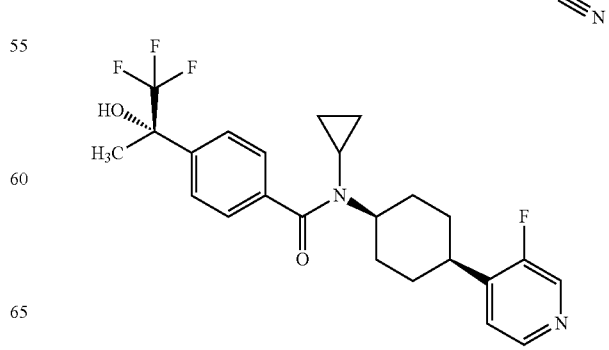

151
-continued
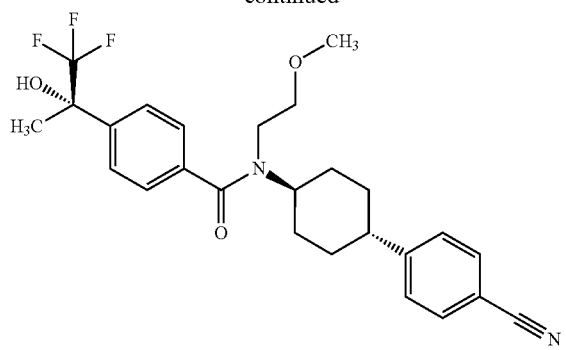
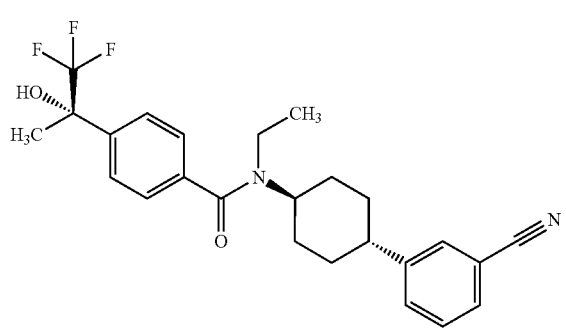
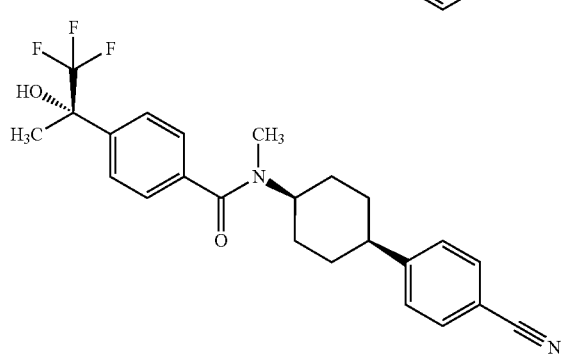
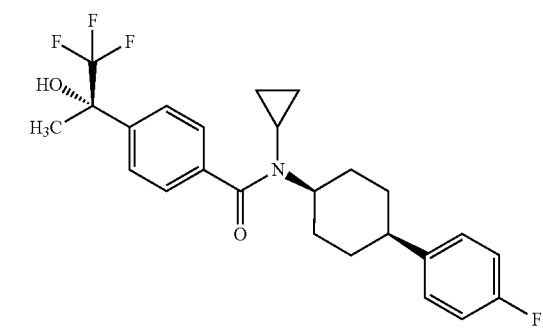
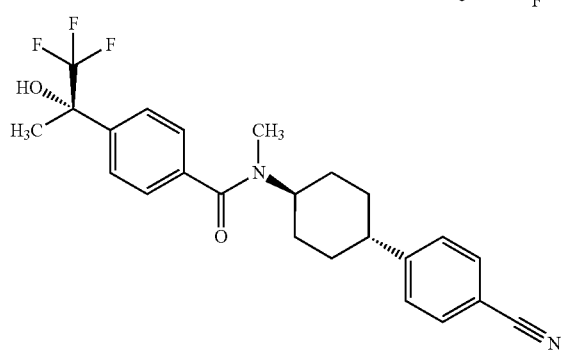
152
-continued
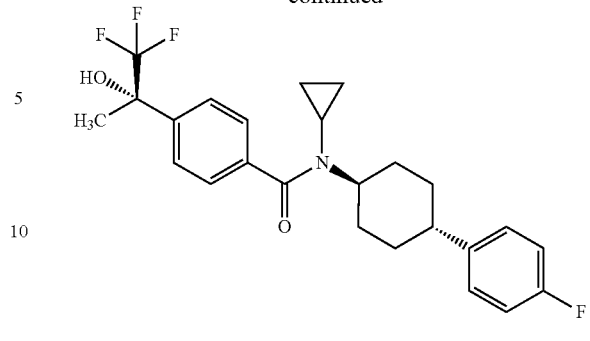
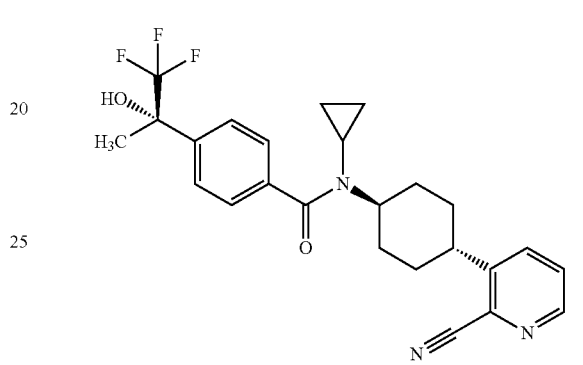
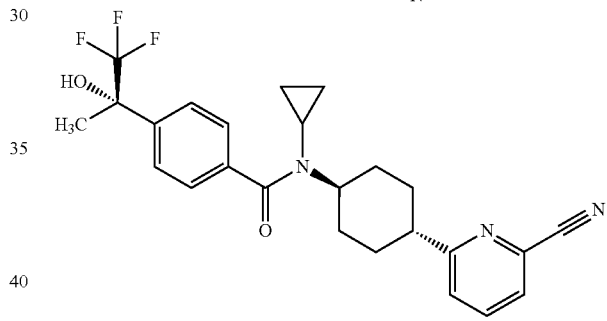
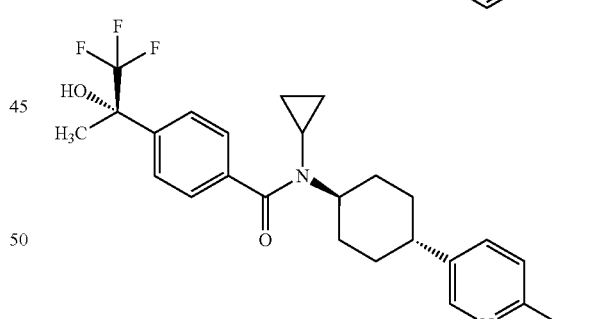
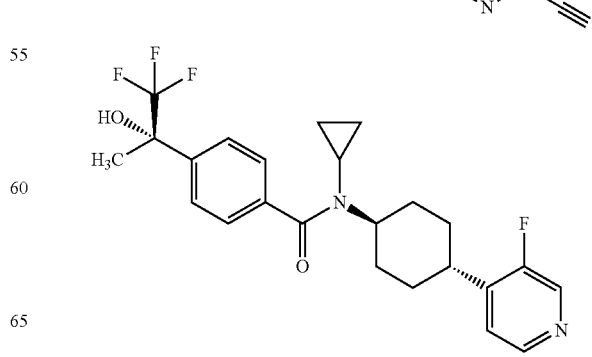

153
-continued
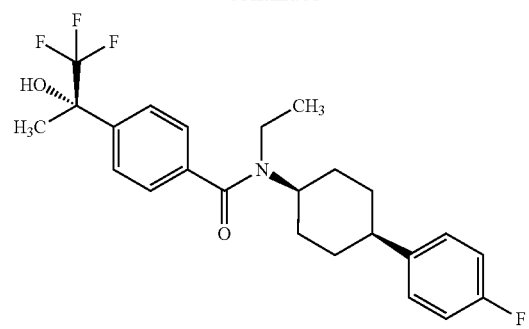
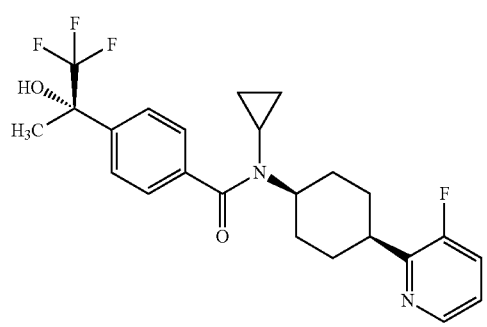
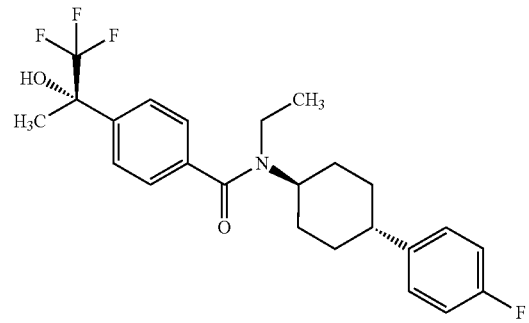
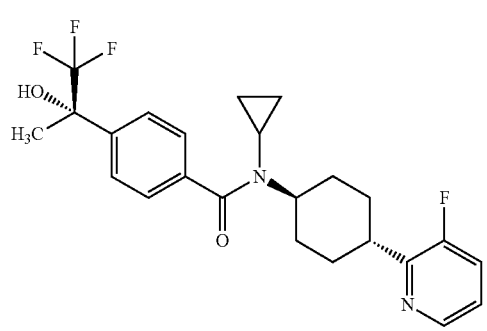
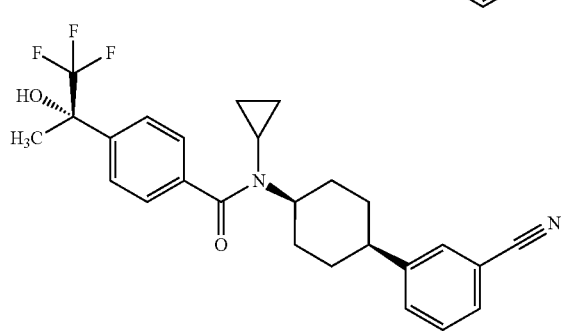
154
-continued
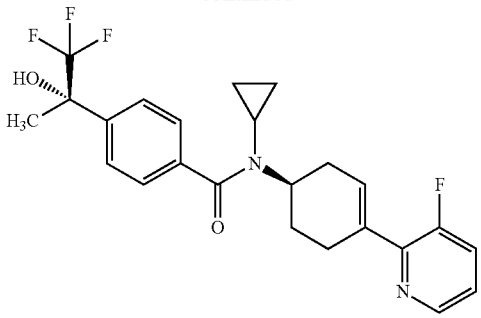
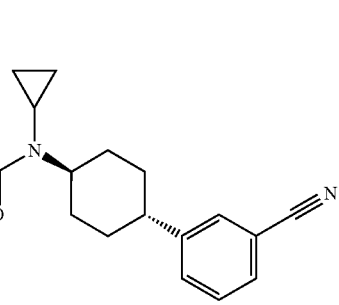
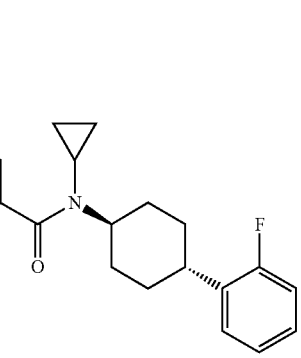
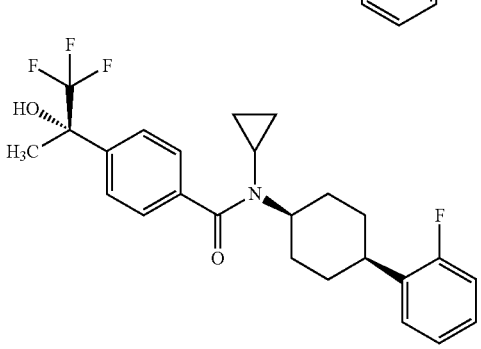

155
-continued
156
-continued
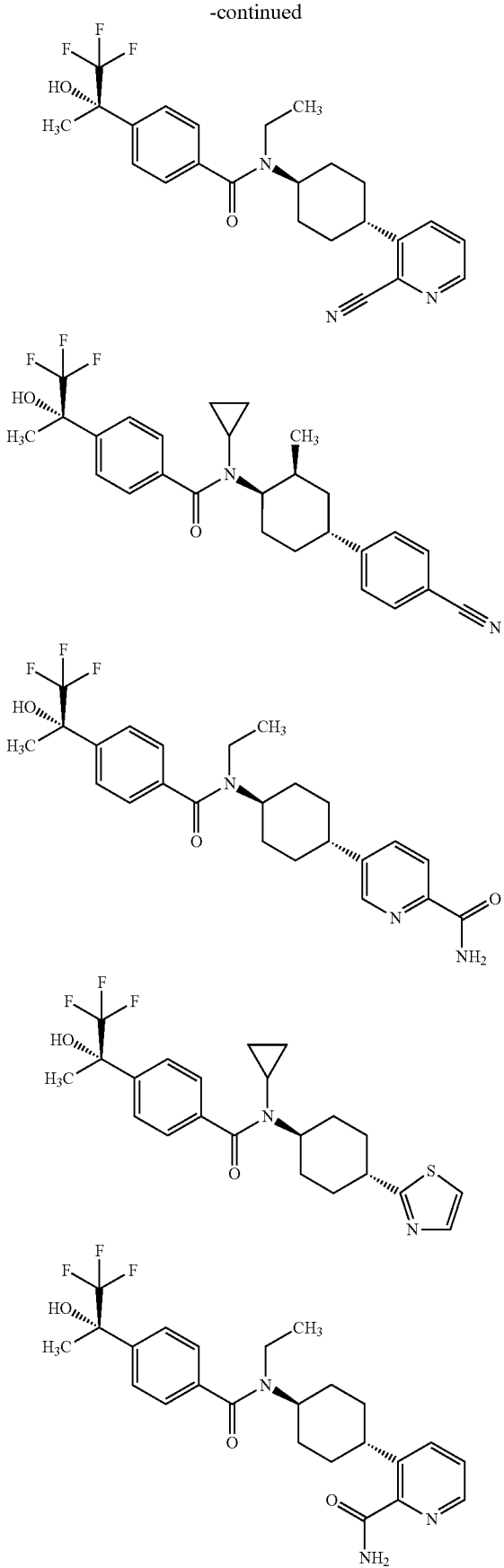
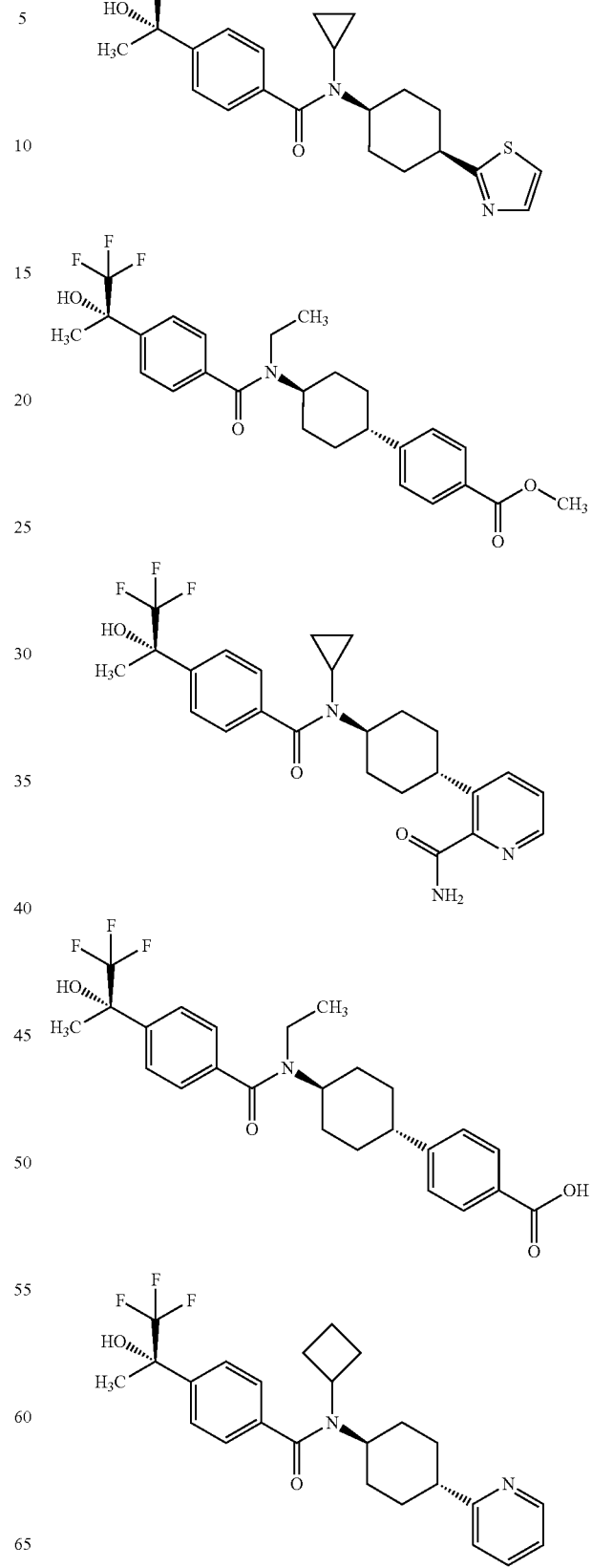

157
-continued
158
-continued
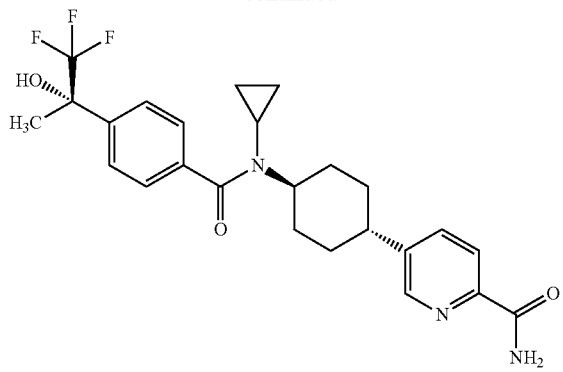
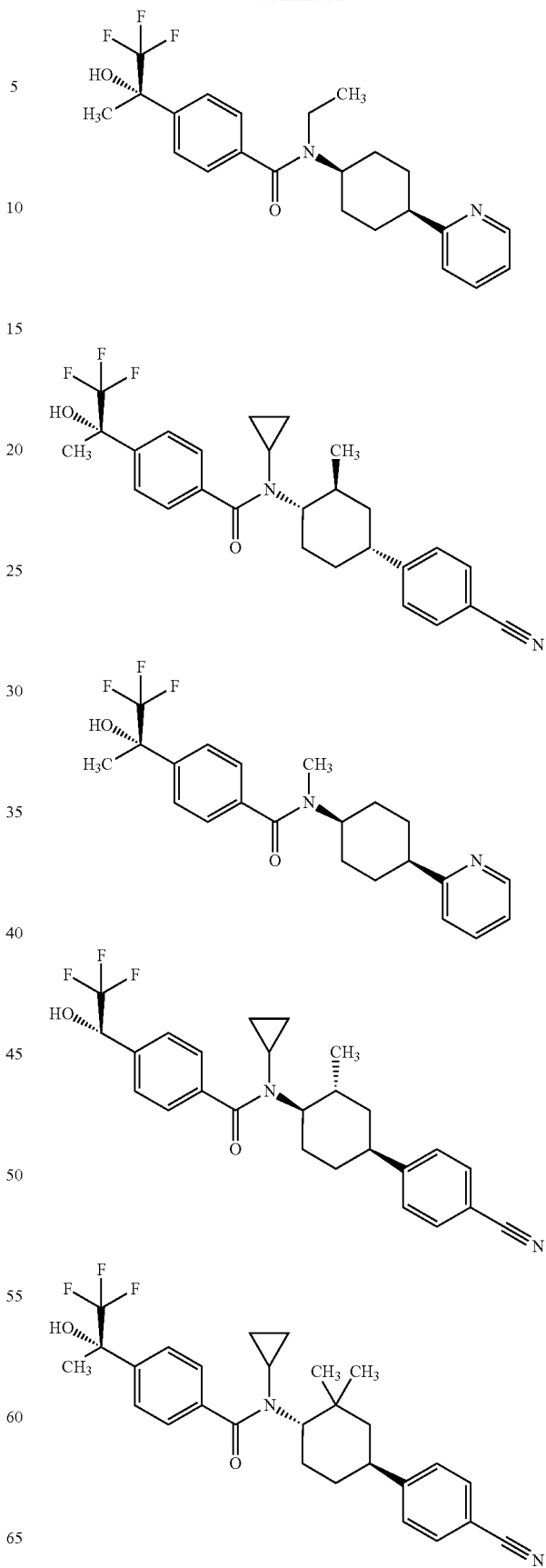

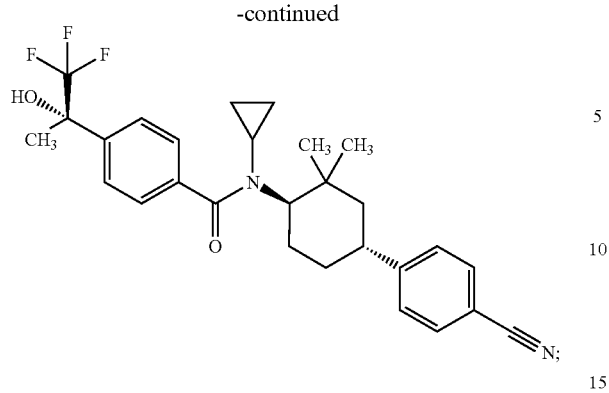
or a pharmaceutically acceptable salt or stereoisomer thereof.
4. The method according to claim 1, wherein the age-related cognitive disorder is Alzheimer's Disease.